(12) United States Patent
Yu et al.

(10) Patent No.: US 9,938,262 B2
(45) Date of Patent: *Apr. 10, 2018

(54) BENZAMIDES

(71) Applicant: Merck Patent GmbH, Darmstadt (DE)

(72) Inventors: Henry Yu, Wellesley, MA (US); Andreas Goutopoulos, Boston, MA (US); Thomas E. Richardson, Chapel HIll, NC (US); Jiezhen Li, Jamaica Plain, MA (US); Brian H. Heasley, Wake Forest, NC (US); Pandi Bharathi, Cary, NC (US)

(73) Assignee: Merck Patent GmbH, Darmstadt (DE)

( * ) Notice: Subject to any disclaimer, the term of this patent is extended or adjusted under 35 U.S.C. 154(b) by 0 days.

This patent is subject to a terminal disclaimer.

(21) Appl. No.: 15/283,938

(22) Filed: Oct. 3, 2016

(65) Prior Publication Data

US 2017/0022191 A1 Jan. 26, 2017

Related U.S. Application Data

(60) Continuation of application No. 14/863,865, filed on Sep. 24, 2015, now Pat. No. 9,498,475, which is a
(Continued)

(51) Int. Cl.
| | |
|---|---|
| *A61K 31/451* | (2006.01) |
| *C07D 417/12* | (2006.01) |
| *C07D 413/12* | (2006.01) |
| *A61K 31/496* | (2006.01) |
| *C07D 403/12* | (2006.01) |
| *C07D 401/14* | (2006.01) |
| *C07D 405/14* | (2006.01) |
| *C07D 413/14* | (2006.01) |
| *C07D 403/14* | (2006.01) |
| *C07D 405/12* | (2006.01) |
| *C07D 409/10* | (2006.01) |
| *C07D 409/12* | (2006.01) |
| *C07D 409/14* | (2006.01) |
| *C07D 417/14* | (2006.01) |
| *A61K 31/454* | (2006.01) |
| *A61K 31/498* | (2006.01) |
| *A61K 31/4985* | (2006.01) |
| *A61K 31/506* | (2006.01) |
| *A61K 31/5377* | (2006.01) |
| *A61K 31/541* | (2006.01) |

(Continued)

(52) U.S. Cl.
CPC .......... *C07D 417/12* (2013.01); *A61K 31/454* (2013.01); *A61K 31/496* (2013.01); *A61K 31/498* (2013.01); *A61K 31/4985* (2013.01); *A61K 31/506* (2013.01); *A61K 31/5377* (2013.01); *A61K 31/541* (2013.01); *A61K 31/551* (2013.01); *C07D 233/64* (2013.01); *C07D 263/34* (2013.01); *C07D 307/68* (2013.01); *C07D 401/14* (2013.01); *C07D 403/12* (2013.01); *C07D 403/14* (2013.01); *C07D 405/12* (2013.01); *C07D 405/14* (2013.01); *C07D 407/12* (2013.01); *C07D 409/10* (2013.01); *C07D 409/12* (2013.01); *C07D 409/14* (2013.01); *C07D 413/12* (2013.01); *C07D 413/14* (2013.01); *C07D 417/14* (2013.01)

(58) Field of Classification Search
CPC ... C07D 239/04; C07D 211/14; C07D 307/48
See application file for complete search history.

(56) References Cited

U.S. PATENT DOCUMENTS

| | | |
|---|---|---|
| 6,653,338 B2 | 11/2003 | El Tayer |
| 7,101,878 B1 | 9/2006 | Anderson et al. |

(Continued)

FOREIGN PATENT DOCUMENTS

| | | |
|---|---|---|
| EP | 0887340 A1 | 12/1998 |
| JP | 1995258224 A | 10/1995 |

(Continued)

OTHER PUBLICATIONS

CAS Registry No. 460735-77-7 (Oct. 11, 2002).*
A. Nefzi et al., Tetrahedron Letters, 4797-4800 (Jun. 30, 2010).*
Beg, M.S.J. et al., Synthesis of 1-(N-Substituted-Carboxamido-2-Aminophenyl) 4-Methyl-Piperazines: D.E.C. Analogs and Their Antifilarial Activity-I, Asian Journal of Chemistry, 2003, pp. 1343-1346, vol. 15, Nos. 3 & 4.
Cole, et al., Identification and initial evaluation of 4-N-aryl-[1,4] diazepane ureas as potent CXCR3 antagonists, Bioorganic & Medicinal Chemistry Letters, 2006, pp. 200-203, vol. 16.
Nefzi, Adel, et al., Diversity-oriented synthesis of N-aryl-N-thiazolyl compounds, Tetrahedron Letters, 2010, pp. 4797-4800, vol. 51.

(Continued)

*Primary Examiner* — Alexander R Pagano
(74) *Attorney, Agent, or Firm* — Dwight D. Kim; EMD Serono Research and Development Institute

(57) ABSTRACT

Novel benzamide derivatives of formula (I)

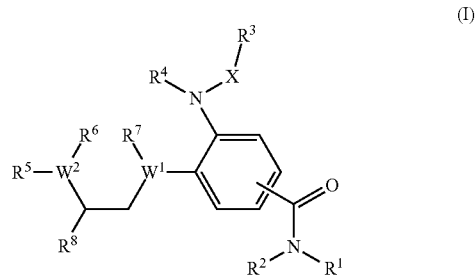

wherein W¹, W², R¹ to R⁷, R⁶, X and Y have the meaning according to the claims, are positive allosteric modulators of the FSH receptor, and can be employed, inter alia, for the treatment of fertility disorders.

6 Claims, No Drawings

Related U.S. Application Data division of application No. 13/551,072, filed on Jul. 17, 2012, now Pat. No. 9,181,226.

(60) Provisional application No. 61/526,342, filed on Aug. 23, 2011, provisional application No. 61/508,861, filed on Jul. 18, 2011.

(51) Int. Cl.
*A61K 31/551* (2006.01)
*C07D 233/64* (2006.01)
*C07D 263/34* (2006.01)
*C07D 307/68* (2006.01)
*C07D 407/12* (2006.01)

(56) References Cited

U.S. PATENT DOCUMENTS

| | | | |
|---|---|---|---|
| 7,718,703 B2 | 5/2010 | Harada et al. | |
| 8,268,828 B2 | 9/2012 | Thorpe et al. | |
| 8,642,660 B2 | 2/2014 | Goldfarb | |
| 8,946,227 B2 * | 2/2015 | Magar | A61K 31/496 514/255.01 |
| 8,969,342 B2 | 3/2015 | Hedstrom et al. | |
| 9,181,226 B2 * | 11/2015 | Yu | C07D 403/12 |
| 9,409,897 B2 * | 8/2016 | Yu | C07D 405/14 |
| 9,498,475 B2 * | 11/2016 | Yu | C07D 403/12 |
| 2004/0010033 A1 | 1/2004 | Anderson et al. | |
| 2004/0014787 A1 | 1/2004 | Anderson et al. | |
| 2004/0053951 A1 | 3/2004 | Christie et al. | |
| 2005/0267147 A1 | 12/2005 | Poitout et al. | |
| 2006/0111366 A1 * | 5/2006 | Andersen | A61K 31/16 514/253.01 |
| 2006/0281784 A1 | 12/2006 | Poitout et al. | |
| 2007/0105899 A1 | 5/2007 | Suzuki et al. | |
| 2010/0069638 A1 * | 3/2010 | Kugimiya | C07D 207/14 544/369 |
| 2010/0137386 A1 | 6/2010 | Yamada et al. | |
| 2010/0184741 A1 | 7/2010 | Ashweek et al. | |
| 2010/0247517 A1 | 9/2010 | Austen et al. | |
| 2013/0023522 A1 * | 1/2013 | Yu | C07D 403/12 514/218 |
| 2013/0172351 A1 | 7/2013 | Yu et al. | |
| 2014/0249135 A1 | 9/2014 | Burger et al. | |
| 2015/0011562 A1 | 1/2015 | Yu et al. | |

FOREIGN PATENT DOCUMENTS

| | | | |
|---|---|---|---|
| JP | 1997059236 A | 3/1997 | |
| JP | 2002506458 A | 2/2002 | |
| WO | WO 9900379 A1 * | 1/1999 | C07D 401/04 |
| WO | 1999020606 A2 | 4/1999 | |
| WO | 2000055153 A1 | 9/2000 | |
| WO | 2001044213 A1 | 6/2001 | |
| WO | 2002/09706 A1 | 2/2002 | |
| WO | 2002085866 A1 | 10/2002 | |
| WO | 2004035548 A1 | 4/2004 | |
| WO | 2006136402 A1 | 12/2006 | |
| WO | 2007/002742 A1 | 1/2007 | |
| WO | 2007/08541 A2 | 1/2007 | |
| WO | 2007115822 A1 | 10/2007 | |
| WO | 2007133983 A2 | 11/2007 | |
| WO | 2008106692 A1 | 9/2008 | |
| WO | 2008/117175 A2 | 10/2008 | |
| WO | 2008123469 A1 | 10/2008 | |
| WO | 2009/105435 A1 | 8/2009 | |
| WO | WO 2009105435 A1 * | 8/2009 | C07D 295/033 |
| WO | 2010034796 A1 | 4/2010 | |
| WO | 2010/136438 A1 | 12/2010 | |

OTHER PUBLICATIONS

Wrobel, J. et al., Synthesis of (bis)Sulfonic Acid, (bis)Benzamides as Follicle-Stimulating Hormone (FSH) Antagonists, Bioorganic & Medicinal Chemistry, 2002, pp. 639-656, vol. 10.

Biscoe, Mark R., A Highly Active Catalyst for Pd-Catalyzed Amination Reactions: Cross-Coupling Reactions Using Aryl Mesylates and the Highly Selective Monoarylation of Primary Amines Using Aryl Chlorides, Journal of the American Chemical Society, 2008, pp. 13552-13554, vol. 130, issue 41.

Biscoe, Mark R., A New Class of Easily Activated Palladium Precatalysts for Facile C−N Cross-Coupling Reactions and the Low Temperature Oxidative Addition of Aryl Chlorides, 2008, pp. 6686-6687, vol. 130, issue 21.

Bundgaard, H., A Textbook of Drug Design and Development, 1991, pp. 131-191, Harwood Academic Publishers.

Bundgaard, H., Design of Prodrugs, 1985, Elsevier Science Ltd.

Yanofsky, Stephen D., Allosteric Activation of the Follicle-stimulating Hormone (FSH) Receptor by Selective, Nonpeptide Agonists, The Journal of Biological Chemistry, 2006, pp. 13226-13233, vol. 281, No. 19.

Compound CAS Registry No. 460735-77-7 (Oct. 11, 2002).

J.H. Poupaert, Drug Design: Basic Principles and Applications, in 2 Encylopedia of Pharmaceutical Technology 1362-1369, 1367 (James Swarbrick ed., 3rd ed., 2007).

B.A. Chabner et al., Chemotherapy of Neoplastic Diseases, Neoplastic Agents in, Goodman & Gilman's: The Pharmalogical Basis of Therapeutics 1315-1403, 1315 (L.L. Brunton et al., eds., 11th ed., 2006).

Yoshida, M. et al., Study of biodegradable copoly(L-lactic acid/glycolic acid) formulations with controlled release of Z-100 for application in radiation therapy, International Journal of Pharmaceutics, 1995, pp. 61-67, vol. 115.

Begunov et al., Izvestiya Vysshikh Uchebnykh Zavedeni i, Khimi ya I Khimicheskaya Tekhnologiya, 2005, 48(11): 56-57.

Bieksa et al, Lietuvos TSR Mokslu Akademijos Darbai, Serija B: Chemija,Technika, Fizine Geografija, 1971, 1: 133-143.

Houben-Weyl, Methoden der organischen Chemie [Methods of Organic Chemistry], Georg-Thieme-Verlag, Stuttgart.

Siddappa et al, Tetrahedron Letters, 2010, 51: 6493-6497.

South et al, Combinatorial Chemistry & High Throughput Screening, 2000, 3: 139-151.

Wermuth et al., The Practice of Medicinal Chemistry, Academic Press, 1996, 31: 671-696.

\* cited by examiner

BENZAMIDES

PRIORITY CLAIM

This application is a Continuation of U.S. Ser. No. 14/863,865, which is a Divisional application of U.S. Ser. No. 13/551,072, filed on Jul. 17, 2012, which claims the benefit of U.S. Provisional application Ser. Nos. 61/508,861, filed on Jul. 18, 2011, and 61/526,342, filed on Aug. 23, 2011, which are hereby incorporated by reference.

FIELD OF THE INVENTION

The present invention relates to compounds of formula (I)

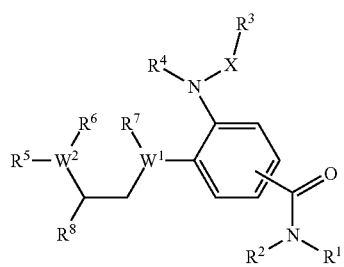

(I)

wherein $W^1$, $W^2$, $R^1$ to $R^7$, $R^6$, X and Y have the meaning according to the claims, and/or physiologically acceptable salts thereof. The compounds of formulas (I) can be used as positive allosteric modulators of the follicle stimulating hormone receptor (FSHR). Objects of the invention are also pharmaceutical compositions comprising the compounds of formula (I), and the use of the compounds of formula (I) for the treatment of fertility disorders.

BACKGROUND

Gonadotropins serve important functions in a variety of bodily functions including metabolism, temperature regulation and the reproductive process. Gonadotropins act on specific gonadal cell types to initiate ovarian and testicular differentiation and steroidogenesis. The gonadotropin FSH (follicle stimulating hormone) is released from the anterior pituitary under the influence of gonadotropin-releasing hormone and estrogens, and from the placenta during pregnancy. FSH is a heterodimeric glycoprotein hormone that shares structural similarities with luteinizing hormone (LH) and thyroid stimulating hormone (TSH), both of which are also produced in the pituitary gland, and chorionic gonadotropin (CG), which is produced in the placenta. In the female, FSH plays a pivotal role in the stimulation of follicle development and maturation and in addition, it is the major hormone regulating secretion of estrogens, whereas LH induces ovulation. In the male, FSH is responsible for the integrity of the seminiferous tubules and acts on Sertoli cells to support gametogenesis.

The hormones are relatively large (28-38 kDa) and are composed of a common α-subunit non-covalently bound to a distinct β-subunit that confers receptor binding specificity. The cellular receptor for these hormones is expressed on testicular Sertoli cells and ovarian granulosa cells. The FSH receptor is known to be members of the G protein-coupled class of membrane-bound receptors, which when activated stimulate an increase in the activity of adenylyl cyclase. This results in an increase in the level of the intracellular second messenger adenosine 3',5'-monophosphate (cAMP), which in turn causes increased steroid synthesis and secretion. Hydropathicity plots of the amino acid sequences of these receptors reveal three general domains: a hydrophilic amino-terminal region, considered to be the amino-terminal extracellular domain; seven hydrophobic segments of membrane-spanning length, considered to be the transmembrane domain; and a carboxy-terminal region that contains potential phosphorylation sites (serine, threonine, and tyrosine residues), considered to be the carboxy-terminal intracellular or cytoplasmic domain. The glycoprotein hormone receptor family is distinguished from other G protein-coupled receptors, such as the β-2-adrenergic, rhodopsin, and substance K receptors, by the large size of the hydrophilic amino-terminal domain, which is involved in hormone binding.

Annually in the U.S. there are 2.4 million couples experiencing infertility that are potential candidates for treatment. FSH, either extracted from urine or produced by recombinant DNA technology, is a parenterally-administered protein product used by specialists for ovulation induction and for controlled ovarian hyperstimulation. Whereas ovulation induction is directed at achieving a single follicle to ovulate, controlled ovarian hyperstimulation is directed at harvesting multiple oocytes for use in various in-vitro assisted reproductive technologies, e.g. in-vitro fertilization (IVF). FSH is also used clinically to treat male hypogonadism and male infertility, e.g. some types of failure of spermatogenesis.

FSHR is a highly specific target in the ovarian follicle growth process and is exclusively expressed in the ovary. However, the use of FSH is limited by its high cost, lack of oral dosing, and need of extensive monitoring by specialist physicians. Hence, identification of a non-peptidic small molecule substitute for FSH that could potentially be developed for oral administration is desirable. Low molecular weight FSH mimetics with agonistic properties are disclosed in the international applications WO 2002/09706 and WO 2010/136438 as well as the U.S. Pat. No. 6,653,338. Furthermore, WO 2009/105435 is directed to 3-(amido or sulphamido)-4-(4-substituted-azinyl)-benzamides which are useful as an inhibitor of the chemokine receptor CXCR3, and for preventing or treating a CXCR3-mediated disease, e.g. inflammation. There is still a need for low molecular weight hormone mimetics that selectively activate FSHR.

SUMMARY OF THE INVENTION

The invention had the object of finding novel compounds having valuable properties, in particular those which can be used for the preparation of medicaments.

It has been surprisingly found that the compounds according to the invention and salts thereof have very valuable pharmacological properties while being well tolerated. In particular, they act as FSHR agonists. The invention relates to compounds of formula (I)

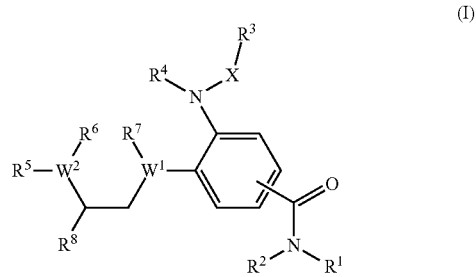

(I)

wherein
$W^1$, $W^2$ denote independently from one another N or $CR^8$, with the proviso that at least one of $W^1$ or $W^2$ denotes N;

$R^1$ denotes —(CY$_2$)$_n$-E-(CY$_2$)$_n$-Het$^3$, —(CY$_2$)$_n$-Cyc-Het$^3$, —(CY$_2$)$_n$—NY-Het$^3$, —(CY$_2$)$_n$—CONH-Het$^3$, —(CY$_2$)$_n$—NHCO-Het$^3$, —(CY$_2$)$_n$—C(Y)(OH)—(CY$_2$)$_n$-Het$^3$, —(CY$_2$)$_n$-Het$^1$, —(CY$_2$)$_n$—CONH-Het$^1$, —(CY$_2$)$_n$—NHCO-Het$^1$, —(CY$_2$)$_n$-Het$^3$, —(CY$_2$)$_n$—NY—Ar, —(CY$_2$)$_n$—CONH—Ar, —(CY$_2$)$_n$—NHCO—Ar, —(CY$_2$)$_n$—C(Y)(OH)—(CY$_2$)$_n$—Ar, —(CY$_2$)$_n$-Cyc, —(CY$_2$)$_n$—NY-Cyc, —(CY$_2$)$_n$—CONH-Cyc, —(CY$_2$)$_n$—NHCO-Cyc, —(CY$_2$)$_n$—NHCO—NH-Cyc, Y, —(CYR$^8$)$_n$—OY, —(CY$_2$)$_n$—COOY, —(CY$_2$)$_n$—SO$_2$Y, —(CYR$^8$)$_n$—CO—(CY$_2$)$_n$—N(R$^8$)$_2$, (CY$_2$)$_n$—[C(Y)(OH)]$_m$—(CYR$^8$)$_n$—NY$_2$, [—(CY$_2$)$_n$—O]—(CYR$^8$)$_n$—NYCOY, —(CY$_2$)$_n$—NYCOOY, —(CY$_2$)$_n$—NYSO$_2$Y, —(CY$_2$)$_n$—NYCON(R$^8$)$_2$, —(CY$_2$)$_n$—NHCO—CH=CH$_2$, —(CY$_2$)$_n$—NHCO—NH—(CY$_2$)$_n$=CH$_2$ or —(CY$_2$)$_n$—CN;

$R^2$ denotes Y;

$R^1$, $R^2$ together also denote —(CY$_2$)$_p$—NH—(CY$_2$)$_p$—, —(CY$_2$)$_p$—NHCO—(CY$_2$)$_p$—, —(CY$_2$)$_p$—CONH—(CY$_2$)$_p$—, —(CY$_2$)$_p$—N(COA)-(CY$_2$)$_p$—, —(CY$_2$)$_p$—N(COOA)-(CY$_2$)$_p$—, —(CY$_2$)$_p$—C(Y)(Het$^3$)-(CY$_2$)$_p$—,

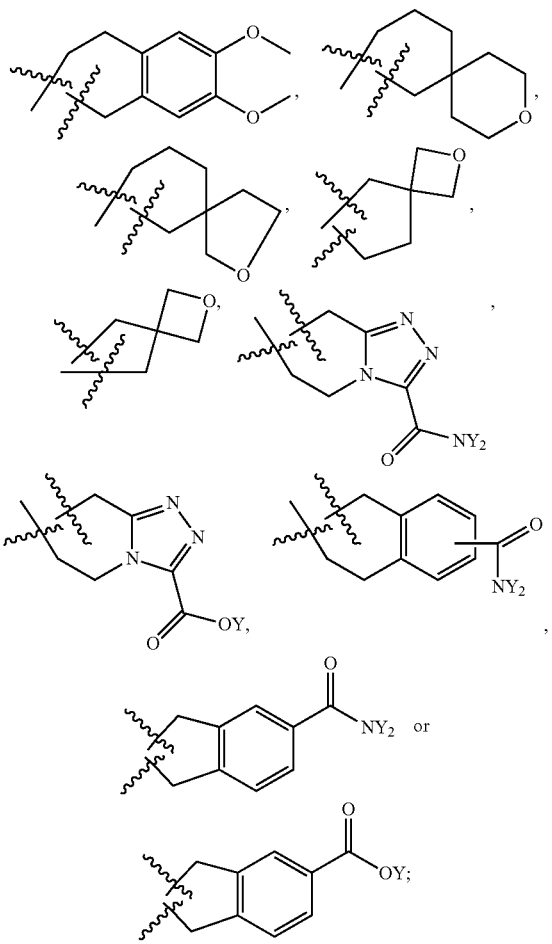

$R^3$ denotes —(CY$_2$)$_n$-Het$^1$, —(CY$_2$)$_n$-Het$^3$, —(CY$_2$)$_n$—Ar, —C(Y)(OY)—Ar, Y or —(CY$_2$)$_n$-Cyc;

$R^4$ denotes Y, COY or SO$_2$Y;

$R^5$ denotes E-Ar, NY—Ar, Cyc, Y, OY, NYY, NYCOOY, NYCOY, COY, COOY, SO$_2$Y, Het$^1$ or Het$^3$;

$R^6$, $R^7$ denote independently from one another H;

$R^6$, $R^7$ together also denote —(CY$_2$)$_p$—;

$R^8$ denotes Y or Ar;

X, E denote independently from one another —(CY$_2$)$_m$—, O, CO, —COO— or SO$_2$;

Y denotes H or A;

A denotes unbranched or branched alkyl having 1-10 C atoms, in which 1-7H atoms can be replaced independently from one another by Hal, =O and/or OH;

Cyc denotes cycloalkyl having 3-7 C atoms, in which 1-4H atoms can be replaced independently from one another by Hal and/or OH;

Ar denotes an unsaturated or aromatic mono- or bicyclic carbocycle having 3-10 C atoms, which can be substituted by at least one substituent selected from the group of A, Hal, —(CY$_2$)$_n$—OY, COOY, CONH$_2$, NHCOY, —(CY$_2$)$_n$—NYCOOY, —(CY$_2$)$_n$—NY$_2$, NO$_2$, SO$_2$Y, SO$_2$NY$_2$, NYSO$_2$Y, —(CY$_2$)$_n$—CN, —(CY$_2$)$_n$-Het$^2$ and Cyc, or which can be fused to Cyc;

Het$^1$ denotes an unsaturated or aromatic mono- or bicyclic heterocycle having 1-10 C atoms and 1-4 N, O and/or S atoms, which can be substituted by at least one substituent selected from the group of Hal, A, Cyc, OY, =O, COOY, CONH$_2$, NHCOY, —(CY$_2$)$_n$—NY$_2$, SO$_2$Y, SO$_2$NY$_2$, NHSO$_2$Y, CN, Ar and —(CY$_2$)$_n$-Het$^3$;

Het$^2$ denotes a saturated or unsaturated monocyclic 5- or 6-membered heterocycle having 1-4 C atoms and 1-4 N, O and/or S atoms, which can be substituted by A and/or =O;

Het$^3$ denotes a saturated mono- or bicyclic heterocycle having 3-7 C atoms and 1-4 N, O and/or S atoms, which can be substituted by at least one substituent selected from the group of =O, A, Hal, —(CY$_2$)$_n$-Cyc, —(CY$_2$)$_n$—OY, COY, COOY, CONY$_2$, NHCOY, —(CY$_2$)$_n$—NY$_2$, CN, SO$_2$Y and —(CY$_2$)$_n$—Ar;

Hal denotes F, Cl, Br or I;

m, n denote independently from one another 0, 1, 2, 3, 4, 5 or 6; and p denotes 1, 2 or 3;

and/or a physiologically acceptable salt thereof, with the proviso that the following compounds are excluded:
3-(3-chloro-benzoylamino)-N-[2-(2,4-dichloro-phenyl)-ethyl]-4-(4-ethyl-piperazin-1-yl)-benzamide;
3-(3-chloro-benzoylamino)-N-[2-(2,4-dichloro-phenyl)-ethyl]-4-[4-(1-methyl-piperidin-4-yl)-piperazin-1-yl]-benzamide; and
4-[1,4']bipiperidinyl-1'-yl-3-(3-chloro-benzoylamino)-N-[2-(4-chloro-phenyl)-ethyl]-benzamide.

In particular, the invention relates to a compound of formula (I)

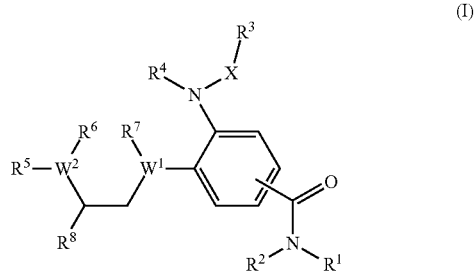

(I)

wherein $W^1$, $W^2$ denote independently from one another N or CH, with the proviso that at least one of $W^1$ or $W^2$ denotes N;

R[1] denotes —(CY$_2$)$_n$-E-Het[3], —(CY$_2$)$_n$-Cyc-Het[3], —(CY$_2$)$_n$-Het[1], —(CY$_2$)$_n$—CONH-Het[1], —(CY$_2$)$_n$—NHCO-Het[1], —(CY$_2$)$_n$—Ar, —(CY$_2$)$_n$-Cyc, —(CY$_2$)$_n$—CONH-Cyc, —(CY$_2$)$_n$—NHCO-Cyc, A, —(CYR[8])$_n$—OY, —(CY$_2$)$_n$—COOY, —(CY$_2$)$_n$—SO$_2$Y, —(CYR[8])$_n$—CONY$_2$, —(CYR[8])$_n$—NY$_2$, —(CYR[8])$_n$—NYCOY, —(CY$_2$)$_n$—NYCOOY, —(CY$_2$)$_n$—NYCONY$_2$, or —(CY$_2$)$_n$—NHCO—CH=CH$_2$;

R[1], R[2] together also denote —(CY$_2$)$_p$—NH—(CY$_2$)$_p$—, —(CY$_2$)$_p$—NHCO—(CY$_2$)$_p$—, —(CY$_2$)$_p$—CONH—(CY$_2$)$_p$—, —(CY$_2$)$_p$—N(COA)-(CY$_2$)$_p$—, —(CY$_2$)$_p$—N(COOA)-(CY$_2$)$_p$—,

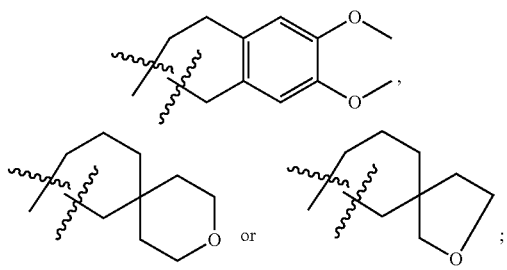

R[3] denotes —(CY$_2$)$_n$-Het[1], —(CY$_2$)$_n$-Het[3], —(CY$_2$)$_n$—Ar, H, A or —(CY$_2$)$_n$-Cyc;

R[4] denotes Y;

R[5] denotes E-Ar, H, A, COOY, SO$_2$Y, Het[1] or Het[3];

R[2], R[6], R[7] denote independently from one another H;

R[6], R[7] together also denote —(CY$_2$)$_p$—;

R[8] denotes H, A or Ar;

X, E denote independently from one another —(CY$_2$)$_m$—, O, CO, —COO— or SO$_2$;

Y denotes H or A;

A denotes unbranched or branched alkyl having 1-10 C atoms, in which 1-7H atoms can be replaced independently from one another by Hal and/or =O;

Cyc denotes cycloalkyl having 3-7 C atoms,
  in which 1-4H atoms can be replaced independently from one another by Hal;

Ar denotes an unsaturated or aromatic mono- or bicyclic carbocycle having 3-10 C atoms,
  which can be substituted by at least one substituent selected from the group of A, Hal, OY, COOY, CONH$_2$, NHCOY, NY$_2$, NO$_2$, SO$_2$Y, CN and Het[2], or which can be fused to Cyc;

Het[1] denotes an unsaturated or aromatic mono- or bicyclic heterocycle having 1-10 C atoms and 1-4 N, O and/or S atoms,
  which can be substituted by at least one substituent selected from the group of Hal, A, Cyc, OY, COOY, CONH$_2$, NHCOY, NY$_2$, SO$_2$Y, SO$_2$NY$_2$, NHSO$_2$Y, CN and Ar;

Het[2] denotes an unsaturated monocyclic 5-membered heterocycle having 1-3 C atoms and 2-4 N and/or S atoms, which can be substituted by A;

Het[3] denotes a saturated mono- or bicyclic heterocycle having 3-7 C atoms and 1-4 N, O and/or S atoms,
  which can be substituted by at least one substituent selected from the group of =O, A, Hal, —(CY$_2$)$_n$-Cyc, —(CY$_2$)$_n$—OY, COY, COOY, CONY$_2$, NHCOY, NY$_2$, CN, SO$_2$Y and —(CY$_2$)$_n$—Ar;

Hal denotes F, Cl, Br or I;

m, n denote independently from one another 0, 1, 2, 3, 4, 5 or 6; and p denotes 1, 2 or 3;

and/or physiologically acceptable salts thereof, with the proviso that the following compounds are excluded:

3-(3-chloro-benzoylamino)-N-[2-(2,4-dichloro-phenyl)-ethyl]-4-(4-ethyl-piperazin-1-yl)-benzamide;

3-(3-chloro-benzoylamino)-N-[2-(2,4-dichloro-phenyl)-ethyl]-4-[4-(1-methyl-piperidin-4-yl)-piperazin-1-yl]-benzamide; and 4-[1,4']bipiperidinyl-1'-yl-3-(3-chloro-benzoylamino)-N-[2-(4-chloro-phenyl)-ethyl]-benzamide.

For the sake of clarity, the fusion of Cyc to the carbocycle in the Ar definition refers to a condensed ring system, wherein another ring system is constructed on the mono- or bicyclic carbocycle with the result of a bi- or tricyclic carbocycle. Moreover, the disclaimer is valid for any embodiment of the invention described herein if appropriate.

DETAILED DESCRIPTION OF THE INVENTION

In the meaning of the present invention, the compound is defined to include pharmaceutically usable derivatives, solvates, prodrugs, tautomers, enantiomers, racemates and stereoisomers thereof, including mixtures thereof in all ratios.

The term "pharmaceutically usable derivatives" is taken to mean, for example, the salts of the compounds according to the invention and also so-called prodrug compounds. The term "solvates" of the compounds is taken to mean adductions of inert solvent molecules onto the compounds, which are formed owing to their mutual attractive force. Solvates are, for example, mono- or dihydrates or alkoxides. The invention also comprises solvates of salts of the compounds according to the invention. The term "prodrug" is taken to mean compounds according to the invention which have been modified by means of, for example, alkyl or acyl groups, sugars or oligopeptides and which are rapidly cleaved in the organism to form the effective compounds according to the invention. These also include biodegradable polymer derivatives of the compounds according to the invention, as described, for example, in Int. J. Pharm. 115, 61-67 (1995). It is likewise possible for the compounds of the invention to be in the form of any desired prodrugs such as, for example, esters, carbonates, carbamates, ureas, amides or phosphates, in which cases the actually biologically active form is released only through metabolism. Any compound that can be converted in-vivo to provide the bioactive agent (i.e. compounds of the invention) is a prodrug within the scope and spirit of the invention. Various forms of prodrugs are well known in the art and are described (e.g. Wermuth C G et al., Chapter 31: 671-696, The Practice of Medicinal Chemistry, Academic Press 1996; Bundgaard H, Design of Prodrugs, Elsevier 1985; Bundgaard H, Chapter 5: 131-191, A Textbook of Drug Design and Development, Harwood Academic Publishers 1991). Said references are incorporated herein by reference. It is further known that chemical substances are converted in the body into metabolites which may where appropriate likewise elicit the desired biological effect—in some circumstances even in more pronounced form. Any biologically active compound that was converted in-vivo by metabolism from any of the compounds of the invention is a metabolite within the scope and spirit of the invention.

The compounds of the invention may be present in the form of their double bond isomers as pure E or Z isomers, or in the form of mixtures of these double bond isomers. Where possible, the compounds of the invention may be in the form of the tautomers, such as keto-enol tautomers. All stereoisomers of the compounds of the invention are contemplated, either in a mixture or in pure or substantially pure form. The compounds of the invention can have asymmetric centers at any of the carbon atoms. Consequently, they can exist in the form of their racemates, in the form of the pure enantiomers and/or diastereomers or in the form of mixtures of these enantiomers and/or diastereomers. The mixtures may have any desired mixing ratio of the stereoisomers. Thus, for example, the compounds of the invention which have one or more centers of chirality and which occur as racemates or as diastereomer mixtures can be fractionated by methods known per se into their optical pure isomers, i.e. enantiomers or diastereomers. The separation of the compounds of the invention can take place by column separation on chiral or nonchiral phases or by recrystallization from an optionally optically active solvent or with use of an optically active acid or base or by derivatization with an optically active reagent such as, for example, an optically active alcohol, and subsequent elimination of the radical.

The invention also relates to the use of mixtures of the compounds according to the invention, for example mixtures of two diastereomers, for example in the ratio 1:1, 1:2, 1:3, 1:4, 1:5, 1:10, 1:100 or 1:1000. These are particularly preferably mixtures of stereoisomeric compounds.

The nomenclature as used herein for defining compounds, especially the compounds according to the invention, is in general based on the rules of the IUPAC-organization for chemical compounds and especially organic compounds. The terms indicated for explanation of the above compounds of the invention always, unless indicated otherwise in the description or in the claims, have the following meanings:

The term "unsubstituted" means that the corresponding radical, group or moiety has no substituents. The term "substituted" means that the corresponding radical, group or moiety has one or more substituents. Where a radical has a plurality of substituents, and a selection of various substituents is specified, the substituents are selected independently of one another and do not need to be identical. Even though a radical has a plurality of a specific-designated substituent (e.g. $Y_2$ or YY) the expression of such substituent may differ from each other (e.g. methyl and ethyl). It shall be understood accordingly that a multiple substitution by any radical of the invention may involve identical or different radicals. Hence, if individual radicals occur several times within a compound, the radicals adopt the meanings indicated, independently of one another. In case of a multiple substitution, the radical could be alternatively designated with R', R", R''', R'''' etc.

The terms "alkyl" or "A" refer to acyclic saturated or unsaturated hydrocarbon radicals, which may be branched or straight-chain and preferably have 1, 2, 3, 4, 5, 6, 7, 8, 9 or 10 carbon atoms, i.e. $C_1$-$C_{10}$-alkanyls. Examples of suitable alkyl radicals are methyl, ethyl, n-propyl, isopropyl, 1,1-, 1,2- or 2,2-dimethylpropyl, 1-ethylpropyl, 1-ethyl-1-methylpropyl, 1-ethyl-2-methylpropyl, 1,1,2- or 1,2,2-trimethylpropyl, n-butyl, isobutyl, sec-butyl, tert-butyl, 1-, 2- or 3-methylbutyl, 1,1-, 1,2-, 1,3-, 2,2-, 2,3- or 3,3-dimethylbutyl, 1- or 2-ethylbutyl, n-pentyl, iso-pentyl, neo-pentyl, tert-pentyl, 1-, 2-, 3- or -methyl-pentyl, n-hexyl, 2-hexyl, isohexyl, n-heptyl, n-octyl, n-nonyl, n-decyl, n-undecyl, n-dodecyl, n-tetradecyl, n-hexadecyl, n-octadecyl, n-icosanyl, n-docosanyl.

In a preferred embodiment of the invention, A denotes unbranched or branched alkyl having 1-10 C atoms, in which 1-7H atoms may be replaced independently from one another by Hal and/or OH. A more preferred A denotes unbranched or branched alkyl having 1-6 C atoms, in which 1-4 atoms may be replaced independently from one another by Hal and/or OH. In a most preferred embodiment of the invention, A denotes unbranched or branched alkyl having 1-5 C atoms, in which 1-3H atoms can be replaced independently from one another by Hal or OH. It is highly preferred that A denotes unbranched or branched alkyl having 1-5 C atoms, in which 1-3H atoms can be replaced independently from one another by F and/or Cl. Particularly preferred is $C_{1-4}$-alkyl. A $C_{1-4}$-alkyl radical is for example a methyl, ethyl, propyl, isopropyl, butyl, isobutyl, tert-butyl, sec-butyl, tert-butyl, fluoromethyl, difluoromethyl, trifluoromethyl, pentafluoroethyl, 1,1,1-trifluoroethyl or bromomethyl, especially methyl, ethyl, propyl or trifluoromethyl. It shall be understood that the respective denotation of A is independently of one another in any radical of the invention.

The terms "cycloalkyl" or "Cyc" for the purposes of this invention refers to saturated and partially unsaturated non-aromatic cyclic hydrocarbon groups/radicals, having 1 to 3 rings, that contain 3 to 20, preferably 3 to 12, more preferably 3 to 9 carbon atoms. The cycloalkyl radical may also be part of a bi- or polycyclic system, where, for example, the cycloalkyl radical is fused to an aryl, heteroaryl or heterocyclyl radical as defined herein by any possible and desired ring member(s). The bonding to the compounds of the general formula (I) can be effected via any possible ring member of the cycloalkyl radical. Examples of suitable cycloalkyl radicals are cyclopropyl, cyclobutyl, cyclopentyl, cyclohexyl, cycloheptyl, cyclooctyl, cyclodecyl, cyclohexenyl, cyclopentenyl and cyclooctadienyl.

In a preferred embodiment of the invention, Cyc denotes cycloalkyl having 3-6 C atoms, in which 1-4H atoms may be replaced by OH. More preferred is $C_3$-$C_6$-cycloalkyl, i.e. cyclopropyl, cyclobutyl, cyclopentyl or cyclohexyl. Moreover, the definition of A shall also comprise cycloalkyls and it is to be applied mutatis mutandis to Cyc. It shall be understood that the respective denotation of Cyc is independently of one another in any radical of the invention.

The term "aryl" or "carboaryl" for the purposes of this invention refers to a mono- or polycyclic aromatic hydrocarbon systems having 3 to 14, preferably 5 to 10, more preferably 6 to 8 carbon atoms, which can be optionally substituted. The term "aryl" also includes systems in which the aromatic cycle is part of a bi- or polycyclic saturated, partially unsaturated and/or aromatic system, such as where the aromatic cycle is fused to an aryl, cycloalkyl, heteroaryl or heterocyclyl group as defined herein via any desired and possible ring member of the aryl radical. The bonding to the compounds of the general formula (I) can be effected via any possible ring member of the aryl radical. Examples of suitable aryl radicals are phenyl, biphenyl, naphthyl, 1-naphthyl, 2-naphthyl and anthracenyl, but likewise in-danyl, indenyl or 1,2,3,4-tetrahydronaphthyl. Preferred carboaryls of the invention are optionally substituted phenyl, naphthyl and biphenyl, more preferably optionally substituted monocylic carboaryl having 6-8 C atoms, most preferably optionally substituted phenyl.

In another embodiment of the invention, a carbocycle, including, but not limited to, carboaryl, is defined as "Ar". Examples of suitable Ar radicals are phenyl, o-, m- or p-tolyl, o-, m- or p-ethylphenyl, o-, m- or p-propylphenyl, o-, m- or p-isopropylphenyl, o-, m- or p-tert.-butylphenyl, o-, m- or p-hydroxyphenyl, o-, m- or p-methoxyphenyl, o-, m- or p-ethoxyphenyl, o-, m- or p-fluorophenyl, o-, m- or p-bromophenyl, o-, m- or p-chlorophenyl, o-, m- or p-sulfonamido-phenyl, o-, m- or p-(N-methyl-sulfonamido)phenyl, o-, m- or p-(N,N-dimethyl-sulfonamido)phenyl, o-, m- or p-(N-ethyl-N-methyl-sulfonamido)phenyl, o-, m- or p-(N,N-diethyl-sulfonamido)-phenyl, particularly 2,3-, 2,4-, 2,5-, 2,6-, 3,4- or 3,5-difluorophenyl, 2,3-, 2,4-, 2,5-, 2,6-, 3,4- or 3,5-dichlorophenyl, 2,3-, 2,4-, 2,5-, 2,6-, 3,4- or 3,5-dibromophenyl, 2,3,4-, 2,3,5-, 2,3,6-, 2,4,6- or 3,4,5-trichlorophenyl, 2,4,6-trimethoxyphenyl, 2-hydroxy-3,5-dichlorophenyl, p-iodophenyl, 4-fluoro-3-chlorophenyl, 2-fluoro-4-bromophenyl, 2,5-difluoro-4-bromophenyl, 3-bromo-6-methoxyphenyl, 3-chloro-6-methoxyphenyl or 2,5-dimethyl-4-chlorophenyl.

Ar preferably denotes an unsaturated or aromatic mono- or bicyclic carbocycle having 3-10 C atoms, which can be substituted by at least one substituent selected from the group of A, Hal, OY, COOY, $CONH_2$, NHCOY, $NY_2$, $NO_2$, $SO_2Y$, CN and $Het^2$, or which can be fused to Cyc. In a more preferred embodiment of the invention, Ar denotes an unsaturated or aromatic mono- or bicyclic carbocycle having 5-10 C atoms, which can be substituted by at least one substituent selected from the group of A, Hal, OY, COOY, $CONH_2$, NHCOY, $NY_2$, $NO_2$, CN and $Het^2$. It is most preferred that Ar denotes an aromatic monocyclic carbocycle having 6-8 C atoms, which can be mono- or disubstituted by at least one substituent selected from the group of A, Hal, OA, $CONH_2$, $NY_2$, $NO_2$ and CN. In another aspect of the invention, Ar preferably denotes an unsaturated or aromatic mono- or bicyclic carbocycle having 3-10 C atoms, which can be substituted by at least one substituent selected from the group of A, Hal, $-(CY_2)_n-OY$, COOY, $CONH_2$, NHCOY, $-(CY_2)_n-NYCOOY$, $-(CY_2)_n-NY_2$, $NO_2$, $SO_2Y$, $SO_2NY_2$, $NYSO_2Y$, $-(CY_2)_n-CN$, $-(CY_2)_n-Het^2$ and Cyc, or which can be fused to Cyc. In another more preferred embodiment of the invention, Ar denotes an unsaturated or aromatic mono- or bicyclic carbocycle having 5-10 C atoms, which can be substituted by at least one substituent selected from the group of A, Hal, OY, COOY, $CONH_2$, NHCOY, $-(CH_2)_n-NY_2$, $SO_2NH_2$, $NO_2$, CN and $Het^2$. It is another most preferred aspect that Ar denotes an aromatic monocyclic carbocycle having 6-8 C atoms, which can be mono- or disubstituted by at least one substituent selected from the group of A, Hal, OY, $CONH_2$, $-(CH_2)_n-NA_2$, $SO_2NH_2$ and $Het^2$. In a highly preferred embodiment of the invention, Ar denotes phenyl, which can be monosubstituted by A, Hal or OA. Particularly preferred Ar is phenyl, which is monosubstituted by A. It shall be understood that the respective denotation of Ar is independently of one another in any radical of the invention.

The term "heteroaryl" for the purposes of this invention refers to a 1-15, preferably 1-9, most preferably 5-, 6- or 7-membered mono- or polycyclic aromatic hydrocarbon radical which comprises at least 1, where appropriate also 2, 3, 4 or 5 heteroatoms, preferably nitrogen, oxygen and/or sulfur, where the heteroatoms are identical or different. Preferably, the number of nitrogen atoms is 0, 1, 2, 3 or 4, and that of the oxygen and sulfur atoms is independently from one another 0 or 1. The term "heteroaryl" also includes systems in which the aromatic cycle is part of a bi- or polycyclic saturated, partially unsaturated and/or aromatic system, such as where the aromatic cycle is fused to an aryl, cycloalkyl, heteroaryl or heterocyclyl group as defined herein via any desired and possible ring member of the heteroaryl radical. The bonding to the compounds of the general formula (I) can be effected via any possible ring member of the heteroaryl radical. Examples of suitable heteroaryl are pyrrolyl, thienyl, furyl, imidazolyl, thiazolyl, isothiazolyl, oxazolyl, oxadiazolyl, isoxazolyl, pyrazolyl, pyridinyl, pyrimidinyl, pyridazinyl, pyrazinyl, indolyl, quinolinyl, isoquinolinyl, imidazolyl, triazolyl, triazinyl, tetrazolyl, phthalazinyl, indazolyl, indolizinyl, quinoxalinyl, quinazolinyl, pteridinyl, carbazolyl, phenazinyl, phenoxazinyl, phenothiazinyl and acridinyl.

It is preferred that heteroaryl in the realms of "$Het^1$" represents an unsaturated or aromatic mono- or bicyclic heterocycle having 1-10 C atoms and 1-4 N, O and/or S atoms, which can be substituted by at least one substituent selected from the group of Hal, A, Cyc, OY, =O, COOY, $CONH_2$, NHCOY, $-(CY_2)_n-NY_2$, $SO_2Y$, $SO_2NY_2$, $NHSO_2Y$, CN, Ar and $-(CY_2)_n-Het^3$. In a more preferred embodiment of the invention, $Het^1$ denotes an unsaturated or aromatic mono- or bicyclic heterocycle having 1-10 C atoms and 1-4 N, O and/or S atoms, which can be substituted by at least one substituent selected from the group of Hal, A, Cyc, OY, COOY, $CONH_2$, NHCOY, $NY_2$, $SO_2Y$, $SO_2NY_2$, $NHSO_2Y$, CN and Ar. In a most preferred embodiment of the invention, $Het^1$ denotes an unsaturated or aromatic mono- or bicyclic heterocycle having 1-9 C atoms and 1-3 N, O and/or S atoms, which can be mono- or disubstituted by at least one substituent selected from the group of Hal, A, Cyc, OY, $CONH_2$, NHCOY, $-(CH_2)_n-NY_2$, $SO_2NY_2$, $NHSO_2Y$, CN and Ar. In another most preferred embodiment of the invention, $Het^1$ denotes an unsaturated or aromatic monocyclic heterocycle having 1-6 C atoms and 1-3 N, O and/or S atoms, which can be mono- or disubstituted by at least one substituent selected from the group of Hal, A, Cyc, OA, $CONH_2$, NHCOA, NHA, $SO_2NH_2$ and CN, or an aromatic bicyclic heterocycle having 6-9 C atoms and 1-3 N and/or S atoms, which can be monosubstituted by A. It is highly preferred that $Het^1$ denotes pyrrolyl, furyl, thiophenyl, imidazolyl, pyrazyl, oxazyl, isoxazyl, thiazyl, thiadiazyl, tetrazyl, pyridyl, pyrimidyl, indolyl, benzimidazolyl, benzothiazyl, quinolyl, isoquinolyl or quinoxalyl, which can be monosubstituted by Hal, A or Cyc. Particularly highly preferred $Het^1$ is pyrrolyl, furyl, thiophenyl, imidazolyl, pyrazyl, oxazyl, isoxazyl, thiazyl, thiadiazyl, tetrazyl, pyridyl or pyrimidyl, which can be monosubstituted by Hal, Cyc or $-(CH_2)_n-NA_2$. It shall be understood that the respective denotation of $Het^1$ is independently of one another in any radical of the invention.

It is preferred that heteroaryl in the realms of "$Het^2$" represents a saturated or unsaturated monocyclic 5- or 6-membered heterocycle having 1-4 C atoms and 1-4 N, O and/or S atoms, which can be substituted by A and/or =O. In a more preferred embodiment of the invention, $Het^2$ denotes an unsaturated monocyclic 5-membered heterocycle having 1-3 C atoms and 2-4 N and/or S atoms, which can be substituted by A. In a most preferred embodiment of the invention, $Het^2$ denotes imidazolyl, pyrazyl, thiazyl or tetrazyl, which can be monosubstituted by methyl. It is a highly preferred embodiment of the invention that $Het^2$ denotes tetrazyl.

The terms "heterocycle" or "heterocyclyl" for the purposes of this invention refers to a mono- or polycyclic system of 3 to 20 ring atoms, preferably 3 to 14 ring atoms, more preferably 3 to 10 ring atoms, comprising carbon atoms and 1, 2, 3, 4 or 5 heteroatoms, which are identical or different, in particular nitrogen, oxygen and/or sulfur. The cyclic system may be saturated or mono- or poly-unsaturated. In the case of a cyclic system consisting of at least two rings the rings may be fused or spiro or otherwise connected. Such heterocyclyl radicals can be linked via any ring member. The term "heterocyclyl" also includes systems in which the heterocycle is part of a bi- or polycyclic saturated, partially unsaturated and/or aromatic system, such as where the heterocycle is fused to an aryl, cycloalkyl, heteroaryl or heterocyclyl group as defined herein via any desired and possible ring member of the heterocyclyl radical. The bonding to the compounds of the general formula (I) can be effected via any possible ring member of the heterocyclyl radical. Examples of suitable heterocyclyl radicals are pyrrolidinyl, thiapyrrolidinyl, piperidinyl, piperazinyl, oxapiperazinyl, oxapiperidinyl, oxadiazolyl, tetrahydrofuryl, imidazolidinyl, thiazolidinyl, tetrahydropyranyl, morpholinyl, tetrahydrothiophenyl, dihydropyranyl.

In a preferred embodiment of the invention, the term "Het$^3$" denotes a saturated mono- or bicyclic heterocycle having 3-7 C atoms and 1-4 N, O and/or S atoms, which can be substituted by at least one substituent selected from the group of =O, A, Hal, —(CY$_2$)$_n$-Cyc, —(CY$_2$)$_n$—OY, COY, COOY, CONY$_2$, NHCOY, —(CH$_2$)$_n$—NY$_2$, CN, SO$_2$Y and —(CY$_2$)$_n$—Ar. In a more preferred embodiment of the invention, Het$^3$ denotes a saturated monocyclic heterocycle having 3-6 C atoms and 1-3 N, O and/or S atoms, which can be mono-, di- or trisubstituted by at least one substituent selected from the group of =O, A, Hal, —(CY$_2$)$_n$-Cyc, —(CY$_2$)$_n$—OY, COY, COOY, CONY$_2$, NHCOY, NY$_2$, CN, SO$_2$Y and —(CY$_2$)$_n$—Ar. In a most preferred embodiment of the invention, Het$^3$ denotes a saturated monocyclic heterocycle having 3-6 C atoms and 1-3 N, O and/or S atoms, which can be mono-, di- or trisubstituted by at least one substituent selected from the group of =O, A, Cyc, OY, COA, COOA, CONHA and SO$_2$A. It is highly preferred that Het$^3$ denotes pyrrolidinyl, oxolanyl, imidazolidinyl, thiazolidinyl, piperidinyl, piperazinyl, thiomorpholinyl, which can be monosubstituted by =O. Particularly preferred Het$^3$ is pyrrolidinyl, oxolanyl, imidazolidinyl, thiazolidinyl, piperidinyl, piperazinyl, thiomorpholinyl, which is monosubstituted by =O. It shall be understood that the respective denotation of Het$^3$ is independently of one another in any radical of the invention.

The term "halogen", "halogen atom", "halogen substituent" or "Hal" for the purposes of this invention refers to one or, where appropriate, a plurality of fluorine (F, fluoro), bromine (Br, bromo), chlorine (Cl, chloro) or iodine (I, iodo) atoms. The designations "dihalogen", "trihalogen" and "perhalogen" refer respectively to two, three and four substituents, where each substituent can be selected independently from the group consisting of fluorine, chlorine, bromine and iodine. Halogen preferably means a fluorine, chlorine or bromine atom. Fluorine and chlorine are more preferred, when the halogens are substituted on an alkyl (haloalkyl) or alkoxy group (e.g. CF$_3$ and CF$_3$O). It shall be understood that the respective denotation of Hal is independently of one another in any radical of the invention.

It is a preferred embodiment of the present invention that both W$^1$ and W$^2$ denote N.

It is another preferred embodiment of the present invention that the phenyl ring in the scaffold of formula (I) is substituted by —CONR$^1$R$^2$ in meta position with regard to the —NXR$^3$R$^4$ moiety.

It is a preferred embodiment of the R$^1$ radical according to the present invention to be —(CY$_2$)$_n$-E-Het$^3$, —(CY$_2$)$_n$-Cyc-Het$^3$, —(CY$_2$)$_n$-Het$^1$, —(CY$_2$)$_n$—NHCO-Het$^1$, —(CY$_2$)$_n$—Ar, —(CY$_2$)$_n$-Cyc, —(CY$_2$)$_n$—CONH-Cyc, A, —(CYR$^8$)$_n$—OY, —(CY$_2$)$_n$—COOY, —(CYR$^8$)$_n$—NY$_2$, —(CYR$^8$)$_n$—NYCOY, —(CY$_2$)$_n$—NYCOOY or —(CY$_2$)$_n$—NHCO—CH=CH$_2$, more preferably —(CY$_2$)$_n$-E-Het$^3$, —(CY$_2$)$_n$-Cyc-Het$^3$, —(CY$_2$)$_n$-Het$^1$, —(CY$_2$)$_n$—NHCO-Het$^1$, —(CY$_2$)$_n$—Ar, —(CY$_2$)$_n$-Cyc, —(CY$_2$)$_n$—CONH-Cyc, A, —(CYR$^8$)$_n$—OH, —(CY$_2$)$_n$—COOA, —(CYR$^8$)$_n$—NY$_2$, —(CYR$^8$)$_n$—NACOA, —(CY$_2$)$_n$—NHCOOA or —(CY$_2$)$_n$—NHCO—CH=CH$_2$, most preferably —(CY$_2$)$_n$-E-Het$^3$, —(CY$_2$)$_n$-Cyc-Het$^3$, —(CY$_2$)$_n$-Het$^1$, —(CY$_2$)$_n$—NHCO-Het$^1$, —(CY$_2$)$_n$—Ar, —(CY$_2$)$_n$-Cyc or —(CY$_2$)$_n$—CONH-Cyc, highly preferably —(CY$_2$)$_n$-E-Het$^3$, —(CY$_2$)$_n$-Het$^1$ or —(CY$_2$)$_n$—Ar, particularly preferably —(CY$_2$)$_n$-Het$^3$.

It is another preferred embodiment of the R$^1$ radical according to the present invention to be —(CY$_2$)$_n$-E-(CY$_2$)$_n$-Het$^3$, —(CY$_2$)$_n$-Cyc-Het$^3$, —(CY$_2$)$_n$—NHCO-Het$^3$, —(CY$_2$)$_n$—C(Y)(OH)—(CY$_2$)$_n$-Het$^3$, —(CY$_2$)$_n$-Het$^1$, —(CY$_2$)$_n$—NHCO-Het$^1$, —(CY$_2$)$_n$—Ar, —(CY$_2$)$_n$—C(Y)(OH)—(CY$_2$)$_n$—Ar, —(CY$_2$)$_n$-Cyc, —(CY$_2$)$_n$—CONH-Cyc, A, —(CYR$^8$)$_n$—OY, —(CY$_2$)$_n$—COOY, —(CYR$^8$)$_n$—CO—(CY$_2$)$_n$—N(R$^8$)$_2$, —(CY$_2$)$_n$—[C(Y)OH]]$_m$—(CYR$^8$)$_n$—NY$_2$, [—(CY$_2$)$_n$—O]$_m$—(CYR$^8$)$_n$—NYCOY, —(CY$_2$)$_n$—NYCOOY, —(CY$_2$)$_n$—NYCON(R$^8$)$_2$, —(CY$_2$)$_n$—NHCO—CH=CH$_2$ or —(CY$_2$)$_n$—NHCO—NH—(CY$_2$)$_n$=CH$_2$, more preferably —(CY$_2$)$_n$-E-Het$^3$, —(CY$_2$)$_n$-Cyc-Het$^3$, —(CY$_2$)$_n$—NHCO-Het$^3$, —(CY$_2$)$_n$—C(Y)(OH)—(CY$_2$)$_n$-Het$^3$, —(CY$_2$)$_n$-Het$^1$, —(CY$_2$)$_n$—NHCO-Het$^1$, —(CY$_2$)$_n$—Ar, —(CY$_2$)$_n$—C(Y)(OH)—(CY$_2$)$_n$—Ar, —(CY$_2$)$_n$-Cyc, —(CY$_2$)$_n$—CONH-Cyc, A, —(CYR$^8$)$_n$—OY, —(CY$_2$)$_n$—COOY, —(CY$_2$)$_n$—CO—NY$_2$, —(CYR$^8$)$_n$—NY$_2$, —(CYR$^8$)$_n$—NYCOY, —(CY$_2$)$_n$—NYCOOY, —(CY$_2$)$_n$—NYCON(R$^8$)$_2$, —(CY$_2$)$_n$—NHCO—CH=CH$_2$ or —(CY$_2$)$_n$—NHCO—NH—(CY$_2$)$_n$=CH$_2$.

It is another more preferred embodiment of the R$^1$ radical according to the present invention to be —(CY$_2$)$_n$-E-(CY$_2$)$_n$-Het$^3$, —(CY$_2$)$_n$—NHCO-Het$^3$, —(CY$_2$)$_n$—C(Y)(OH)—(CY$_2$)$_n$-Het$^3$, —(CY$_2$)$_n$-Het$^1$, —(CY$_2$)$_n$—Ar, —(CY$_2$)$_n$—C(Y)(OH)—(CY$_2$)$_n$—Ar, —(CY$_2$)$_n$-Cyc, —(CYR$^8$)$_n$—CO—(CY$_2$)$_n$—N(R$^8$)$_2$, [—(CY$_2$)$_n$—O]$_m$—(CYR$^8$)$_n$—NYCOY, —(CY$_2$)$_n$—NYCON(R$^8$)$_2$ or —(CY$_2$)$_n$—NHCO—NH—(CY$_2$)$_n$=CH$_2$, most preferably —(CY$_2$)$_n$-Het$^3$, —(CY$_2$)$_n$—NHCO-Het$^3$, —(CY$_2$)$_n$—C(Y)(OH)—(CY$_2$)$_n$-Het$^3$, —(CY$_2$)$_n$-Het$^1$, —(CY$_2$)$_n$—Ar, —(CY$_2$)$_n$—C(Y)(OH)—Ar, Cyc, —(CY$_2$)$_n$—CO—NY$_2$, (CY$_2$)$_n$—NYCOY, —(CY$_2$)$_n$—NYCONY$_2$ or —(CY$_2$)$_n$—NHCO—NH—(CY$_2$)$_n$=CH$_2$.

It is a preferred embodiment of the R$^2$ radical according to the present invention to be H.

It is another preferred embodiment that R$^1$, R$^2$ together also denote —(CY$_2$)$_p$—NH—(CY$_2$)$_p$—, —(CY$_2$)$_p$—NHCO—(CY$_2$)$_p$—, —(CY$_2$)$_p$—CONH—(CY$_2$)$_p$—, —(CY$_2$)$_p$—N(COA)-(CY$_2$)$_p$—, —(CY$_2$)$_p$—N(COOA)-(CY$_2$)$_p$—,

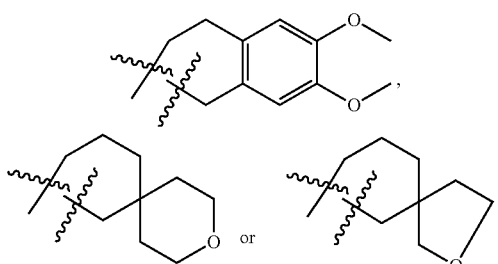

It is a preferred embodiment of the R$^3$ radical according to the present invention to be Het$^1$, Het$^3$, Ar, H, A or Cyc, more preferably Het$^1$, Het$^3$ or Ar, highly preferably Het$^1$ or Het$^3$, particularly highly preferably Het$^1$.

It is a preferred embodiment of the R$^4$ radical according to the present invention to be Y, more preferably H.

It is a preferred embodiment of the $R^5$ radical according to the present invention to be E-Ar, H, A, COOA or Het$^1$, more preferably E-Ar, H or COOA. It is another more preferred embodiment of the $R^5$ radical according to the present invention to be E-Ar or Het$^1$, most preferably E-Ar, highly preferably Ar.

It is another highly preferred embodiment of the $R^1$, $R^3$, $R^5$ radicals according to the present invention to be independently from one another —(CY$_2$)$_n$-Het$^3$, —(CY$_2$)$_n$-Het$^1$, —(CY$_2$)$_n$—Ar or Cyc, particularly highly preferably —(CY$_2$)$_n$-Het$^3$, Het$^1$ or Ar. The aforesaid disclaimer is applicable.

It is a preferred embodiment of the $R^6$, $R^7$ radicals according to the present invention to be together —(CY$_2$)$_p$—.

It is a preferred embodiment of the $R^8$ radical according to the present invention to be Y, more preferably H. It shall be understood that the respective denotation of $R^8$ is independently of one another in any radical of the invention.

It is another more preferred embodiment of the $R^2$, $R^4$, $R^8$ radicals according to the present invention to be independently of one another H, more preferably to be H.

It is a preferred embodiment of the X radical according to the present invention to be —(CY$_2$)$_m$—, CO or SO$_2$, more preferably CO, SO$_2$ or a single bond, most preferably CO or SO$_2$. It is another more preferred embodiment of the X radical according to the present invention to be —(CY$_2$)$_m$— or CO. A highly preferred X is CO.

It is a preferred embodiment of the E radical according to the present invention to be —(CY$_2$)$_m$—, CO, —COO— or SO$_2$, more preferably —(CY$_2$)$_m$—, CO or SO$_2$, most preferably —(CY$_2$)$_m$—. It shall be understood that the respective denotation of E is independently of one another in any radical of the invention.

In an aspect of the invention, Y denotes H or A. It shall be understood that the respective denotation of Y is independently of one another in any radical of the invention.

It is a preferred embodiment of the m index according to the present invention to be 0, 1, 2 or 3, more preferably 0, 1 or 2, most preferably 0 or 1.

It is a preferred embodiment of the n index according to the present invention to be 0, 1, 2, 3, 4 or 5, more preferably 0, 1, 2, 3 or 4, most preferably 0, 1, 2 or 3. It shall be understood that the respective denotation of n is independently of one another in any radical of the invention.

It is a preferred embodiment of the p index according to the present invention to be 1, 2 or 3, more preferably 2 or 3, most preferably 2. It shall be understood that the respective denotation of p is independently of one another in any radical of the invention.

In another preferred embodiment of the present invention, both W$^1$ and W$^2$ denote N, and $R^6$ and $R^7$ together denote —(CY$_2$)$_p$—, and p denotes 2.

Accordingly, the subject-matter of the invention relates to compounds of formula (I), in which at least one of the aforementioned radicals has any meaning, particularly realize any preferred embodiment, as described above. Radicals, which are not explicitly specified in the context of any embodiment of formula (I), sub-formulae thereof or other radicals thereto, shall be construed to represent any respective denotations according to formula (I) as disclosed hereunder for solving the problem of the invention. That means that the aforementioned radicals may adopt all designated meanings as each described in the prior or following course of the present specification, irrespective of the context to be found, including, but not limited to, any preferred embodiments. It shall be particularly understood that any embodiment of a certain radical can be combined with any embodiment of one or more other radicals.

In another preferred embodiment of the present invention, benzamide derivatives of sub-formula (I-A) are provided

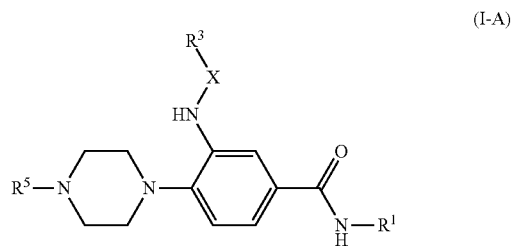

(I-A)

wherein
$R^1$ denotes —(CY$_2$)$_n$-E-(CY$_2$)$_n$-Het$^3$, —(CY$_2$)$_n$-Cyc-Het$^3$, —(CY$_2$)$_n$—NHCO-Het$^3$, —(CY$_2$)$_n$—C(Y)(OH)—(CY$_2$)$_n$-Het$^3$, —(CY$_2$)$_n$-Het$^1$, —(CY$_2$)$_n$—NHCO-Het$^1$, —(CY$_2$)$_n$—Ar, —(CY$_2$)$_n$—C(Y)(OH)—(CY$_2$)$_n$—Ar, —(CY$_2$)$_n$-Cyc, —(CY$_2$)$_n$—CONH-Cyc, A, —(CYR$^8$)$_n$—OY, —(CY$_2$)$_n$—COOY, —(CYR$^8$)$_n$—CO—(CY$_2$)$_n$—N(R$^8$)$_2$, —(CY$_2$)$_n$—[C(Y)OH]]$_m$—(CYR$^8$)$_n$—NY$_2$, [—(CY$_2$)$_n$—O]$_m$—(CYR$^8$)$_n$—NYCOY, —(CY$_2$)$_n$—NY-COOY, —(CY$_2$)$_n$—NYCON(R$^8$)$_2$, —(CY$_2$)$_n$—NHCO—CH=CH$_2$ or —(CY$_2$)$_n$—NHCO—NH—(CY$_2$)$_n$=CH$_2$;
$R^3$ denotes Het$^1$, Het$^3$, Ar, H, A or Cyc;
$R^5$ denotes E-Ar, H, A, COOA or Het$^1$;
$R^8$, Y denote independently from one another H or A;
X denotes CO or —(CY$_2$)$_m$;
E denotes —(CY$_2$)$_m$—, CO, —COO— or SO$_2$;
A denotes unbranched or branched alkyl having 1-10 C atoms, in which 1-7H atoms can be replaced independently from one another by Hal and/or OH;
Cyc denotes cycloalkyl having 3-7 C atoms, in which 1-4H atoms can be replaced independently from one another by Hal and/or OH;
Ar denotes an unsaturated or aromatic mono- or bicyclic carbocycle having 5-10 C atoms, which can be substituted by at least one substituent selected from the group of A, Hal, OY, COOY, CONH$_2$, NHCOY, —(CH$_2$)$_n$—NY$_2$, SO$_2$NH$_2$, NO$_2$, CN and Het$^2$;
Het$^1$ denotes an unsaturated or aromatic mono- or bicyclic heterocycle having 1-9 C atoms and 1-3 N, O and/or S atoms, which can be mono- or disubstituted by at least one substituent selected from the group of Hal, A, Cyc, OY, CONH$_2$, NHCOY, —(CH$_2$)$_n$—NY$_2$, SO$_2$NY$_2$, NHSO$_2$Y, CN and Ar;
Het$^2$ denotes imidazolyl, pyrazyl, thiazyl or tetrazyl, which can be monosubstituted by methyl;
Het$^3$ denotes a saturated monocyclic heterocycle having 3-6 C atoms and 1-3 N, O and/or S atoms, which can be mono-, di- or trisubstituted by at least one substituent selected from the group of =O, A, Hal, —(CY$_2$)$_n$-Cyc, —(CY$_2$)$_n$—OY, COY, COOY, CONY$_2$, NHCOY, NY$_2$, CN, SO$_2$Y and —(CY$_2$)$_n$—Ar;
Hal denotes F, Cl, Br or I; and
m, n denote independently from one another 0, 1, 2 or 3;
and/or a physiologically acceptable salt thereof,
with the proviso that 3-(3-chloro-benzoylamino)-N-[2-(2,4-dichloro-phenyl)-ethyl]-4-(4-ethyl-piperazin-1-yl)-benzamide is excluded.

In another more preferred embodiment of the present invention, benzamide derivatives of sub-formula (I-B) are provided (I-B)

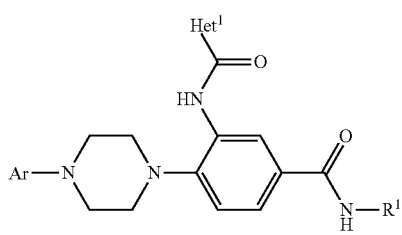

wherein
R¹ denotes —(CY$_2$)$_n$-Het³, —(CY$_2$)$_n$—NHCO-Het³, —(CY$_2$)$_n$—C(Y)(OH)—(CY$_2$)$_n$-Het³, —(CY$_2$)$_n$-Het¹, —(CY$_2$)$_n$—Ar, —(CY$_2$)$_n$—C(Y)(OH)—Ar, Cyc, —(CY$_2$)$_n$—CO—NY$_2$, —(CY$_2$)$_n$—NYCOY, —(CY$_2$)$_n$—NYCONY$_2$ or —(CY$_2$)$_n$—NHCO—NH—(CY$_2$)$_n$=CH$_2$;

Y denotes H or A;
A denotes unbranched or branched alkyl having 1-6 C atoms, in which 1-4H atoms can be replaced independently from one another by Hal and/or OH;
Cyc denotes cycloalkyl having 3-6 C atoms, in which 1-4H atoms can be replaced by OH;
Ar denotes an aromatic monocyclic carbocycle having 6-8 C atoms, which can be mono- or disubstituted by at least one substituent selected from the group of A, Hal, OY, CONH$_2$, —(CH$_2$)$_n$-NA$_2$, SO$_2$NH$_2$ and Het²;
Het¹ denotes an unsaturated or aromatic monocyclic heterocycle having 1-6 C atoms and 1-3 N, O and/or S atoms, which can be mono- or disubstituted by at least one substituent selected from the group of Hal, A, Cyc and —(CH$_2$)$_n$-NA$_2$;
Het² denotes tetrazyl;
Het³ denotes a saturated monocyclic heterocycle having 3-6 C atoms and 1-3 N, O and/or S atoms, which can be mono-, di- or trisubstituted by at least one substituent selected from the group of =O, A and OY;
Hal denotes F, Cl or Br; and
n denotes 0, 1, 2 or 3;
and/or a physiologically acceptable salt thereof.

In still another more preferred embodiment of the present invention, benzamide derivatives of sub-formula (I-C) are provided (I-C)

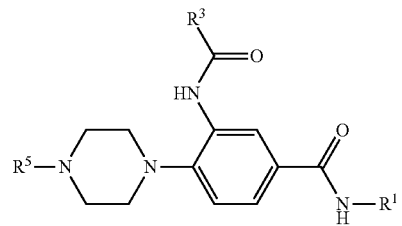

wherein
R¹ denotes —(CY$_2$)$_n$-E-Het³, —(CY$_2$)$_n$-Cyc-Het³, —(CY$_2$)$_n$-Het¹, —(CY$_2$)$_n$—NHCO-Het¹, —(CY$_2$)$_n$—Ar, —(CY$_2$)$_n$-Cyc, —(CY$_2$)$_n$—CONH-Cyc, A, —(CYR⁸)$_n$—OY, —(CY$_2$)$_n$—COOY, —(CYR⁸)$_n$—NY$_2$, —(CYR⁸)$_n$—NYCOY, —(CY$_2$)$_n$—NYCOOY or —(CY$_2$)$_n$—NHCO—CH=CH$_2$;

R³ denotes Het¹, Het³, Ar, H, A or Cyc;
R⁵ denotes E-Ar, H, A, COOA or Het¹;
R⁸, Y denote independently from one another H or A;
E denotes —(CY$_2$)$_m$—, CO, —COO— or SO$_2$;
A denotes unbranched or branched alkyl having 1-10 C atoms, in which 1-7H atoms can be replaced independently from one another by Hal and/or OH;
Cyc denotes cycloalkyl having 3-7 C atoms, in which 1-4H atoms can be replaced independently from one another by Hal;
Ar denotes an unsaturated or aromatic mono- or bicyclic carbocycle having 5-10 C atoms, which can be substituted by at least one substituent selected from the group of A, Hal, OY, COOY, CONH$_2$, NHCOY, NY$_2$, NO$_2$, CN and Het²;
Het¹ denotes an unsaturated or aromatic mono- or bicyclic heterocycle having 1-9 C atoms and 1-3 N, O and/or S atoms, which can be mono- or disubstituted by at least one substituent selected from the group of Hal, A, Cyc, OY, CONH$_2$, NHCOY, NY$_2$, SO$_2$NY$_2$, NHSO$_2$Y, CN and Ar;
Het² denotes imidazolyl, pyrazyl, thiazyl or tetrazyl, which can be monosubstituted by methyl;
Het³ denotes a saturated monocyclic heterocycle having 3-6 C atoms and 1-3 N, O and/or S atoms, which can be mono-, di- or trisubstituted by at least one substituent selected from the group of =O, A, Hal, —(CY$_2$)$_n$-Cyc, —(CY$_2$)$_n$—OY, COY, COOY, CONY$_2$, NHCOY, NY$_2$, CN, SO$_2$Y and —(CY$_2$)$_n$—Ar;
Hal denotes F, Cl, Br or I; and
m, n denote independently from one another 0, 1, 2 or 3;
and/or physiologically acceptable salts thereof,
with the proviso that 3-(3-chloro-benzoylamino)-N-[2-(2,4-dichloro-phenyl)-ethyl]-4-(4-ethyl-piperazin-1-yl)-benzamide is excluded.

In another most preferred embodiment of the present invention, benzamide derivatives of sub-formula (I-D) are provided (I-D)

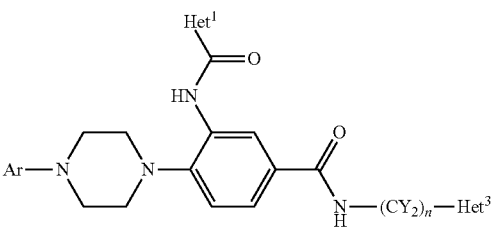

wherein
Y denotes H or A;
A denotes unbranched or branched alkyl having 1-6 C atoms, in which 1-4H atoms can be replaced independently from one another by Hal and/or OH;
Cyc denotes cycloalkyl having 3-6 C atoms;
Ar denotes an aromatic monocyclic carbocycle having 6-8 C atoms, which can be mono- or disubstituted by at least one substituent selected from the group of A, Hal, OA, CONH$_2$, NY$_2$, NO$_2$ and CN;

Het$^1$ denotes an unsaturated or aromatic monocyclic heterocycle having 1-6 C atoms and 1-3 N, O and/or S atoms, which can be mono- or disubstituted by at least one substituent selected from the group of Hal, A, Cyc, OA, CONH$_2$, NHCOA, NHA, SO$_2$NH$_2$ and CN, or an aromatic bicyclic heterocycle having 6-9 C atoms and 1-3 N and/or S atoms, which can be monosubstituted by A;

Het$^3$ denotes a saturated monocyclic heterocycle having 3-6 C atoms and 1-3 N, O and/or S atoms, which can be mono- or disubstituted by at least one substituent selected from the group of =O, A, Cyc, OY, COA, COOA, CONHA and SO$_2$A;

Hal denotes F, Cl or Br; and n denotes 0, 1, 2 or 3;

and/or physiologically acceptable salts thereof.

The prior teaching of the present specification concerning the compounds of formula (I), including any radical definition and preferred embodiment thereof, is valid and applicable without restrictions to the compounds according to sub-formulae (I-A), (I-B) and their salts if expedient.

Most preferred embodiments are those compounds of formulae (I), (I-A), (I-B) and (I-C) as listed in Table 1 and 2.

TABLE 1

Compounds of formulae (I), (I-A), (I-B), (I-C).
Assay A: Example 10; Assay B: Example 11.

| | Structure | Assay A<br>0 > 10 μM<br>+ > 1-10 μM<br>++ 0.1-1 μM<br>+++ < 0.1 μM<br>% at 5 μM | Assay B<br>0 > 10 μM<br>+ > 1-10 μM<br>++ 0.1-1 μM<br>+++ < 0.1 μM<br>% at 5 μM |
|---|---|---|---|
| 1 | 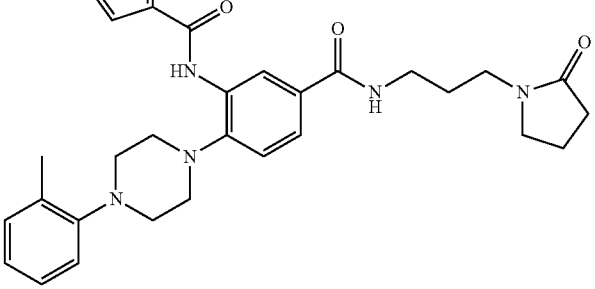 | ++ | |
| 2 | 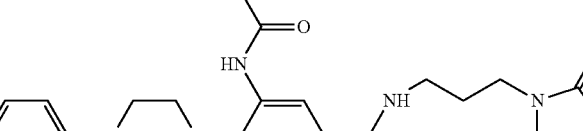 | +++ | + |
| 3 | 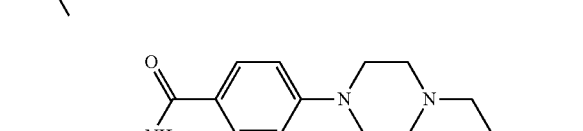 | ++ | 10% |

TABLE 1-continued

Compounds of formulae (I), (I-A), (I-B), (I-C).
Assay A: Example 10; Assay B: Example 11.

| | Structure | Assay A<br>0 > 10 μM<br>+ > 1-10 μM<br>++ 0.1-1 μM<br>+++ < 0.1 μM<br>% at 5 μM | Assay B<br>0 > 10 μM<br>+ > 1-10 μM<br>++ 0.1-1 μM<br>+++ < 0.1 μM<br>% at 5 μM |
|---|---|---|---|
| 4 | 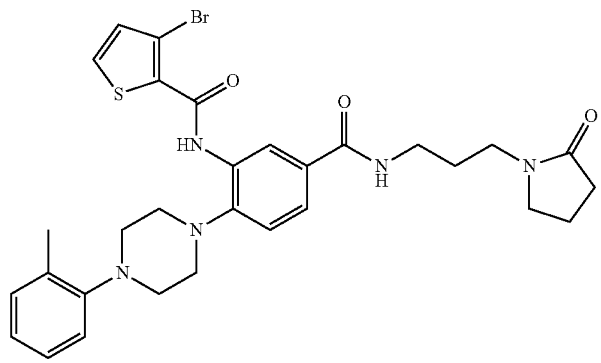 [SMILES: Cc1ccccc1N1CCN(c2ccc(C(=O)NCCCN3CCCC3=O)cc2NC(=O)c2sccc2Br)CC1] | + | |
| 5 | 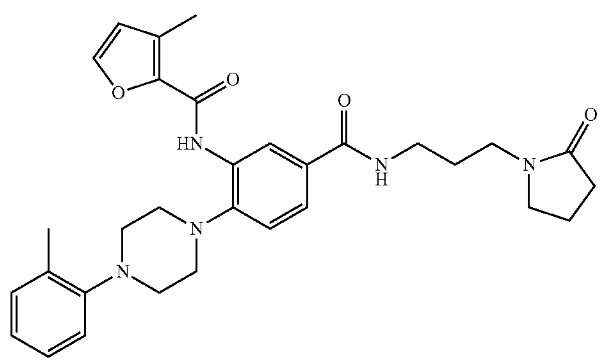 [SMILES: Cc1ccccc1N1CCN(c2ccc(C(=O)NCCCN3CCCC3=O)cc2NC(=O)c2occc2C)CC1] | ++ | + |
| 6 | 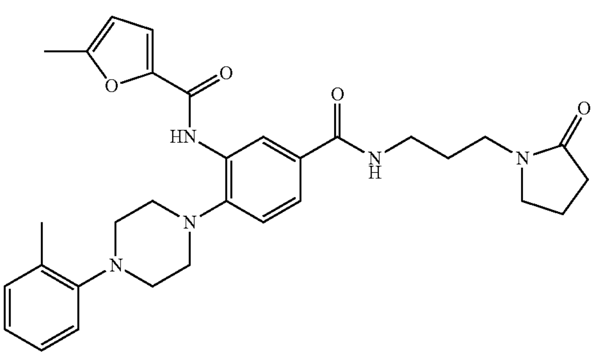 [SMILES: Cc1ccc(C(=O)Nc2cc(C(=O)NCCCN3CCCC3=O)ccc2N2CCN(c3ccccc3C)CC2)o1] | ++ | ++ |
| 7 | 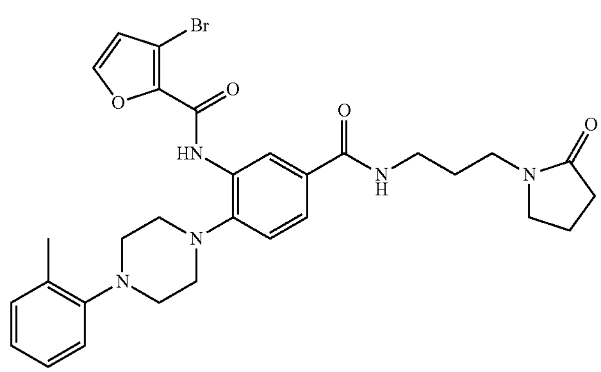 [SMILES: Cc1ccccc1N1CCN(c2ccc(C(=O)NCCCN3CCCC3=O)cc2NC(=O)c2occc2Br)CC1] | + | |

TABLE 1-continued

Compounds of formulae (I), (I-A), (I-B), (I-C).
Assay A: Example 10; Assay B: Example 11.

| | Structure | Assay A<br>0 > 10 μM<br>+ > 1-10 μM<br>++ 0.1-1 μM<br>+++ < 0.1 μM<br>% at 5 μM | Assay B<br>0 > 10 μM<br>+ > 1-10 μM<br>++ 0.1-1 μM<br>+++ < 0.1 μM<br>% at 5 μM |
|---|---|---|---|
| 8 | 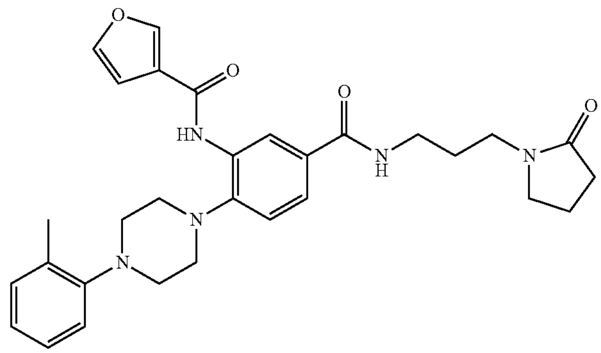 [SMILES: Cc1ccccc1N1CCN(c2ccc(C(=O)NCCCN3CCCC3=O)cc2NC(=O)c2ccoc2)CC1] | | ++ |
| 9 | 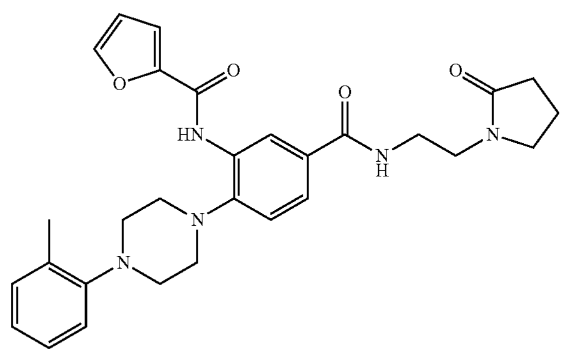 [SMILES: Cc1ccccc1N1CCN(c2ccc(C(=O)NCCN3CCCC3=O)cc2NC(=O)c2ccco2)CC1] | | +++ |
| 10 | 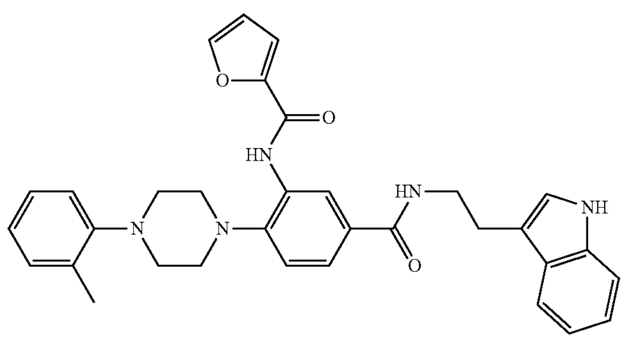 [SMILES: Cc1ccccc1N1CCN(c2ccc(C(=O)NCCc3c[nH]c4ccccc34)cc2NC(=O)c2ccco2)CC1] | | 39% |
| 11 | 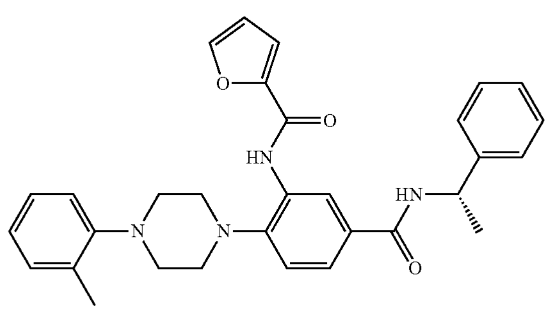 [SMILES: Cc1ccccc1N1CCN(c2ccc(C(=O)N[C@@H](C)c3ccccc3)cc2NC(=O)c2ccco2)CC1] | | ++ |

US 9,938,262 B2
23
24
TABLE 1-continued
Compounds of formulae (I), (I-A), (I-B), (I-C).
Assay A: Example 10; Assay B: Example 11.
| Structure | Assay A<br>0 > 10 μM<br>+ > 1-10 μM<br>++ 0.1-1 μM<br>+++ < 0.1 μM<br>% at 5 μM | Assay B<br>0 > 10 μM<br>+ > 1-10 μM<br>++ 0.1-1 μM<br>+++ < 0.1 μM<br>% at 5 μM |
|---|---|---|
| 12 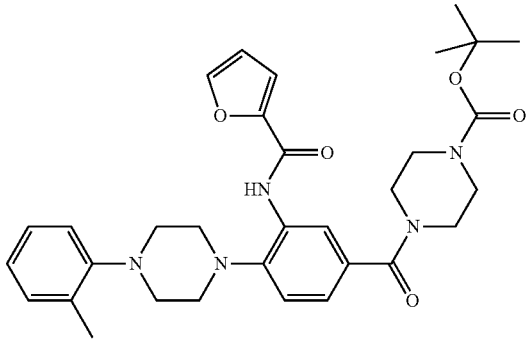 [SMILES: Cc1ccccc1N1CCN(c2ccc(C(=O)N3CCN(C(=O)OC(C)(C)C)CC3)cc2NC(=O)c2ccco2)CC1] | 7% | |
| 13 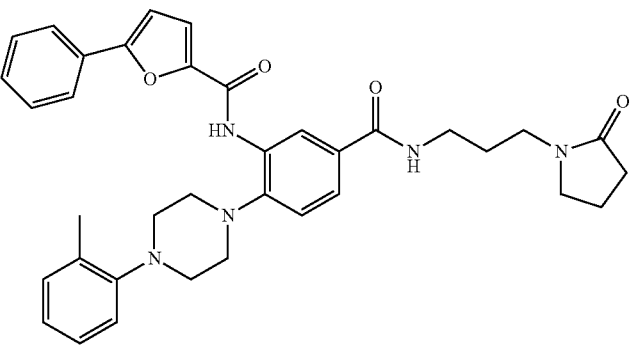 [SMILES: Cc1ccccc1N1CCN(c2ccc(C(=O)NCCCN3CCCC3=O)cc2NC(=O)c2ccc(-c3ccccc3)o2)CC1] | 14% | |
| 14 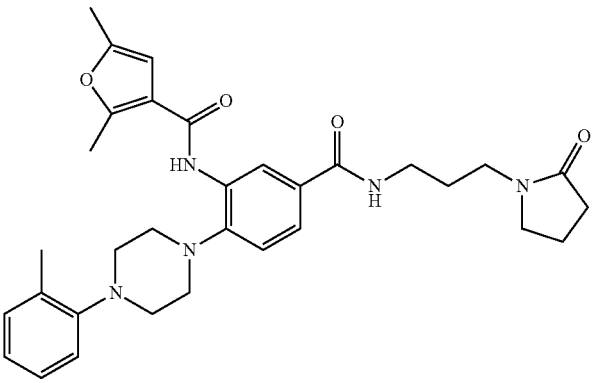 [SMILES: Cc1cc(C(=O)Nc2cc(C(=O)NCCCN3CCCC3=O)ccc2N2CCN(c3ccccc3C)CC2)c(C)o1] | ++ | |
| 15 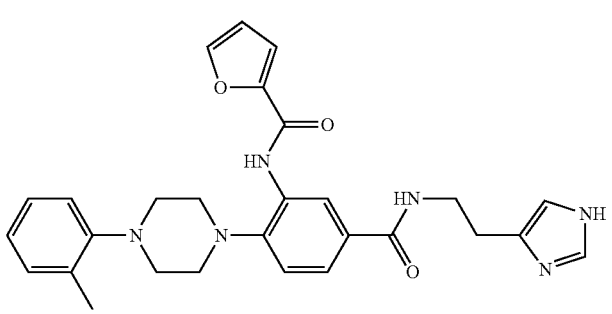 [SMILES: Cc1ccccc1N1CCN(c2ccc(C(=O)NCCc3c[nH]cn3)cc2NC(=O)c2ccco2)CC1] | ++ | ++ |

TABLE 1-continued

Compounds of formulae (I), (I-A), (I-B), (I-C).
Assay A: Example 10; Assay B: Example 11.

| Structure | Assay A<br>0 > 10 μM<br>+ > 1-10 μM<br>++ 0.1-1 μM<br>+++ < 0.1 μM<br>% at 5 μM | Assay B<br>0 > 10 μM<br>+ > 1-10 μM<br>++ 0.1-1 μM<br>+++ < 0.1 μM<br>% at 5 μM |
|---|---|---|
| 16 | | |
| 17 | | ++ |
| 18 | | |
| 19 | | + |

TABLE 1-continued

Compounds of formulae (I), (I-A), (I-B), (I-C).
Assay A: Example 10; Assay B: Example 11.

| Structure | Assay A<br>0 > 10 μM<br>+ > 1-10 μM<br>++ 0.1-1 μM<br>+++ < 0.1 μM<br>% at 5 μM | Assay B<br>0 > 10 μM<br>+ > 1-10 μM<br>++ 0.1-1 μM<br>+++ < 0.1 μM<br>% at 5 μM |
| --- | --- | --- |
| 20 | | ++ |
| 21 | | 22% |
| 22 | | + |
| 23 | | 4% |

TABLE 1-continued

Compounds of formulae (I), (I-A), (I-B), (I-C).
Assay A: Example 10; Assay B: Example 11.

| Structure | Assay A<br>0 > 10 μM<br>+ > 1-10 μM<br>++ 0.1-1 μM<br>+++ < 0.1 μM<br>% at 5 μM | Assay B<br>0 > 10 μM<br>+ > 1-10 μM<br>++ 0.1-1 μM<br>+++ < 0.1 μM<br>% at 5 μM |
|---|---|---|
| 24 | + | |
| 25 | + | |
| 26 | + | |
| 27 | ++ | + |

TABLE 1-continued

Compounds of formulae (I), (I-A), (I-B), (I-C).
Assay A: Example 10; Assay B: Example 11.

| Structure | Assay A<br>0 > 10 μM<br>+ > 1-10 μM<br>++ 0.1-1 μM<br>+++ < 0.1 μM<br>% at 5 μM | Assay B<br>0 > 10 μM<br>+ > 1-10 μM<br>++ 0.1-1 μM<br>+++ < 0.1 μM<br>% at 5 μM |
|---|---|---|
| 28 | + | |
| 29 | ++ | |
| 30 | + | |
| 31 | ++ | ++ |

TABLE 1-continued

Compounds of formulae (I), (I-A), (I-B), (I-C).
Assay A: Example 10; Assay B: Example 11.

| | Structure | Assay A<br>0 > 10 μM<br>+ > 1-10 μM<br>++ 0.1-1 μM<br>+++ < 0.1 μM<br>% at 5 μM | Assay B<br>0 > 10 μM<br>+ > 1-10 μM<br>++ 0.1-1 μM<br>+++ < 0.1 μM<br>% at 5 μM |
|---|---|---|---|
| 32 | 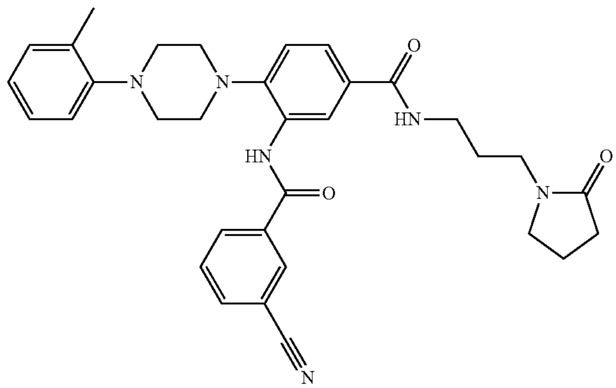 [SMILES: Cc1ccccc1N1CCN(c2ccc(C(=O)NCCCN3CCCC3=O)cc2NC(=O)c2cccc(C#N)c2)CC1] | | |
| 33 | 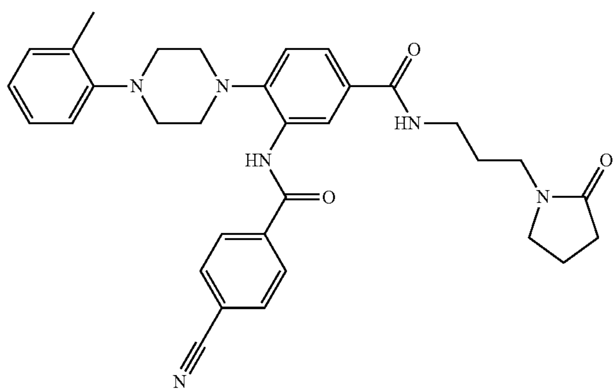 [SMILES: Cc1ccccc1N1CCN(c2ccc(C(=O)NCCCN3CCCC3=O)cc2NC(=O)c2ccc(C#N)cc2)CC1] | | + |
| 34 | 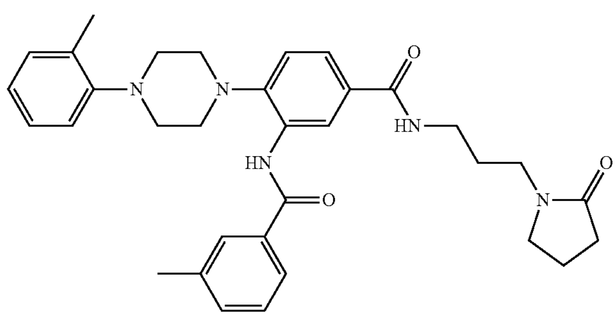 [SMILES: Cc1cccc(C(=O)Nc2cc(C(=O)NCCCN3CCCC3=O)ccc2N2CCN(c3ccccc3C)CC2)c1] | | + |
| 35 | 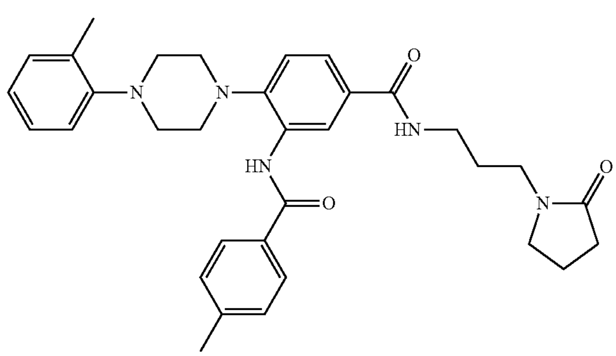 [SMILES: Cc1ccc(C(=O)Nc2cc(C(=O)NCCCN3CCCC3=O)ccc2N2CCN(c3ccccc3C)CC2)cc1] | ++ | + |

TABLE 1-continued

Compounds of formulae (I), (I-A), (I-B), (I-C).
Assay A: Example 10; Assay B: Example 11.

| | Structure | Assay A<br>0 > 10 μM<br>+ > 1-10 μM<br>++ 0.1-1 μM<br>+++ < 0.1 μM<br>% at 5 μM | Assay B<br>0 > 10 μM<br>+ > 1-10 μM<br>++ 0.1-1 μM<br>+++ < 0.1 μM<br>% at 5 μM |
|---|---|---|---|
| 36 | 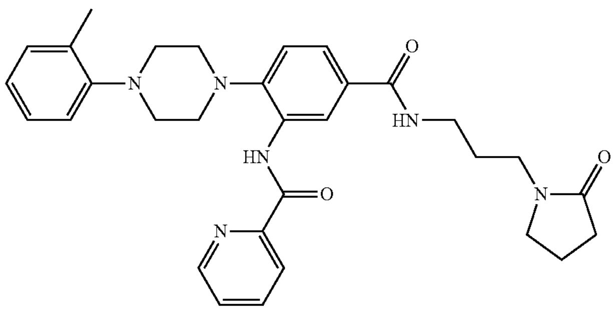 [SMILES: Cc1ccccc1N1CCN(c2ccc(C(=O)NCCCN3CCCC3=O)cc2NC(=O)c2ccccn2)CC1] | ++ | ++ |
| 37 | 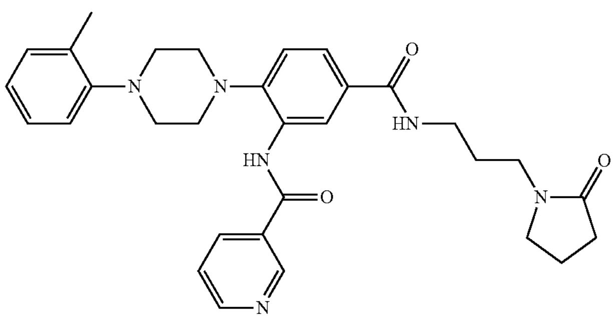 [SMILES: Cc1ccccc1N1CCN(c2ccc(C(=O)NCCCN3CCCC3=O)cc2NC(=O)c2cccnc2)CC1] | 37% | |
| 38 | 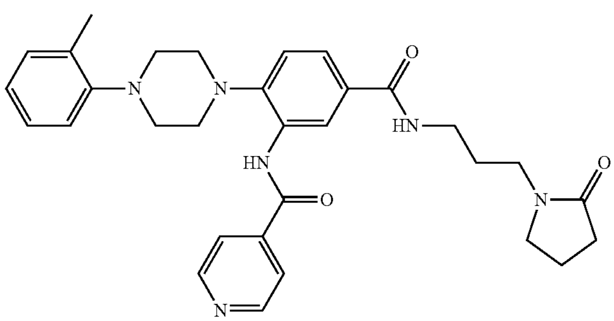 [SMILES: Cc1ccccc1N1CCN(c2ccc(C(=O)NCCCN3CCCC3=O)cc2NC(=O)c2ccncc2)CC1] | | |
| 39 | 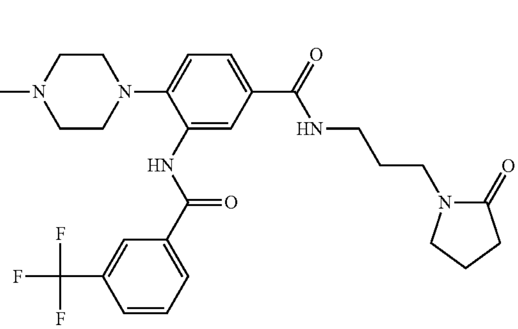 | 15% | |

TABLE 1-continued
Compounds of formulae (I), (I-A), (I-B), (I-C).
Assay A: Example 10; Assay B: Example 11.
| Structure | Assay A<br>0 > 10 μM<br>+ > 1-10 μM<br>++ 0.1-1 μM<br>+++ < 0.1 μM<br>% at 5 μM | Assay B<br>0 > 10 μM<br>+ > 1-10 μM<br>++ 0.1-1 μM<br>+++ < 0.1 μM<br>% at 5 μM |
|---|---|---|
| 40 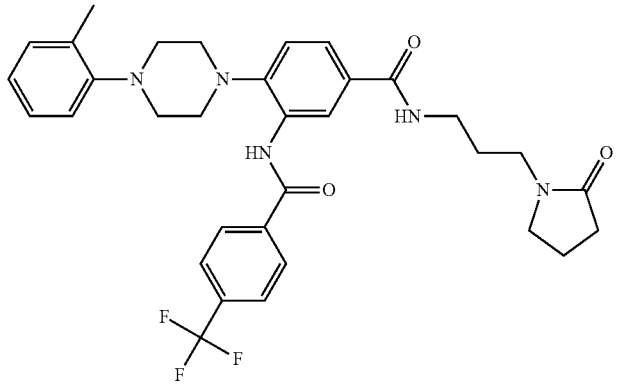 [SMILES: Cc1ccccc1N1CCN(c2ccc(C(=O)NCCCN3CCCC3=O)cc2NC(=O)c2ccc(C(F)(F)F)cc2)CC1] | 40% | |
| 41 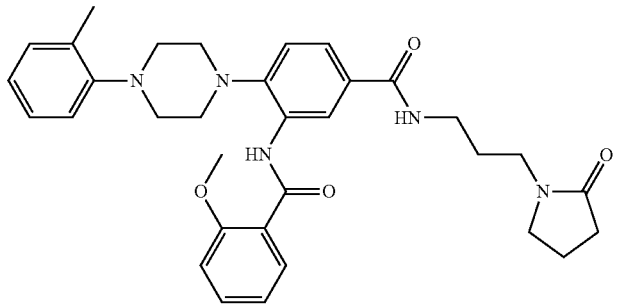 [SMILES: COc1ccccc1C(=O)Nc1cc(C(=O)NCCCN2CCCC2=O)ccc1N1CCN(c2ccccc2C)CC1] | + | |
| 42 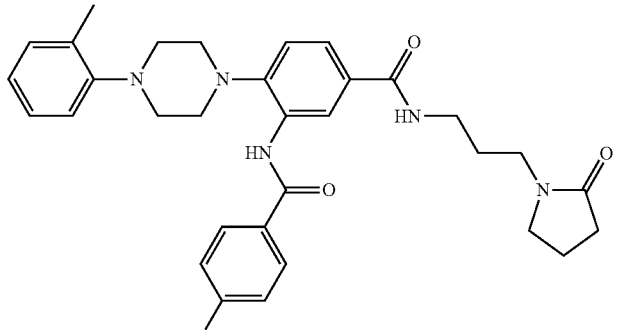 | ++ | |
| 43 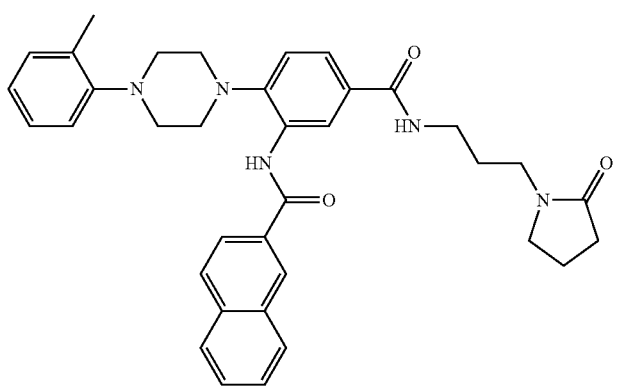 [SMILES: Cc1ccccc1N1CCN(c2ccc(C(=O)NCCCN3CCCC3=O)cc2NC(=O)c2ccc3ccccc3c2)CC1] | 44% | |

TABLE 1-continued

Compounds of formulae (I), (I-A), (I-B), (I-C).
Assay A: Example 10; Assay B: Example 11.

| Structure | Assay A<br>0 > 10 μM<br>+ > 1-10 μM<br>++ 0.1-1 μM<br>+++ < 0.1 μM<br>% at 5 μM | Assay B<br>0 > 10 μM<br>+ > 1-10 μM<br>++ 0.1-1 μM<br>+++ < 0.1 μM<br>% at 5 μM |
|---|---|---|
| 44 | 44% | |
| 45 | ++ | ++ |
| 46 | 10% | |
| 47 | | |

TABLE 1-continued

Compounds of formulae (I), (I-A), (I-B), (I-C).
Assay A: Example 10; Assay B: Example 11.

| | Structure | Assay A<br>0 > 10 μM<br>+ > 1-10 μM<br>++ 0.1-1 μM<br>+++ < 0.1 μM<br>% at 5 μM | Assay B<br>0 > 10 μM<br>+ > 1-10 μM<br>++ 0.1-1 μM<br>+++ < 0.1 μM<br>% at 5 μM |
|---|---|---|---|
| 48 | 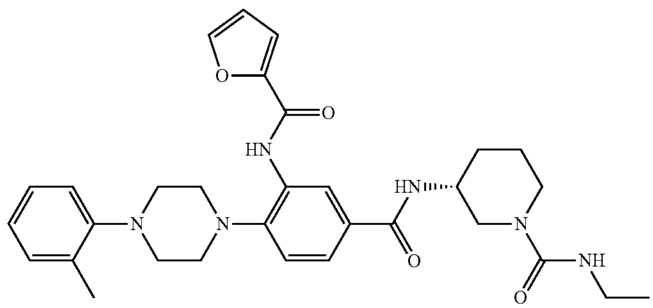 [SMILES: CCNC(=O)N1CCC[C@@H](NC(=O)c2ccc(N3CCN(c4ccccc4C)CC3)c(NC(=O)c3ccco3)c2)C1] | | + |
| 49 | 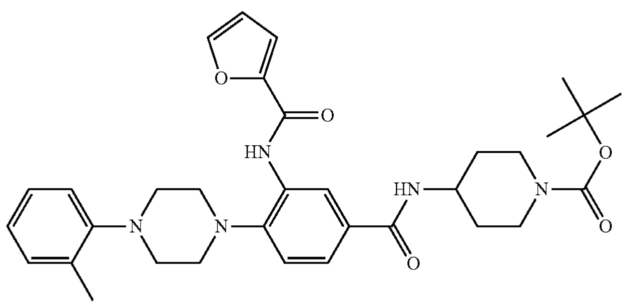 [SMILES: Cc1ccccc1N1CCN(c2ccc(C(=O)NC3CCN(C(=O)OC(C)(C)C)CC3)cc2NC(=O)c2ccco2)CC1] | | ++ |
| 50 | 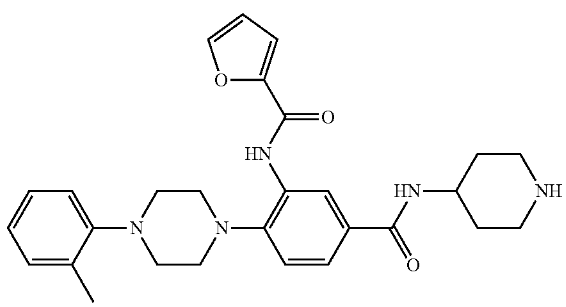 [SMILES: Cc1ccccc1N1CCN(c2ccc(C(=O)NC3CCNCC3)cc2NC(=O)c2ccco2)CC1] | | |
| 51 | 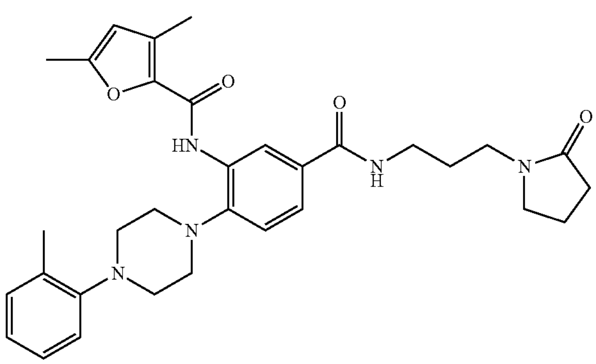 [SMILES: Cc1cc(C)c(C(=O)Nc2cc(C(=O)NCCCN3CCCC3=O)ccc2N2CCN(c3ccccc3C)CC2)o1] | | 39% |

TABLE 1-continued

Compounds of formulae (I), (I-A), (I-B), (I-C).
Assay A: Example 10; Assay B: Example 11.

| Structure | Assay A<br>0 > 10 μM<br>+ > 1-10 μM<br>++ 0.1-1 μM<br>+++ < 0.1 μM<br>% at 5 μM | Assay B<br>0 > 10 μM<br>+ > 1-10 μM<br>++ 0.1-1 μM<br>+++ < 0.1 μM<br>% at 5 μM |
|---|---|---|
| 52 | | |
| 53 | | |
| 54 | | |
| 55 | + | |

TABLE 1-continued

Compounds of formulae (I), (I-A), (I-B), (I-C).
Assay A: Example 10; Assay B: Example 11.

| Structure | Assay A<br>0 > 10 μM<br>+ > 1-10 μM<br>++ 0.1-1 μM<br>+++ < 0.1 μM<br>% at 5 μM | Assay B<br>0 > 10 μM<br>+ > 1-10 μM<br>++ 0.1-1 μM<br>+++ < 0.1 μM<br>% at 5 μM |
| --- | --- | --- |
| 56 | | + |
| 57 | | + |
| 58 | | ++ 27% |
| 59 | | + |

TABLE 1-continued
Compounds of formulae (I), (I-A), (I-B), (I-C).
Assay A: Example 10; Assay B: Example 11.
| Structure | Assay A<br>0 > 10 μM<br>+ > 1-10 μM<br>++ 0.1-1 μM<br>+++ < 0.1 μM<br>% at 5 μM | Assay B<br>0 > 10 μM<br>+ > 1-10 μM<br>++ 0.1-1 μM<br>+++ < 0.1 μM<br>% at 5 μM |
|---|---|---|
| 60 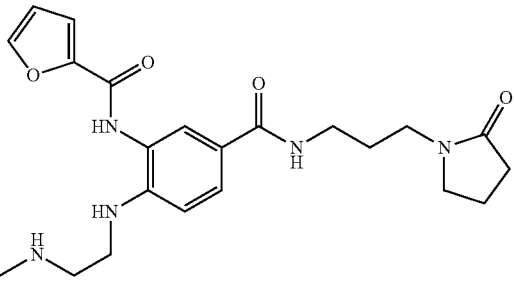 | | |
| 61 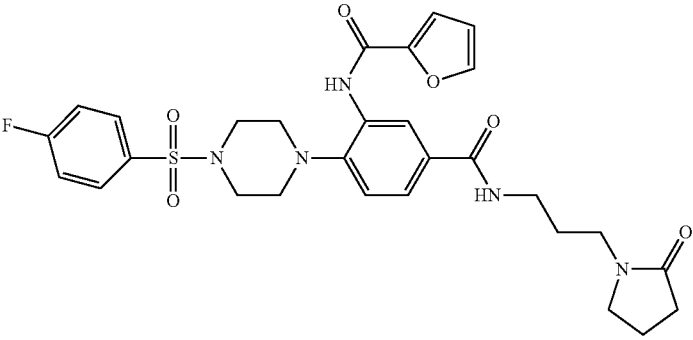 [SMILES: O=C(NCCCN1CCCC1=O)c1ccc(N2CCN(S(=O)(=O)c3ccc(F)cc3)CC2)c(NC(=O)c2ccco2)c1] | | |
| 62 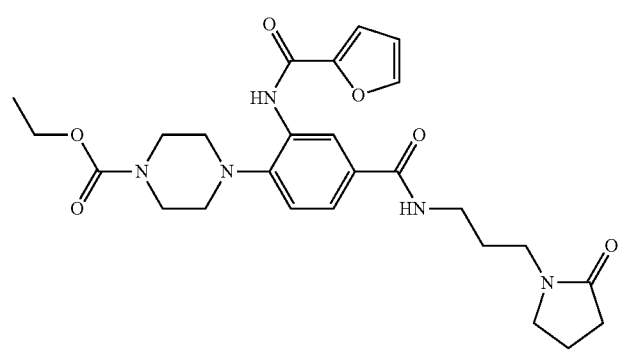 [SMILES: CCOC(=O)N1CCN(c2ccc(C(=O)NCCCN3CCCC3=O)cc2NC(=O)c2ccco2)CC1] | | 42% |
| 63 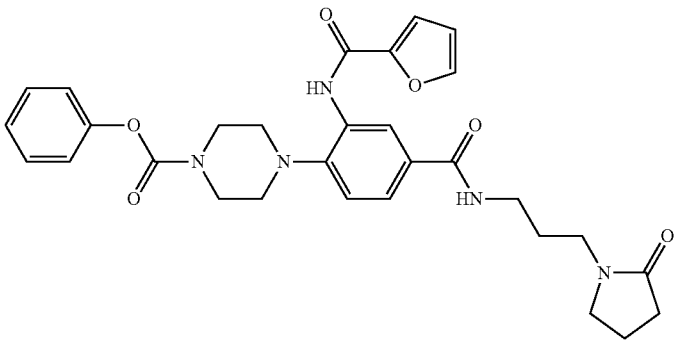 [SMILES: O=C(NCCCN1CCCC1=O)c1ccc(N2CCN(C(=O)Oc3ccccc3)CC2)c(NC(=O)c2ccco2)c1] | | |

TABLE 1-continued

Compounds of formulae (I), (I-A), (I-B), (I-C).
Assay A: Example 10; Assay B: Example 11.

| Structure | Assay A<br>0 > 10 μM<br>+ > 1-10 μM<br>++ 0.1-1 μM<br>+++ < 0.1 μM<br>% at 5 μM | Assay B<br>0 > 10 μM<br>+ > 1-10 μM<br>++ 0.1-1 μM<br>+++ < 0.1 μM<br>% at 5 μM |
|---|---|---|
| 64 | 72% | |
| 65 | | + |
| 66 | | |
| 67 | | ++ |
| 68 | | + |

TABLE 1-continued

Compounds of formulae (I), (I-A), (I-B), (I-C).
Assay A: Example 10; Assay B: Example 11.

| | Structure | Assay A<br>0 > 10 μM<br>+ > 1-10 μM<br>++ 0.1-1 μM<br>+++ < 0.1 μM<br>% at 5 μM | Assay B<br>0 > 10 μM<br>+ > 1-10 μM<br>++ 0.1-1 μM<br>+++ < 0.1 μM<br>% at 5 μM |
|---|---|---|---|
| 69 | 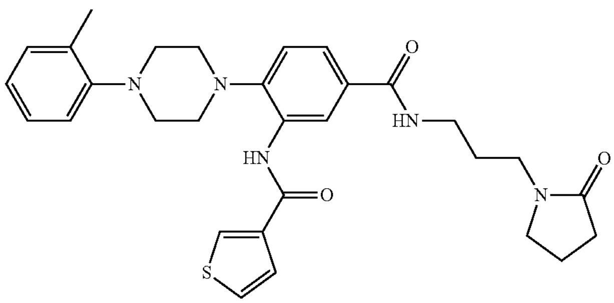 [SMILES: Cc1ccccc1N1CCN(c2ccc(C(=O)NCCCN3CCCC3=O)cc2NC(=O)c2ccsc2)CC1] | | ++ |
| 70 | 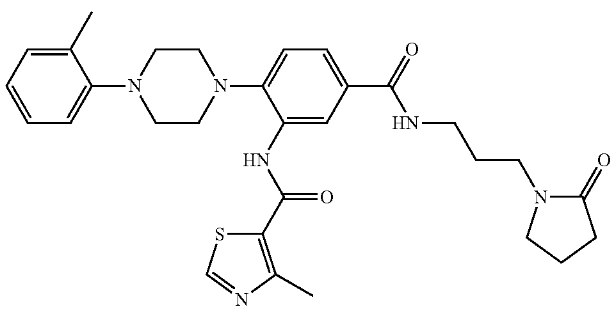 [SMILES: Cc1ccccc1N1CCN(c2ccc(C(=O)NCCCN3CCCC3=O)cc2NC(=O)c2scnc2C)CC1] | | 0 |
| 71 | 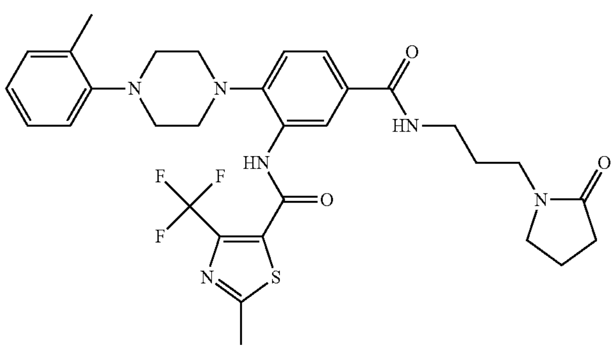 [SMILES: Cc1nc(C(F)(F)F)c(C(=O)Nc2cc(C(=O)NCCCN3CCCC3=O)ccc2N2CCN(c3ccccc3C)CC2)s1] | | + |
| 72 | 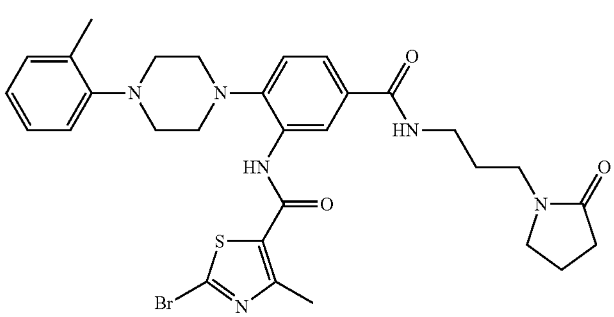 [SMILES: Cc1ccccc1N1CCN(c2ccc(C(=O)NCCCN3CCCC3=O)cc2NC(=O)c2sc(Br)nc2C)CC1] | | 0 |

TABLE 1-continued

Compounds of formulae (I), (I-A), (I-B), (I-C).
Assay A: Example 10; Assay B: Example 11.

| | Structure | Assay A<br>0 > 10 μM<br>+ > 1-10 μM<br>++ 0.1-1 μM<br>+++ < 0.1 μM<br>% at 5 μM | Assay B<br>0 > 10 μM<br>+ > 1-10 μM<br>++ 0.1-1 μM<br>+++ < 0.1 μM<br>% at 5 μM |
|---|---|---|---|
| 73 | 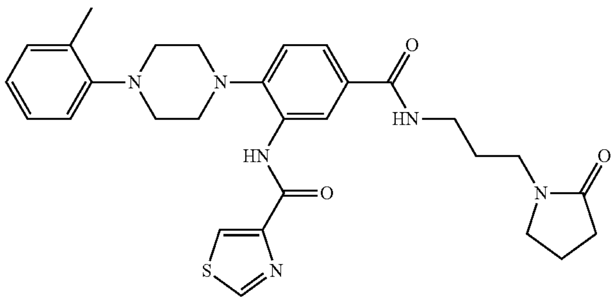 | ++ | + |
| 74 | 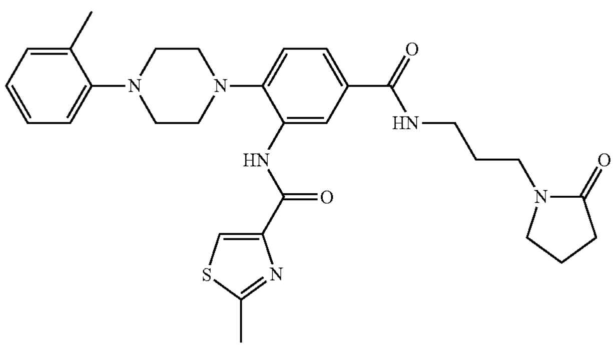 [SMILES: Cc1nc(C(=O)Nc2cc(C(=O)NCCCN3CCCC3=O)ccc2N2CCN(c3ccccc3C)CC2)co1] | ++ | ++ |
| 75 | 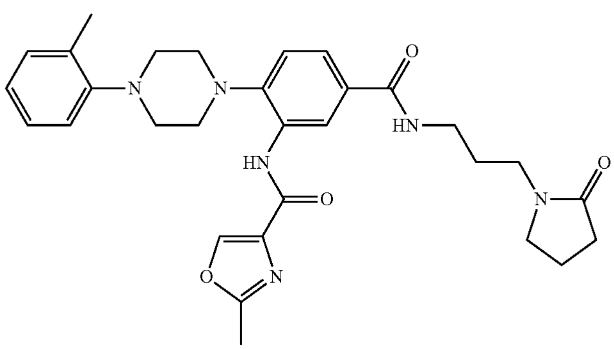 | ++ | 0 |
| 76 | 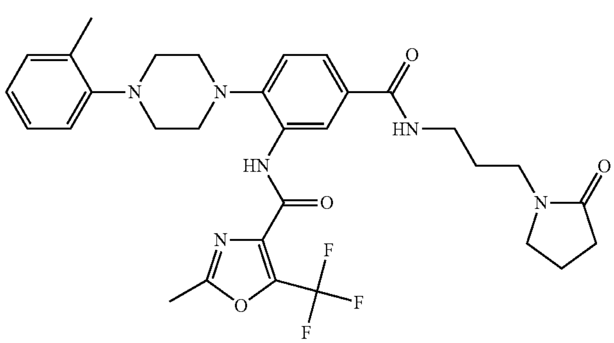 [SMILES: Cc1nc(C(=O)Nc2cc(C(=O)NCCCN3CCCC3=O)ccc2N2CCN(c3ccccc3C)CC2)c(C(F)(F)F)o1] | | + |

TABLE 1-continued

Compounds of formulae (I), (I-A), (I-B), (I-C).
Assay A: Example 10; Assay B: Example 11.

| | Structure | Assay A<br>0 > 10 μM<br>+ > 1-10 μM<br>++ 0.1-1 μM<br>+++ < 0.1 μM<br>% at 5 μM | Assay B<br>0 > 10 μM<br>+ > 1-10 μM<br>++ 0.1-1 μM<br>+++ < 0.1 μM<br>% at 5 μM |
|---|---|---|---|
| 77 | 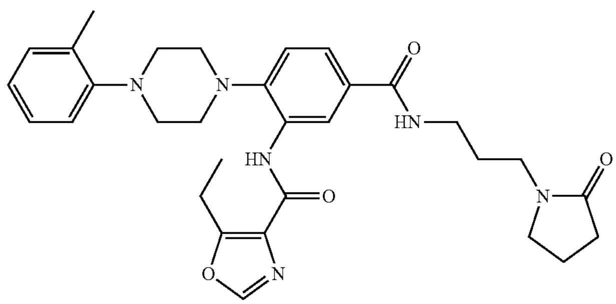 | | + |
| 78 | 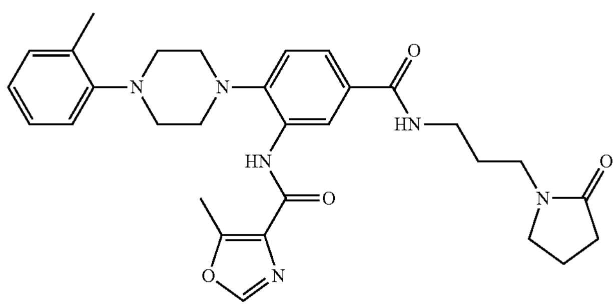 [SMILES: Cc1ccccc1N1CCN(c2ccc(C(=O)NCCCN3CCCC3=O)cc2NC(=O)c2ncoc2C)CC1] | | ++ |
| 79 | 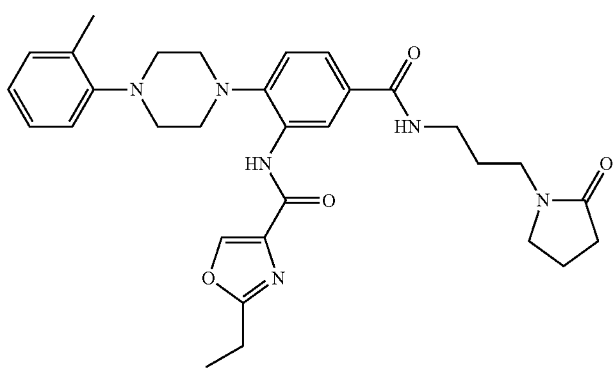 [SMILES: CCc1nc(C(=O)Nc2cc(C(=O)NCCCN3CCCC3=O)ccc2N2CCN(c3ccccc3C)CC2)co1] | ++ | ++ |
| 80 | 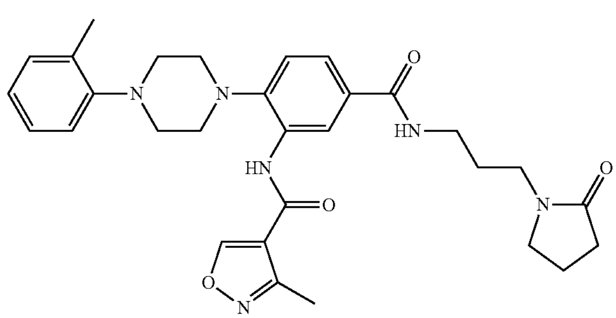 [SMILES: Cc1ccccc1N1CCN(c2ccc(C(=O)NCCCN3CCCC3=O)cc2NC(=O)c2conc2C)CC1] | | 22% |

TABLE 1-continued
Compounds of formulae (I), (I-A), (I-B), (I-C).
Assay A: Example 10; Assay B: Example 11.
| | Structure | Assay A<br>0 > 10 μM<br>+ > 1-10 μM<br>++ 0.1-1 μM<br>+++ < 0.1 μM<br>% at 5 μM | Assay B<br>0 > 10 μM<br>+ > 1-10 μM<br>++ 0.1-1 μM<br>+++ < 0.1 μM<br>% at 5 μM |
|---|---|---|---|
| 81 | 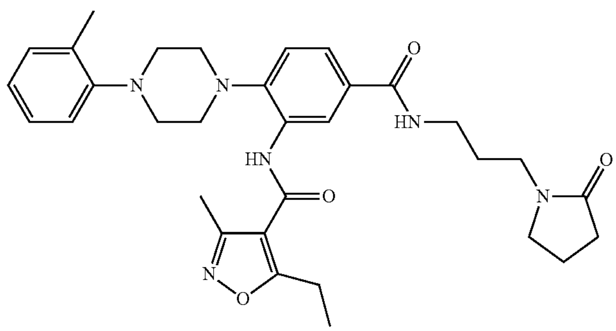 [SMILES: CCc1onc(C)c1C(=O)Nc1cc(C(=O)NCCCN2CCCC2=O)ccc1N1CCN(c2ccccc2C)CC1] | 11% | |
| 82 | 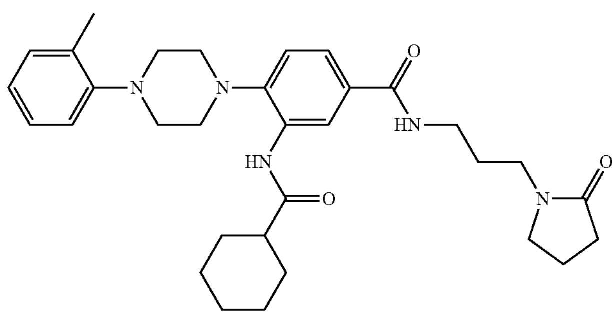 [SMILES: Cc1ccccc1N1CCN(c2ccc(C(=O)NCCCN3CCCC3=O)cc2NC(=O)C2CCCCC2)CC1] | + | |
| 83 | 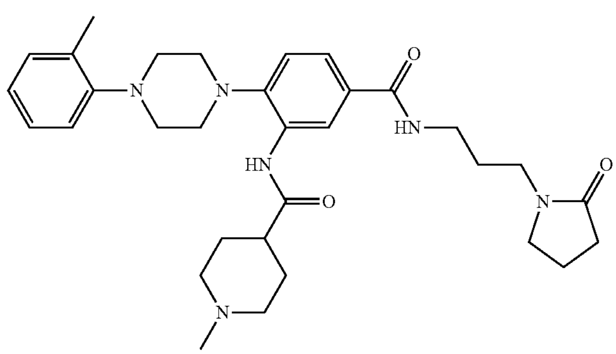 [SMILES: Cc1ccccc1N1CCN(c2ccc(C(=O)NCCCN3CCCC3=O)cc2NC(=O)C2CCN(C)CC2)CC1] | 8% | |
| 84 | 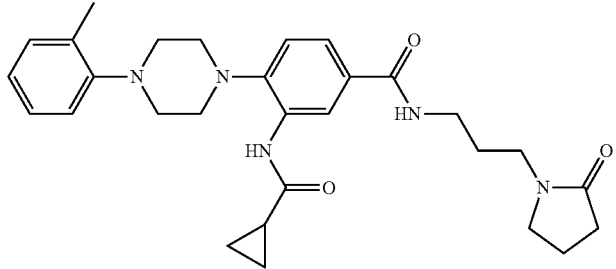 [SMILES: Cc1ccccc1N1CCN(c2ccc(C(=O)NCCCN3CCCC3=O)cc2NC(=O)C2CC2)CC1] | ++ | ++ |

TABLE 1-continued

Compounds of formulae (I), (I-A), (I-B), (I-C).
Assay A: Example 10; Assay B: Example 11.

| Structure | Assay A<br>0 > 10 μM<br>+ > 1-10 μM<br>++ 0.1-1 μM<br>+++ < 0.1 μM<br>% at 5 μM | Assay B<br>0 > 10 μM<br>+ > 1-10 μM<br>++ 0.1-1 μM<br>+++ < 0.1 μM<br>% at 5 μM |
|---|---|---|
| 85 | ++ | + |
| 86 | 47% | |
| 87 | | + |
| 88 | 34% | |

TABLE 1-continued

Compounds of formulae (I), (I-A), (I-B), (I-C).
Assay A: Example 10; Assay B: Example 11.

| Structure | Assay A<br>0 > 10 μM<br>+ > 1-10 μM<br>++ 0.1-1 μM<br>+++ < 0.1 μM<br>% at 5 μM | Assay B<br>0 > 10 μM<br>+ > 1-10 μM<br>++ 0.1-1 μM<br>+++ < 0.1 μM<br>% at 5 μM |
| --- | --- | --- |
| 89 | | ++ |
| 90 | | ++ |
| 91 | | + |
| 92 | | + |

TABLE 1-continued

Compounds of formulae (I), (I-A), (I-B), (I-C).
Assay A: Example 10; Assay B: Example 11.

| Structure | Assay A<br>0 > 10 μM<br>+ > 1-10 μM<br>++ 0.1-1 μM<br>+++ < 0.1 μM<br>% at 5 μM | Assay B<br>0 > 10 μM<br>+ > 1-10 μM<br>++ 0.1-1 μM<br>+++ < 0.1 μM<br>% at 5 μM |
|---|---|---|
| 93 | | ++ |
| 94 | | 48% |
| 95 | | ++ |
| 96 | | 0 |

TABLE 1-continued

Compounds of formulae (I), (I-A), (I-B), (I-C).
Assay A: Example 10; Assay B: Example 11.

| Structure | Assay A<br>0 > 10 μM<br>+ > 1-10 μM<br>++ 0.1-1 μM<br>+++ < 0.1 μM<br>% at 5 μM | Assay B<br>0 > 10 μM<br>+ > 1-10 μM<br>++ 0.1-1 μM<br>+++ < 0.1 μM<br>% at 5 μM |
|---|---|---|
| 97 | | |
| 98 | | + |
| 99 | | 35% |
| 100 | | 12% |

TABLE 1-continued
Compounds of formulae (I), (I-A), (I-B), (I-C).
Assay A: Example 10; Assay B: Example 11.
| Structure | Assay A<br>0 > 10 μM<br>+ > 1-10 μM<br>++ 0.1-1 μM<br>+++ < 0.1 μM<br>% at 5 μM | Assay B<br>0 > 10 μM<br>+ > 1-10 μM<br>++ 0.1-1 μM<br>+++ < 0.1 μM<br>% at 5 μM |
|---|---|---|
| 101 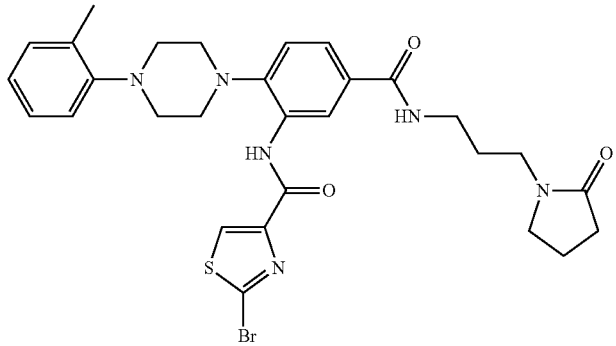 [SMILES: Cc1ccccc1N1CCN(c2ccc(C(=O)NCCCN3CCCC3=O)cc2NC(=O)c2csc(Br)n2)CC1] | | + |
| 102 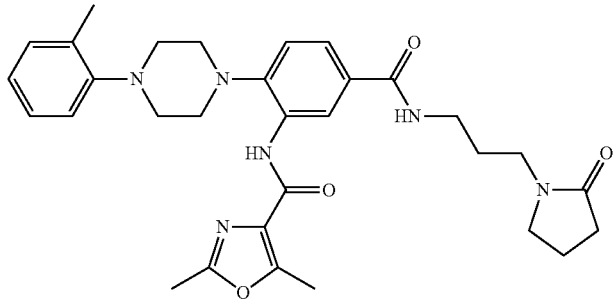 [SMILES: Cc1nc(C(=O)Nc2cc(C(=O)NCCCN3CCCC3=O)ccc2N2CCN(c3ccccc3C)CC2)c(C)o1] | | + |
| 103 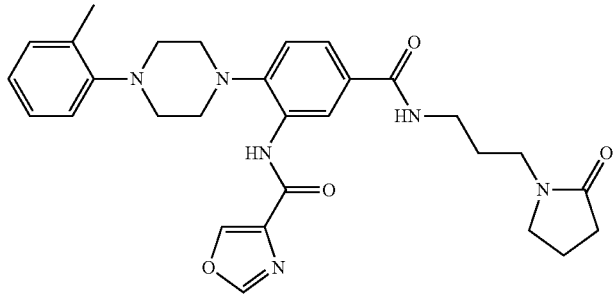 [SMILES: Cc1ccccc1N1CCN(c2ccc(C(=O)NCCCN3CCCC3=O)cc2NC(=O)c2cocn2)CC1] | | + |
| 104 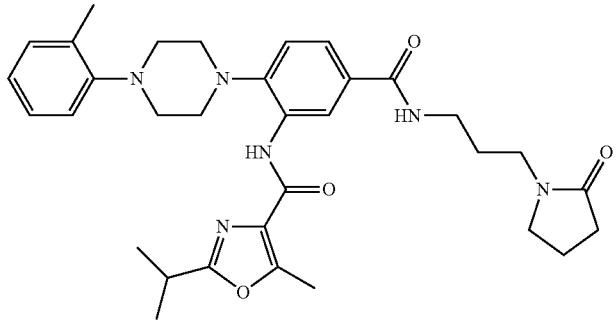 [SMILES: Cc1ccccc1N1CCN(c2ccc(C(=O)NCCCN3CCCC3=O)cc2NC(=O)c2nc(C(C)C)oc2C)CC1] | | |

TABLE 1-continued

Compounds of formulae (I), (I-A), (I-B), (I-C).
Assay A: Example 10; Assay B: Example 11.

| | Structure | Assay A<br>0 > 10 μM<br>+ > 1-10 μM<br>++ 0.1-1 μM<br>+++ < 0.1 μM<br>% at 5 μM | Assay B<br>0 > 10 μM<br>+ > 1-10 μM<br>++ 0.1-1 μM<br>+++ < 0.1 μM<br>% at 5 μM |
|---|---|---|---|
| 105 | 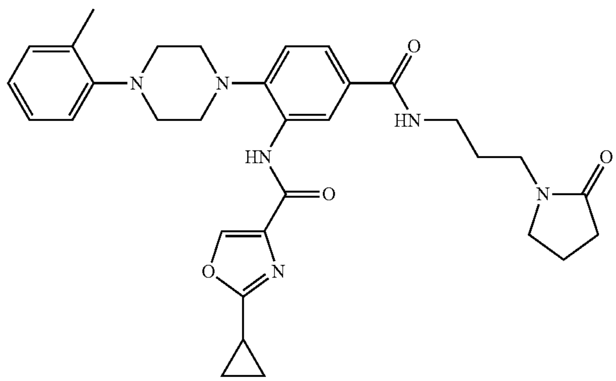 [SMILES: Cc1ccccc1N1CCN(c2ccc(C(=O)NCCCN3CCCC3=O)cc2NC(=O)c2coc(C3CC3)n2)CC1] | +++ | ++ |
| 106 | 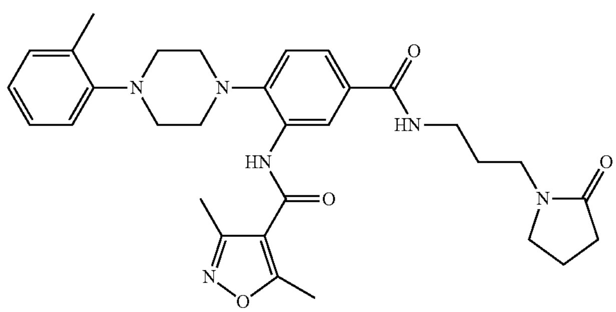 [SMILES: Cc1ccccc1N1CCN(c2ccc(C(=O)NCCCN3CCCC3=O)cc2NC(=O)c2c(C)noc2C)CC1] | 33% | |
| 107 | 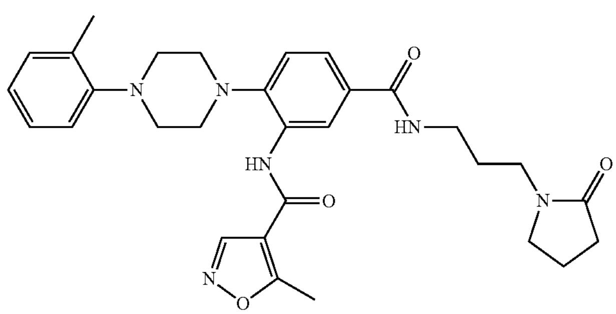 [SMILES: Cc1ccccc1N1CCN(c2ccc(C(=O)NCCCN3CCCC3=O)cc2NC(=O)c2cnoc2C)CC1] | 15% | |
| 108 | 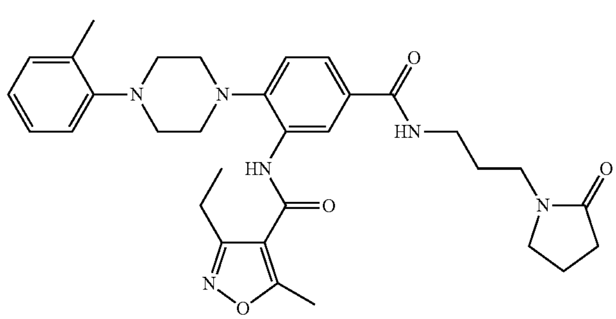 [SMILES: CCc1noc(C)c1C(=O)Nc1cc(C(=O)NCCCN2CCCC2=O)ccc1N1CCN(c2ccccc2C)CC1] | | |

TABLE 1-continued
Compounds of formulae (I), (I-A), (I-B), (I-C).
Assay A: Example 10; Assay B: Example 11.
| | Structure | Assay A<br>0 > 10 μM<br>+ > 1-10 μM<br>++ 0.1-1 μM<br>+++ < 0.1 μM<br>% at 5 μM | Assay B<br>0 > 10 μM<br>+ > 1-10 μM<br>++ 0.1-1 μM<br>+++ < 0.1 μM<br>% at 5 μM |
|---|---|---|---|
| 109 | 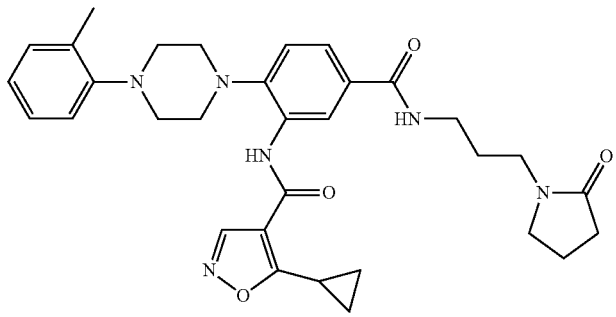 [SMILES: Cc1ccccc1N1CCN(c2ccc(C(=O)NCCCN3CCCC3=O)cc2NC(=O)c2cnoc2C2CC2)CC1] | | 10% |
| 110 | 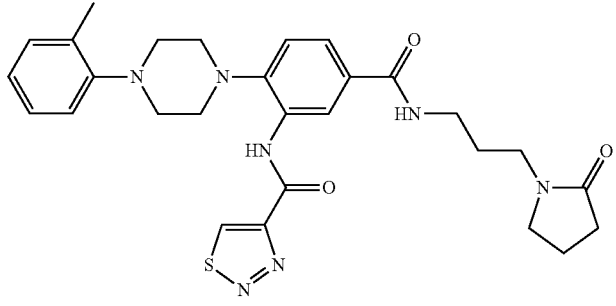 [SMILES: Cc1ccccc1N1CCN(c2ccc(C(=O)NCCCN3CCCC3=O)cc2NC(=O)c2csnn2)CC1] | | + |
| 111 | 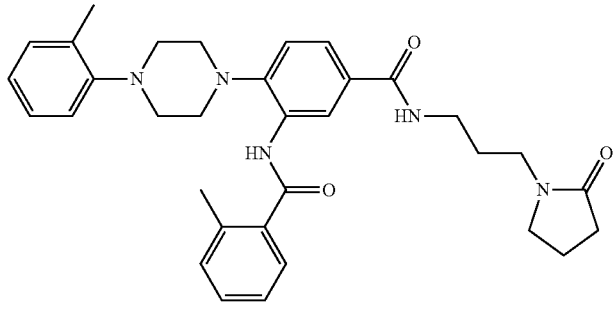 | | + |
| 112 | 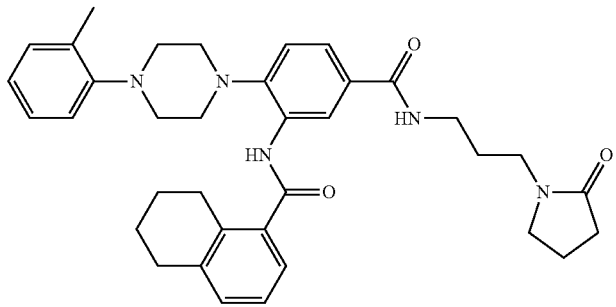 [SMILES: Cc1ccccc1N1CCN(c2ccc(C(=O)NCCCN3CCCC3=O)cc2NC(=O)c2cccc3c2CCCC3)CC1] | | 21% |

TABLE 1-continued

Compounds of formulae (I), (I-A), (I-B), (I-C).
Assay A: Example 10; Assay B: Example 11.

| | Structure | Assay A<br>0 > 10 μM<br>+ > 1-10 μM<br>++ 0.1-1 μM<br>+++ < 0.1 μM<br>% at 5 μM | Assay B<br>0 > 10 μM<br>+ > 1-10 μM<br>++ 0.1-1 μM<br>+++ < 0.1 μM<br>% at 5 μM |
|---|---|---|---|
| 113 | | | |
| 114 | | | 40% |
| 115 | | | 39% |
| 116 | | | ++ |

TABLE 1-continued

Compounds of formulae (I), (I-A), (I-B), (I-C).
Assay A: Example 10; Assay B: Example 11.

| | Structure | Assay A<br>0 > 10 μM<br>+ > 1-10 μM<br>++ 0.1-1 μM<br>+++ < 0.1 μM<br>% at 5 μM | Assay B<br>0 > 10 μM<br>+ > 1-10 μM<br>++ 0.1-1 μM<br>+++ < 0.1 μM<br>% at 5 μM |
|---|---|---|---|
| 117 | 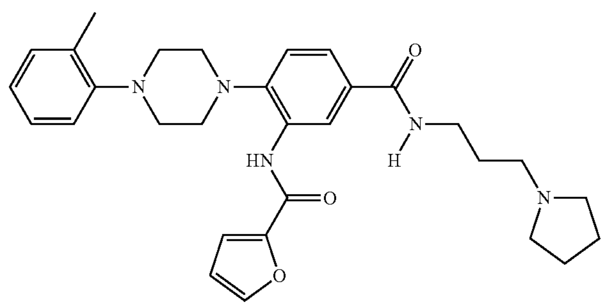 | | + |
| 118 | 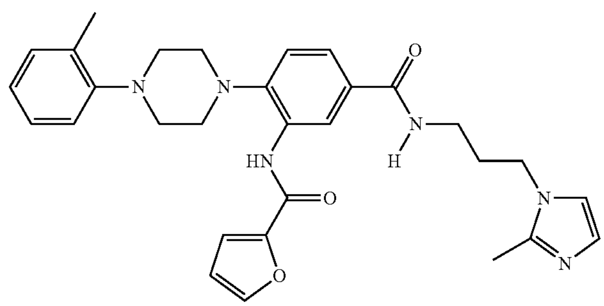 [SMILES: Cc1ccccc1N1CCN(c2ccc(C(=O)NCCCn3ccnc3C)cc2NC(=O)c2ccco2)CC1] | | ++ |
| 119 | 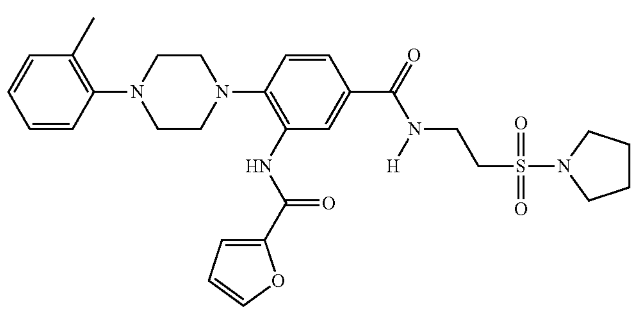 [SMILES: Cc1ccccc1N1CCN(c2ccc(C(=O)NCCS(=O)(=O)N3CCCC3)cc2NC(=O)c2ccco2)CC1] | | ++ |
| 120 | 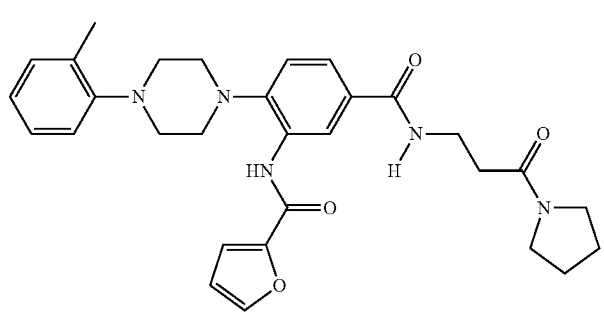 [SMILES: Cc1ccccc1N1CCN(c2ccc(C(=O)NCCC(=O)N3CCCC3)cc2NC(=O)c2ccco2)CC1] | | ++ |

TABLE 1-continued

Compounds of formulae (I), (I-A), (I-B), (I-C).
Assay A: Example 10; Assay B: Example 11.

| Structure | Assay A<br>0 > 10 μM<br>+ > 1-10 μM<br>++ 0.1-1 μM<br>+++ < 0.1 μM<br>% at 5 μM | Assay B<br>0 > 10 μM<br>+ > 1-10 μM<br>++ 0.1-1 μM<br>+++ < 0.1 μM<br>% at 5 μM |
|---|---|---|
| 121 | | |
| 122 | | 24% |
| 123 | | |
| 124 | | 82% |

TABLE 1-continued

Compounds of formulae (I), (I-A), (I-B), (I-C).
Assay A: Example 10; Assay B: Example 11.

| Structure | Assay A<br>0 > 10 μM<br>+ > 1-10 μM<br>++ 0.1-1 μM<br>+++ < 0.1 μM<br>% at 5 μM | Assay B<br>0 > 10 μM<br>+ > 1-10 μM<br>++ 0.1-1 μM<br>+++ < 0.1 μM<br>% at 5 μM |
|---|---|---|
| 125 | | |
| 126 | 33% | |
| 127 | 33% | |
| 128 | ++ | ++ |

TABLE 1-continued

Compounds of formulae (I), (I-A), (I-B), (I-C).
Assay A: Example 10; Assay B: Example 11.

| Structure | Assay A<br>0 > 10 μM<br>+ > 1-10 μM<br>++ 0.1-1 μM<br>+++ < 0.1 μM<br>% at 5 μM | Assay B<br>0 > 10 μM<br>+ > 1-10 μM<br>++ 0.1-1 μM<br>+++ < 0.1 μM<br>% at 5 μM |
|---|---|---|
| 129 | | ++ |
| 130 | | + |
| 131 | | ++ |
| 132 | | + |

TABLE 1-continued

Compounds of formulae (I), (I-A), (I-B), (I-C).
Assay A: Example 10; Assay B: Example 11.

| Structure | Assay A<br>0 > 10 μM<br>+ > 1-10 μM<br>++ 0.1-1 μM<br>+++ < 0.1 μM<br>% at 5 μM | Assay B<br>0 > 10 μM<br>+ > 1-10 μM<br>++ 0.1-1 μM<br>+++ < 0.1 μM<br>% at 5 μM |
|---|---|---|
| 133 | | ++ |
| 134 | | + |
| 135 | ++ | ++ |
| 136 | | |

TABLE 1-continued
Compounds of formulae (I), (I-A), (I-B), (I-C).
Assay A: Example 10; Assay B: Example 11.
| | Assay A<br>0 > 10 μM<br>+ > 1-10 μM<br>++ 0.1-1 μM<br>+++ < 0.1 μM | Assay B<br>0 > 10 μM<br>+ > 1-10 μM<br>++ 0.1-1 μM<br>+++ < 0.1 μM |
|---|---|---|
| Structure | % at 5 μM | % at 5 μM |
137 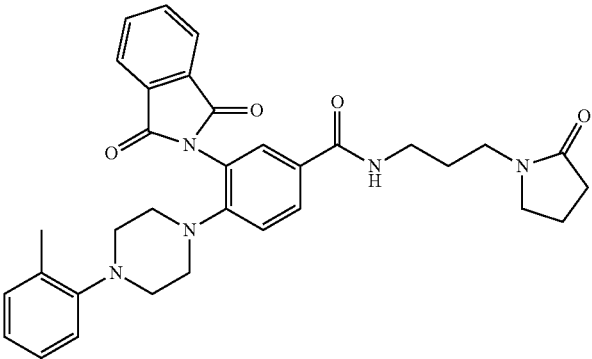 [SMILES: Cc1ccccc1N1CCN(c2ccc(C(=O)NCCCN3CCCC3=O)cc2N2C(=O)c3ccccc3C2=O)CC1]
138 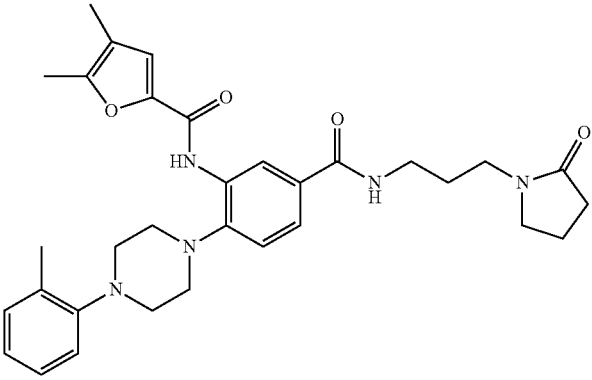 [SMILES: Cc1ccccc1N1CCN(c2ccc(C(=O)NCCCN3CCCC3=O)cc2NC(=O)c2cc(C)c(C)o2)CC1]  41%
139 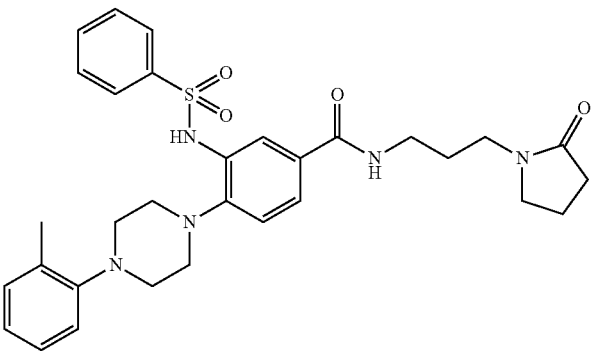 [SMILES: Cc1ccccc1N1CCN(c2ccc(C(=O)NCCCN3CCCC3=O)cc2NS(=O)(=O)c2ccccc2)CC1]

TABLE 1-continued

Compounds of formulae (I), (I-A), (I-B), (I-C).
Assay A: Example 10; Assay B: Example 11.

| | Structure | Assay A<br>0 > 10 μM<br>+ > 1-10 μM<br>++ 0.1-1 μM<br>+++ < 0.1 μM<br>% at 5 μM | Assay B<br>0 > 10 μM<br>+ > 1-10 μM<br>++ 0.1-1 μM<br>+++ < 0.1 μM<br>% at 5 μM |
|---|---|---|---|
| 140 | 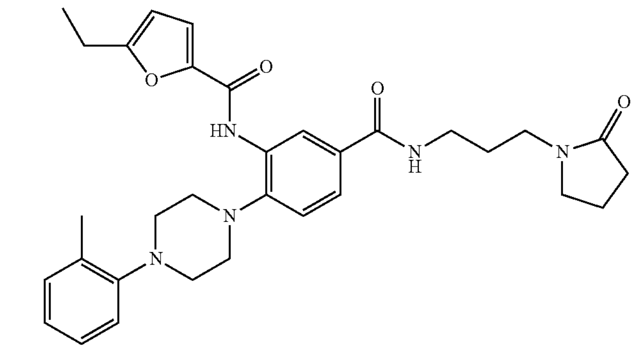 [SMILES: CCc1ccc(C(=O)Nc2cc(C(=O)NCCCN3CCCC3=O)ccc2N2CCN(c3ccccc3C)CC2)o1] | | ++ |
| 141 | 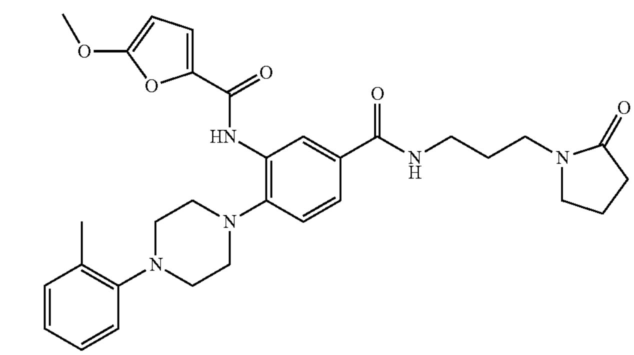 [SMILES: COc1ccc(C(=O)Nc2cc(C(=O)NCCCN3CCCC3=O)ccc2N2CCN(c3ccccc3C)CC2)o1] | | ++ |
| 142 | 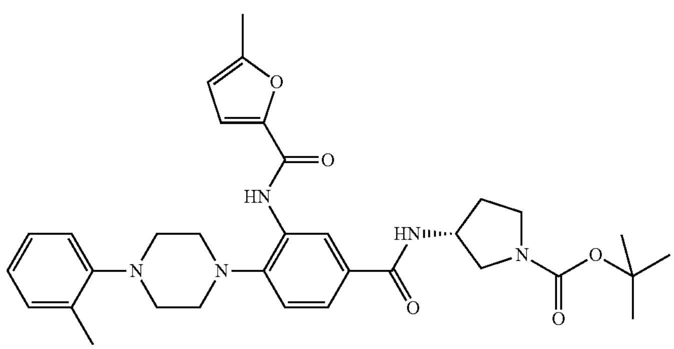 [SMILES: Cc1ccc(C(=O)Nc2cc(C(=O)N[C@@H]3CCN(C(=O)OC(C)(C)C)C3)ccc2N2CCN(c3ccccc3C)CC2)o1] | | + |
| 143 | 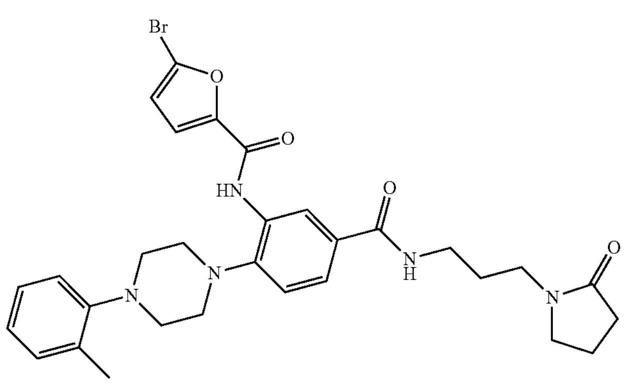 [SMILES: Cc1ccccc1N1CCN(c2ccc(C(=O)NCCCN3CCCC3=O)cc2NC(=O)c2ccc(Br)o2)CC1] | ++ | ++ |

TABLE 1-continued

Compounds of formulae (I), (I-A), (I-B), (I-C).
Assay A: Example 10; Assay B: Example 11.

| | Structure | Assay A<br>0 > 10 μM<br>+ > 1-10 μM<br>++ 0.1-1 μM<br>+++ < 0.1 μM<br>% at 5 μM | Assay B<br>0 > 10 μM<br>+ > 1-10 μM<br>++ 0.1-1 μM<br>+++ < 0.1 μM<br>% at 5 μM |
|---|---|---|---|
| 144 | | | |
| 145 | | 16% | |
| 146 | | 0 | |
| 147 | | ++ | ++ |

TABLE 1-continued
Compounds of formulae (I), (I-A), (I-B), (I-C).
Assay A: Example 10; Assay B: Example 11.
| | Structure | Assay A<br>0 > 10 μM<br>+ > 1-10 μM<br>++ 0.1-1 μM<br>+++ < 0.1 μM<br>% at 5 μM | Assay B<br>0 > 10 μM<br>+ > 1-10 μM<br>++ 0.1-1 μM<br>+++ < 0.1 μM<br>% at 5 μM |
|---|---|---|---|
| 148 | 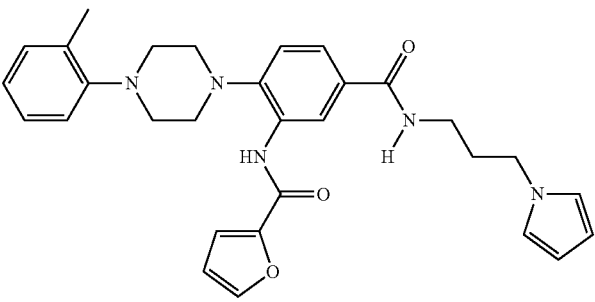 [SMILES: Cc1ccccc1N1CCN(c2ccc(C(=O)NCCCn3cccc3)cc2NC(=O)c2ccco2)CC1] | ++ | |
| 149 | 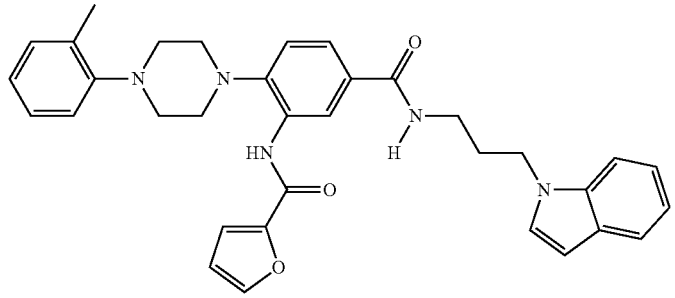 [SMILES: Cc1ccccc1N1CCN(c2ccc(C(=O)NCCCn3ccc4ccccc43)cc2NC(=O)c2ccco2)CC1] | 24% | |
| 150 | 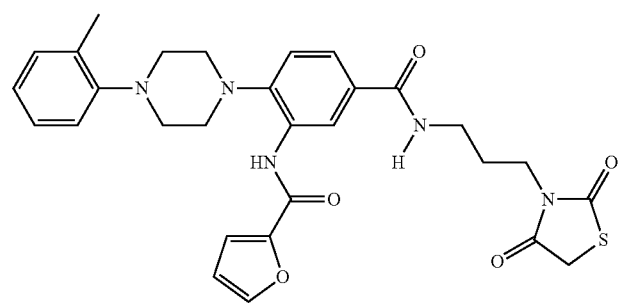 [SMILES: Cc1ccccc1N1CCN(c2ccc(C(=O)NCCCN3C(=O)CSC3=O)cc2NC(=O)c2ccco2)CC1] | ++ | ++ |
| 151 | 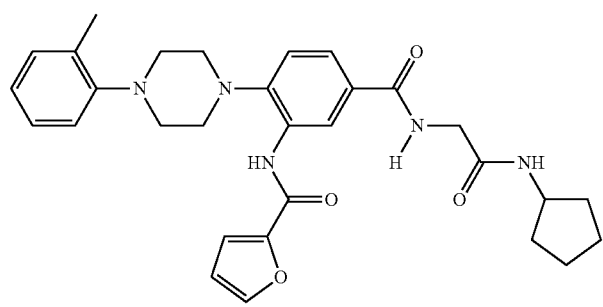 [SMILES: Cc1ccccc1N1CCN(c2ccc(C(=O)NCC(=O)NC3CCCC3)cc2NC(=O)c2ccco2)CC1] | ++ | |

TABLE 1-continued

Compounds of formulae (I), (I-A), (I-B), (I-C).
Assay A: Example 10; Assay B: Example 11.

| Structure | Assay A<br>0 > 10 μM<br>+ > 1-10 μM<br>++ 0.1-1 μM<br>+++ < 0.1 μM<br>% at 5 μM | Assay B<br>0 > 10 μM<br>+ > 1-10 μM<br>++ 0.1-1 μM<br>+++ < 0.1 μM<br>% at 5 μM |
|---|---|---|
| 152 | ++ | +++ |
| 153 | ++ | |
| 154 | + | |
| 155 | ++ | + |

TABLE 1-continued

Compounds of formulae (I), (I-A), (I-B), (I-C).
Assay A: Example 10; Assay B: Example 11.

| Structure | Assay A<br>0 > 10 μM<br>+ > 1-10 μM<br>++ 0.1-1 μM<br>+++ < 0.1 μM<br>% at 5 μM | Assay B<br>0 > 10 μM<br>+ > 1-10 μM<br>++ 0.1-1 μM<br>+++ < 0.1 μM<br>% at 5 μM |
|---|---|---|
| 156 | ++ | |
| 157 | ++ | |
| 158 | +++ | ++ |
| 159 | | |

TABLE 1-continued
Compounds of formulae (I), (I-A), (I-B), (I-C).
Assay A: Example 10; Assay B: Example 11.
| | Structure | Assay A<br>0 > 10 μM<br>+ > 1-10 μM<br>++ 0.1-1 μM<br>+++ < 0.1 μM<br>% at 5 μM | Assay B<br>0 > 10 μM<br>+ > 1-10 μM<br>++ 0.1-1 μM<br>+++ < 0.1 μM<br>% at 5 μM |
|---|---|---|---|
| 160 | 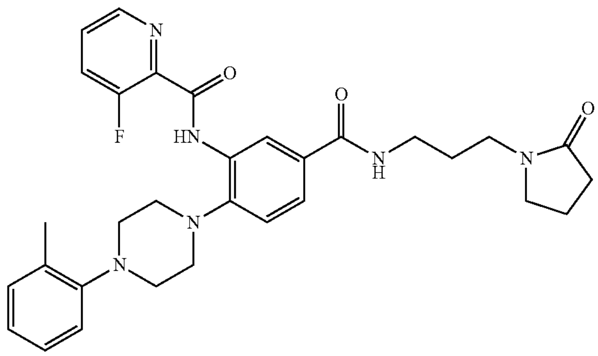 [SMILES: Cc1ccccc1N1CCN(c2ccc(C(=O)NCCCN3CCCC3=O)cc2NC(=O)c2ncccc2F)CC1] | | + |
| 161 | 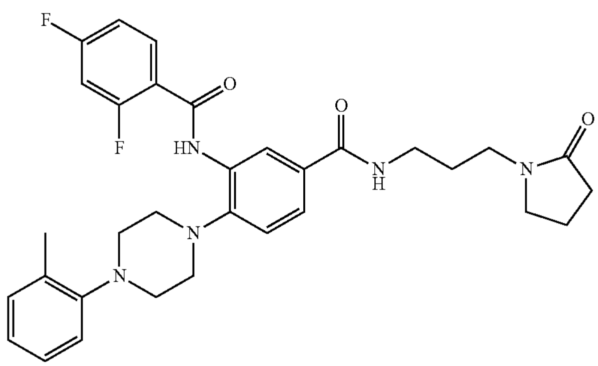 [SMILES: Cc1ccccc1N1CCN(c2ccc(C(=O)NCCCN3CCCC3=O)cc2NC(=O)c2ccc(F)cc2F)CC1] | | ++ |
| 162 | 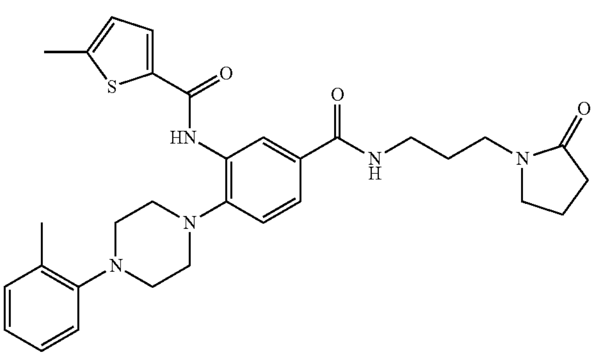 | | ++ |

TABLE 1-continued

Compounds of formulae (I), (I-A), (I-B), (I-C).
Assay A: Example 10; Assay B: Example 11.

| | Structure | Assay A<br>0 > 10 μM<br>+ > 1-10 μM<br>++ 0.1-1 μM<br>+++ < 0.1 μM<br>% at 5 μM | Assay B<br>0 > 10 μM<br>+ > 1-10 μM<br>++ 0.1-1 μM<br>+++ < 0.1 μM<br>% at 5 μM |
|---|---|---|---|
| 163 | 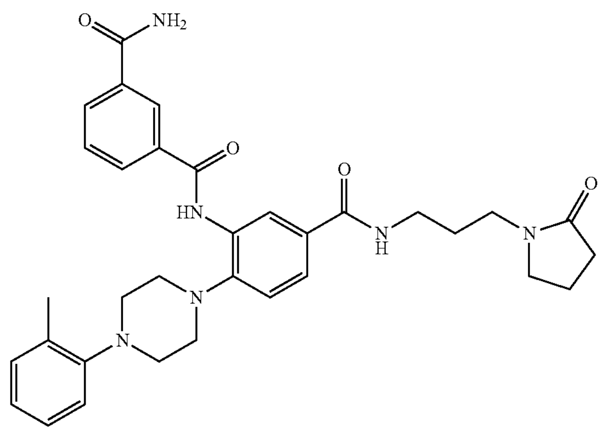 [SMILES: Cc1ccccc1N1CCN(c2ccc(C(=O)NCCCN3CCCC3=O)cc2NC(=O)c2cccc(C(N)=O)c2)CC1] | | 8% |
| 164 | 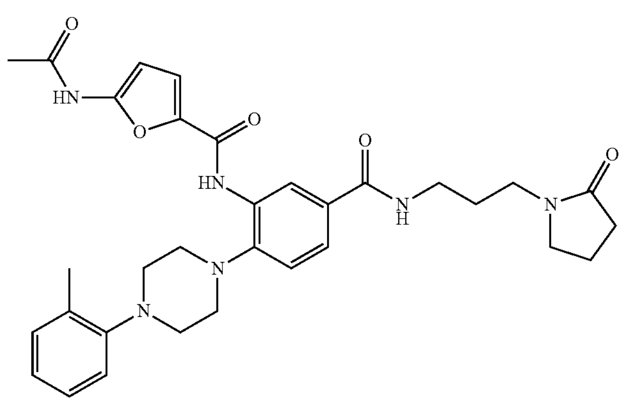 [SMILES: CC(=O)Nc1ccc(C(=O)Nc2cc(C(=O)NCCCN3CCCC3=O)ccc2N2CCN(c3ccccc3C)CC2)o1] | | + |
| 165 | 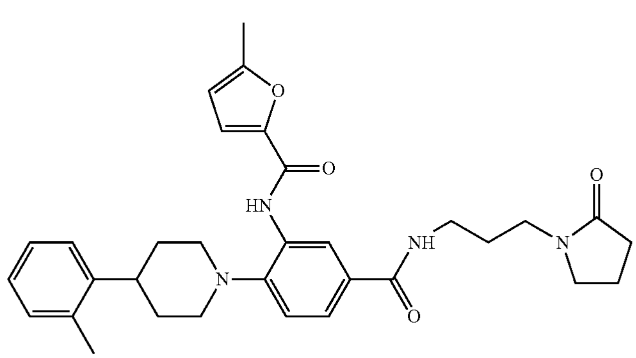 [SMILES: Cc1ccc(C(=O)Nc2cc(C(=O)NCCCN3CCCC3=O)ccc2N2CCC(c3ccccc3C)CC2)o1] | | 0 |

TABLE 1-continued

Compounds of formulae (I), (I-A), (I-B), (I-C).
Assay A: Example 10; Assay B: Example 11.

| | Structure | Assay A<br>0 > 10 μM<br>+ > 1-10 μM<br>++ 0.1-1 μM<br>+++ < 0.1 μM<br>% at 5 μM | Assay B<br>0 > 10 μM<br>+ > 1-10 μM<br>++ 0.1-1 μM<br>+++ < 0.1 μM<br>% at 5 μM |
|---|---|---|---|
| 166 | 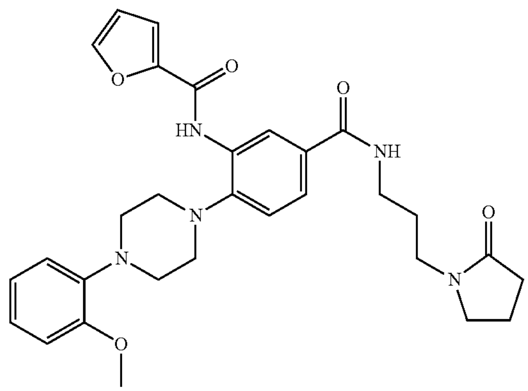 [SMILES: COc1ccccc1N1CCN(c2ccc(C(=O)NCCCN3CCCC3=O)cc2NC(=O)c2ccco2)CC1] | | 20% |
| 167 | 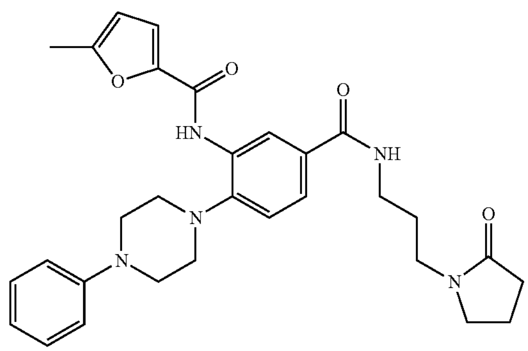 [SMILES: Cc1ccc(C(=O)Nc2cc(C(=O)NCCCN3CCCC3=O)ccc2N2CCN(c3ccccc3)CC2)o1] | | + |
| 168 | 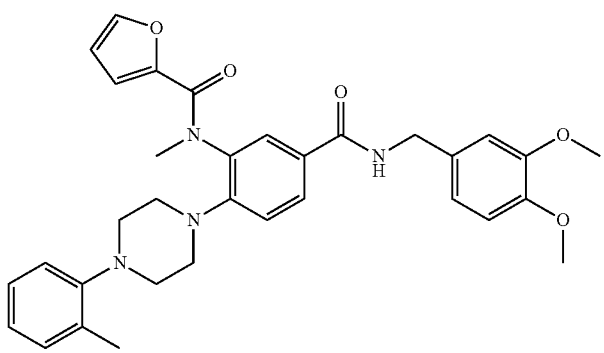 [SMILES: COc1ccc(CNC(=O)c2ccc(N3CCN(c4ccccc4C)CC3)c(N(C)C(=O)c3ccco3)c2)cc1OC] | | |
| 169 | 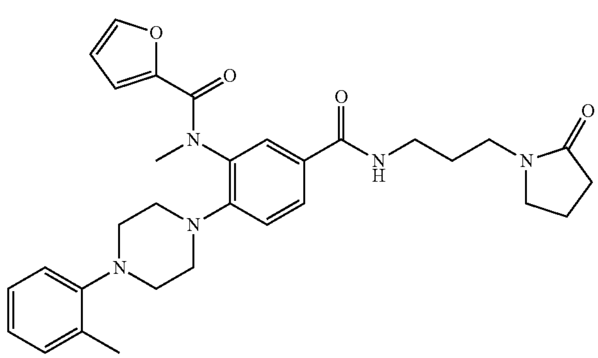 [SMILES: Cc1ccccc1N1CCN(c2ccc(C(=O)NCCCN3CCCC3=O)cc2N(C)C(=O)c2ccco2)CC1] | | + |

TABLE 1-continued

Compounds of formulae (I), (I-A), (I-B), (I-C).
Assay A: Example 10; Assay B: Example 11.

| Structure | Assay A<br>0 > 10 μM<br>+ > 1-10 μM<br>++ 0.1-1 μM<br>+++ < 0.1 μM<br>% at 5 μM | Assay B<br>0 > 10 μM<br>+ > 1-10 μM<br>++ 0.1-1 μM<br>+++ < 0.1 μM<br>% at 5 μM |
| --- | --- | --- |
| 170 | 32% | |
| 171 | + | |
| 172 | + | |
| 173 | + | |
| 174 | + | |

TABLE 1-continued

Compounds of formulae (I), (I-A), (I-B), (I-C).
Assay A: Example 10; Assay B: Example 11.

| Structure | Assay A<br>0 > 10 μM<br>+ > 1-10 μM<br>++ 0.1-1 μM<br>+++ < 0.1 μM<br>% at 5 μM | Assay B<br>0 > 10 μM<br>+ > 1-10 μM<br>++ 0.1-1 μM<br>+++ < 0.1 μM<br>% at 5 μM |
|---|---|---|
| 175 | + | |
| 176 | ++ | + |
| 177 | + | |
| 178 | + | |

TABLE 1-continued
Compounds of formulae (I), (I-A), (I-B), (I-C).
Assay A: Example 10; Assay B: Example 11.
| Structure | Assay A<br>0 > 10 μM<br>+ > 1-10 μM<br>++ 0.1-1 μM<br>+++ < 0.1 μM<br>% at 5 μM | Assay B<br>0 > 10 μM<br>+ > 1-10 μM<br>++ 0.1-1 μM<br>+++ < 0.1 μM<br>% at 5 μM |
|---|---|---|
| 179 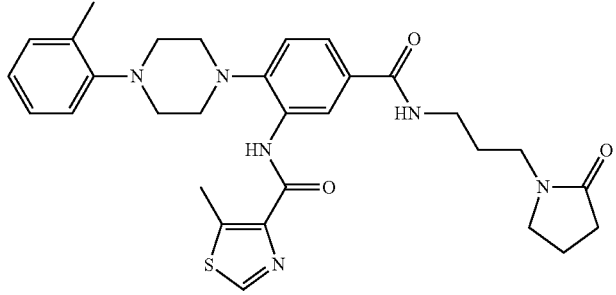 [SMILES: Cc1ccccc1N1CCN(c2ccc(C(=O)NCCCN3CCCC3=O)cc2NC(=O)c2ncsc2C)CC1] | | ++ |
| 180 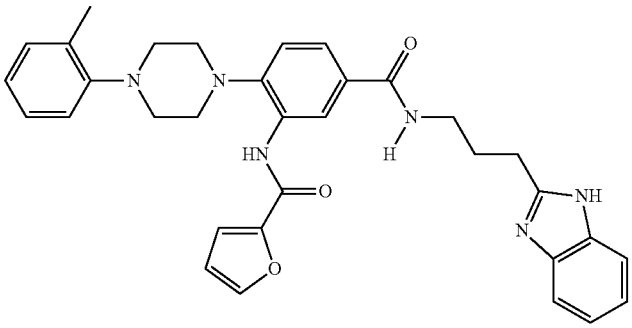 [SMILES: Cc1ccccc1N1CCN(c2ccc(C(=O)NCCCc3nc4ccccc4[nH]3)cc2NC(=O)c2ccco2)CC1] | | |
| 181 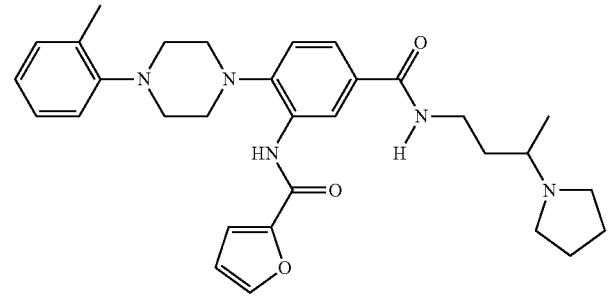 | | + |
| 182 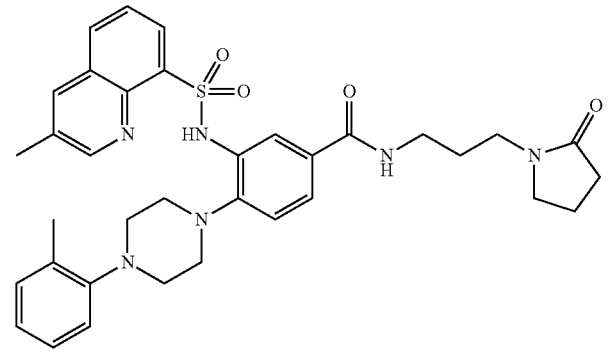 [SMILES: Cc1cnc2c(S(=O)(=O)Nc3cc(C(=O)NCCCN4CCCC4=O)ccc3N3CCN(c4ccccc4C)CC3)cccc2c1] | | |

TABLE 1-continued

Compounds of formulae (I), (I-A), (I-B), (I-C).
Assay A: Example 10; Assay B: Example 11.

| Structure | Assay A<br>0 > 10 μM<br>+ > 1-10 μM<br>++ 0.1-1 μM<br>+++ < 0.1 μM<br>% at 5 μM | Assay B<br>0 > 10 μM<br>+ > 1-10 μM<br>++ 0.1-1 μM<br>+++ < 0.1 μM<br>% at 5 μM |
|---|---|---|
| 183 | | |
| 184 | | |
| 185 | + | |
| 186 | + | |

TABLE 1-continued
Compounds of formulae (I), (I-A), (I-B), (I-C).
Assay A: Example 10; Assay B: Example 11.
| Structure | Assay A<br>0 > 10 μM<br>+ > 1-10 μM<br>++ 0.1-1 μM<br>+++ < 0.1 μM<br>% at 5 μM | Assay B<br>0 > 10 μM<br>+ > 1-10 μM<br>++ 0.1-1 μM<br>+++ < 0.1 μM<br>% at 5 μM |
|---|---|---|
| 187 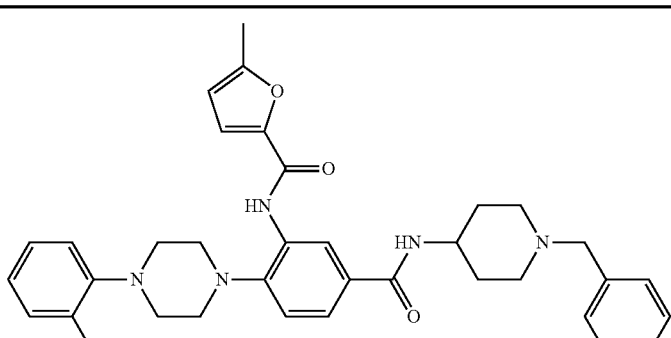 | | |
| 188 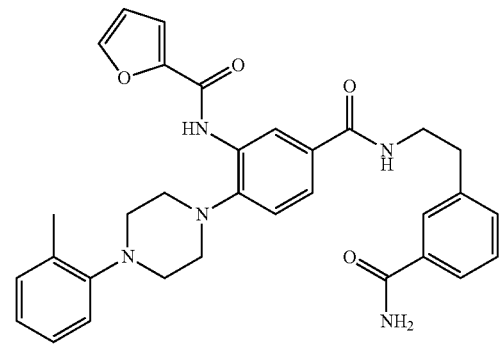 [SMILES: Cc1ccccc1N1CCN(c2ccc(C(=O)NCCc3cccc(C(N)=O)c3)cc2NC(=O)c2ccco2)CC1] | ++ | ++ |
| 189 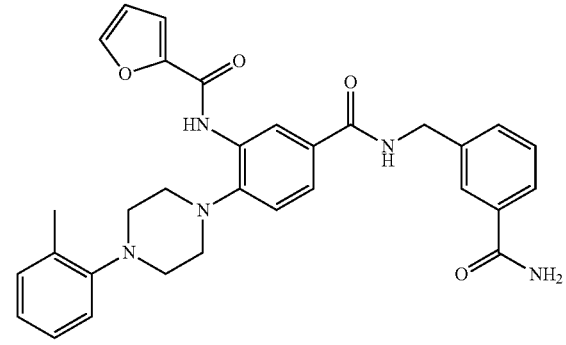 [SMILES: Cc1ccccc1N1CCN(c2ccc(C(=O)NCc3cccc(C(N)=O)c3)cc2NC(=O)c2ccco2)CC1] | +++ | ++ |
| 190 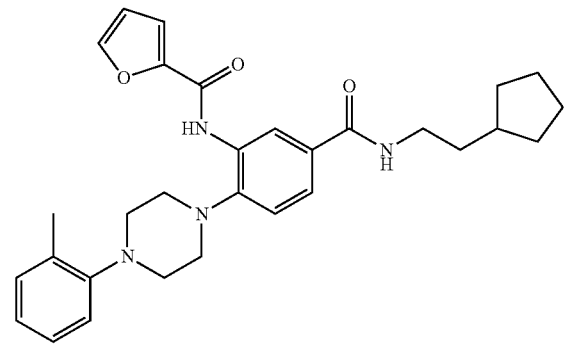 [SMILES: Cc1ccccc1N1CCN(c2ccc(C(=O)NCCC3CCCC3)cc2NC(=O)c2ccco2)CC1] | ++ | |

TABLE 1-continued

Compounds of formulae (I), (I-A), (I-B), (I-C).
Assay A: Example 10; Assay B: Example 11.

| Structure | Assay A<br>0 > 10 μM<br>+ > 1-10 μM<br>++ 0.1-1 μM<br>+++ < 0.1 μM<br>% at 5 μM | Assay B<br>0 > 10 μM<br>+ > 1-10 μM<br>++ 0.1-1 μM<br>+++ < 0.1 μM<br>% at 5 μM |
|---|---|---|
| 191 | ++ | |
| 192 | ++ | |
| 193 | + | |
| 194 | + | |

TABLE 1-continued

Compounds of formulae (I), (I-A), (I-B), (I-C).
Assay A: Example 10; Assay B: Example 11.

| | Assay A<br>0 > 10 μM<br>+ > 1-10 μM<br>++ 0.1-1 μM<br>+++ < 0.1 μM | Assay B<br>0 > 10 μM<br>+ > 1-10 μM<br>++ 0.1-1 μM<br>+++ < 0.1 μM |
|---|---|---|
| Structure | % at 5 μM | % at 5 μM |

195

| | + |

196

| | 22% |

197

| | + |

198

| | ++ |

TABLE 1-continued

Compounds of formulae (I), (I-A), (I-B), (I-C).
Assay A: Example 10; Assay B: Example 11.

| Structure | Assay A<br>0 > 10 μM<br>+ > 1-10 μM<br>++ 0.1-1 μM<br>+++ < 0.1 μM<br>% at 5 μM | Assay B<br>0 > 10 μM<br>+ > 1-10 μM<br>++ 0.1-1 μM<br>+++ < 0.1 μM<br>% at 5 μM |
|---|---|---|
| 199 | | |
| 200 | | + |
| 201 | | 0 |
| 202 | | + |

TABLE 1-continued

Compounds of formulae (I), (I-A), (I-B), (I-C).
Assay A: Example 10; Assay B: Example 11.

| Structure | Assay A<br>0 > 10 μM<br>+ > 1-10 μM<br>++ 0.1-1 μM<br>+++ < 0.1 μM<br>% at 5 μM | Assay B<br>0 > 10 μM<br>+ > 1-10 μM<br>++ 0.1-1 μM<br>+++ < 0.1 μM<br>% at 5 μM |
|---|---|---|
| 203 | ++ | ++ |
| 204 | | |
| 205 | | ++ |
| 206 | | |

TABLE 1-continued

Compounds of formulae (I), (I-A), (I-B), (I-C).
Assay A: Example 10; Assay B: Example 11.

| Structure | Assay A<br>0 > 10 μM<br>+ > 1-10 μM<br>++ 0.1-1 μM<br>+++ < 0.1 μM<br>% at 5 μM | Assay B<br>0 > 10 μM<br>+ > 1-10 μM<br>++ 0.1-1 μM<br>+++ < 0.1 μM<br>% at 5 μM |
| --- | --- | --- |
| 207 | ++ | ++ |
| 208 | | + |
| 209 | | |
| 210 | | + |

US 9,938,262 B2
TABLE 1-continued
Compounds of formulae (I), (I-A), (I-B), (I-C).
Assay A: Example 10; Assay B: Example 11.
| Structure | Assay A<br>0 > 10 μM<br>+ > 1-10 μM<br>++ 0.1-1 μM<br>+++ < 0.1 μM<br>% at 5 μM | Assay B<br>0 > 10 μM<br>+ > 1-10 μM<br>++ 0.1-1 μM<br>+++ < 0.1 μM<br>% at 5 μM |
|---|---|---|
| 211 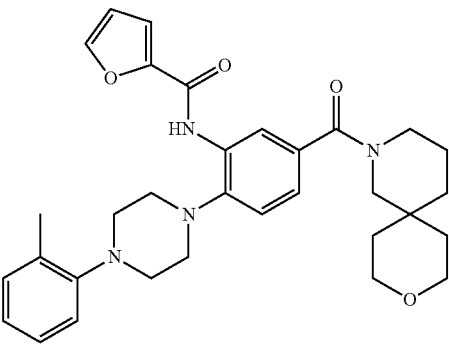 [SMILES: Cc1ccccc1N1CCN(c2ccc(C(=O)N3CCCC4(CCOCC4)C3)cc2NC(=O)c2ccco2)CC1] | | |
| 212 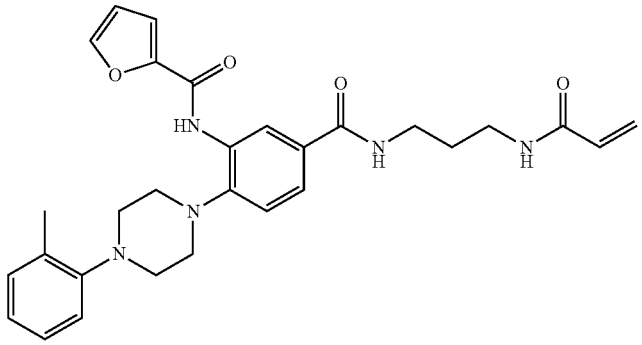 [SMILES: C=CC(=O)NCCCNC(=O)c1ccc(N2CCN(c3ccccc3C)CC2)c(NC(=O)c2ccco2)c1] | | ++ |
| 213 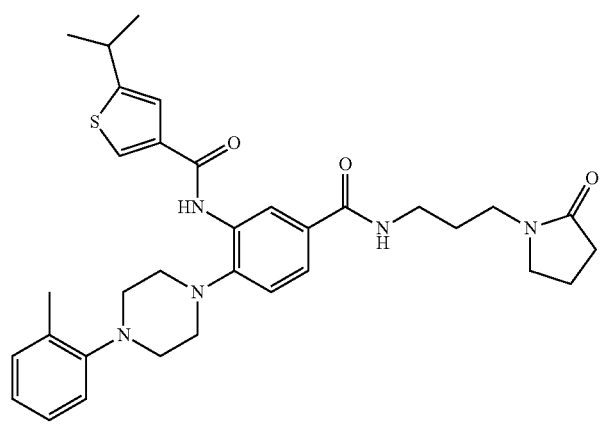 [SMILES: Cc1ccccc1N1CCN(c2ccc(C(=O)NCCCN3CCCC3=O)cc2NC(=O)c2csc(C(C)C)c2)CC1] | | 0 |

TABLE 1-continued

Compounds of formulae (I), (I-A), (I-B), (I-C).
Assay A: Example 10; Assay B: Example 11.

| Structure | Assay A<br>0 > 10 μM<br>+ > 1-10 μM<br>++ 0.1-1 μM<br>+++ < 0.1 μM<br>% at 5 μM | Assay B<br>0 > 10 μM<br>+ > 1-10 μM<br>++ 0.1-1 μM<br>+++ < 0.1 μM<br>% at 5 μM |
|---|---|---|
| 214 | + | |
| 215 | | |
| 216 | | 0 |
| 217 | | |

TABLE 1-continued
Compounds of formulae (I), (I-A), (I-B), (I-C).
Assay A: Example 10; Assay B: Example 11.
| Structure | Assay A<br>0 > 10 μM<br>+ > 1-10 μM<br>++ 0.1-1 μM<br>+++ < 0.1 μM<br>% at 5 μM | Assay B<br>0 > 10 μM<br>+ > 1-10 μM<br>++ 0.1-1 μM<br>+++ < 0.1 μM<br>% at 5 μM |
|---|---|---|
| 218 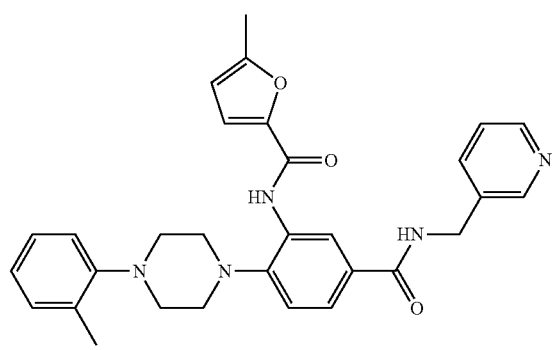 [SMILES: Cc1ccc(C(=O)Nc2cc(C(=O)NCc3cccnc3)ccc2N2CCN(c3ccccc3C)CC2)o1] | | ++ |
| 219 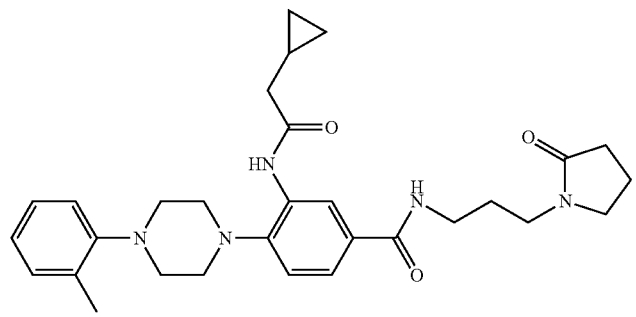 [SMILES: Cc1ccccc1N1CCN(c2ccc(C(=O)NCCCN3CCCC3=O)cc2NC(=O)CC2CC2)CC1] | | + |
| 220 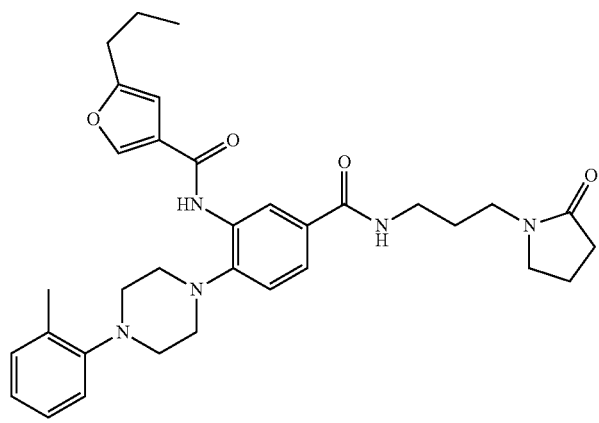 [SMILES: CCCc1cc(C(=O)Nc2cc(C(=O)NCCCN3CCCC3=O)ccc2N2CCN(c3ccccc3C)CC2)co1] | | + |

TABLE 1-continued
Compounds of formulae (I), (I-A), (I-B), (I-C).
Assay A: Example 10; Assay B: Example 11.
| Structure | Assay A<br>0 > 10 μM<br>+ > 1-10 μM<br>++ 0.1-1 μM<br>+++ < 0.1 μM<br>% at 5 μM | Assay B<br>0 > 10 μM<br>+ > 1-10 μM<br>++ 0.1-1 μM<br>+++ < 0.1 μM<br>% at 5 μM |
|---|---|---|
| 221 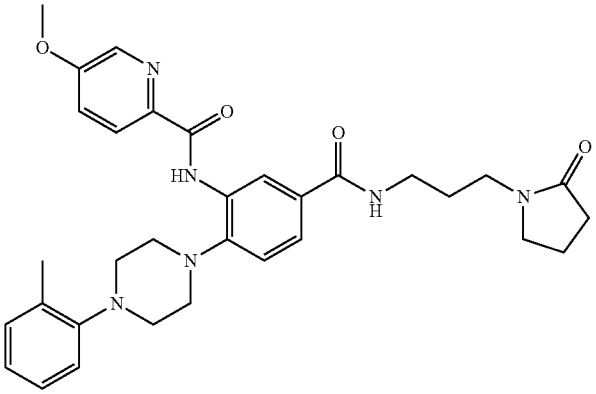 [SMILES: COc1ccc(C(=O)Nc2cc(C(=O)NCCCN3CCCC3=O)ccc2N2CCN(c3ccccc3C)CC2)nc1] | ++ | |
| 222 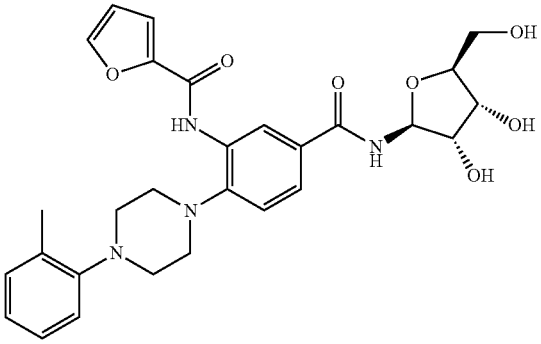 [SMILES: Cc1ccccc1N1CCN(c2ccc(C(=O)N[C@H]3O[C@@H](CO)[C@H](O)[C@@H]3O)cc2NC(=O)c2ccco2)CC1] | ++ | |
| 223 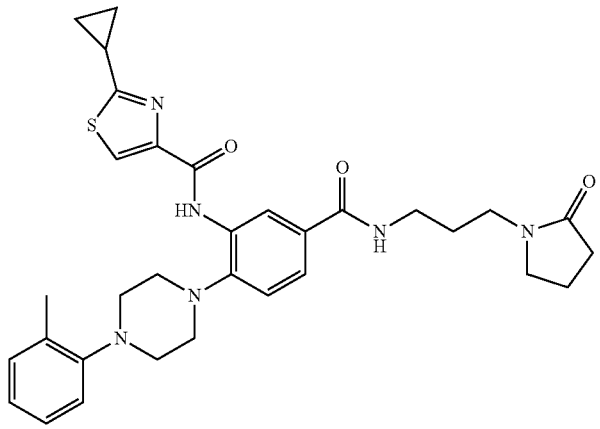 [SMILES: Cc1ccccc1N1CCN(c2ccc(C(=O)NCCCN3CCCC3=O)cc2NC(=O)c2csc(C3CC3)n2)CC1] | ++ | |

TABLE 1-continued

Compounds of formulae (I), (I-A), (I-B), (I-C).
Assay A: Example 10; Assay B: Example 11.

| Structure | Assay A<br>0 > 10 μM<br>+ > 1-10 μM<br>++ 0.1-1 μM<br>+++ < 0.1 μM<br>% at 5 μM | Assay B<br>0 > 10 μM<br>+ > 1-10 μM<br>++ 0.1-1 μM<br>+++ < 0.1 μM<br>% at 5 μM |
|---|---|---|
| 224 | 10% | + |
| 225 | | ++ |
| 226 | | |

TABLE 1-continued

Compounds of formulae (I), (I-A), (I-B), (I-C).
Assay A: Example 10; Assay B: Example 11.

| Structure | Assay A<br>0 > 10 μM<br>+ > 1-10 μM<br>++ 0.1-1 μM<br>+++ < 0.1 μM<br>% at 5 μM | Assay B<br>0 > 10 μM<br>+ > 1-10 μM<br>++ 0.1-1 μM<br>+++ < 0.1 μM<br>% at 5 μM |
|---|---|---|
| 227 | | |
| 228 | | |
| 229 | | 41% |
| 230 | | |

TABLE 1-continued
Compounds of formulae (I), (I-A), (I-B), (I-C).
Assay A: Example 10; Assay B: Example 11.
| Structure | Assay A<br>0 > 10 μM<br>+ > 1-10 μM<br>++ 0.1-1 μM<br>+++ < 0.1 μM<br>% at 5 μM | Assay B<br>0 > 10 μM<br>+ > 1-10 μM<br>++ 0.1-1 μM<br>+++ < 0.1 μM<br>% at 5 μM |
|---|---|---|
| 231 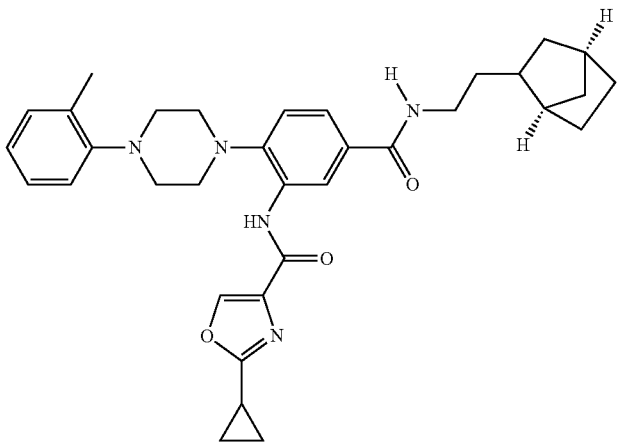 [SMILES: Cc1ccccc1N1CCN(c2ccc(C(=O)NCCC3C[C@H]4CC[C@@H]3C4)cc2NC(=O)c2coc(C3CC3)n2)CC1] | | ++ |
| 232 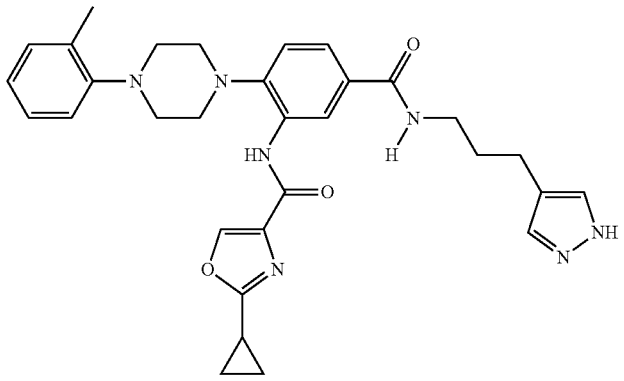 [SMILES: Cc1ccccc1N1CCN(c2ccc(C(=O)NCCCc3cn[nH]c3)cc2NC(=O)c2coc(C3CC3)n2)CC1] | | ++ |
| 233 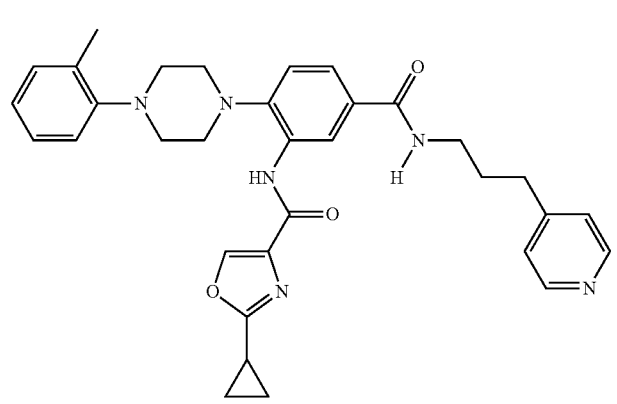 [SMILES: Cc1ccccc1N1CCN(c2ccc(C(=O)NCCCc3ccncc3)cc2NC(=O)c2coc(C3CC3)n2)CC1] | | ++ |

TABLE 1-continued

Compounds of formulae (I), (I-A), (I-B), (I-C).
Assay A: Example 10; Assay B: Example 11.

| Structure | Assay A<br>0 > 10 μM<br>+ > 1-10 μM<br>++ 0.1-1 μM<br>+++ < 0.1 μM<br>% at 5 μM | Assay B<br>0 > 10 μM<br>+ > 1-10 μM<br>++ 0.1-1 μM<br>+++ < 0.1 μM<br>% at 5 μM |
|---|---|---|
| 234 | | + |
| 235 | | + |
| 236 | | ++ |

TABLE 1-continued

Compounds of formulae (I), (I-A), (I-B), (I-C).
Assay A: Example 10; Assay B: Example 11.

| Structure | Assay A<br>0 > 10 μM<br>+ > 1-10 μM<br>++ 0.1-1 μM<br>+++ < 0.1 μM<br>% at 5 μM | Assay B<br>0 > 10 μM<br>+ > 1-10 μM<br>++ 0.1-1 μM<br>+++ < 0.1 μM<br>% at 5 μM |
|---|---|---|
| 237 | ++ | |
| 238 | ++ | |
| 239 | 43% | |

TABLE 1-continued

Compounds of formulae (I), (I-A), (I-B), (I-C).
Assay A: Example 10; Assay B: Example 11.

| Structure | Assay A<br>0 > 10 μM<br>+ > 1-10 μM<br>++ 0.1-1 μM<br>+++ < 0.1 μM<br>% at 5 μM | Assay B<br>0 > 10 μM<br>+ > 1-10 μM<br>++ 0.1-1 μM<br>+++ < 0.1 μM<br>% at 5 μM |
|---|---|---|
| 240 | ++ | |
| 241 | ++ | 177% |
| 242 | + | |
| 243 | + | |

TABLE 1-continued
Compounds of formulae (I), (I-A), (I-B), (I-C).
Assay A: Example 10; Assay B: Example 11.
| Structure | Assay A<br>0 > 10 μM<br>+ > 1-10 μM<br>++ 0.1-1 μM<br>+++ < 0.1 μM<br>% at 5 μM | Assay B<br>0 > 10 μM<br>+ > 1-10 μM<br>++ 0.1-1 μM<br>+++ < 0.1 μM<br>% at 5 μM |
|---|---|---|
| 244 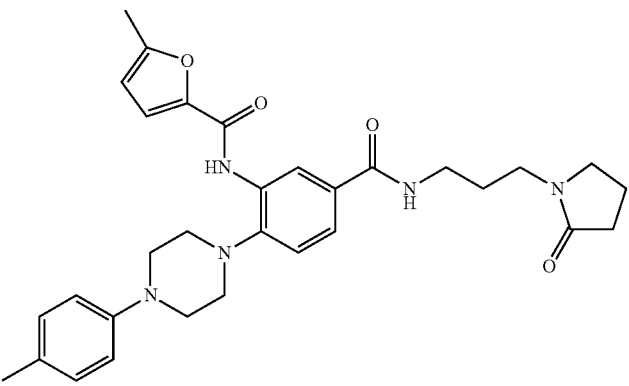 [SMILES: Cc1ccc(N2CCN(c3ccc(C(=O)NCCCN4CCCC4=O)cc3NC(=O)c3ccc(C)o3)CC2)cc1] | | |
| 245 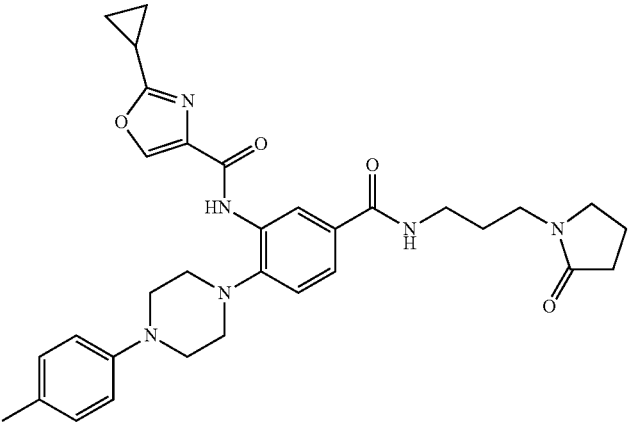 | | 12% |
| 246 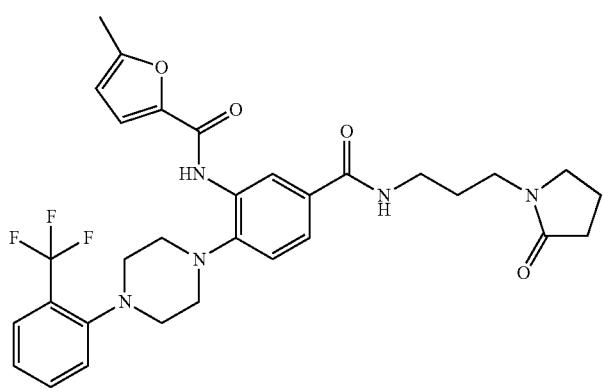 [SMILES: Cc1ccc(C(=O)Nc2cc(C(=O)NCCCN3CCCC3=O)ccc2N2CCN(c3ccccc3C(F)(F)F)CC2)o1] | + | + |

TABLE 1-continued

Compounds of formulae (I), (I-A), (I-B), (I-C).
Assay A: Example 10; Assay B: Example 11.

| Structure | Assay A<br>0 > 10 μM<br>+ > 1-10 μM<br>++ 0.1-1 μM<br>+++ < 0.1 μM<br>% at 5 μM | Assay B<br>0 > 10 μM<br>+ > 1-10 μM<br>++ 0.1-1 μM<br>+++ < 0.1 μM<br>% at 5 μM |
|---|---|---|
| 247 | | +++ |
| 248 | | +++ |
| 249 | | + |

TABLE 1-continued

Compounds of formulae (I), (I-A), (I-B), (I-C).
Assay A: Example 10; Assay B: Example 11.

| Structure | Assay A<br>0 > 10 μM<br>+ > 1-10 μM<br>++ 0.1-1 μM<br>+++ < 0.1 μM<br>% at 5 μM | Assay B<br>0 > 10 μM<br>+ > 1-10 μM<br>++ 0.1-1 μM<br>+++ < 0.1 μM<br>% at 5 μM |
|---|---|---|
| 250 | | + |
| 251 | | |
| 252 | | 14% | ns

TABLE 1-continued

Compounds of formulae (I), (I-A), (I-B), (I-C).
Assay A: Example 10; Assay B: Example 11.

| Structure | Assay A<br>0 > 10 μM<br>+ > 1-10 μM<br>++ 0.1-1 μM<br>+++ < 0.1 μM<br>% at 5 μM | Assay B<br>0 > 10 μM<br>+ > 1-10 μM<br>++ 0.1-1 μM<br>+++ < 0.1 μM<br>% at 5 μM |
|---|---|---|
| 253 | 24% | |
| 254 | 20% | |
| 255 | 22% | |

TABLE 1-continued
Compounds of formulae (I), (I-A), (I-B), (I-C).
Assay A: Example 10; Assay B: Example 11.
| Structure | Assay A<br>0 > 10 μM<br>+ > 1-10 μM<br>++ 0.1-1 μM<br>+++ < 0.1 μM<br>% at 5 μM | Assay B<br>0 > 10 μM<br>+ > 1-10 μM<br>++ 0.1-1 μM<br>+++ < 0.1 μM<br>% at 5 μM |
|---|---|---|
| 256 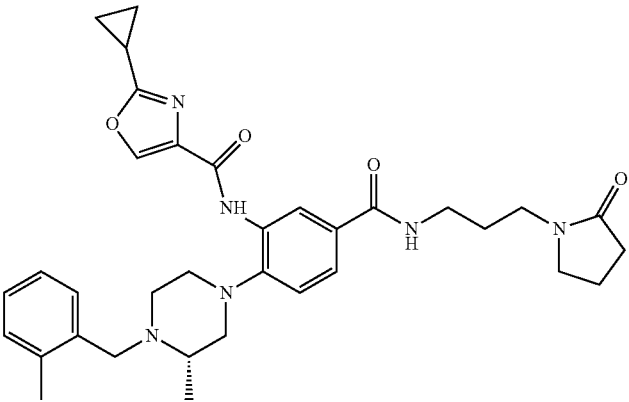 [SMILES: Cc1ccccc1CN1CCN(c2ccc(C(=O)NCCCN3CCCC3=O)cc2NC(=O)c2coc(C3CC3)n2)C[C@@H]1C] | | 26% |
| 257 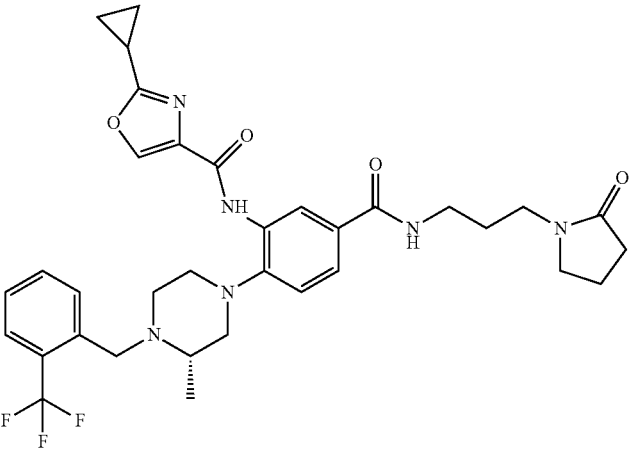 [SMILES: C[C@H]1CN(c2ccc(C(=O)NCCCN3CCCC3=O)cc2NC(=O)c2coc(C3CC3)n2)CCN1Cc1ccccc1C(F)(F)F] | | 21% |
| 258 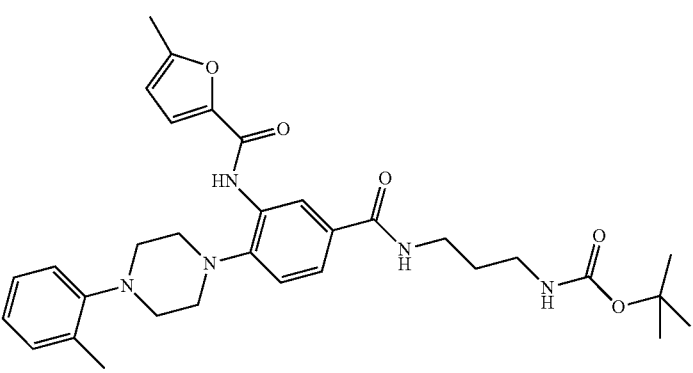 [SMILES: Cc1ccc(C(=O)Nc2cc(C(=O)NCCCNC(=O)OC(C)(C)C)ccc2N2CCN(c3ccccc3C)CC2)o1] | | + |

TABLE 1-continued

Compounds of formulae (I), (I-A), (I-B), (I-C).
Assay A: Example 10; Assay B: Example 11.

| | Structure | Assay A<br>0 > 10 μM<br>+ > 1-10 μM<br>++ 0.1-1 μM<br>+++ < 0.1 μM<br>% at 5 μM | Assay B<br>0 > 10 μM<br>+ > 1-10 μM<br>++ 0.1-1 μM<br>+++ < 0.1 μM<br>% at 5 μM |
|---|---|---|---|
| 259 | 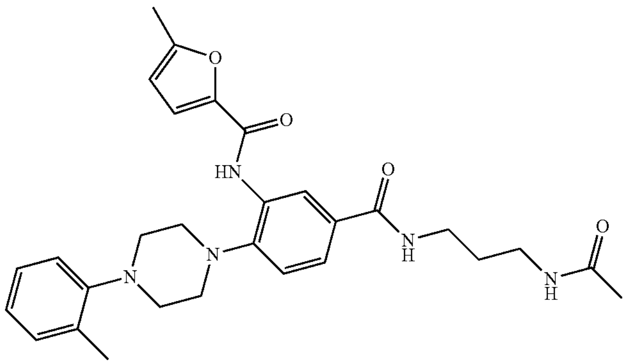 [SMILES: CC(=O)NCCCNC(=O)c1ccc(N2CCN(c3ccccc3C)CC2)c(NC(=O)c2ccc(C)o2)c1] | | ++ |
| 260 | 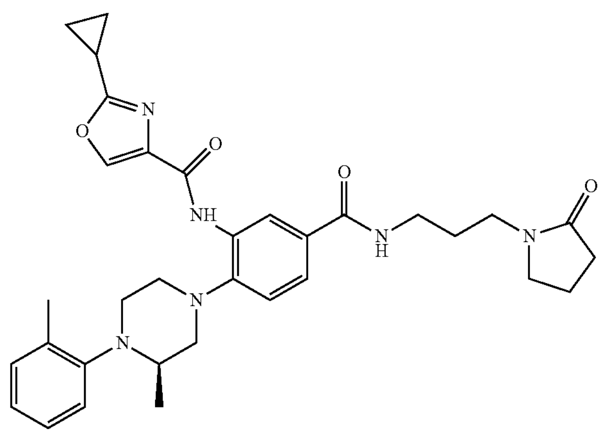 [SMILES: Cc1ccccc1N1CCN(c2ccc(C(=O)NCCCN3CCCC3=O)cc2NC(=O)c2coc(C3CC3)n2)C[C@H]1C] | | |
| 261 | 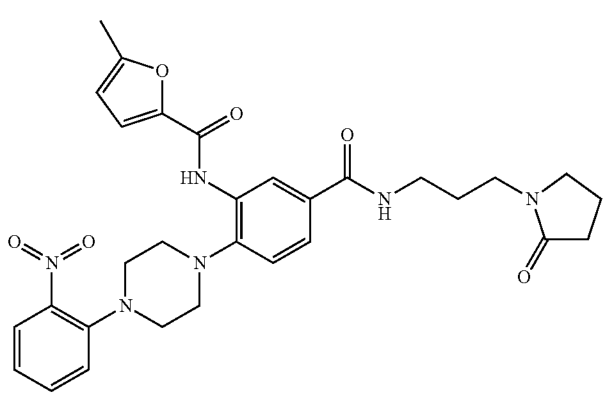 [SMILES: Cc1ccc(C(=O)Nc2cc(C(=O)NCCCN3CCCC3=O)ccc2N2CCN(c3ccccc3[N+](=O)[O-])CC2)o1] | | + |

TABLE 1-continued
Compounds of formulae (I), (I-A), (I-B), (I-C).
Assay A: Example 10; Assay B: Example 11.
| | Structure | Assay A<br>0 > 10 μM<br>+ > 1-10 μM<br>++ 0.1-1 μM<br>+++ < 0.1 μM<br>% at 5 μM | Assay B<br>0 > 10 μM<br>+ > 1-10 μM<br>++ 0.1-1 μM<br>+++ < 0.1 μM<br>% at 5 μM |
|---|---|---|---|
| 262 | 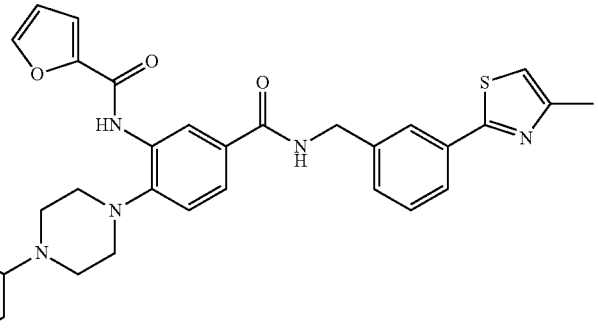 | | ++ |
| 263 | 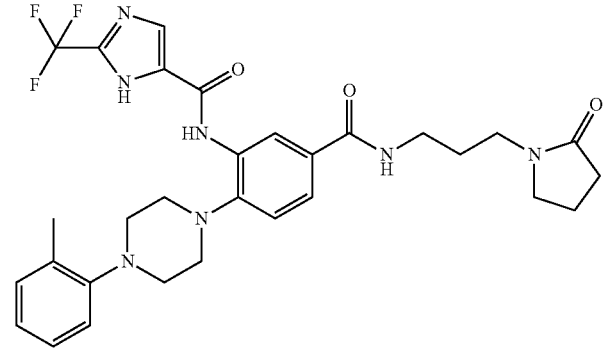 [SMILES: Cc1ccccc1N1CCN(c2ccc(C(=O)NCCCN3CCCC3=O)cc2NC(=O)c2cnc(C(F)(F)F)[nH]2)CC1] | | |
| 264 | 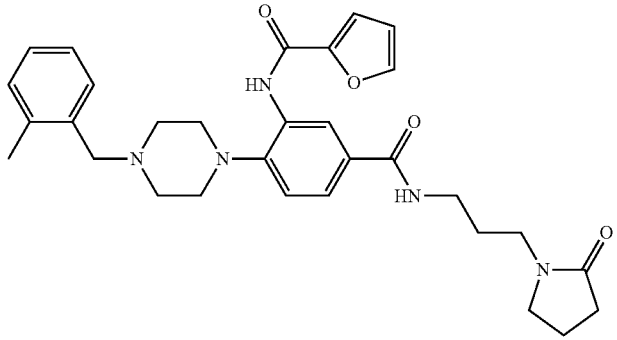 [SMILES: Cc1ccccc1CN1CCN(c2ccc(C(=O)NCCCN3CCCC3=O)cc2NC(=O)c2ccco2)CC1] | | |
| 265 | 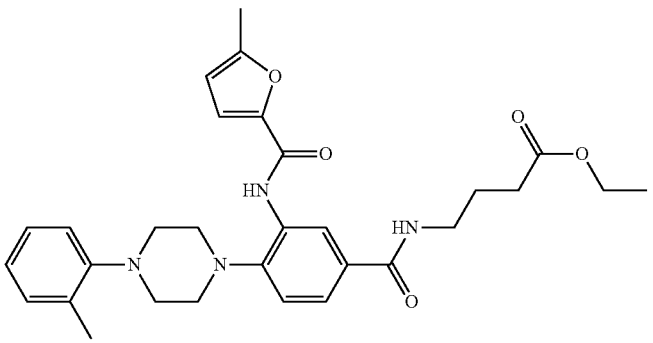 [SMILES: CCOC(=O)CCCNC(=O)c1ccc(N2CCN(c3ccccc3C)CC2)c(NC(=O)c2ccc(C)o2)c1] | | |

TABLE 2
Further compounds of formulae (I), (I-A), (I-B), (I-C).
Assay A: Example 10; Assay B: Example 11.
| Structure | Assay A<br>0 > 10 µM<br>+ > 1-10 µM<br>++ 0.1-1 µM<br>+++ < 0.1 µM<br>% at 5 µM | Assay B<br>0 > 10 µM<br>+ > 1-10 µM<br>++ 0.1-1 µM<br>+++ < 0.1 µM<br>% at 1.25 µM |
|---|---|---|
| 266 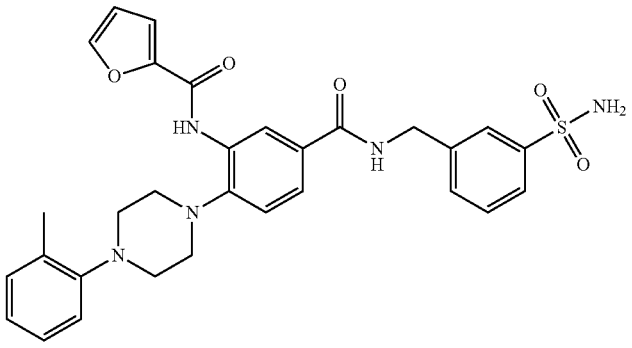 [SMILES: Cc1ccccc1N1CCN(c2ccc(C(=O)NCc3cccc(S(N)(=O)=O)c3)cc2NC(=O)c2ccco2)CC1] | | +++ |
| 267 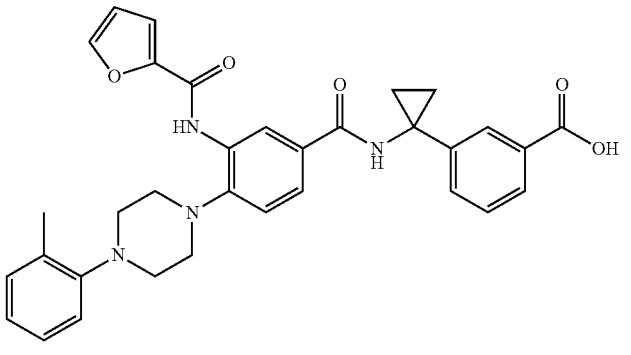 [SMILES: Cc1ccccc1N1CCN(c2ccc(C(=O)NC3(c4cccc(C(=O)O)c4)CC3)cc2NC(=O)c2ccco2)CC1] | | + |
| 268 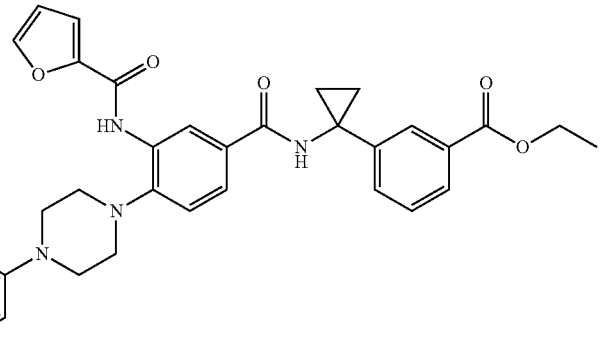 | | |
| 269 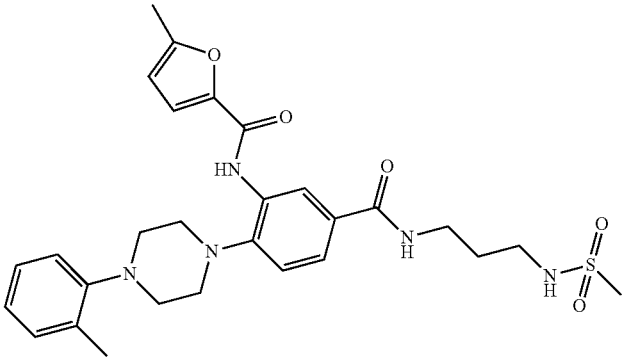 [SMILES: Cc1ccc(C(=O)Nc2cc(C(=O)NCCCNS(C)(=O)=O)ccc2N2CCN(c3ccccc3C)CC2)o1] | | |

TABLE 2-continued

Further compounds of formulae (I), (I-A), (I-B), (I-C).
Assay A: Example 10; Assay B: Example 11.

| Structure | Assay A<br>0 > 10 µM<br>+ > 1-10 µM<br>++ 0.1-1 µM<br>+++ < 0.1 µM<br>% at 5 µM | Assay B<br>0 > 10 µM<br>+ > 1-10 µM<br>++ 0.1-1 µM<br>+++ < 0.1 µM<br>% at 1.25 µM |
|---|---|---|
| 270 | | ++ |
| 271 | | ++ |
| 272 | | 30% |

TABLE 2-continued
Further compounds of formulae (I), (I-A), (I-B), (I-C).
Assay A: Example 10; Assay B: Example 11.
| Structure | Assay A<br>0 > 10 μM<br>+ > 1-10 μM<br>++ 0.1-1 μM<br>+++ < 0.1 μM<br>% at 5 μM | Assay B<br>0 > 10 μM<br>+ > 1-10 μM<br>++ 0.1-1 μM<br>+++ < 0.1 μM<br>% at 1.25 μM |
|---|---|---|
| 273 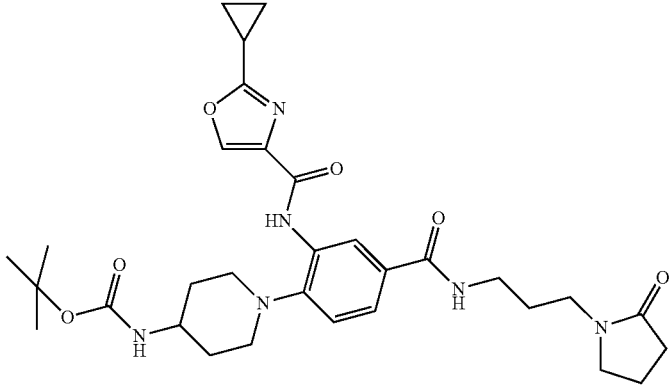 [SMILES: CC(C)(C)OC(=O)NC1CCN(c2ccc(C(=O)NCCCN3CCCC3=O)cc2NC(=O)c2coc(C3CC3)n2)CC1] | | + |
| 274 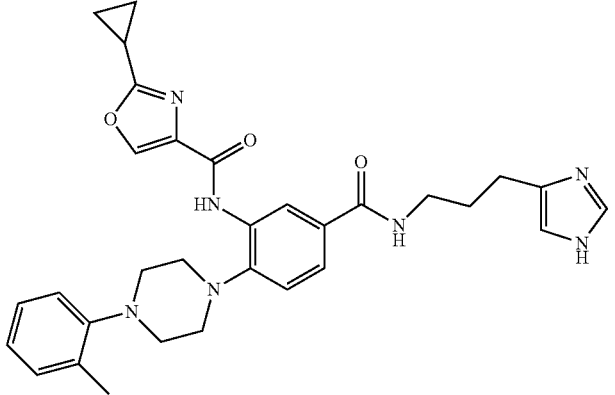 [SMILES: Cc1ccccc1N1CCN(c2ccc(C(=O)NCCCc3c[nH]cn3)cc2NC(=O)c2coc(C3CC3)n2)CC1] | | ++ |
| 275 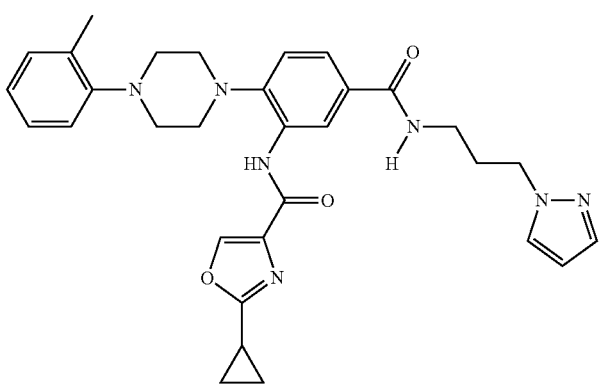 [SMILES: Cc1ccccc1N1CCN(c2ccc(C(=O)NCCCn3cccn3)cc2NC(=O)c2coc(C3CC3)n2)CC1] | | ++ |

TABLE 2-continued
Further compounds of formulae (I), (I-A), (I-B), (I-C).
Assay A: Example 10; Assay B: Example 11.
| Structure | Assay A<br>0 > 10 μM<br>+ > 1-10 μM<br>++ 0.1-1 μM<br>+++ < 0.1 μM<br>% at 5 μM | Assay B<br>0 > 10 μM<br>+ > 1-10 μM<br>++ 0.1-1 μM<br>+++ < 0.1 μM<br>% at 1.25 μM |
|---|---|---|
| 276 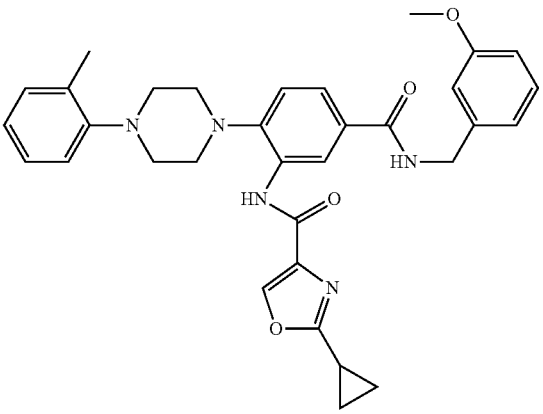 [SMILES: COc1cccc(CNC(=O)c2ccc(N3CCN(c4ccccc4C)CC3)c(NC(=O)c3coc(C4CC4)n3)c2)c1] | | ++ |
| 277 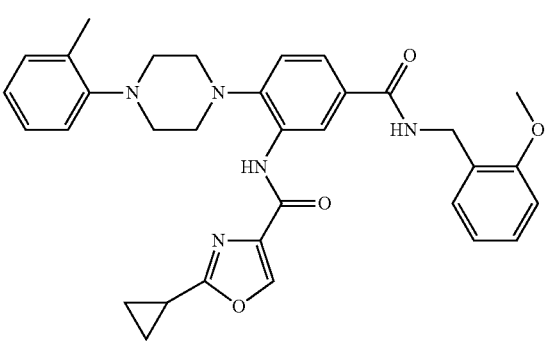 [SMILES: COc1ccccc1CNC(=O)c1ccc(N2CCN(c3ccccc3C)CC2)c(NC(=O)c2coc(C3CC3)n2)c1] | | ++ |
| 278 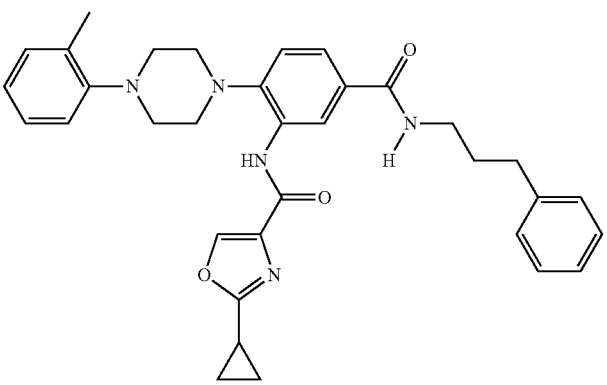 [SMILES: Cc1ccccc1N1CCN(c2ccc(C(=O)NCCCc3ccccc3)cc2NC(=O)c2coc(C3CC3)n2)CC1] | | + |

TABLE 2-continued

Further compounds of formulae (I), (I-A), (I-B), (I-C).
Assay A: Example 10; Assay B: Example 11.

| Structure | Assay A<br>0 > 10 μM<br>+ > 1-10 μM<br>++ 0.1-1 μM<br>+++ < 0.1 μM<br>% at 5 μM | Assay B<br>0 > 10 μM<br>+ > 1-10 μM<br>++ 0.1-1 μM<br>+++ < 0.1 μM<br>% at 1.25 μM |
|---|---|---|
| 279 | | ++ |
| 280 | | ++ |
| 281 | | ++ |
| 282 | | ++ |

TABLE 2-continued
Further compounds of formulae (I), (I-A), (I-B), (I-C).
Assay A: Example 10; Assay B: Example 11.
| Structure | Assay A<br>0 > 10 μM<br>+ > 1-10 μM<br>++ 0.1-1 μM<br>+++ < 0.1 μM<br>% at 5 μM | Assay B<br>0 > 10 μM<br>+ > 1-10 μM<br>++ 0.1-1 μM<br>+++ < 0.1 μM<br>% at 1.25 μM |
|---|---|---|
| 283 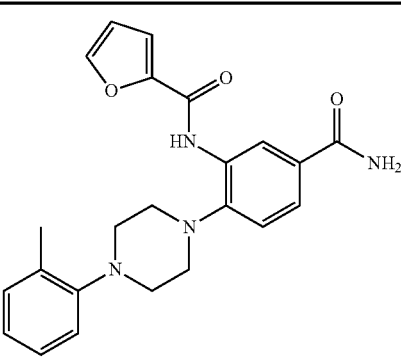 | | + |
| 284 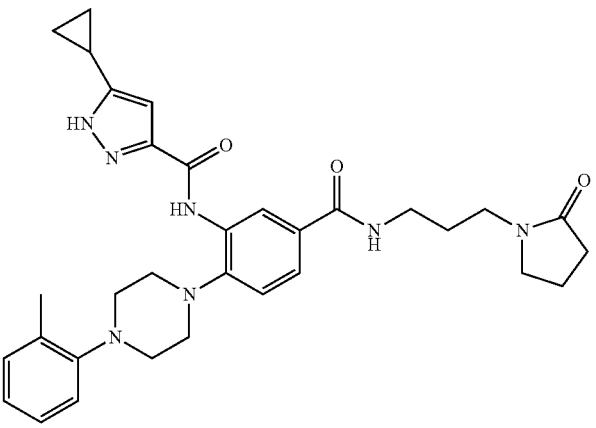 | | ++ |
| 285 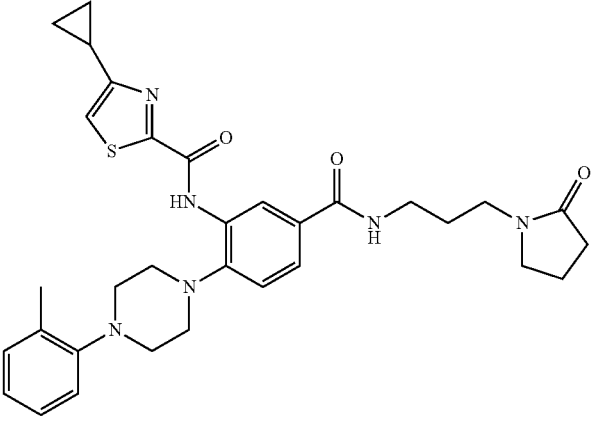 [SMILES: Cc1ccccc1N1CCN(c2ccc(C(=O)NCCCN3CCCC3=O)cc2NC(=O)c2nc(C3CC3)cs2)CC1] | | ++ |

TABLE 2-continued
Further compounds of formulae (I), (I-A), (I-B), (I-C).
Assay A: Example 10; Assay B: Example 11.
| Structure | Assay A<br>0 > 10 μM<br>+ > 1-10 μM<br>++ 0.1-1 μM<br>+++ < 0.1 μM<br>% at 5 μM | Assay B<br>0 > 10 μM<br>+ > 1-10 μM<br>++ 0.1-1 μM<br>+++ < 0.1 μM<br>% at 1.25 μM |
|---|---|---|
| 286 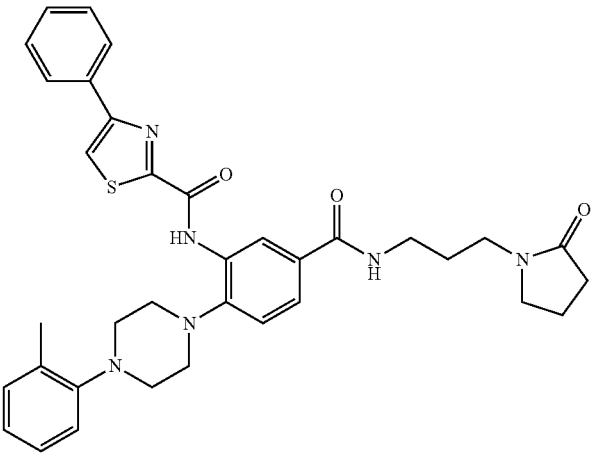 [SMILES: Cc1ccccc1N1CCN(c2ccc(C(=O)NCCCN3CCCC3=O)cc2NC(=O)c2nc(-c3ccccc3)cs2)CC1] | | |
| 287 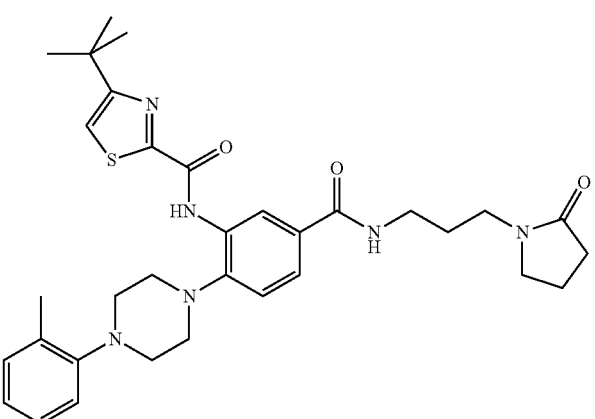 | | |
| 288 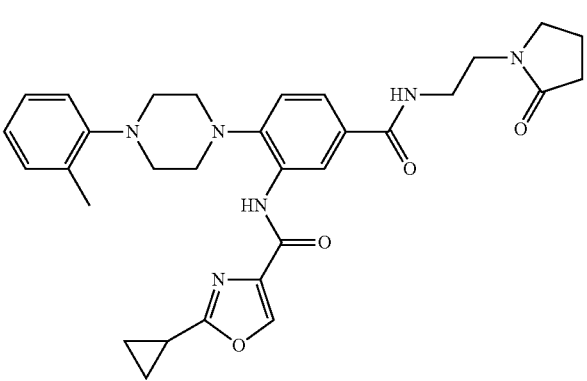 [SMILES: Cc1ccccc1N1CCN(c2ccc(C(=O)NCCN3CCCC3=O)cc2NC(=O)c2coc(C3CC3)n2)CC1] | | ++ |

TABLE 2-continued
Further compounds of formulae (I), (I-A), (I-B), (I-C).
Assay A: Example 10; Assay B: Example 11.
| Structure | Assay A<br>0 > 10 μM<br>+ > 1-10 μM<br>++ 0.1-1 μM<br>+++ < 0.1 μM<br>% at 5 μM | Assay B<br>0 > 10 μM<br>+ > 1-10 μM<br>++ 0.1-1 μM<br>+++ < 0.1 μM<br>% at 1.25 μM |
|---|---|---|
| 289 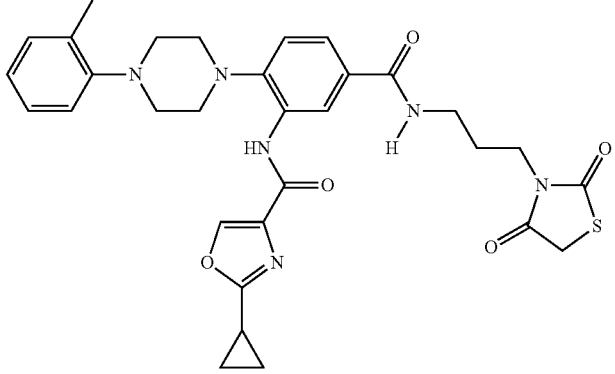 [SMILES: Cc1ccccc1N1CCN(c2ccc(C(=O)NCCCN3C(=O)CSC3=O)cc2NC(=O)c2coc(C3CC3)n2)CC1] | | ++ |
| 290 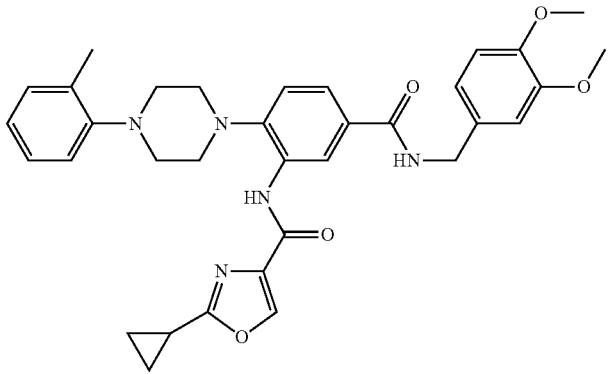 [SMILES: COc1ccc(CNC(=O)c2ccc(N3CCN(c4ccccc4C)CC3)c(NC(=O)c3coc(C4CC4)n3)c2)cc1OC] | | ++ |
| 291 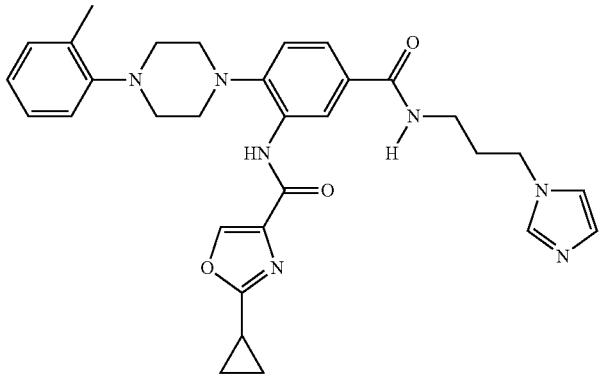 [SMILES: Cc1ccccc1N1CCN(c2ccc(C(=O)NCCCn3ccnc3)cc2NC(=O)c2coc(C3CC3)n2)CC1] | | ++ |

TABLE 2-continued

Further compounds of formulae (I), (I-A), (I-B), (I-C).
Assay A: Example 10; Assay B: Example 11.

| Structure | Assay A<br>0 > 10 μM<br>+ > 1-10 μM<br>++ 0.1-1 μM<br>+++ < 0.1 μM<br>% at 5 μM | Assay B<br>0 > 10 μM<br>+ > 1-10 μM<br>++ 0.1-1 μM<br>+++ < 0.1 μM<br>% at 1.25 μM |
|---|---|---|
| 292 | | ++ |
| 293 | | ++ |
| 294 | | + |
| 295 | | ++ |

TABLE 2-continued
Further compounds of formulae (I), (I-A), (I-B), (I-C).
Assay A: Example 10; Assay B: Example 11.
| Structure | Assay A<br>0 > 10 μM<br>+ > 1-10 μM<br>++ 0.1-1 μM<br>+++ < 0.1 μM<br>% at 5 μM | Assay B<br>0 > 10 μM<br>+ > 1-10 μM<br>++ 0.1-1 μM<br>+++ < 0.1 μM<br>% at 1.25 μM |
|---|---|---|
| 296 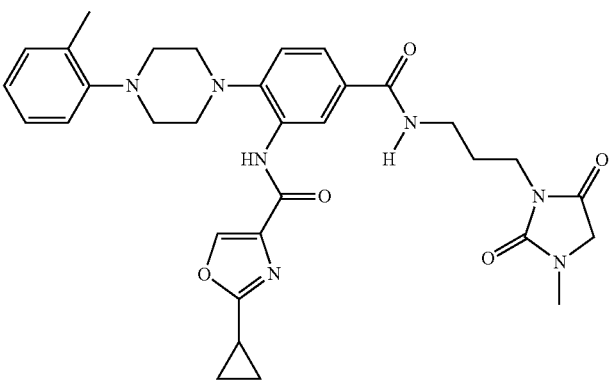 [SMILES: Cc1ccccc1N1CCN(c2ccc(C(=O)NCCCN3C(=O)CN(C)C3=O)cc2NC(=O)c2coc(C3CC3)n2)CC1] | | ++ |
| 297 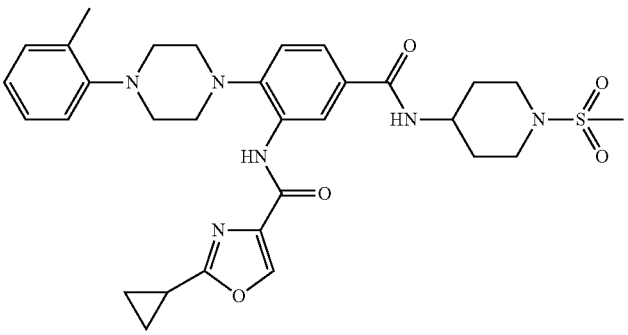 [SMILES: Cc1ccccc1N1CCN(c2ccc(C(=O)NC3CCN(S(C)(=O)=O)CC3)cc2NC(=O)c2coc(C3CC3)n2)CC1] | | ++ |
| 298 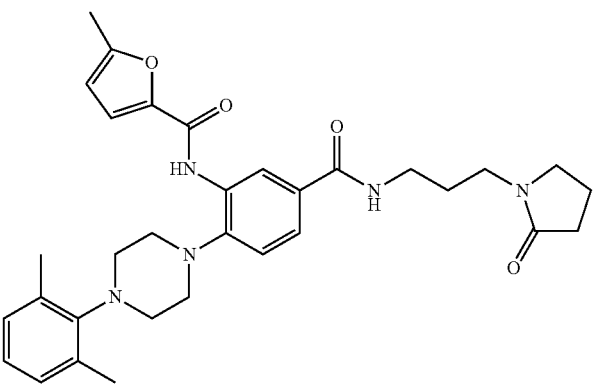 [SMILES: Cc1ccc(C(=O)Nc2cc(C(=O)NCCCN3CCCC3=O)ccc2N2CCN(c3c(C)cccc3C)CC2)o1] | | + |

TABLE 2-continued

Further compounds of formulae (I), (I-A), (I-B), (I-C).
Assay A: Example 10; Assay B: Example 11.

| Structure | Assay A<br>0 > 10 μM<br>+ > 1-10 μM<br>++ 0.1-1 μM<br>+++ < 0.1 μM<br>% at 5 μM | Assay B<br>0 > 10 μM<br>+ > 1-10 μM<br>++ 0.1-1 μM<br>+++ < 0.1 μM<br>% at 1.25 μM |
|---|---|---|
| 299 | | + |
| 300 | | |
| 301 | | + |

TABLE 2-continued
Further compounds of formulae (I), (I-A), (I-B), (I-C).
Assay A: Example 10; Assay B: Example 11.
| Structure | Assay A<br>0 > 10 μM<br>+ > 1-10 μM<br>++ 0.1-1 μM<br>+++ < 0.1 μM<br>% at 5 μM | Assay B<br>0 > 10 μM<br>+ > 1-10 μM<br>++ 0.1-1 μM<br>+++ < 0.1 μM<br>% at 1.25 μM |
|---|---|---|
| 302 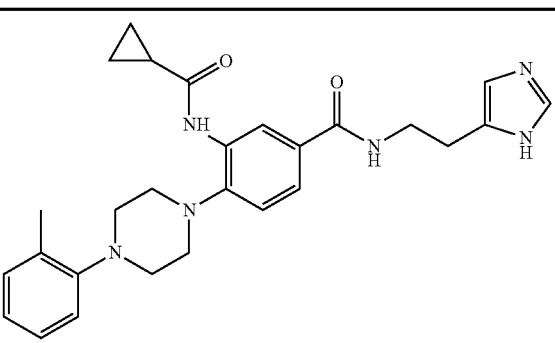 | | + |
| 303 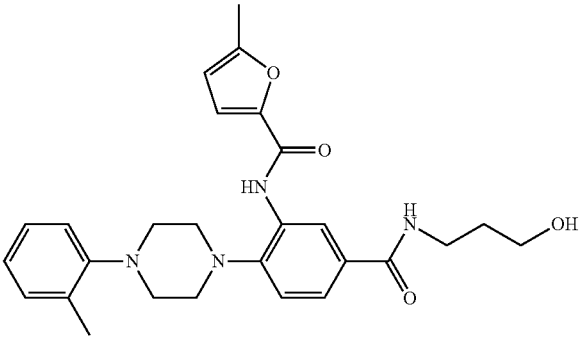 [SMILES: Cc1ccc(C(=O)Nc2cc(C(=O)NCCCO)ccc2N2CCN(c3ccccc3C)CC2)o1] | | + |
| 304 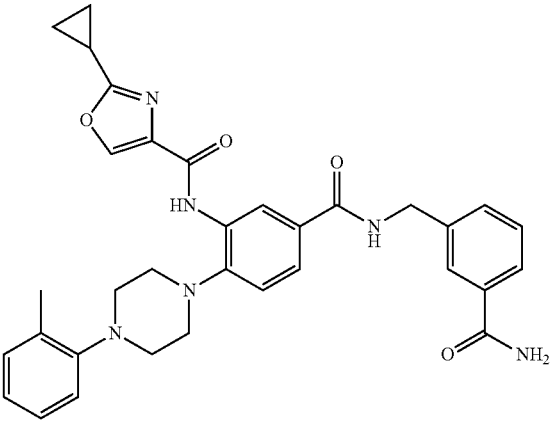 [SMILES: Cc1ccccc1N1CCN(c2ccc(C(=O)NCc3cccc(C(N)=O)c3)cc2NC(=O)c2coc(C3CC3)n2)CC1] | | +++ 79% |
| 305 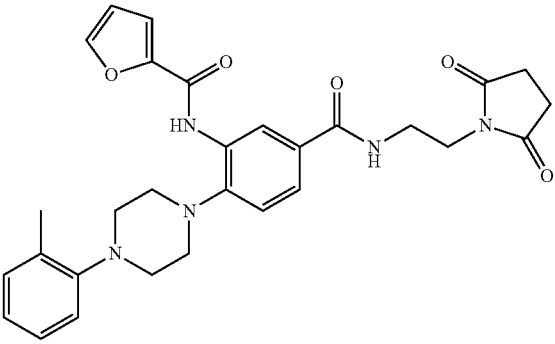 [SMILES: Cc1ccccc1N1CCN(c2ccc(C(=O)NCCN3C(=O)CCC3=O)cc2NC(=O)c2ccco2)CC1] | | +++ |

TABLE 2-continued

Further compounds of formulae (I), (I-A), (I-B), (I-C).
Assay A: Example 10; Assay B: Example 11.

| Structure | Assay A<br>0 > 10 μM<br>+ > 1-10 μM<br>++ 0.1-1 μM<br>+++ < 0.1 μM<br>% at 5 μM | Assay B<br>0 > 10 μM<br>+ > 1-10 μM<br>++ 0.1-1 μM<br>+++ < 0.1 μM<br>% at 1.25 μM |
|---|---|---|
| 306 | | ++ |
| 307 | ++ | + |
| 308 | | ++ |

TABLE 2-continued
Further compounds of formulae (I), (I-A), (I-B), (I-C).
Assay A: Example 10; Assay B: Example 11.
| Structure | Assay A<br>0 > 10 µM<br>+ > 1-10 µM<br>++ 0.1-1 µM<br>+++ < 0.1 µM<br>% at 5 µM | Assay B<br>0 > 10 µM<br>+ > 1-10 µM<br>++ 0.1-1 µM<br>+++ < 0.1 µM<br>% at 1.25 µM |
|---|---|---|
| 309 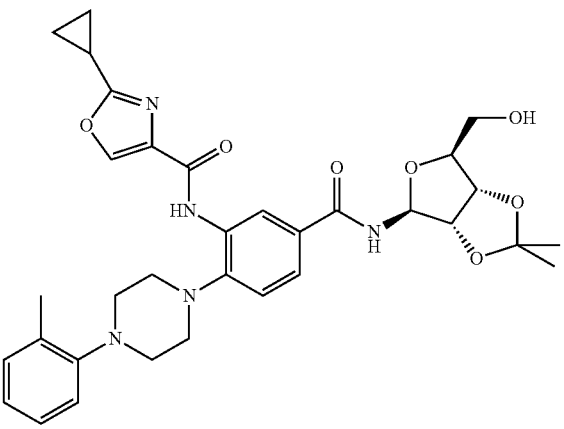 [SMILES: Cc1ccccc1N1CCN(c2ccc(C(=O)N[C@H]3O[C@@H](CO)[C@@H]4OC(C)(C)O[C@@H]43)cc2NC(=O)c2coc(C3CC3)n2)CC1] | | ++ |
| 310 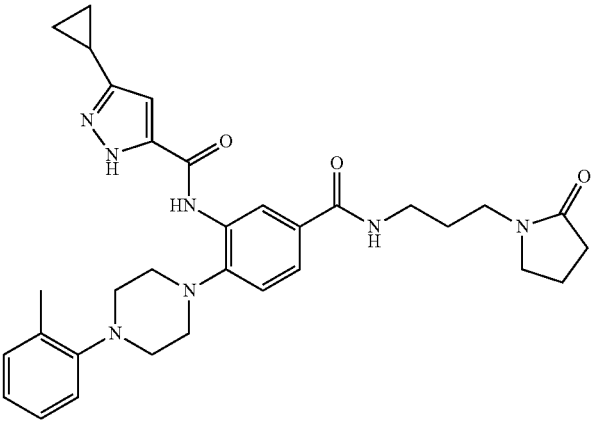 [SMILES: Cc1ccccc1N1CCN(c2ccc(C(=O)NCCCN3CCCC3=O)cc2NC(=O)c2cc(C3CC3)n[nH]2)CC1] | | ++ |
| 311 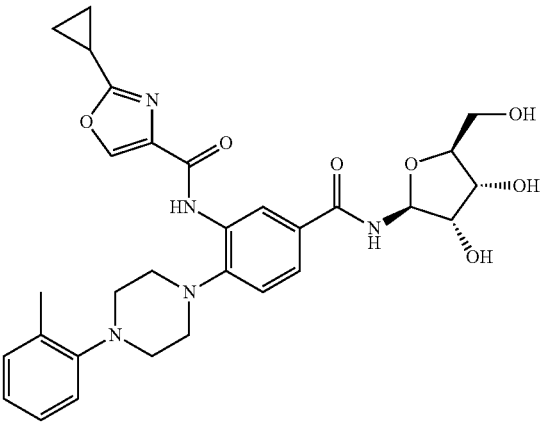 [SMILES: Cc1ccccc1N1CCN(c2ccc(C(=O)N[C@H]3O[C@@H](CO)[C@H](O)[C@@H]3O)cc2NC(=O)c2coc(C3CC3)n2)CC1] | ++ | ++ |

US 9,938,262 B2
185
186
TABLE 2-continued
Further compounds of formulae (I), (I-A), (I-B), (I-C).
Assay A: Example 10; Assay B: Example 11.
| Structure | Assay A<br>0 > 10 μM<br>+ > 1-10 μM<br>++ 0.1-1 μM<br>+++ < 0.1 μM<br>% at 5 μM | Assay B<br>0 > 10 μM<br>+ > 1-10 μM<br>++ 0.1-1 μM<br>+++ < 0.1 μM<br>% at 1.25 μM |
|---|---|---|
| 312 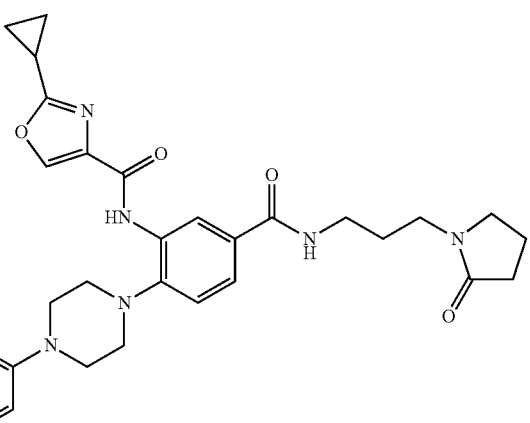 | | ++ |
| 313 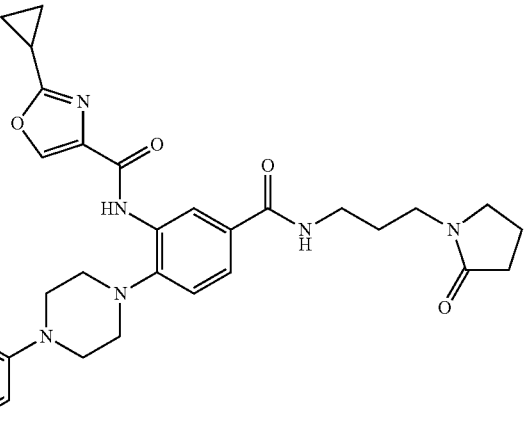 | | ++ |
| 314 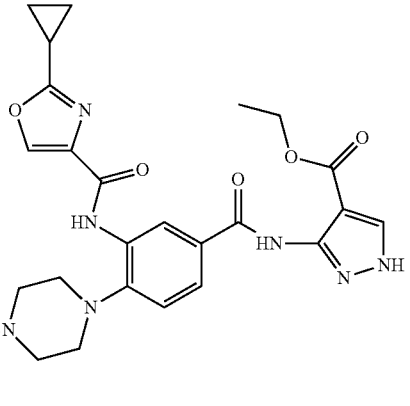 | | 38% |

TABLE 2-continued
Further compounds of formulae (I), (I-A), (I-B), (I-C).
Assay A: Example 10; Assay B: Example 11.
| Structure | Assay A<br>0 > 10 μM<br>+ > 1-10 μM<br>++ 0.1-1 μM<br>+++ < 0.1 μM<br>% at 5 μM | Assay B<br>0 > 10 μM<br>+ > 1-10 μM<br>++ 0.1-1 μM<br>+++ < 0.1 μM<br>% at 1.25 μM |
|---|---|---|
| 315 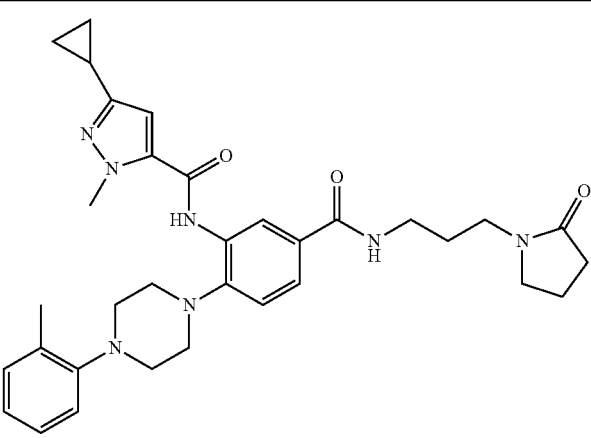 | | 47% |
| 316 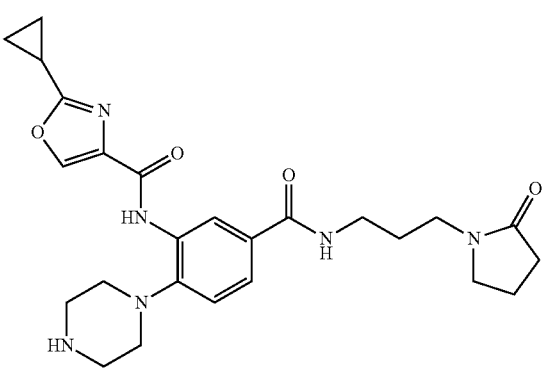 [SMILES: O=C(NCCCN1CCCC1=O)c1ccc(N2CCNCC2)c(NC(=O)c2coc(C3CC3)n2)c1] | | |
| 317 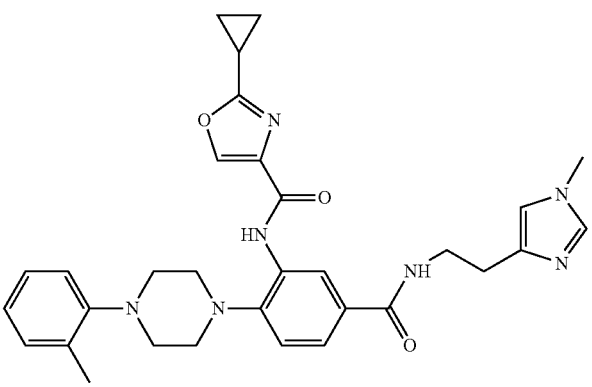 [SMILES: Cc1ccccc1N1CCN(c2ccc(C(=O)NCCc3cn(C)cn3)cc2NC(=O)c2coc(C3CC3)n2)CC1] | | ++ |

TABLE 2-continued

Further compounds of formulae (I), (I-A), (I-B), (I-C).
Assay A: Example 10; Assay B: Example 11.

| Structure | Assay A<br>0 > 10 μM<br>+ > 1-10 μM<br>++ 0.1-1 μM<br>+++ < 0.1 μM<br>% at 5 μM | Assay B<br>0 > 10 μM<br>+ > 1-10 μM<br>++ 0.1-1 μM<br>+++ < 0.1 μM<br>% at 1.25 μM |
|---|---|---|
| 318 | | ++ |
| 319 | | |
| 320 | ++ | ++ |

… TABLE 2-continued

Further compounds of formulae (I), (I-A), (I-B), (I-C).
Assay A: Example 10; Assay B: Example 11.

| Structure | Assay A<br>0 > 10 μM<br>+ > 1-10 μM<br>++ 0.1-1 μM<br>+++ < 0.1 μM<br>% at 5 μM | Assay B<br>0 > 10 μM<br>+ > 1-10 μM<br>++ 0.1-1 μM<br>+++ < 0.1 μM<br>% at 1.25 μM |
|---|---|---|
| 321 | | ++ |
| 322 | ++ | + |
| 323 | | ++ |

TABLE 2-continued
Further compounds of formulae (I), (I-A), (I-B), (I-C).
Assay A: Example 10; Assay B: Example 11.
| Structure | Assay A<br>0 > 10 μM<br>+ > 1-10 μM<br>++ 0.1-1 μM<br>+++ < 0.1 μM<br>% at 5 μM | Assay B<br>0 > 10 μM<br>+ > 1-10 μM<br>++ 0.1-1 μM<br>+++ < 0.1 μM<br>% at 1.25 μM |
|---|---|---|
| 324 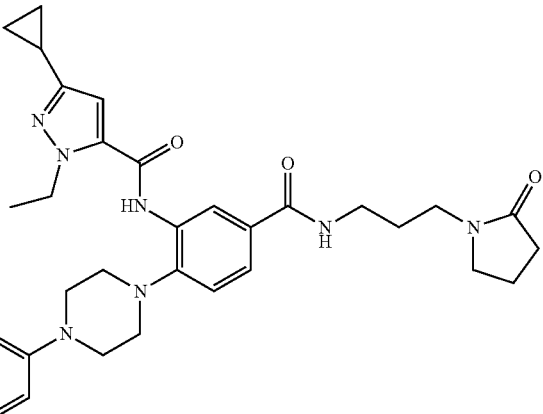 | | + |
| 325 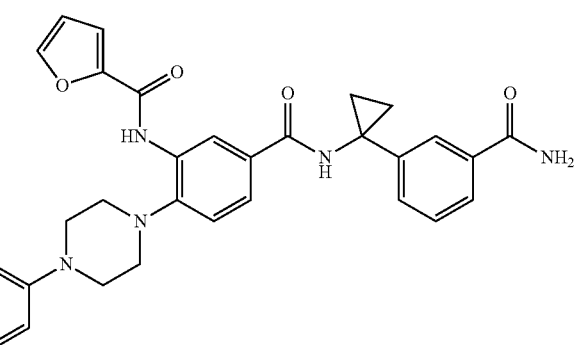 | | ++ |
| 326 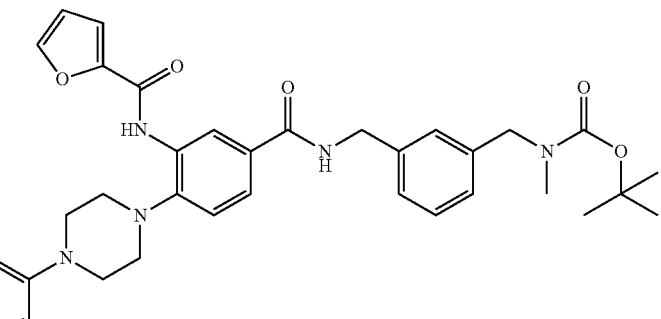 | | 0 |

TABLE 2-continued
Further compounds of formulae (I), (I-A), (I-B), (I-C).
Assay A: Example 10; Assay B: Example 11.
| Structure | Assay A<br>0 > 10 μM<br>+ > 1-10 μM<br>++ 0.1-1 μM<br>+++ < 0.1 μM<br>% at 5 μM | Assay B<br>0 > 10 μM<br>+ > 1-10 μM<br>++ 0.1-1 μM<br>+++ < 0.1 μM<br>% at 1.25 μM |
|---|---|---|
| 327 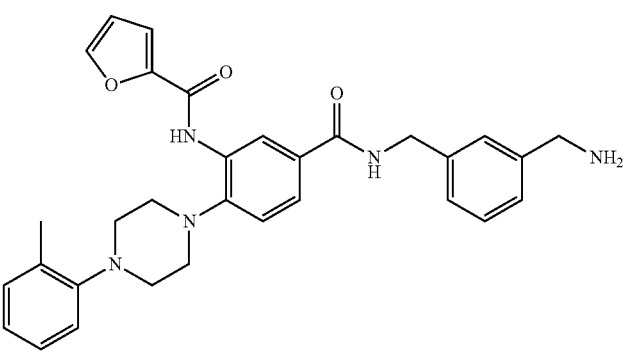 [SMILES: Cc1ccccc1N1CCN(c2ccc(C(=O)NCc3cccc(CN)c3)cc2NC(=O)c2ccco2)CC1] | | ++ |
| 328 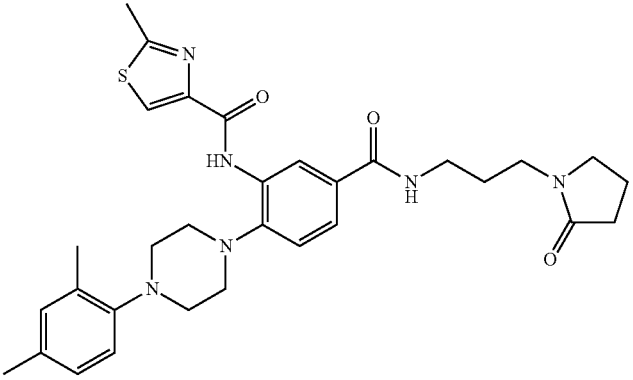 [SMILES: Cc1ccc(N2CCN(c3ccc(C(=O)NCCCN4CCCC4=O)cc3NC(=O)c3csc(C)n3)CC2)c(C)c1] | | |
| 329 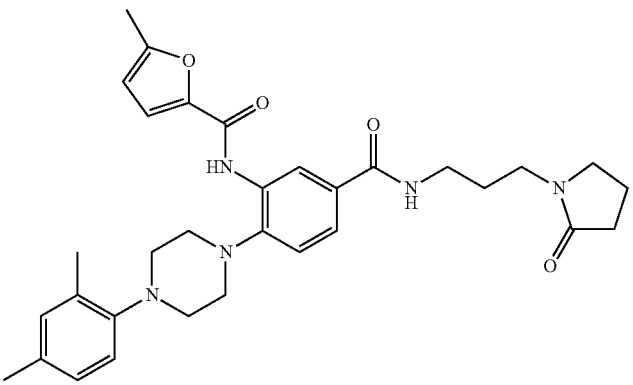 [SMILES: Cc1ccc(N2CCN(c3ccc(C(=O)NCCCN4CCCC4=O)cc3NC(=O)c3ccc(C)o3)CC2)c(C)c1] | | |

TABLE 2-continued

Further compounds of formulae (I), (I-A), (I-B), (I-C).
Assay A: Example 10; Assay B: Example 11.

| Structure | Assay A<br>0 > 10 μM<br>+ > 1-10 μM<br>++ 0.1-1 μM<br>+++ < 0.1 μM<br>% at 5 μM | Assay B<br>0 > 10 μM<br>+ > 1-10 μM<br>++ 0.1-1 μM<br>+++ < 0.1 μM<br>% at 1.25 μM |
| --- | --- | --- |
| 330 | | ++ |
| 331 | | +++ |
| 332 | | ++ |

TABLE 2-continued

Further compounds of formulae (I), (I-A), (I-B), (I-C).
Assay A: Example 10; Assay B: Example 11.

| Structure | Assay A<br>0 > 10 μM<br>+ > 1-10 μM<br>++ 0.1-1 μM<br>+++ < 0.1 μM<br>% at 5 μM | Assay B<br>0 > 10 μM<br>+ > 1-10 μM<br>++ 0.1-1 μM<br>+++ < 0.1 μM<br>% at 1.25 μM |
|---|---|---|
| 333 | | ++ |
| 334 | | ++ |
| 335 | | |
| 336 | | |

TABLE 2-continued

Further compounds of formulae (I), (I-A), (I-B), (I-C).
Assay A: Example 10; Assay B: Example 11.

| Structure | Assay A<br>0 > 10 μM<br>+ > 1-10 μM<br>++ 0.1-1 μM<br>+++ < 0.1 μM<br>% at 5 μM | Assay B<br>0 > 10 μM<br>+ > 1-10 μM<br>++ 0.1-1 μM<br>+++ < 0.1 μM<br>% at 1.25 μM |
|---|---|---|
| 337 | | |
| 338 | | |
| 339 | | |
| 340 | | |

TABLE 2-continued
Further compounds of formulae (I), (I-A), (I-B), (I-C).
Assay A: Example 10; Assay B: Example 11.
| Structure | Assay A<br>0 > 10 µM<br>+ > 1-10 µM<br>++ 0.1-1 µM<br>+++ < 0.1 µM<br>% at 5 µM | Assay B<br>0 > 10 µM<br>+ > 1-10 µM<br>++ 0.1-1 µM<br>+++ < 0.1 µM<br>% at 1.25 µM |
|---|---|---|
| 341 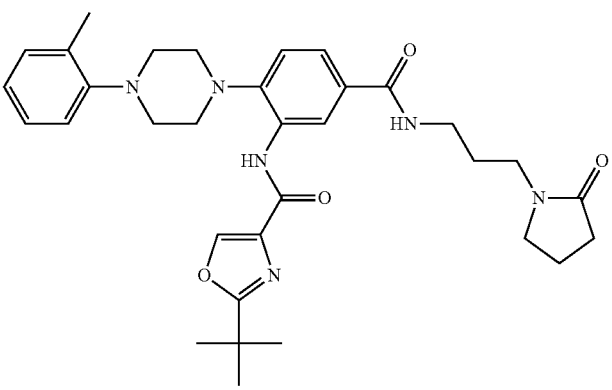 [SMILES: Cc1ccccc1N1CCN(c2ccc(C(=O)NCCCN3CCCC3=O)cc2NC(=O)c2coc(C(C)(C)C)n2)CC1] | | |
| 342 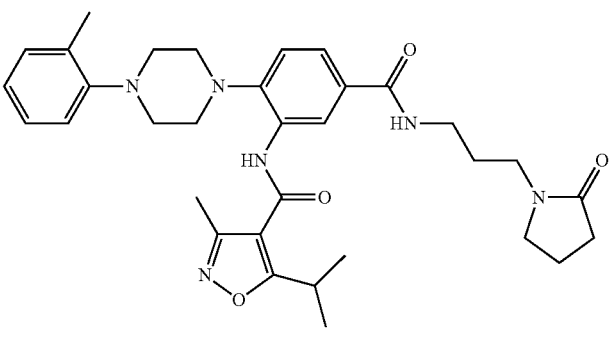 | | |
| 343 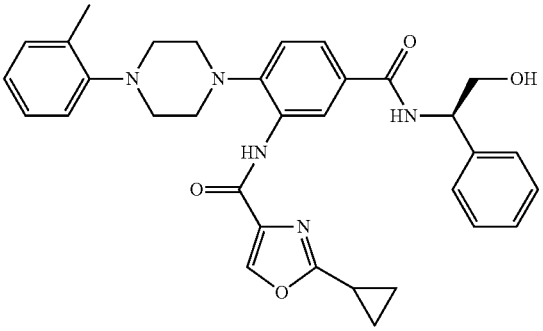 [SMILES: Cc1ccccc1N1CCN(c2ccc(C(=O)N[C@@H](CO)c3ccccc3)cc2NC(=O)c2coc(C3CC3)n2)CC1] | + | |
| 344 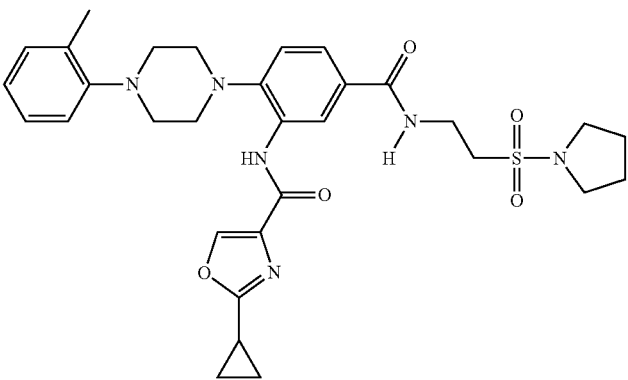 [SMILES: Cc1ccccc1N1CCN(c2ccc(C(=O)NCCS(=O)(=O)N3CCCC3)cc2NC(=O)c2coc(C3CC3)n2)CC1] | + | ++ |

TABLE 2-continued
Further compounds of formulae (I), (I-A), (I-B), (I-C).
Assay A: Example 10; Assay B: Example 11.
| Structure | Assay A<br>0 > 10 µM<br>+ > 1-10 µM<br>++ 0.1-1 µM<br>+++ < 0.1 µM<br>% at 5 µM | Assay B<br>0 > 10 µM<br>+ > 1-10 µM<br>++ 0.1-1 µM<br>+++ < 0.1 µM<br>% at 1.25 µM |
|---|---|---|
| 345 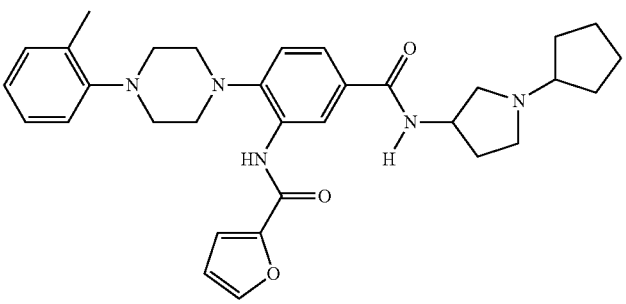 [SMILES: Cc1ccccc1N1CCN(c2ccc(C(=O)NC3CCN(C4CCCC4)C3)cc2NC(=O)c2ccco2)CC1] | | + |
| 346 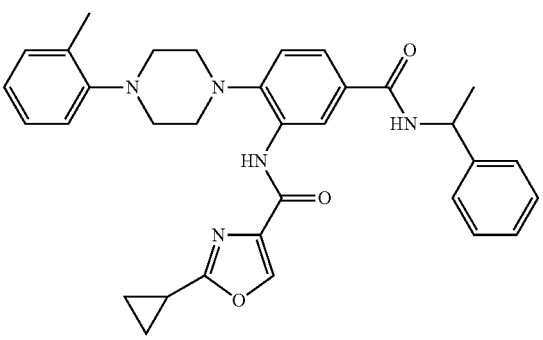 [SMILES: Cc1ccccc1N1CCN(c2ccc(C(=O)NC(C)c3ccccc3)cc2NC(=O)c2coc(C3CC3)n2)CC1] | | ++ |
| 347 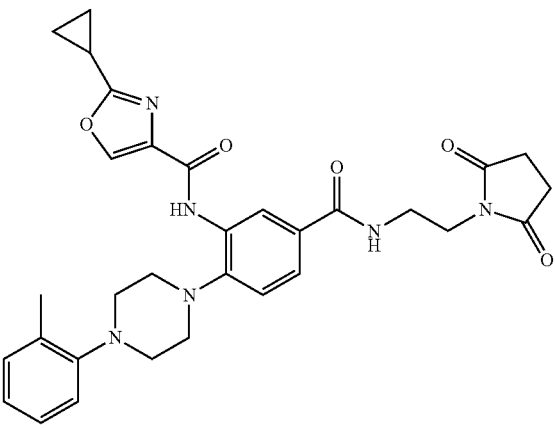 [SMILES: Cc1ccccc1N1CCN(c2ccc(C(=O)NCCN3C(=O)CCC3=O)cc2NC(=O)c2coc(C3CC3)n2)CC1] | | 0 |

TABLE 2-continued

Further compounds of formulae (I), (I-A), (I-B), (I-C).
Assay A: Example 10; Assay B: Example 11.

| Structure | Assay A<br>0 > 10 μM<br>+ > 1-10 μM<br>++ 0.1-1 μM<br>+++ < 0.1 μM<br>% at 5 μM | Assay B<br>0 > 10 μM<br>+ > 1-10 μM<br>++ 0.1-1 μM<br>+++ < 0.1 μM<br>% at 1.25 μM |
|---|---|---|
| 348 | | ++ |
| 349 | ++ | + |
| 350 | | ++ |

TABLE 2-continued

Further compounds of formulae (I), (I-A), (I-B), (I-C).
Assay A: Example 10; Assay B: Example 11.

| Structure | Assay A<br>0 > 10 μM<br>+ > 1-10 μM<br>++ 0.1-1 μM<br>+++ < 0.1 μM<br>% at 5 μM | Assay B<br>0 > 10 μM<br>+ > 1-10 μM<br>++ 0.1-1 μM<br>+++ < 0.1 μM<br>% at 1.25 μM |
|---|---|---|
| 351 | ++ | |
| 352 | ++ | |
| 353 | ++ | |

TABLE 2-continued
Further compounds of formulae (I), (I-A), (I-B), (I-C).
Assay A: Example 10; Assay B: Example 11.
| Structure | Assay A<br>0 > 10 μM<br>+ > 1-10 μM<br>++ 0.1-1 μM<br>+++ < 0.1 μM<br>% at 5 μM | Assay B<br>0 > 10 μM<br>+ > 1-10 μM<br>++ 0.1-1 μM<br>+++ < 0.1 μM<br>% at 1.25 μM |
|---|---|---|
| 354 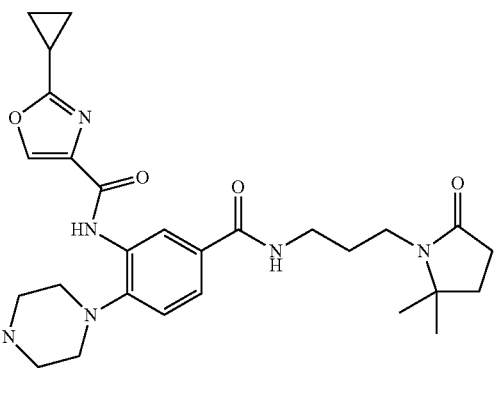 | | ++ |
| 355 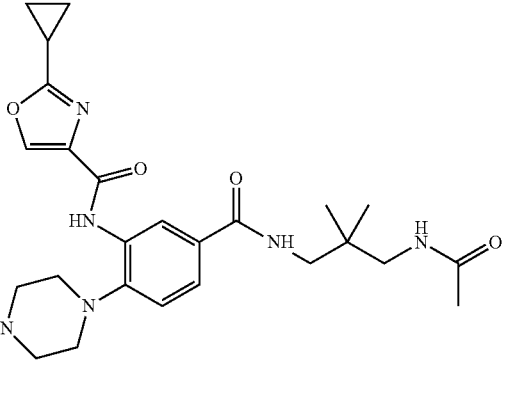 | | ++ |
| 356 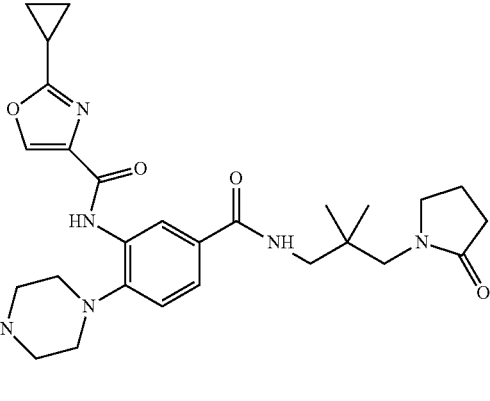 | | ++ |

TABLE 2-continued

Further compounds of formulae (I), (I-A), (I-B), (I-C).
Assay A: Example 10; Assay B: Example 11.

| Structure | Assay A<br>0 > 10 μM<br>+ > 1-10 μM<br>++ 0.1-1 μM<br>+++ < 0.1 μM<br>% at 5 μM | Assay B<br>0 > 10 μM<br>+ > 1-10 μM<br>++ 0.1-1 μM<br>+++ < 0.1 μM<br>% at 1.25 μM |
|---|---|---|
| 357 | | ++ |
| 358 | | ++ |
| 359 | | ++ |

TABLE 2-continued
Further compounds of formulae (I), (I-A), (I-B), (I-C).
Assay A: Example 10; Assay B: Example 11.
| Structure | Assay A<br>0 > 10 µM<br>+ > 1-10 µM<br>++ 0.1-1 µM<br>+++ < 0.1 µM<br>% at 5 µM | Assay B<br>0 > 10 µM<br>+ > 1-10 µM<br>++ 0.1-1 µM<br>+++ < 0.1 µM<br>% at 1.25 µM |
|---|---|---|
| 360 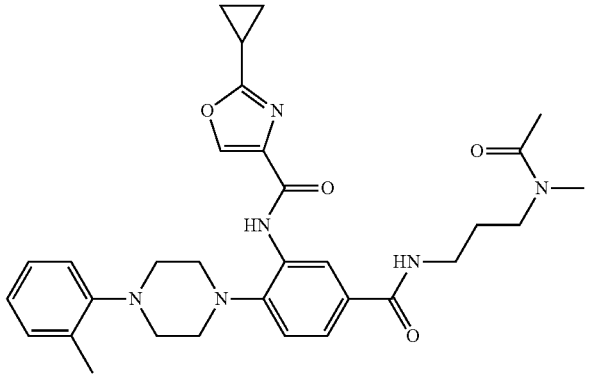 [SMILES: CC(=O)N(C)CCCNC(=O)c1ccc(N2CCN(c3ccccc3C)CC2)c(NC(=O)c2coc(C3CC3)n2)c1] | | +++ |
| 361 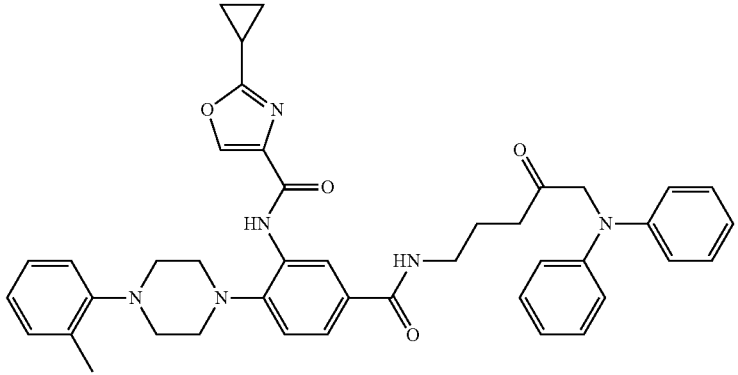 [SMILES: Cc1ccccc1N1CCN(c2ccc(C(=O)NCCCC(=O)CN(c3ccccc3)c3ccccc3)cc2NC(=O)c2coc(C3CC3)n2)CC1] | | + |
| 362 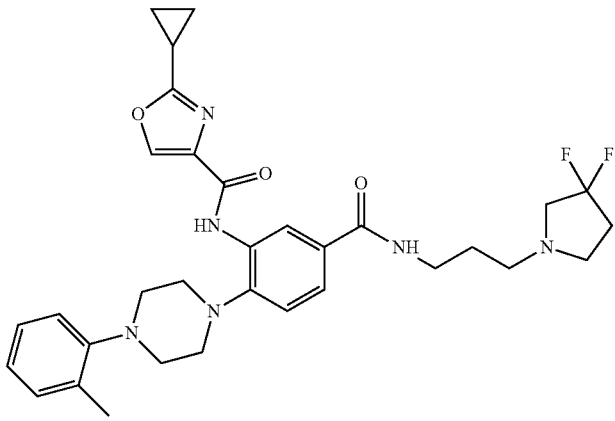 [SMILES: Cc1ccccc1N1CCN(c2ccc(C(=O)NCCCN3CCC(F)(F)C3)cc2NC(=O)c2coc(C3CC3)n2)CC1] | | ++ |

TABLE 2-continued
Further compounds of formulae (I), (I-A), (I-B), (I-C).
Assay A: Example 10; Assay B: Example 11.
| Structure | Assay A<br>0 > 10 μM<br>+ > 1-10 μM<br>++ 0.1-1 μM<br>+++ < 0.1 μM<br>% at 5 μM | Assay B<br>0 > 10 μM<br>+ > 1-10 μM<br>++ 0.1-1 μM<br>+++ < 0.1 μM<br>% at 1.25 μM |
|---|---|---|
| 363 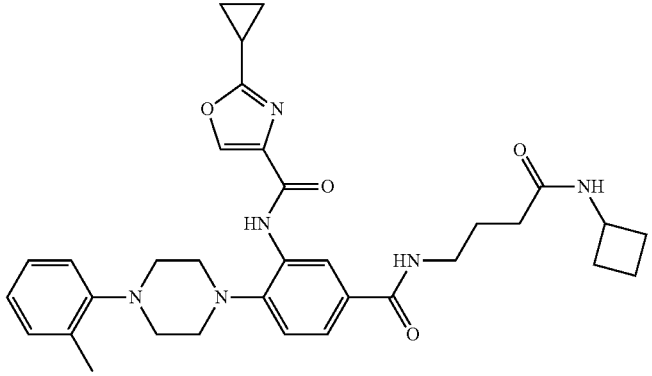 [SMILES: Cc1ccccc1N1CCN(c2ccc(C(=O)NCCCC(=O)NC3CCC3)cc2NC(=O)c2coc(C3CC3)n2)CC1] | | ++ |
| 364 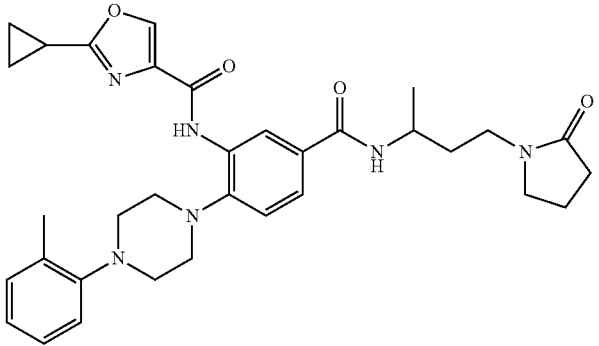 [SMILES: Cc1ccccc1N1CCN(c2ccc(C(=O)NC(C)CCN3CCCC3=O)cc2NC(=O)c2coc(C3CC3)n2)CC1] | | ++ |
| 365 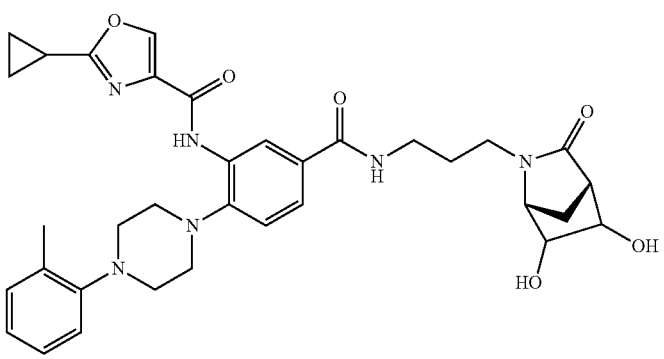 [SMILES: Cc1ccccc1N1CCN(c2ccc(C(=O)NCCCN3C(=O)[C@H]4C[C@@H]3C(O)C4O)cc2NC(=O)c2coc(C3CC3)n2)CC1] | ++ | +++ |

TABLE 2-continued

Further compounds of formulae (I), (I-A), (I-B), (I-C).
Assay A: Example 10; Assay B: Example 11.

| Structure | Assay A<br>0 > 10 μM<br>+ > 1-10 μM<br>++ 0.1-1 μM<br>+++ < 0.1 μM<br>% at 5 μM | Assay B<br>0 > 10 μM<br>+ > 1-10 μM<br>++ 0.1-1 μM<br>+++ < 0.1 μM<br>% at 1.25 μM |
|---|---|---|
| 366 | | ++ |
| 367 | | ++ |
| 368 | | ++ |

US 9,938,262 B2
221 222
TABLE 2-continued
Further compounds of formulae (I), (I-A), (I-B), (I-C).
Assay A: Example 10; Assay B: Example 11.
| Structure | Assay A<br>0 > 10 μM<br>+ > 1-10 μM<br>++ 0.1-1 μM<br>+++ < 0.1 μM<br>% at 5 μM | Assay B<br>0 > 10 μM<br>+ > 1-10 μM<br>++ 0.1-1 μM<br>+++ < 0.1 μM<br>% at 1.25 μM |
|---|---|---|
| 369 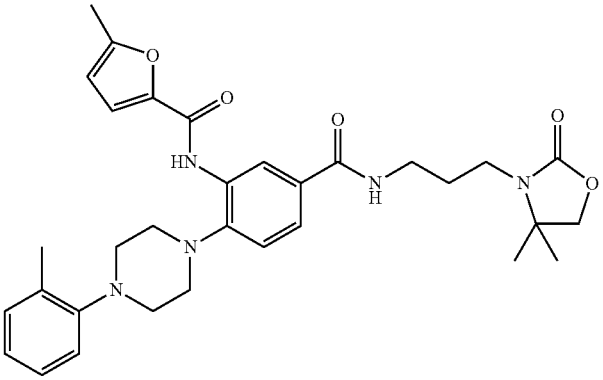 [SMILES: Cc1ccc(C(=O)Nc2cc(C(=O)NCCCN3C(=O)OCC3(C)C)ccc2N2CCN(c3ccccc3C)CC2)o1] | | + |
| 370 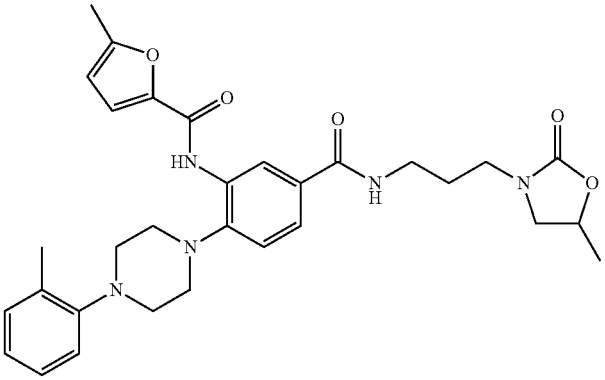 [SMILES: Cc1ccc(C(=O)Nc2cc(C(=O)NCCCN3CC(C)OC3=O)ccc2N2CCN(c3ccccc3C)CC2)o1] | | + |
| 371 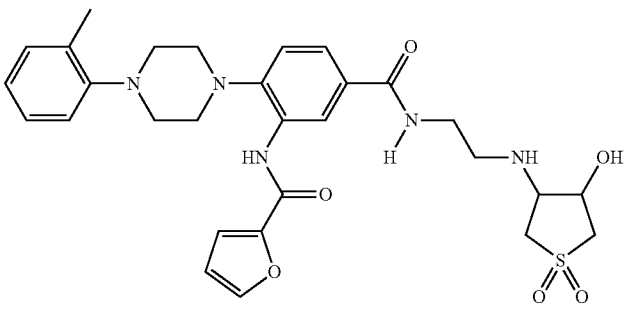 [SMILES: Cc1ccccc1N1CCN(c2ccc(C(=O)NCCNC3CS(=O)(=O)CC3O)cc2NC(=O)c2ccco2)CC1] | | ++ |
| 372 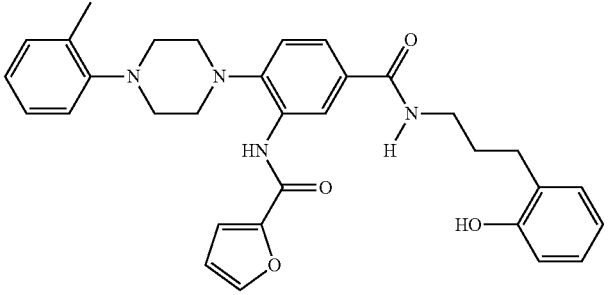 [SMILES: Cc1ccccc1N1CCN(c2ccc(C(=O)NCCCc3ccccc3O)cc2NC(=O)c2ccco2)CC1] | | ++ |

TABLE 2-continued
Further compounds of formulae (I), (I-A), (I-B), (I-C).
Assay A: Example 10; Assay B: Example 11.
| Structure | Assay A<br>0 > 10 μM<br>+ > 1-10 μM<br>++ 0.1-1 μM<br>+++ < 0.1 μM<br>% at 5 μM | Assay B<br>0 > 10 μM<br>+ > 1-10 μM<br>++ 0.1-1 μM<br>+++ < 0.1 μM<br>% at 1.25 μM |
|---|---|---|
| 373 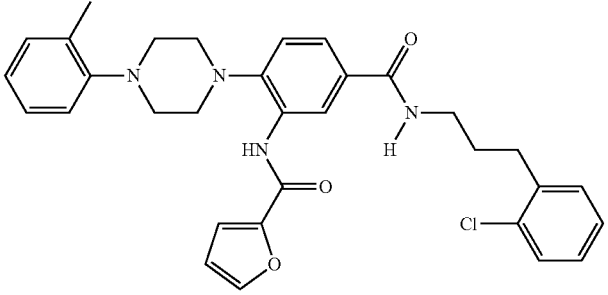 [SMILES: Cc1ccccc1N1CCN(c2ccc(C(=O)NCCCc3ccccc3Cl)cc2NC(=O)c2ccco2)CC1] | | + |
| 374 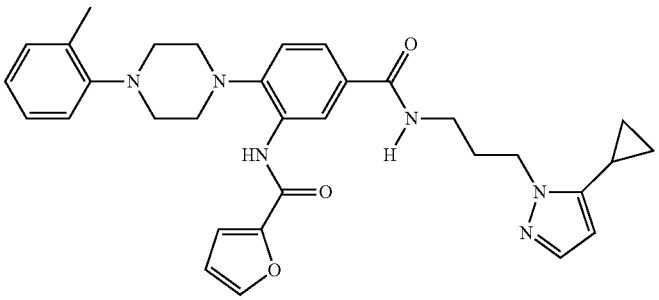 [SMILES: Cc1ccccc1N1CCN(c2ccc(C(=O)NCCCn3nccc3C3CC3)cc2NC(=O)c2ccco2)CC1] | | ++ |
| 375 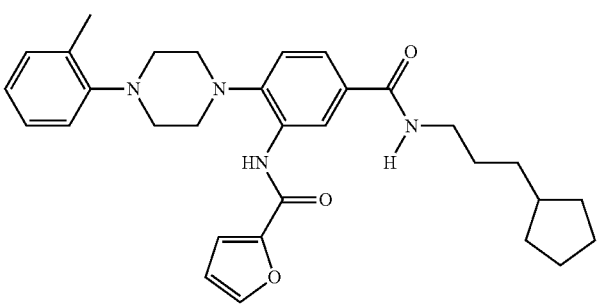 [SMILES: Cc1ccccc1N1CCN(c2ccc(C(=O)NCCCC3CCCC3)cc2NC(=O)c2ccco2)CC1] | | ++ |
| 376 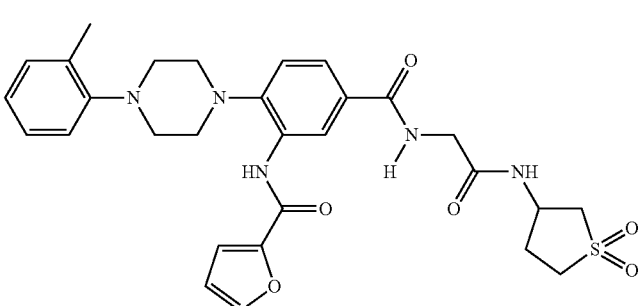 | | ++ |

TABLE 2-continued
Further compounds of formulae (I), (I-A), (I-B), (I-C).
Assay A: Example 10; Assay B: Example 11.
| Structure | Assay A<br>0 > 10 μM<br>+ > 1-10 μM<br>++ 0.1-1 μM<br>+++ < 0.1 μM<br>% at 5 μM | Assay B<br>0 > 10 μM<br>+ > 1-10 μM<br>++ 0.1-1 μM<br>+++ < 0.1 μM<br>% at 1.25 μM |
|---|---|---|
| 377 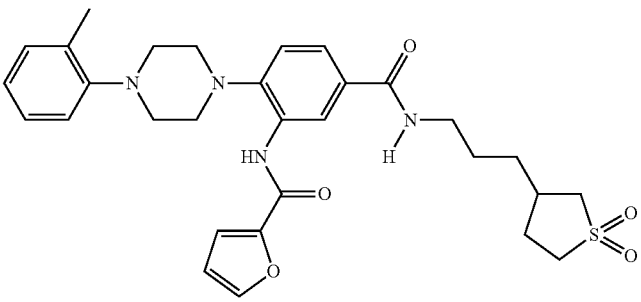 [SMILES: Cc1ccccc1N1CCN(c2ccc(C(=O)NCCCC3CCS(=O)(=O)C3)cc2NC(=O)c2ccco2)CC1] | | ++ |
| 378 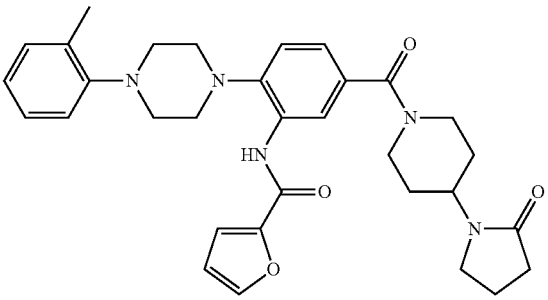 [SMILES: Cc1ccccc1N1CCN(c2ccc(C(=O)N3CCC(N4CCCC4=O)CC3)cc2NC(=O)c2ccco2)CC1] | | |
| 379 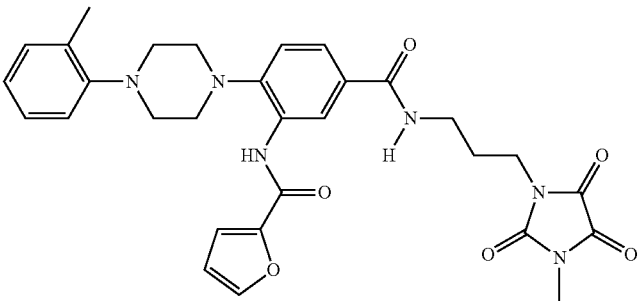 [SMILES: Cc1ccccc1N1CCN(c2ccc(C(=O)NCCCN3C(=O)C(=O)N(C)C3=O)cc2NC(=O)c2ccco2)CC1] | | ++ |
| 380 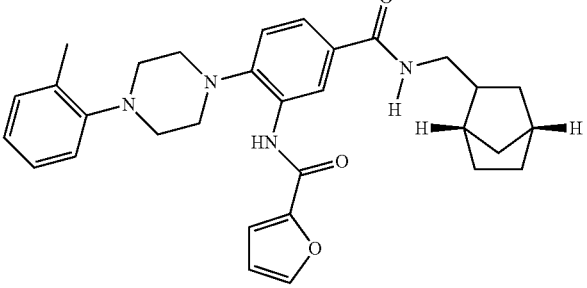 | | ++ |

TABLE 2-continued

Further compounds of formulae (I), (I-A), (I-B), (I-C).
Assay A: Example 10; Assay B: Example 11.

| Structure | Assay A<br>0 > 10 μM<br>+ > 1-10 μM<br>++ 0.1-1 μM<br>+++ < 0.1 μM<br>% at 5 μM | Assay B<br>0 > 10 μM<br>+ > 1-10 μM<br>++ 0.1-1 μM<br>+++ < 0.1 μM<br>% at 1.25 μM |
|---|---|---|
| 381 | | |
| 382 | | ++ |
| 383 | | ++ |

TABLE 2-continued
Further compounds of formulae (I), (I-A), (I-B), (I-C).
Assay A: Example 10; Assay B: Example 11.
| Structure | Assay A<br>0 > 10 μM<br>+ > 1-10 μM<br>++ 0.1-1 μM<br>+++ < 0.1 μM<br>% at 5 μM | Assay B<br>0 > 10 μM<br>+ > 1-10 μM<br>++ 0.1-1 μM<br>+++ < 0.1 μM<br>% at 1.25 μM |
|---|---|---|
| 384 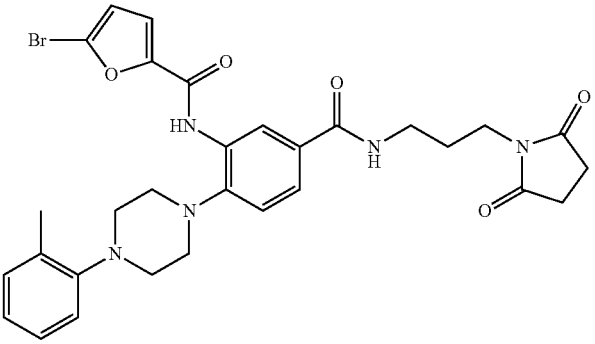 [SMILES: Cc1ccccc1N1CCN(c2ccc(C(=O)NCCCN3C(=O)CCC3=O)cc2NC(=O)c2ccc(Br)o2)CC1] | | ++ |
| 385 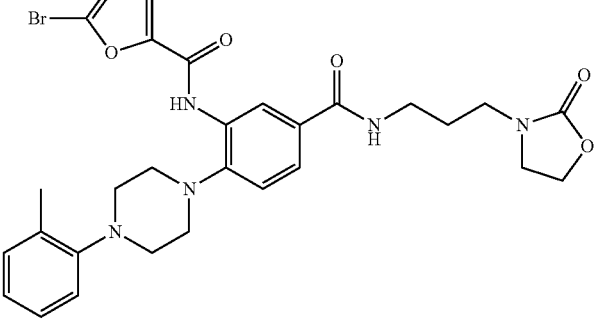 | | ++ |
| 386 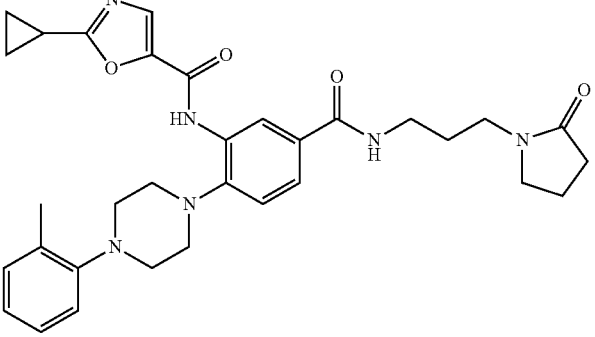 | | ++ |
| 387 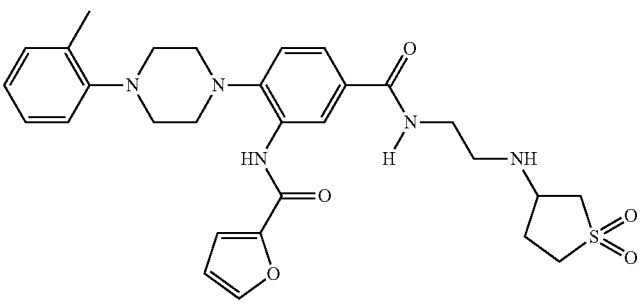 [SMILES: Cc1ccccc1N1CCN(c2ccc(C(=O)NCCNC3CCS(=O)(=O)C3)cc2NC(=O)c2ccco2)CC1] | | ++ |

TABLE 2-continued
Further compounds of formulae (I), (I-A), (I-B), (I-C).
Assay A: Example 10; Assay B: Example 11.
| Structure | Assay A<br>0 > 10 μM<br>+ > 1-10 μM<br>++ 0.1-1 μM<br>+++ < 0.1 μM<br>% at 5 μM | Assay B<br>0 > 10 μM<br>+ > 1-10 μM<br>++ 0.1-1 μM<br>+++ < 0.1 μM<br>% at 1.25 μM |
|---|---|---|
| 388 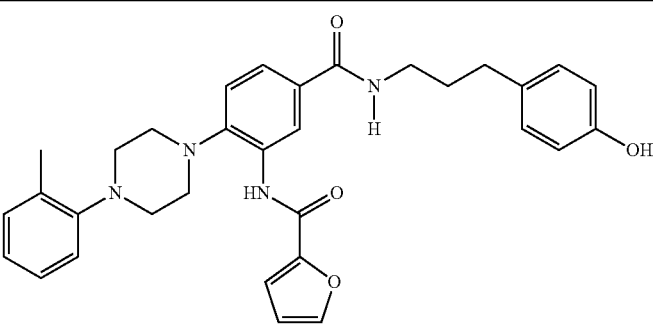 | | +++ |
| 389 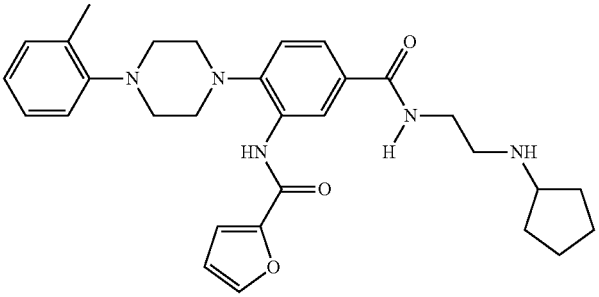 [SMILES: Cc1ccccc1N1CCN(c2ccc(C(=O)NCCNC3CCCC3)cc2NC(=O)c2ccco2)CC1] | | 0 |
| 390 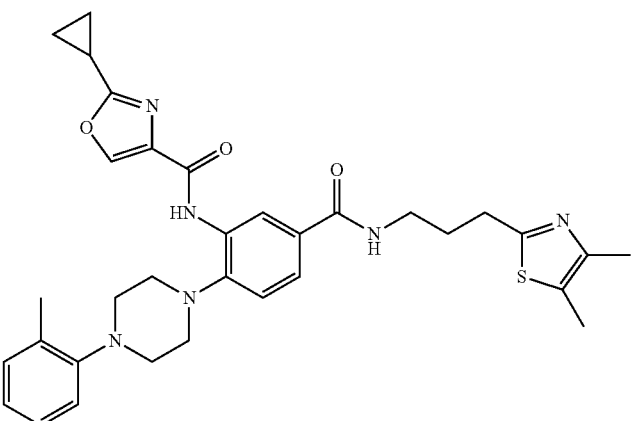 | | ++ |

US 9,938,262 B2
233 234
TABLE 2-continued
Further compounds of formulae (I), (I-A), (I-B), (I-C).
Assay A: Example 10; Assay B: Example 11.
| Structure | Assay A<br>0 > 10 μM<br>+ > 1-10 μM<br>++ 0.1-1 μM<br>+++ < 0.1 μM<br>% at 5 μM | Assay B<br>0 > 10 μM<br>+ > 1-10 μM<br>++ 0.1-1 μM<br>+++ < 0.1 μM<br>% at 1.25 μM |
|---|---|---|
| 391 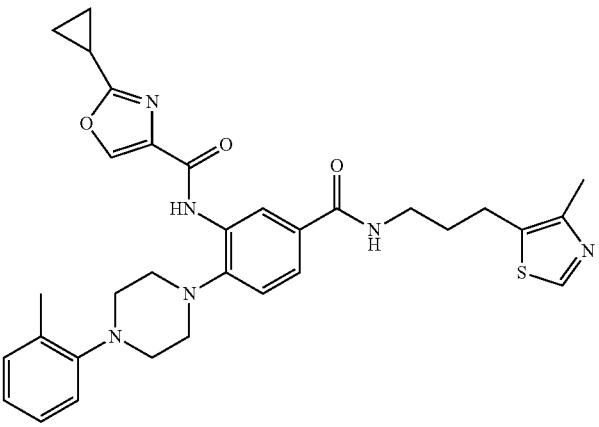 [SMILES: Cc1ccccc1N1CCN(c2ccc(C(=O)NCCCc3scnc3C)cc2NC(=O)c2coc(C3CC3)n2)CC1] | | ++ |
| 392 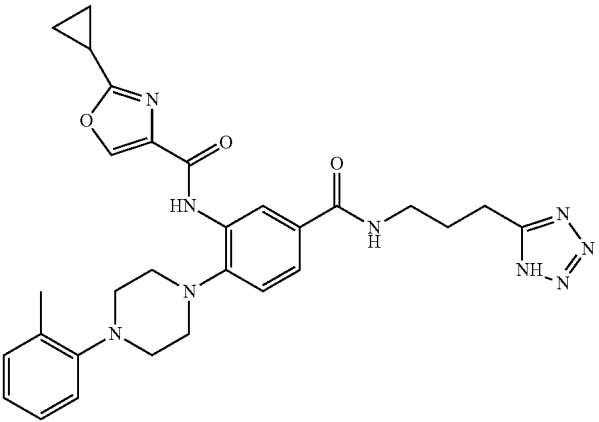 [SMILES: Cc1ccccc1N1CCN(c2ccc(C(=O)NCCCc3nnn[nH]3)cc2NC(=O)c2coc(C3CC3)n2)CC1] | +++ | ++ |
| 393 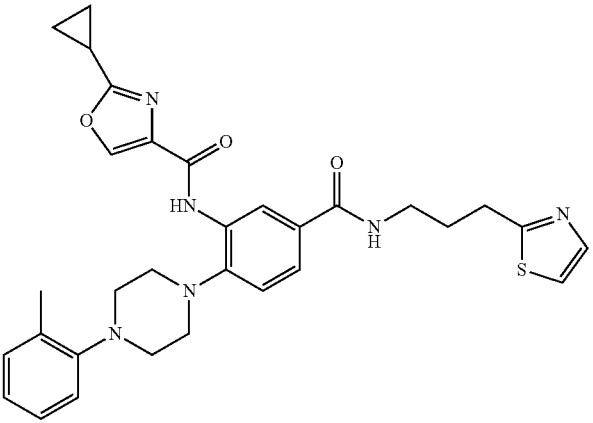 [SMILES: Cc1ccccc1N1CCN(c2ccc(C(=O)NCCCc3nccs3)cc2NC(=O)c2coc(C3CC3)n2)CC1] | | ++ |

TABLE 2-continued
Further compounds of formulae (I), (I-A), (I-B), (I-C).
Assay A: Example 10; Assay B: Example 11.
| Structure | Assay A<br>0 > 10 µM<br>+ > 1-10 µM<br>++ 0.1-1 µM<br>+++ < 0.1 µM<br>% at 5 µM | Assay B<br>0 > 10 µM<br>+ > 1-10 µM<br>++ 0.1-1 µM<br>+++ < 0.1 µM<br>% at 1.25 µM |
|---|---|---|
| 394 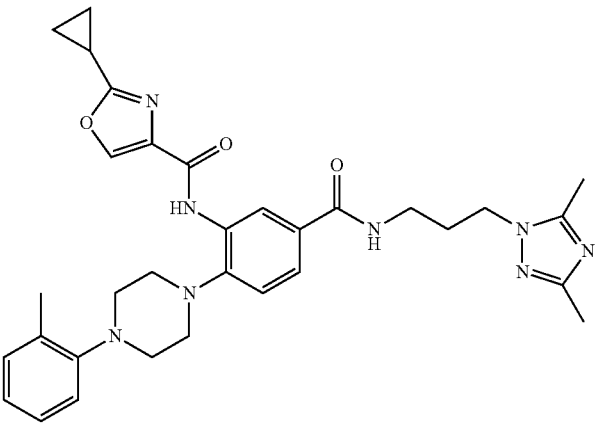 [SMILES: Cc1nc(C)n(CCCNC(=O)c2ccc(N3CCN(c4ccccc4C)CC3)c(NC(=O)c3coc(C4CC4)n3)c2)n1] | ++ | 50% |
| 395 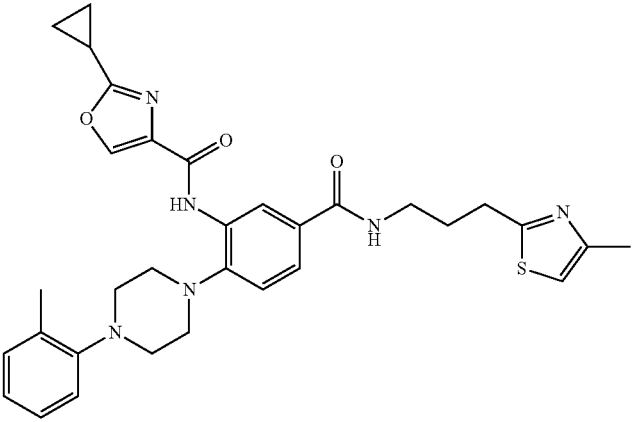 [SMILES: Cc1csc(CCCNC(=O)c2ccc(N3CCN(c4ccccc4C)CC3)c(NC(=O)c3coc(C4CC4)n3)c2)n1] | ++ | |
| 396 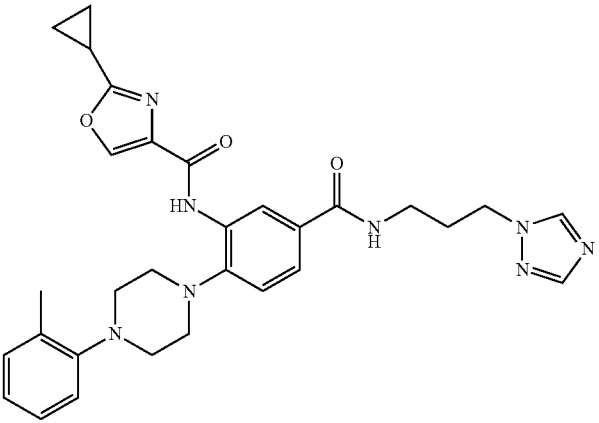 [SMILES: Cc1ccccc1N1CCN(c2ccc(C(=O)NCCCn3cncn3)cc2NC(=O)c2coc(C3CC3)n2)CC1] | ++ | |

TABLE 2-continued

Further compounds of formulae (I), (I-A), (I-B), (I-C).
Assay A: Example 10; Assay B: Example 11.

| Structure | Assay A<br>0 > 10 μM<br>+ > 1-10 μM<br>++ 0.1-1 μM<br>+++ < 0.1 μM<br>% at 5 μM | Assay B<br>0 > 10 μM<br>+ > 1-10 μM<br>++ 0.1-1 μM<br>+++ < 0.1 μM<br>% at 1.25 μM |
|---|---|---|
| 397 | | ++ |
| 398 | | ++ |
| 399 | | ++ |

TABLE 2-continued

Further compounds of formulae (I), (I-A), (I-B), (I-C).
Assay A: Example 10; Assay B: Example 11.

| Structure | Assay A<br>0 > 10 μM<br>+ > 1-10 μM<br>++ 0.1-1 μM<br>+++ < 0.1 μM<br>% at 5 μM | Assay B<br>0 > 10 μM<br>+ > 1-10 μM<br>++ 0.1-1 μM<br>+++ < 0.1 μM<br>% at 1.25 μM |
|---|---|---|
| 400 | | 0 |
| 401 | | 0 |
| 402 | | ++ |

TABLE 2-continued
Further compounds of formulae (I), (I-A), (I-B), (I-C).
Assay A: Example 10; Assay B: Example 11.
| Structure | Assay A<br>0 > 10 µM<br>+ > 1-10 µM<br>++ 0.1-1 µM<br>+++ < 0.1 µM<br>% at 5 µM | Assay B<br>0 > 10 µM<br>+ > 1-10 µM<br>++ 0.1-1 µM<br>+++ < 0.1 µM<br>% at 1.25 µM |
|---|---|---|
| 403 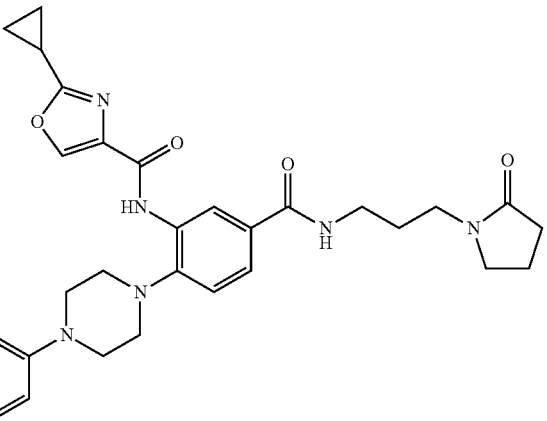 | | + |
| 404 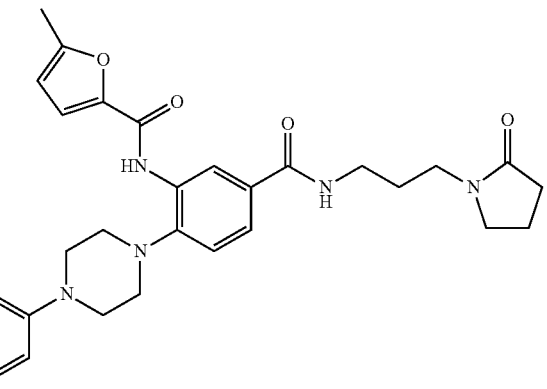 | | + |
| 405 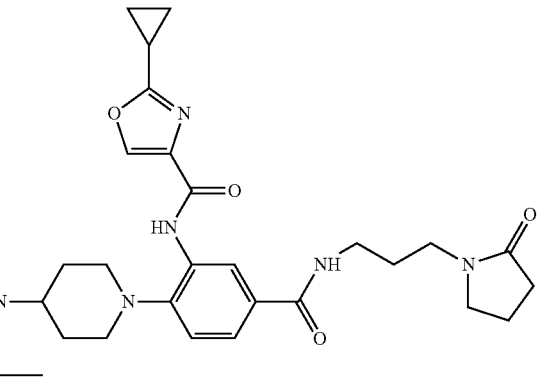 | | ++ |

TABLE 2-continued

Further compounds of formulae (I), (I-A), (I-B), (I-C).
Assay A: Example 10; Assay B: Example 11.

| Structure | Assay A<br>0 > 10 μM<br>+ > 1-10 μM<br>++ 0.1-1 μM<br>+++ < 0.1 μM<br>% at 5 μM | Assay B<br>0 > 10 μM<br>+ > 1-10 μM<br>++ 0.1-1 μM<br>+++ < 0.1 μM<br>% at 1.25 μM |
|---|---|---|
| 406 | | ++ |
| 407 | | 0 |
| 408 | | ++ |

TABLE 2-continued

Further compounds of formulae (I), (I-A), (I-B), (I-C).
Assay A: Example 10; Assay B: Example 11.

| Structure | Assay A<br>0 > 10 μM<br>+ > 1-10 μM<br>++ 0.1-1 μM<br>+++ < 0.1 μM<br>% at 5 μM | Assay B<br>0 > 10 μM<br>+ > 1-10 μM<br>++ 0.1-1 μM<br>+++ < 0.1 μM<br>% at 1.25 μM |
|---|---|---|
| 409 | 0 | |
| 410 | ++ | + |
| 411 | ++ | |

TABLE 2-continued
Further compounds of formulae (I), (I-A), (I-B), (I-C).
Assay A: Example 10; Assay B: Example 11.
| Structure | Assay A<br>0 > 10 μM<br>+ > 1-10 μM<br>++ 0.1-1 μM<br>+++ < 0.1 μM<br>% at 5 μM | Assay B<br>0 > 10 μM<br>+ > 1-10 μM<br>++ 0.1-1 μM<br>+++ < 0.1 μM<br>% at 1.25 μM |
|---|---|---|
| 412 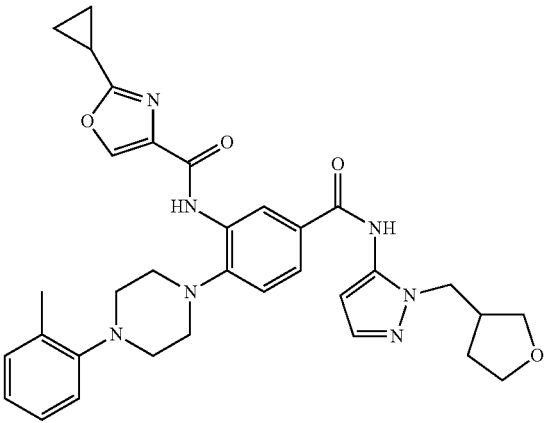 [SMILES: Cc1ccccc1N1CCN(c2ccc(C(=O)Nc3ccnn3CC3CCOC3)cc2NC(=O)c2coc(C3CC3)n2)CC1] | | + |
| 413 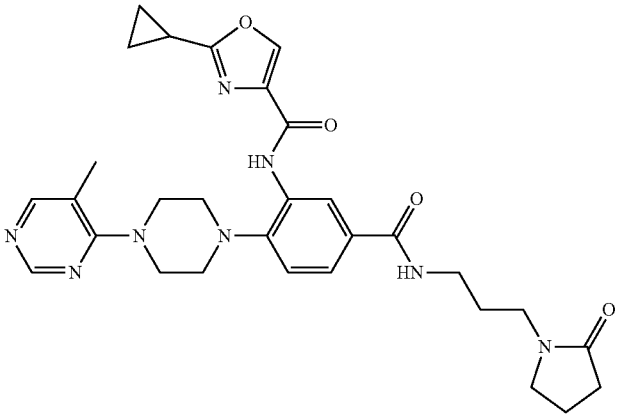 [SMILES: Cc1cncnc1N1CCN(c2ccc(C(=O)NCCCN3CCCC3=O)cc2NC(=O)c2coc(C3CC3)n2)CC1] | | + |
| 414 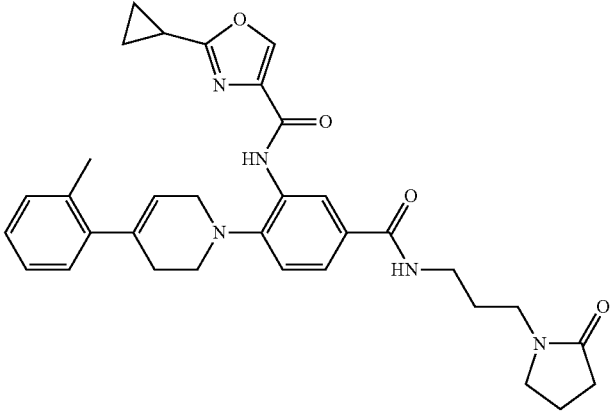 [SMILES: Cc1ccccc1C1=CCN(c2ccc(C(=O)NCCCN3CCCC3=O)cc2NC(=O)c2coc(C3CC3)n2)CC1] | | ++ |

TABLE 2-continued
Further compounds of formulae (I), (I-A), (I-B), (I-C).
Assay A: Example 10; Assay B: Example 11.
| Structure | Assay A<br>0 > 10 μM<br>+ > 1-10 μM<br>++ 0.1-1 μM<br>+++ < 0.1 μM<br>% at 5 μM | Assay B<br>0 > 10 μM<br>+ > 1-10 μM<br>++ 0.1-1 μM<br>+++ < 0.1 μM<br>% at 1.25 μM |
|---|---|---|
| 415 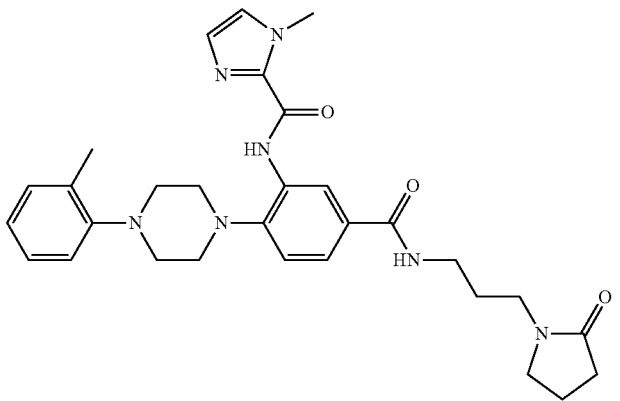 [SMILES: Cc1ccccc1N1CCN(c2ccc(C(=O)NCCCN3CCCC3=O)cc2NC(=O)c2nccn2C)CC1] | 0 | |
| 416 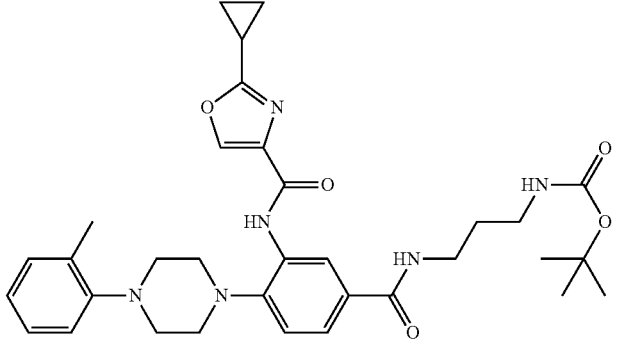 [SMILES: Cc1ccccc1N1CCN(c2ccc(C(=O)NCCCNC(=O)OC(C)(C)C)cc2NC(=O)c2coc(C3CC3)n2)CC1] | | ++ |
| 417 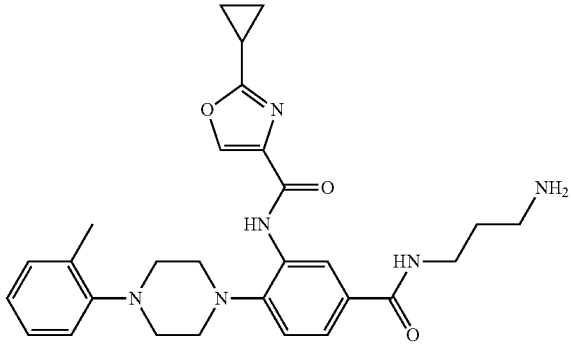 [SMILES: Cc1ccccc1N1CCN(c2ccc(C(=O)NCCCN)cc2NC(=O)c2coc(C3CC3)n2)CC1] | | + |

TABLE 2-continued
Further compounds of formulae (I), (I-A), (I-B), (I-C).
Assay A: Example 10; Assay B: Example 11.
| Structure | Assay A<br>0 > 10 μM<br>+ > 1-10 μM<br>++ 0.1-1 μM<br>+++ < 0.1 μM<br>% at 5 μM | Assay B<br>0 > 10 μM<br>+ > 1-10 μM<br>++ 0.1-1 μM<br>+++ < 0.1 μM<br>% at 1.25 μM |
|---|---|---|
| 418 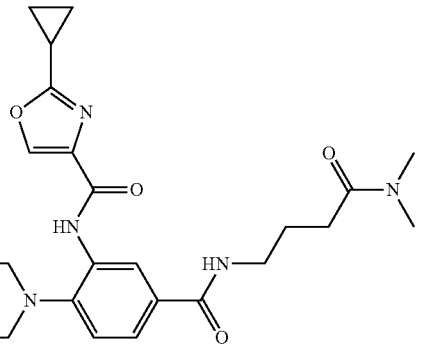 | | ++ |
| 419 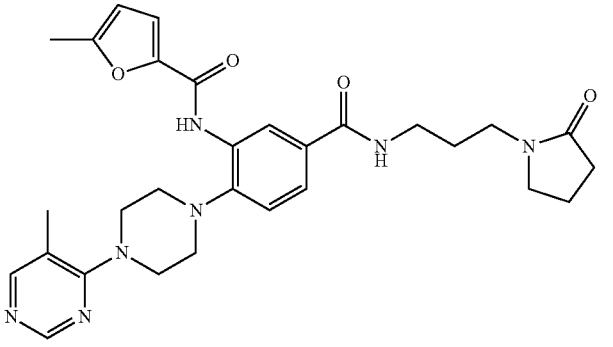 [SMILES: Cc1ccc(C(=O)Nc2cc(C(=O)NCCCN3CCCC3=O)ccc2N2CCN(c3ncncc3C)CC2)o1] | | 0 |
| 420 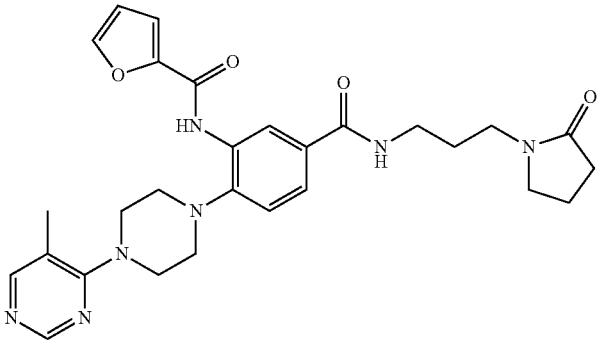 [SMILES: Cc1cncnc1N1CCN(c2ccc(C(=O)NCCCN3CCCC3=O)cc2NC(=O)c2ccco2)CC1] | | 0 |
| 421 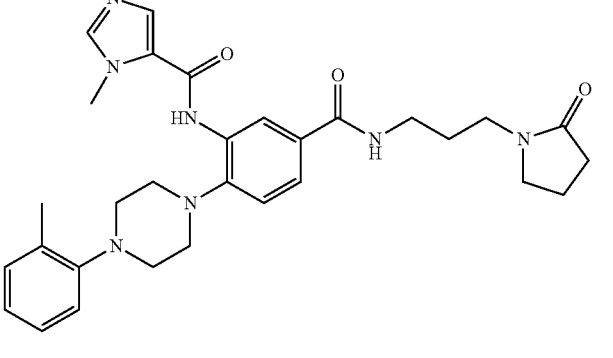 | | 0 |

TABLE 2-continued

Further compounds of formulae (I), (I-A), (I-B), (I-C).
Assay A: Example 10; Assay B: Example 11.

| Structure | Assay A<br>0 > 10 μM<br>+ > 1-10 μM<br>++ 0.1-1 μM<br>+++ < 0.1 μM<br>% at 5 μM | Assay B<br>0 > 10 μM<br>+ > 1-10 μM<br>++ 0.1-1 μM<br>+++ < 0.1 μM<br>% at 1.25 μM |
|---|---|---|
| 422 | | 0 |
| 423 | | 0 |
| 424 | | ++ |

TABLE 2-continued

Further compounds of formulae (I), (I-A), (I-B), (I-C).
Assay A: Example 10; Assay B: Example 11.

| Structure | Assay A<br>0 > 10 μM<br>+ > 1-10 μM<br>++ 0.1-1 μM<br>+++ < 0.1 μM<br>% at 5 μM | Assay B<br>0 > 10 μM<br>+ > 1-10 μM<br>++ 0.1-1 μM<br>+++ < 0.1 μM<br>% at 1.25 μM |
|---|---|---|
| 425 | | ++ |
| 426 | | ++ |
| 427 | | ++ |

TABLE 2-continued
Further compounds of formulae (I), (I-A), (I-B), (I-C).
Assay A: Example 10; Assay B: Example 11.
| Structure | Assay A<br>0 > 10 μM<br>+ > 1-10 μM<br>++ 0.1-1 μM<br>+++ < 0.1 μM<br>% at 5 μM | Assay B<br>0 > 10 μM<br>+ > 1-10 μM<br>++ 0.1-1 μM<br>+++ < 0.1 μM<br>% at 1.25 μM |
|---|---|---|
| 428 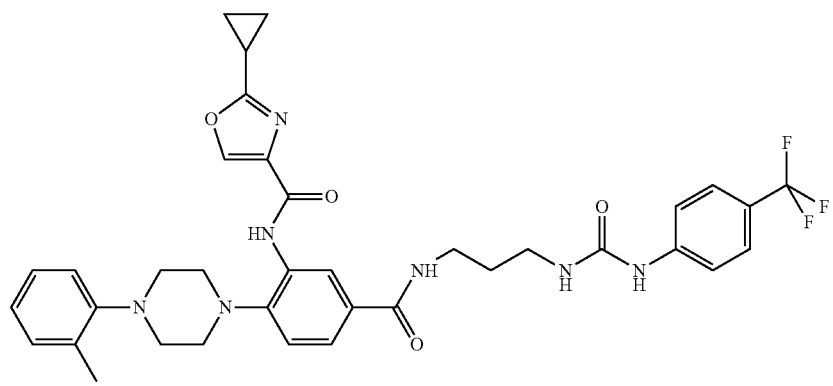 [SMILES: Cc1ccccc1N1CCN(c2ccc(C(=O)NCCCNC(=O)Nc3ccc(C(F)(F)F)cc3)cc2NC(=O)c2coc(C3CC3)n2)CC1] | | 0 |
| 429 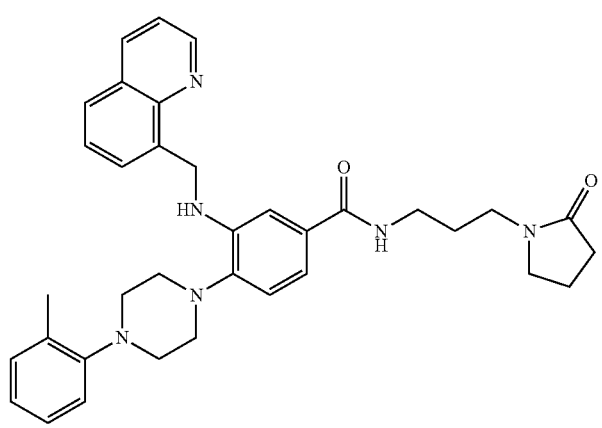 [SMILES: Cc1ccccc1N1CCN(c2ccc(C(=O)NCCCN3CCCC3=O)cc2NCc2cccc3cccnc23)CC1] | | ++ |
| 430 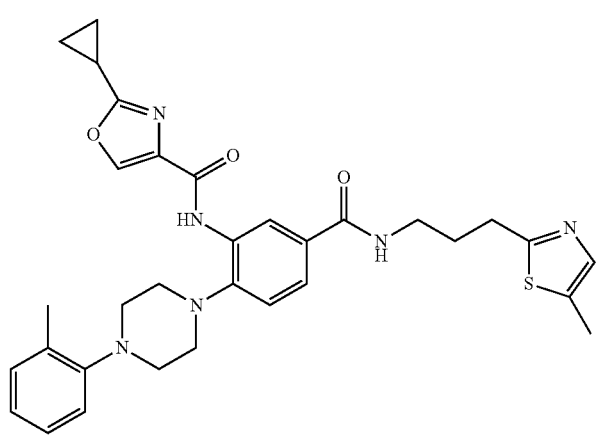 [SMILES: Cc1cnc(CCCNC(=O)c2ccc(N3CCN(c4ccccc4C)CC3)c(NC(=O)c3coc(C4CC4)n3)c2)s1] | | ++ |

TABLE 2-continued

Further compounds of formulae (I), (I-A), (I-B), (I-C).
Assay A: Example 10; Assay B: Example 11.

| Structure | Assay A<br>0 > 10 μM<br>+ > 1-10 μM<br>++ 0.1-1 μM<br>+++ < 0.1 μM<br>% at 5 μM | Assay B<br>0 > 10 μM<br>+ > 1-10 μM<br>++ 0.1-1 μM<br>+++ < 0.1 μM<br>% at 1.25 μM |
|---|---|---|
| 431 | | 0 |
| 432 | | + |
| 433 | | ++ |

TABLE 2-continued
Further compounds of formulae (I), (I-A), (I-B), (I-C).
Assay A: Example 10; Assay B: Example 11.
| Structure | Assay A<br>0 > 10 μM<br>+ > 1-10 μM<br>++ 0.1-1 μM<br>+++ < 0.1 μM<br>% at 5 μM | Assay B<br>0 > 10 μM<br>+ > 1-10 μM<br>++ 0.1-1 μM<br>+++ < 0.1 μM<br>% at 1.25 μM |
|---|---|---|
| 434 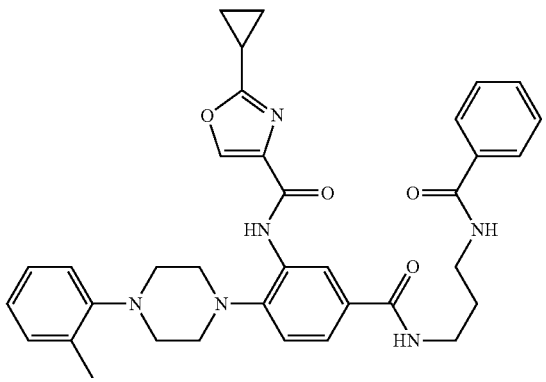 [SMILES: Cc1ccccc1N1CCN(c2ccc(C(=O)NCCCNC(=O)c3ccccc3)cc2NC(=O)c2coc(C3CC3)n2)CC1] | ++ | |
| 435 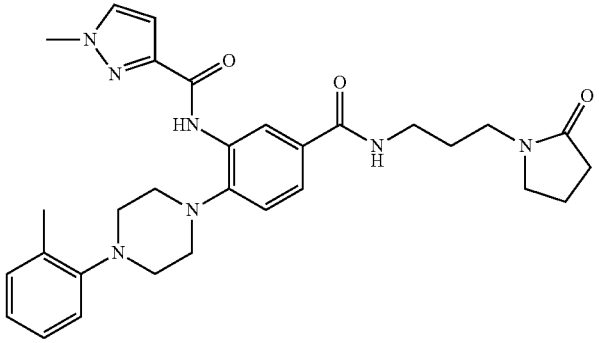 [SMILES: Cc1ccccc1N1CCN(c2ccc(C(=O)NCCCN3CCCC3=O)cc2NC(=O)c2ccn(C)n2)CC1] | ++ | ++ |
| 436 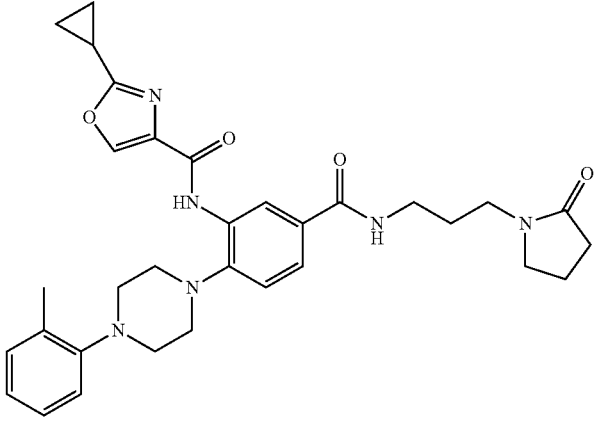 [SMILES: Cc1ccccc1N1CCN(c2ccc(C(=O)NCCCN3CCCC3=O)cc2NC(=O)c2coc(C3CC3)n2)CC1] | ++ | |

TABLE 2-continued
Further compounds of formulae (I), (I-A), (I-B), (I-C).
Assay A: Example 10; Assay B: Example 11.
| Structure | Assay A<br>0 > 10 µM<br>+ > 1-10 µM<br>++ 0.1-1 µM<br>+++ < 0.1 µM<br>% at 5 µM | Assay B<br>0 > 10 µM<br>+ > 1-10 µM<br>++ 0.1-1 µM<br>+++ < 0.1 µM<br>% at 1.25 µM |
|---|---|---|
| 437 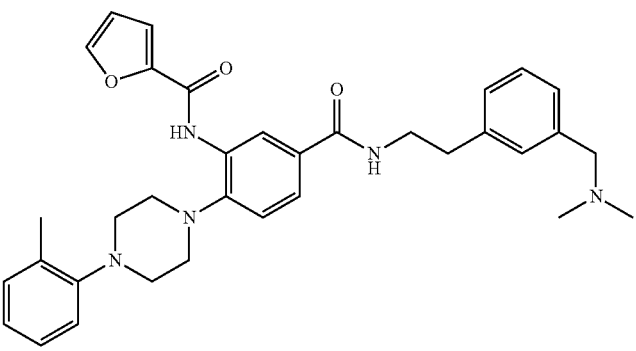 [SMILES: Cc1ccccc1N1CCN(c2ccc(C(=O)NCCc3cccc(CN(C)C)c3)cc2NC(=O)c2ccco2)CC1] | | ++ |
| 438 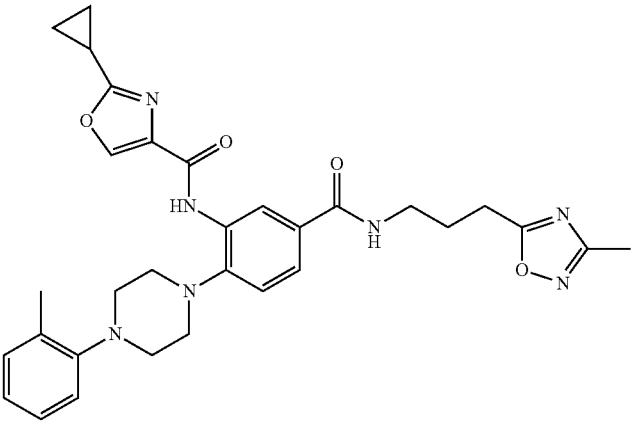 [SMILES: Cc1noc(CCCNC(=O)c2ccc(N3CCN(c4ccccc4C)CC3)c(NC(=O)c3coc(C4CC4)n3)c2)n1] | | ++ |
| 439 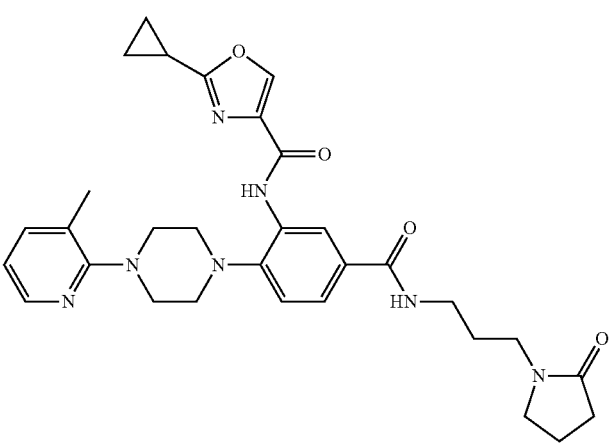 [SMILES: Cc1cccnc1N1CCN(c2ccc(C(=O)NCCCN3CCCC3=O)cc2NC(=O)c2coc(C3CC3)n2)CC1] | | +++ |

TABLE 2-continued

Further compounds of formulae (I), (I-A), (I-B), (I-C).
Assay A: Example 10; Assay B: Example 11.

| Structure | Assay A<br>0 > 10 μM<br>+ > 1-10 μM<br>++ 0.1-1 μM<br>+++ < 0.1 μM<br>% at 5 μM | Assay B<br>0 > 10 μM<br>+ > 1-10 μM<br>++ 0.1-1 μM<br>+++ < 0.1 μM<br>% at 1.25 μM |
|---|---|---|
| 440 | | ++ |
| 441 | | +++ |
| 442 | | ++ |

TABLE 2-continued
Further compounds of formulae (I), (I-A), (I-B), (I-C).
Assay A: Example 10; Assay B: Example 11.
| Structure | Assay A<br>0 > 10 μM<br>+ > 1-10 μM<br>++ 0.1-1 μM<br>+++ < 0.1 μM<br>% at 5 μM | Assay B<br>0 > 10 μM<br>+ > 1-10 μM<br>++ 0.1-1 μM<br>+++ < 0.1 μM<br>% at 1.25 μM |
|---|---|---|
| 443 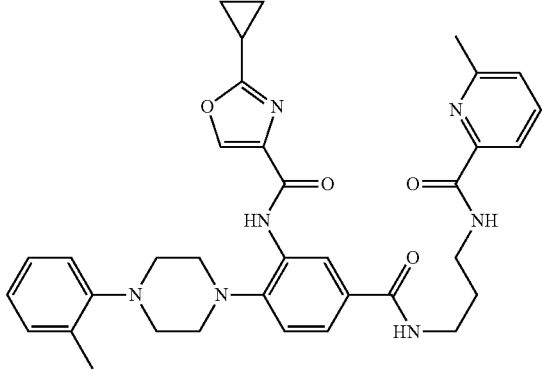 [SMILES: Cc1cccc(C(=O)NCCCNC(=O)c2ccc(N3CCN(c4ccccc4C)CC3)c(NC(=O)c3coc(C4CC4)n3)c2)n1] | | ++ |
| 444 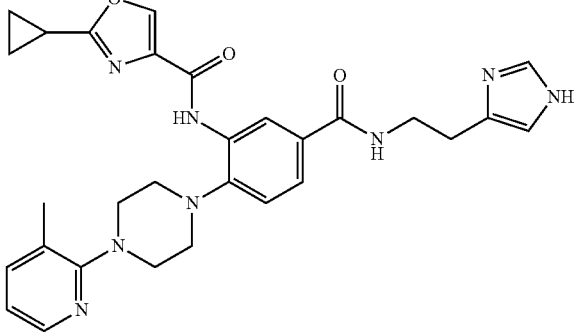 | | ++ |
| 445 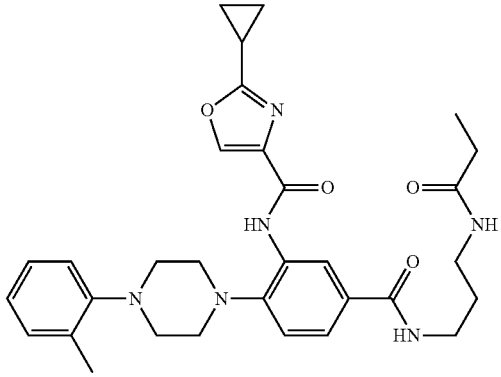 [SMILES: CCC(=O)NCCCNC(=O)c1ccc(N2CCN(c3ccccc3C)CC2)c(NC(=O)c2coc(C3CC3)n2)c1] | | +++ |

TABLE 2-continued
Further compounds of formulae (I), (I-A), (I-B), (I-C).
Assay A: Example 10; Assay B: Example 11.
| Structure | Assay A<br>0 > 10 μM<br>+ > 1-10 μM<br>++ 0.1-1 μM<br>+++ < 0.1 μM<br>% at 5 μM | Assay B<br>0 > 10 μM<br>+ > 1-10 μM<br>++ 0.1-1 μM<br>+++ < 0.1 μM<br>% at 1.25 μM |
|---|---|---|
| 446 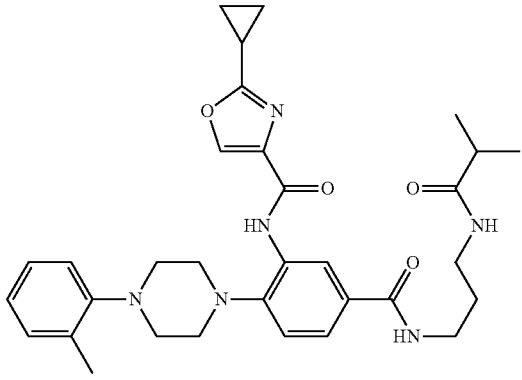 [SMILES: Cc1ccccc1N1CCN(c2ccc(C(=O)NCCCNC(=O)C(C)C)cc2NC(=O)c2coc(C3CC3)n2)CC1] | | ++ |
| 447 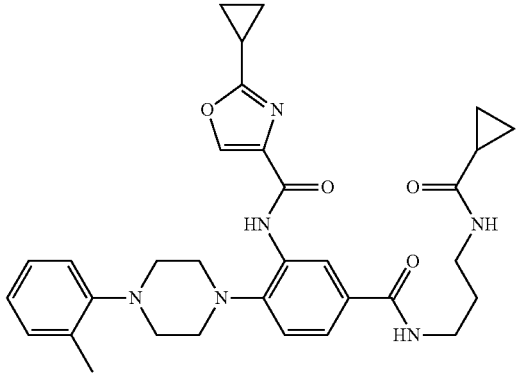 [SMILES: Cc1ccccc1N1CCN(c2ccc(C(=O)NCCCNC(=O)C3CC3)cc2NC(=O)c2coc(C3CC3)n2)CC1] | | ++ |
| 448 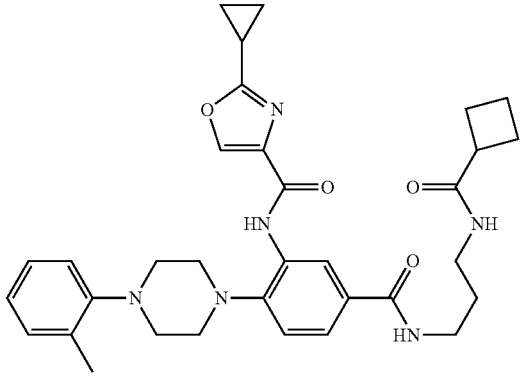 [SMILES: Cc1ccccc1N1CCN(c2ccc(C(=O)NCCCNC(=O)C3CCC3)cc2NC(=O)c2coc(C3CC3)n2)CC1] | | ++ |

TABLE 2-continued

Further compounds of formulae (I), (I-A), (I-B), (I-C).
Assay A: Example 10; Assay B: Example 11.

| Structure | Assay A<br>0 > 10 μM<br>+ > 1-10 μM<br>++ 0.1-1 μM<br>+++ < 0.1 μM<br>% at 5 μM | Assay B<br>0 > 10 μM<br>+ > 1-10 μM<br>++ 0.1-1 μM<br>+++ < 0.1 μM<br>% at 1.25 μM |
|---|---|---|
| 449 | | ++ |
| 450 | | |
| 451 | | ++ |
| 452 | | + |

TABLE 2-continued

Further compounds of formulae (I), (I-A), (I-B), (I-C).
Assay A: Example 10; Assay B: Example 11.

| Structure | Assay A<br>0 > 10 μM<br>+ > 1-10 μM<br>++ 0.1-1 μM<br>+++ < 0.1 μM<br>% at 5 μM | Assay B<br>0 > 10 μM<br>+ > 1-10 μM<br>++ 0.1-1 μM<br>+++ < 0.1 μM<br>% at 1.25 μM |
|---|---|---|
| 453 | | ++ |
| 454 | | ++ |
| 455 | | ++ |
| 456 | | ++ |

TABLE 2-continued
Further compounds of formulae (I), (I-A), (I-B), (I-C).
Assay A: Example 10; Assay B: Example 11.
| Structure | Assay A<br>0 > 10 μM<br>+ > 1-10 μM<br>++ 0.1-1 μM<br>+++ < 0.1 μM<br>% at 5 μM | Assay B<br>0 > 10 μM<br>+ > 1-10 μM<br>++ 0.1-1 μM<br>+++ < 0.1 μM<br>% at 1.25 μM |
|---|---|---|
| 457 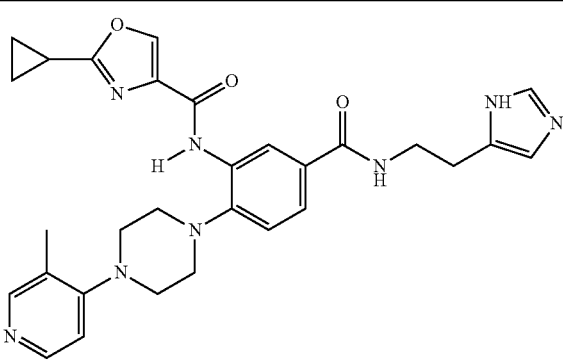 | | + |
| 458 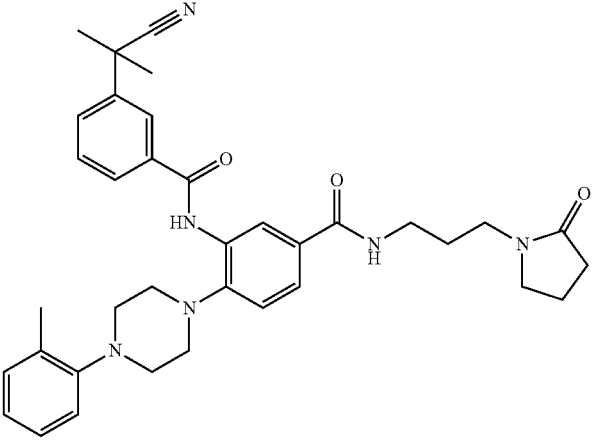 [SMILES: Cc1ccccc1N1CCN(c2ccc(C(=O)NCCCN3CCCC3=O)cc2NC(=O)c2cccc(C(C)(C)C#N)c2)CC1] | | |
| 459 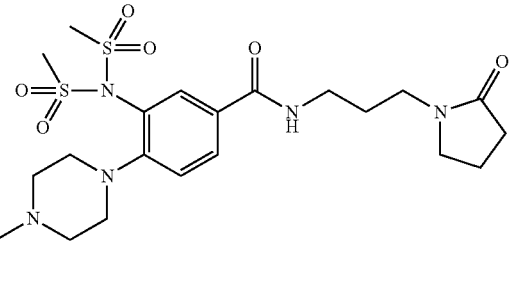 | | |

TABLE 2-continued
Further compounds of formulae (I), (I-A), (I-B), (I-C).
Assay A: Example 10; Assay B: Example 11.
| Structure | Assay A<br>0 > 10 μM<br>+ > 1-10 μM<br>++ 0.1-1 μM<br>+++ < 0.1 μM<br>% at 5 μM | Assay B<br>0 > 10 μM<br>+ > 1-10 μM<br>++ 0.1-1 μM<br>+++ < 0.1 μM<br>% at 1.25 μM |
|---|---|---|
| 460 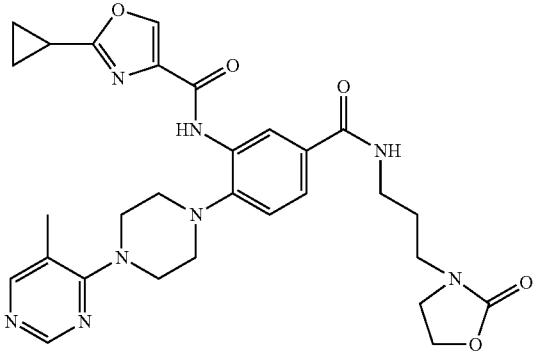 [SMILES: Cc1cncnc1N1CCN(c2ccc(C(=O)NCCCN3CCOC3=O)cc2NC(=O)c2coc(C3CC3)n2)CC1] | | ++ |
| 461 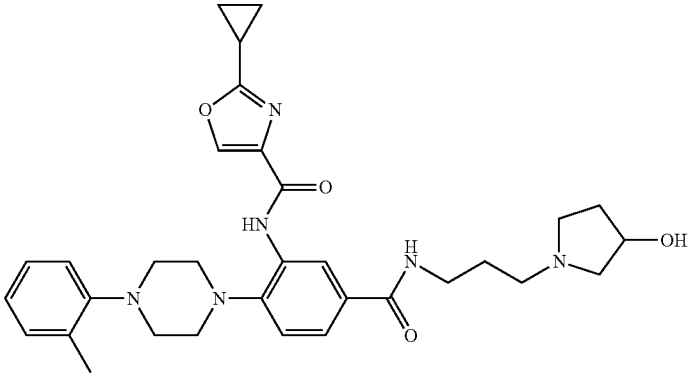 [SMILES: Cc1ccccc1N1CCN(c2ccc(C(=O)NCCCN3CCC(O)C3)cc2NC(=O)c2coc(C3CC3)n2)CC1] | | ++ |
| 462 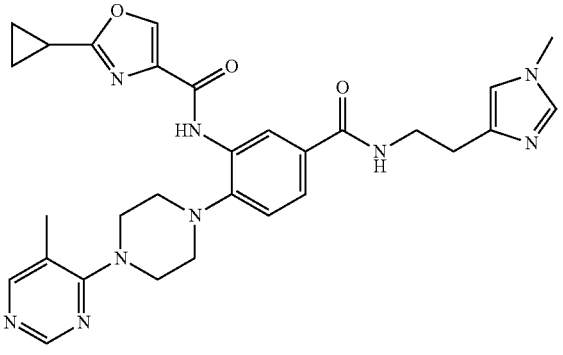 [SMILES: Cc1cncnc1N1CCN(c2ccc(C(=O)NCCc3cn(C)cn3)cc2NC(=O)c2coc(C3CC3)n2)CC1] | | + |
| 463 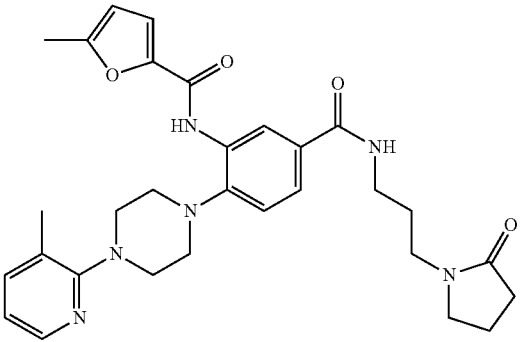 [SMILES: Cc1ccc(C(=O)Nc2cc(C(=O)NCCCN3CCCC3=O)ccc2N2CCN(c3ncccc3C)CC2)o1] | | ++ |

TABLE 2-continued
Further compounds of formulae (I), (I-A), (I-B), (I-C).
Assay A: Example 10; Assay B: Example 11.
| Structure | Assay A<br>0 > 10 μM<br>+ > 1-10 μM<br>++ 0.1-1 μM<br>+++ < 0.1 μM<br>% at 5 μM | Assay B<br>0 > 10 μM<br>+ > 1-10 μM<br>++ 0.1-1 μM<br>+++ < 0.1 μM<br>% at 1.25 μM |
|---|---|---|
| 464 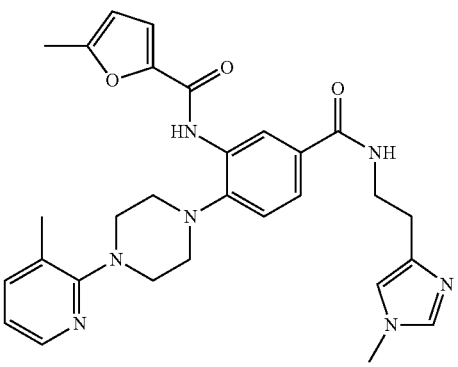 [SMILES: Cc1ccc(C(=O)Nc2cc(C(=O)NCCc3cn(C)cn3)ccc2N2CCN(c3ncccc3C)CC2)o1] | | + |
| 465 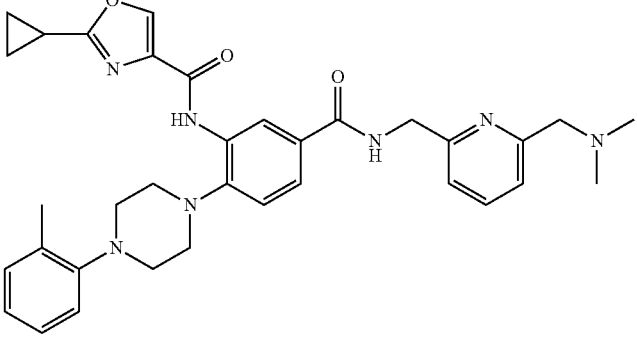 | | ++ |
| 466 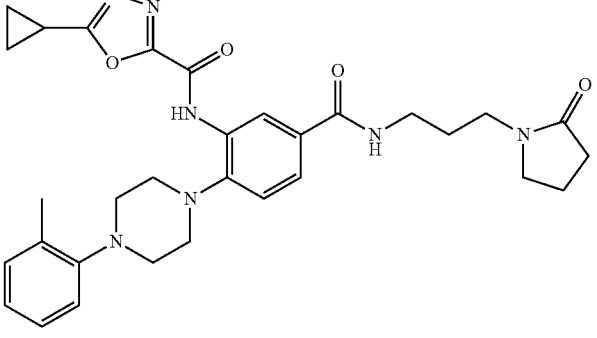 | | + |
| 467 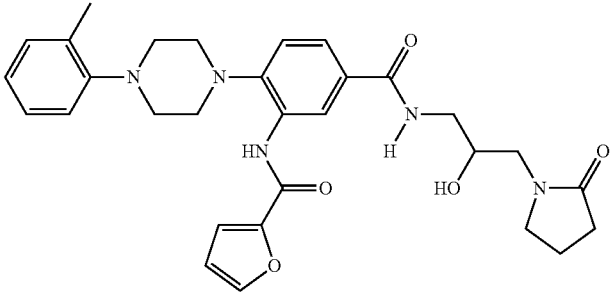 [SMILES: Cc1ccccc1N1CCN(c2ccc(C(=O)NCC(O)CN3CCCC3=O)cc2NC(=O)c2ccco2)CC1] | | +++ |

TABLE 2-continued
Further compounds of formulae (I), (I-A), (I-B), (I-C).
Assay A: Example 10; Assay B: Example 11.
| Structure | Assay A<br>0 > 10 µM<br>+ > 1-10 µM<br>++ 0.1-1 µM<br>+++ < 0.1 µM<br>% at 5 µM | Assay B<br>0 > 10 µM<br>+ > 1-10 µM<br>++ 0.1-1 µM<br>+++ < 0.1 µM<br>% at 1.25 µM |
|---|---|---|
| 468 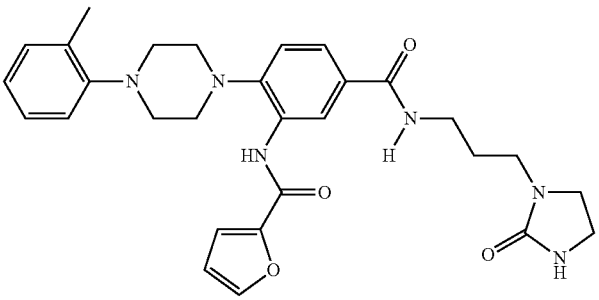 | | +++ |
| 469 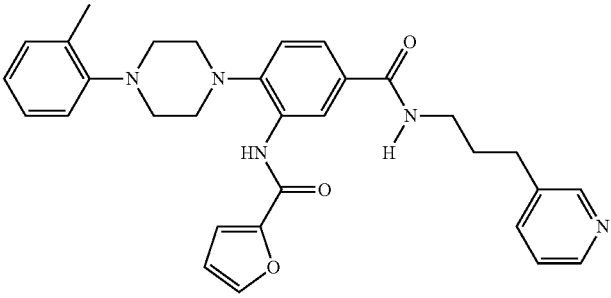 [SMILES: Cc1ccccc1N1CCN(c2ccc(C(=O)NCCCc3cccnc3)cc2NC(=O)c2ccco2)CC1] | | ++ |
| 470 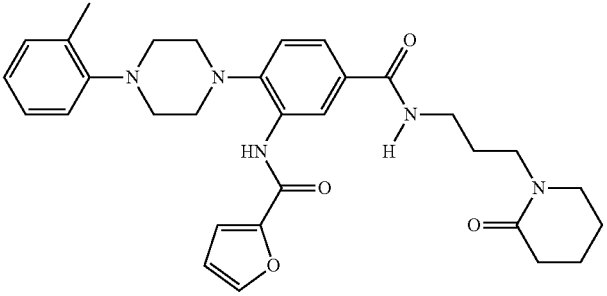 [SMILES: Cc1ccccc1N1CCN(c2ccc(C(=O)NCCCN3CCCCC3=O)cc2NC(=O)c2ccco2)CC1] | | ++ |
| 471 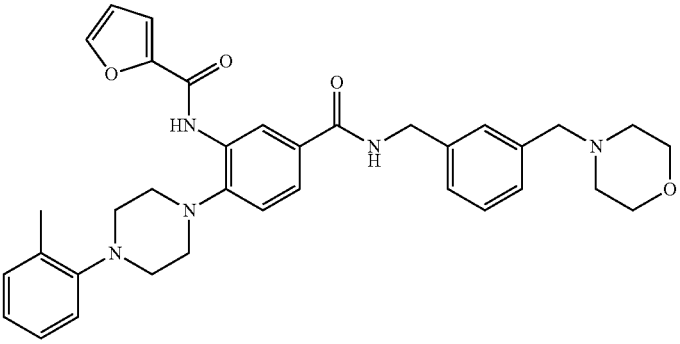 [SMILES: Cc1ccccc1N1CCN(c2ccc(C(=O)NCc3cccc(CN4CCOCC4)c3)cc2NC(=O)c2ccco2)CC1] | | ++ |

TABLE 2-continued
Further compounds of formulae (I), (I-A), (I-B), (I-C).
Assay A: Example 10; Assay B: Example 11.
| Structure | Assay A<br>0 > 10 μM<br>+ > 1-10 μM<br>++ 0.1-1 μM<br>+++ < 0.1 μM<br>% at 5 μM | Assay B<br>0 > 10 μM<br>+ > 1-10 μM<br>++ 0.1-1 μM<br>+++ < 0.1 μM<br>% at 1.25 μM |
|---|---|---|
| 472 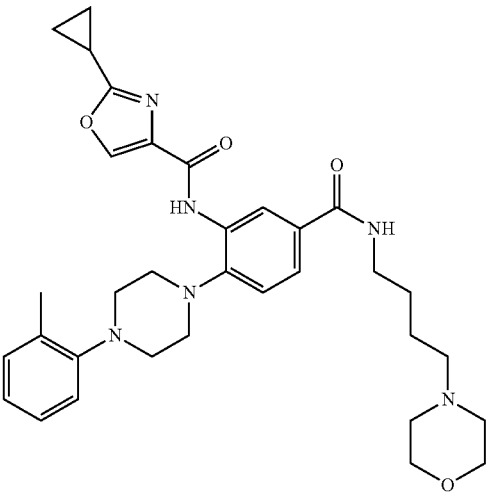 [SMILES: Cc1ccccc1N1CCN(c2ccc(C(=O)NCCCCN3CCOCC3)cc2NC(=O)c2coc(C3CC3)n2)CC1] | | ++ |
| 473 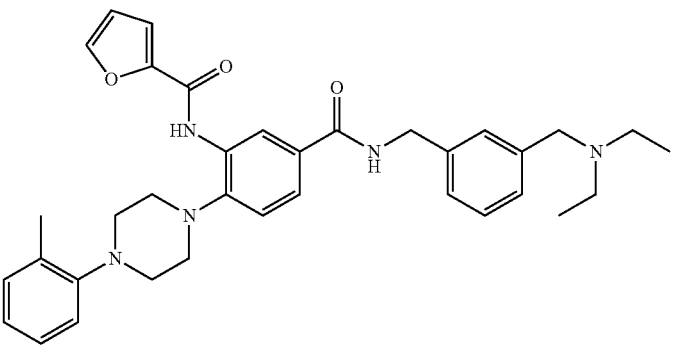 [SMILES: CCN(CC)Cc1cccc(CNC(=O)c2ccc(N3CCN(c4ccccc4C)CC3)c(NC(=O)c3ccco3)c2)c1] | | ++ |
| 474 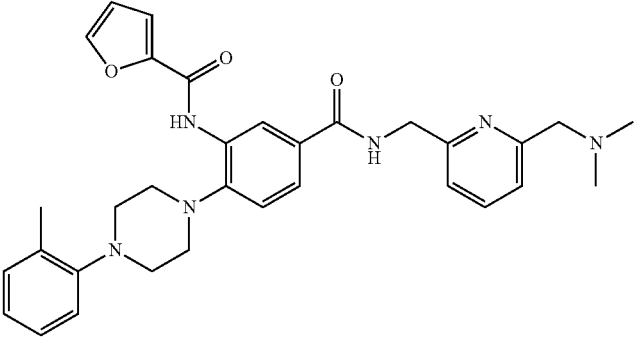 [SMILES: Cc1ccccc1N1CCN(c2ccc(C(=O)NCc3cccc(CN(C)C)n3)cc2NC(=O)c2ccco2)CC1] | | +++ |

TABLE 2-continued

Further compounds of formulae (I), (I-A), (I-B), (I-C).
Assay A: Example 10; Assay B: Example 11.

| Structure | Assay A<br>0 > 10 μM<br>+ > 1-10 μM<br>++ 0.1-1 μM<br>+++ < 0.1 μM<br>% at 5 μM | Assay B<br>0 > 10 μM<br>+ > 1-10 μM<br>++ 0.1-1 μM<br>+++ < 0.1 μM<br>% at 1.25 μM |
|---|---|---|
| 475 | | 0 |
| 476 | | |
| 477 | | +++ |
| 478 | | +++ |

TABLE 2-continued

Further compounds of formulae (I), (I-A), (I-B), (I-C).
Assay A: Example 10; Assay B: Example 11.

| Structure | Assay A<br>0 > 10 μM<br>+ > 1-10 μM<br>++ 0.1-1 μM<br>+++ < 0.1 μM<br>% at 5 μM | Assay B<br>0 > 10 μM<br>+ > 1-10 μM<br>++ 0.1-1 μM<br>+++ < 0.1 μM<br>% at 1.25 μM |
|---|---|---|
| 479 | | ++ |
| 480 (2 HCl) | | +++ |
| 481 | | ++ |

TABLE 2-continued
Further compounds of formulae (I), (I-A), (I-B), (I-C).
Assay A: Example 10; Assay B: Example 11.
| Structure | Assay A<br>0 > 10 μM<br>+ > 1-10 μM<br>++ 0.1-1 μM<br>+++ < 0.1 μM<br>% at 5 μM | Assay B<br>0 > 10 μM<br>+ > 1-10 μM<br>++ 0.1-1 μM<br>+++ < 0.1 μM<br>% at 1.25 μM |
|---|---|---|
| 482 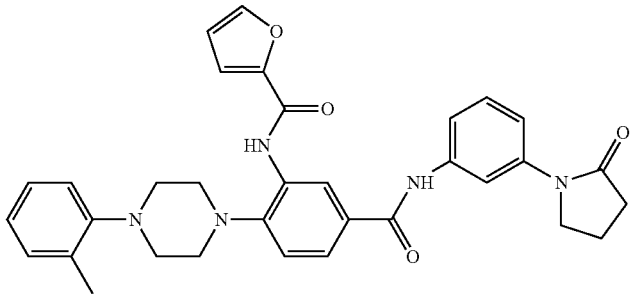 [SMILES: Cc1ccccc1N1CCN(c2ccc(C(=O)Nc3cccc(N4CCCC4=O)c3)cc2NC(=O)c2ccco2)CC1] | | + |
| 483 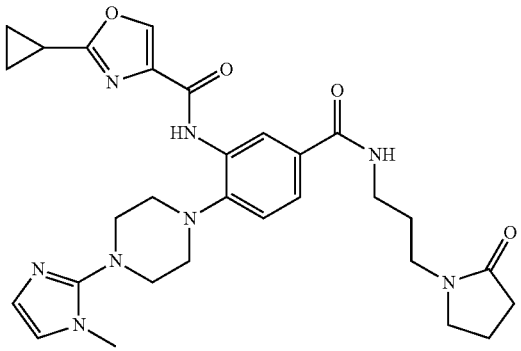 [SMILES: Cn1ccnc1N1CCN(c2ccc(C(=O)NCCCN3CCCC3=O)cc2NC(=O)c2coc(C3CC3)n2)CC1] | | + |
| 484 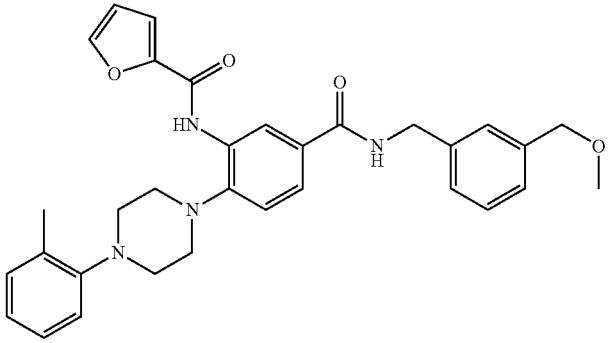 [SMILES: COCc1cccc(CNC(=O)c2ccc(N3CCN(c4ccccc4C)CC3)c(NC(=O)c3ccco3)c2)c1] | | ++ |
| 485 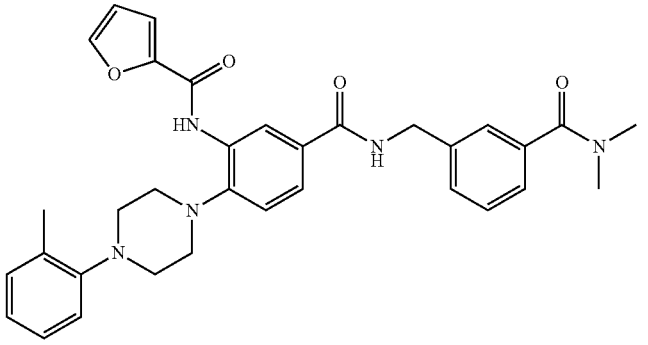 [SMILES: Cc1ccccc1N1CCN(c2ccc(C(=O)NCc3cccc(C(=O)N(C)C)c3)cc2NC(=O)c2ccco2)CC1] | | ++ |

TABLE 2-continued
Further compounds of formulae (I), (I-A), (I-B), (I-C).
Assay A: Example 10; Assay B: Example 11.
| Structure | Assay A<br>0 > 10 μM<br>+ > 1-10 μM<br>++ 0.1-1 μM<br>+++ < 0.1 μM<br>% at 5 μM | Assay B<br>0 > 10 μM<br>+ > 1-10 μM<br>++ 0.1-1 μM<br>+++ < 0.1 μM<br>% at 1.25 μM |
|---|---|---|
| 486 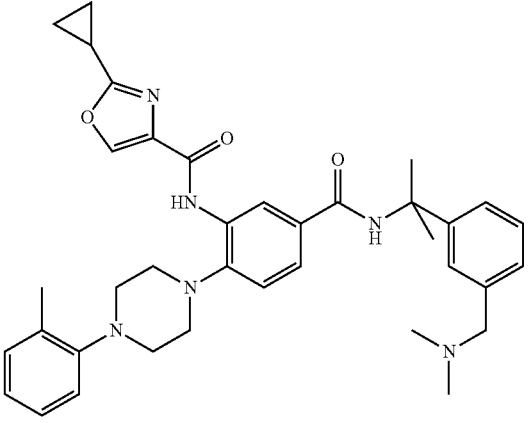 [SMILES: Cc1ccccc1N1CCN(c2ccc(C(=O)NC(C)(C)c3cccc(CN(C)C)c3)cc2NC(=O)c2coc(C3CC3)n2)CC1] | | + |
| 487 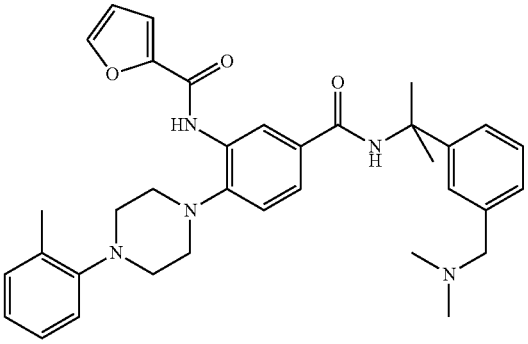 [SMILES: Cc1ccccc1N1CCN(c2ccc(C(=O)NC(C)(C)c3cccc(CN(C)C)c3)cc2NC(=O)c2ccco2)CC1] | | + |
| 488 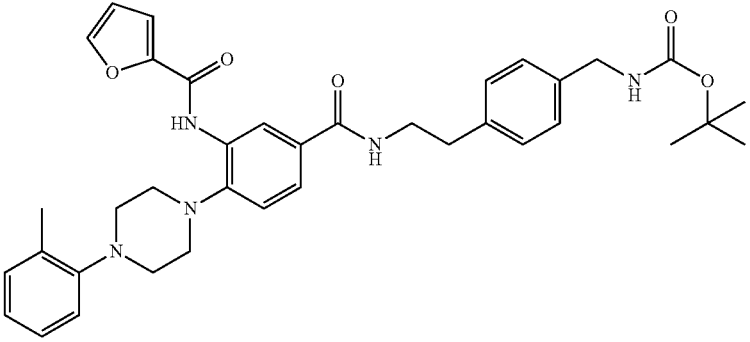 [SMILES: Cc1ccccc1N1CCN(c2ccc(C(=O)NCCc3ccc(CNC(=O)OC(C)(C)C)cc3)cc2NC(=O)c2ccco2)CC1] | | |

TABLE 2-continued

Further compounds of formulae (I), (I-A), (I-B), (I-C).
Assay A: Example 10; Assay B: Example 11.

| Structure | Assay A<br>0 > 10 μM<br>+ > 1-10 μM<br>++ 0.1-1 μM<br>+++ < 0.1 μM<br>% at 5 μM | Assay B<br>0 > 10 μM<br>+ > 1-10 μM<br>++ 0.1-1 μM<br>+++ < 0.1 μM<br>% at 1.25 μM |
|---|---|---|
| 489 | | + |
| 490 | | +++ |
| 491 | | ++ |
| 492 | | ++ |

TABLE 2-continued

Further compounds of formulae (I), (I-A), (I-B), (I-C).
Assay A: Example 10; Assay B: Example 11.

| Structure | Assay A<br>0 > 10 μM<br>+ > 1-10 μM<br>++ 0.1-1 μM<br>+++ < 0.1 μM<br>% at 5 μM | Assay B<br>0 > 10 μM<br>+ > 1-10 μM<br>++ 0.1-1 μM<br>+++ < 0.1 μM<br>% at 1.25 μM |
|---|---|---|
| 493 | | ++ |
| 494 | | ++ |
| 495 | | ++ |
| 496 | | ++ |

TABLE 2-continued
Further compounds of formulae (I), (I-A), (I-B), (I-C).
Assay A: Example 10; Assay B: Example 11.
| Structure | Assay A<br>0 > 10 μM<br>+ > 1-10 μM<br>++ 0.1-1 μM<br>+++ < 0.1 μM<br>% at 5 μM | Assay B<br>0 > 10 μM<br>+ > 1-10 μM<br>++ 0.1-1 μM<br>+++ < 0.1 μM<br>% at 1.25 μM |
|---|---|---|
| 497 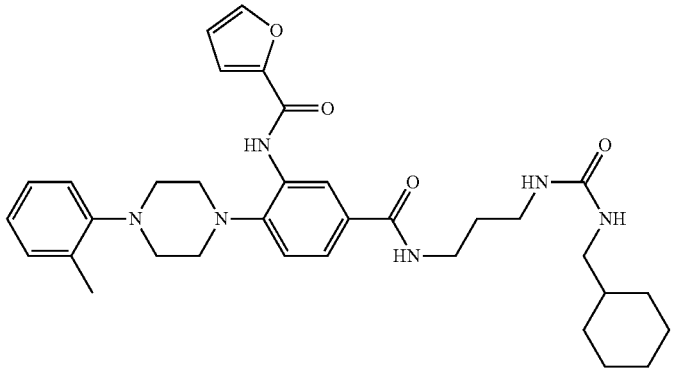 [SMILES: Cc1ccccc1N1CCN(c2ccc(C(=O)NCCCNC(=O)NCC3CCCCC3)cc2NC(=O)c2ccco2)CC1] | | + |
| 498 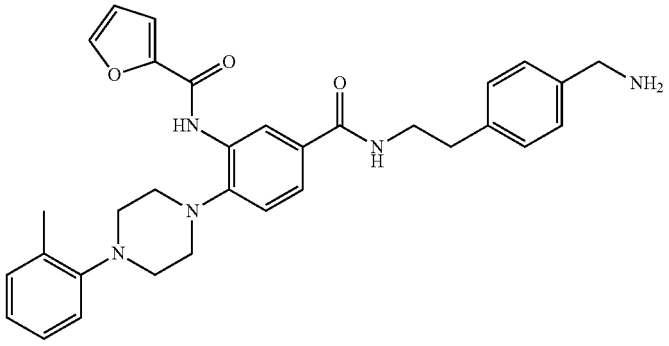 [SMILES: Cc1ccccc1N1CCN(c2ccc(C(=O)NCCc3ccc(CN)cc3)cc2NC(=O)c2ccco2)CC1] | | |
| 499 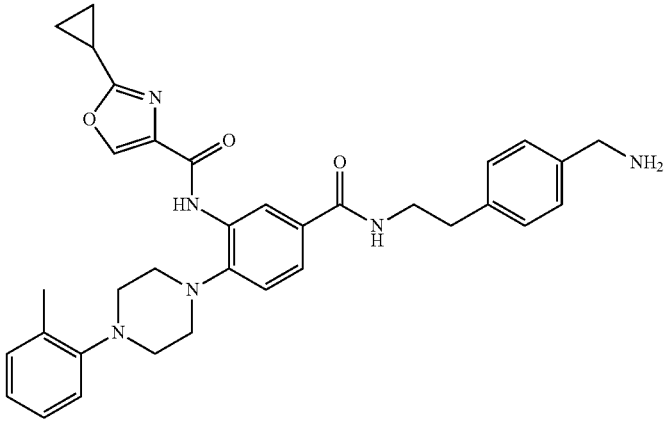 [SMILES: Cc1ccccc1N1CCN(c2ccc(C(=O)NCCc3ccc(CN)cc3)cc2NC(=O)c2coc(C3CC3)n2)CC1] | | ++ |

US 9,938,262 B2

TABLE 2-continued

Further compounds of formulae (I), (I-A), (I-B), (I-C).
Assay A: Example 10; Assay B: Example 11.

| Structure | Assay A<br>0 > 10 μM<br>+ > 1-10 μM<br>++ 0.1-1 μM<br>+++ < 0.1 μM<br>% at 5 μM | Assay B<br>0 > 10 μM<br>+ > 1-10 μM<br>++ 0.1-1 μM<br>+++ < 0.1 μM<br>% at 1.25 μM |
|---|---|---|
| 500 | | ++ |
| 501 | | ++ |
| 502 | | ++ |
| 503 | | ++ |

TABLE 2-continued
Further compounds of formulae (I), (I-A), (I-B), (I-C).
Assay A: Example 10; Assay B: Example 11.
| Structure | Assay A<br>0 > 10 μM<br>+ > 1-10 μM<br>++ 0.1-1 μM<br>+++ < 0.1 μM<br>% at 5 μM | Assay B<br>0 > 10 μM<br>+ > 1-10 μM<br>++ 0.1-1 μM<br>+++ < 0.1 μM<br>% at 1.25 μM |
|---|---|---|
| 504 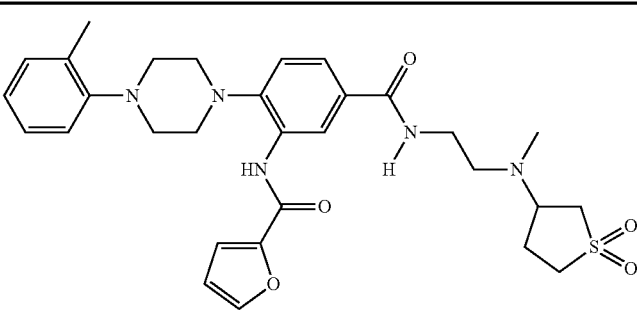 | | ++ |
| 505 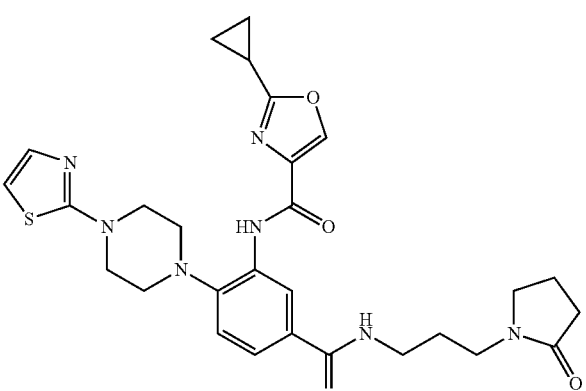 | | + |
| 506 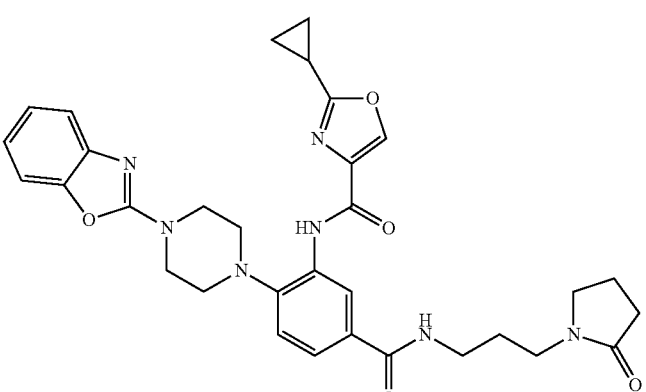 | | |

TABLE 2-continued
Further compounds of formulae (I), (I-A), (I-B), (I-C).
Assay A: Example 10; Assay B: Example 11.
| Structure | Assay A<br>0 > 10 μM<br>+ > 1-10 μM<br>++ 0.1-1 μM<br>+++ < 0.1 μM<br>% at 5 μM | Assay B<br>0 > 10 μM<br>+ > 1-10 μM<br>++ 0.1-1 μM<br>+++ < 0.1 μM<br>% at 1.25 μM |
|---|---|---|
| 507 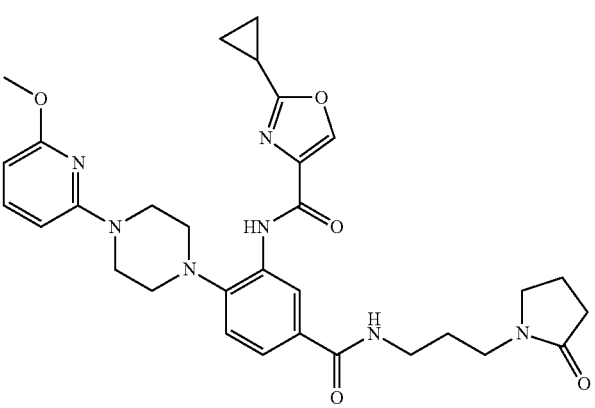 [SMILES: COc1cccc(N2CCN(c3ccc(C(=O)NCCCN4CCCC4=O)cc3NC(=O)c3coc(C4CC4)n3)CC2)n1] | | ++ |
| 508 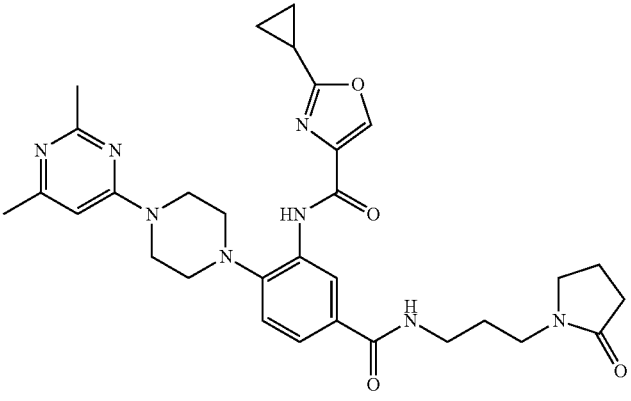 [SMILES: Cc1cc(N2CCN(c3ccc(C(=O)NCCCN4CCCC4=O)cc3NC(=O)c3coc(C4CC4)n3)CC2)nc(C)n1] | | |
| 509 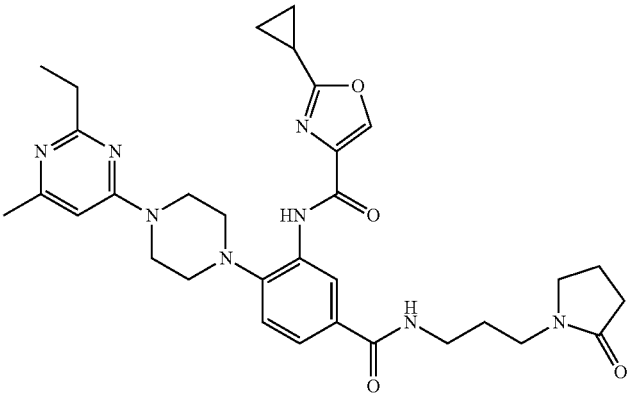 [SMILES: CCc1nc(C)cc(N2CCN(c3ccc(C(=O)NCCCN4CCCC4=O)cc3NC(=O)c3coc(C4CC4)n3)CC2)n1] | | |

TABLE 2-continued

Further compounds of formulae (I), (I-A), (I-B), (I-C).
Assay A: Example 10; Assay B: Example 11.

| Structure | Assay A<br>0 > 10 µM<br>+ > 1-10 µM<br>++ 0.1-1 µM<br>+++ < 0.1 µM<br>% at 5 µM | Assay B<br>0 > 10 µM<br>+ > 1-10 µM<br>++ 0.1-1 µM<br>+++ < 0.1 µM<br>% at 1.25 µM |
|---|---|---|
| 510 | +++ | + |
| 511 |  | ++ |
| 512 |  | +++ |
| 513 |  | + |

TABLE 2-continued

Further compounds of formulae (I), (I-A), (I-B), (I-C).
Assay A: Example 10; Assay B: Example 11.

| Structure | Assay A<br>0 > 10 μM<br>+ > 1-10 μM<br>++ 0.1-1 μM<br>+++ < 0.1 μM<br>% at 5 μM | Assay B<br>0 > 10 μM<br>+ > 1-10 μM<br>++ 0.1-1 μM<br>+++ < 0.1 μM<br>% at 1.25 μM |
|---|---|---|
| 514 | | 48% |
| 515 | | +++ |
| 516 | | ++ |

TABLE 2-continued
Further compounds of formulae (I), (I-A), (I-B), (I-C).
Assay A: Example 10; Assay B: Example 11.
| Structure | Assay A<br>0 > 10 μM<br>+ > 1-10 μM<br>++ 0.1-1 μM<br>+++ < 0.1 μM<br>% at 5 μM | Assay B<br>0 > 10 μM<br>+ > 1-10 μM<br>++ 0.1-1 μM<br>+++ < 0.1 μM<br>% at 1.25 μM |
|---|---|---|
| 517 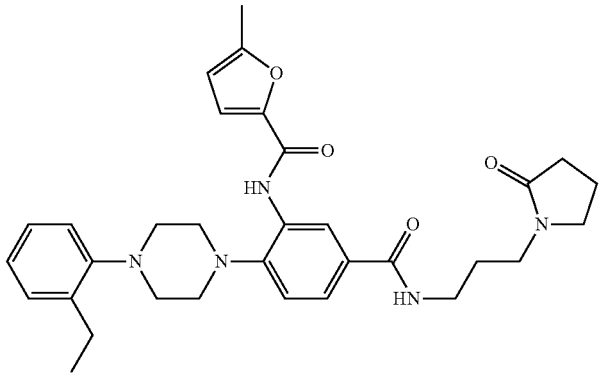 [SMILES: CCc1ccccc1N1CCN(c2ccc(C(=O)NCCCN3CCCC3=O)cc2NC(=O)c2ccc(C)o2)CC1] | | ++ |
| 518 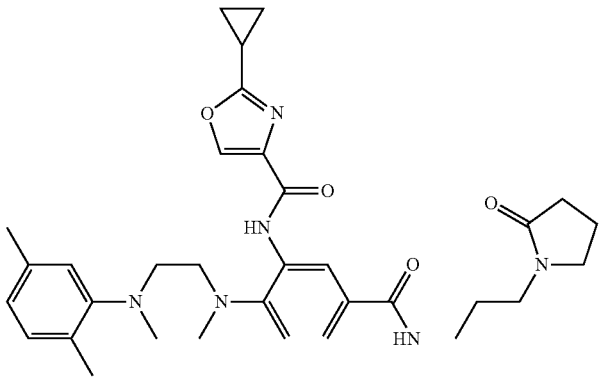 | | ++ |
| 519 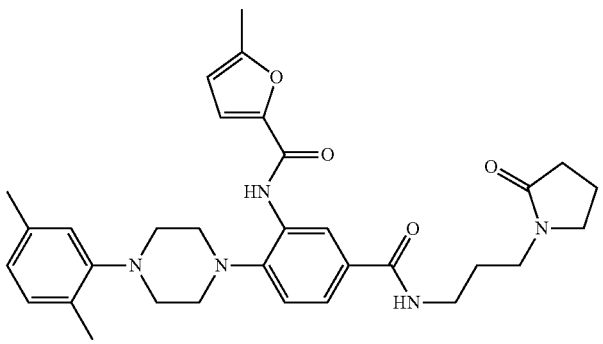 [SMILES: Cc1ccc(C)c(N2CCN(c3ccc(C(=O)NCCCN4CCCC4=O)cc3NC(=O)c3ccc(C)o3)CC2)c1] | | ++ |

TABLE 2-continued
Further compounds of formulae (I), (I-A), (I-B), (I-C).
Assay A: Example 10; Assay B: Example 11.
| Structure | Assay A<br>0 > 10 μM<br>+ > 1-10 μM<br>++ 0.1-1 μM<br>+++ < 0.1 μM<br>% at 5 μM | Assay B<br>0 > 10 μM<br>+ > 1-10 μM<br>++ 0.1-1 μM<br>+++ < 0.1 μM<br>% at 1.25 μM |
|---|---|---|
| 520 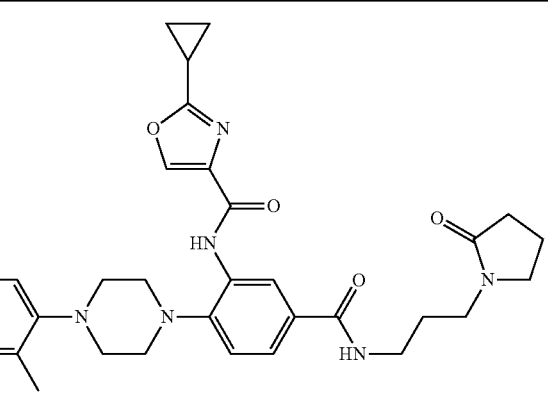 | | |
| 521 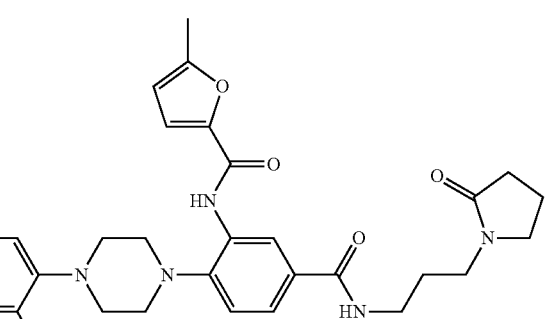 | | ++ |
| 522 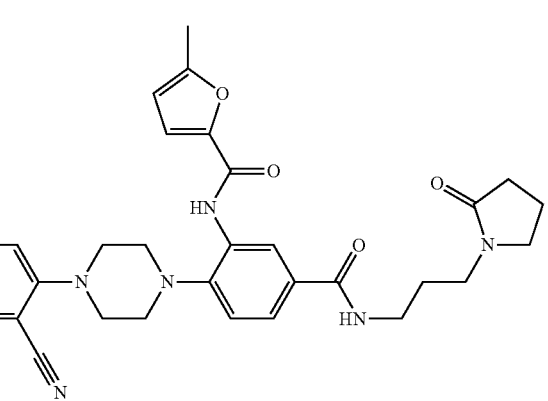 | | + |

TABLE 2-continued

Further compounds of formulae (I), (I-A), (I-B), (I-C).
Assay A: Example 10; Assay B: Example 11.

| Structure | Assay A<br>0 > 10 μM<br>+ > 1-10 μM<br>++ 0.1-1 μM<br>+++ < 0.1 μM<br>% at 5 μM | Assay B<br>0 > 10 μM<br>+ > 1-10 μM<br>++ 0.1-1 μM<br>+++ < 0.1 μM<br>% at 1.25 μM |
|---|---|---|
| 523 | ++ | ++ |
| 524 | ++ | |
| 525 | ++ | |

TABLE 2-continued
Further compounds of formulae (I), (I-A), (I-B), (I-C).
Assay A: Example 10; Assay B: Example 11.
| Structure | Assay A<br>0 > 10 μM<br>+ > 1-10 μM<br>++ 0.1-1 μM<br>+++ < 0.1 μM<br>% at 5 μM | Assay B<br>0 > 10 μM<br>+ > 1-10 μM<br>++ 0.1-1 μM<br>+++ < 0.1 μM<br>% at 1.25 μM |
|---|---|---|
| 526 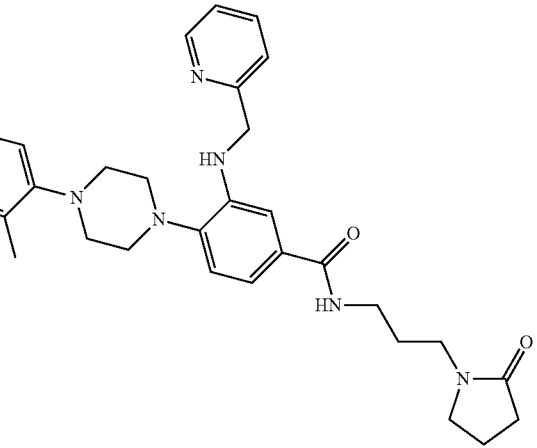 | ++ | 0 |
| 527 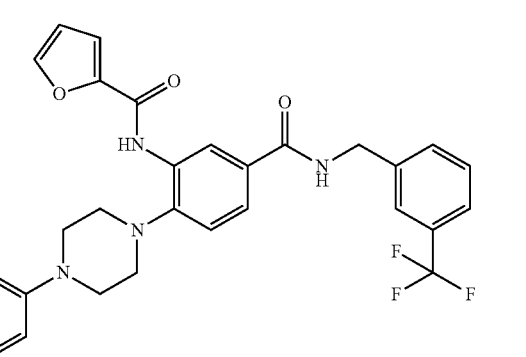 | | ++ |
| 528 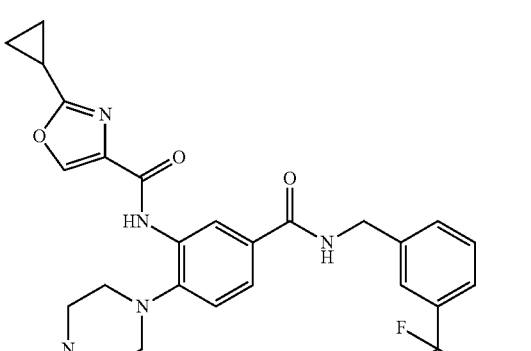 | | + |

TABLE 2-continued

Further compounds of formulae (I), (I-A), (I-B), (I-C).
Assay A: Example 10; Assay B: Example 11.

| Structure | Assay A<br>0 > 10 μM<br>+ > 1-10 μM<br>++ 0.1-1 μM<br>+++ < 0.1 μM<br>% at 5 μM | Assay B<br>0 > 10 μM<br>+ > 1-10 μM<br>++ 0.1-1 μM<br>+++ < 0.1 μM<br>% at 1.25 μM |
|---|---|---|
| 529 | ++ | + |
| 530 |  | + |
| 531 |  |  |

TABLE 2-continued

Further compounds of formulae (I), (I-A), (I-B), (I-C).
Assay A: Example 10; Assay B: Example 11.

| Structure | Assay A<br>0 > 10 μM<br>+ > 1-10 μM<br>++ 0.1-1 μM<br>+++ < 0.1 μM<br>% at 5 μM | Assay B<br>0 > 10 μM<br>+ > 1-10 μM<br>++ 0.1-1 μM<br>+++ < 0.1 μM<br>% at 1.25 μM |
|---|---|---|
| 532 | | 0 |
| 533 | | + |
| 534 | | |

TABLE 2-continued
Further compounds of formulae (I), (I-A), (I-B), (I-C).
Assay A: Example 10; Assay B: Example 11.
| Structure | Assay A<br>0 > 10 μM<br>+ > 1-10 μM<br>++ 0.1-1 μM<br>+++ < 0.1 μM<br>% at 5 μM | Assay B<br>0 > 10 μM<br>+ > 1-10 μM<br>++ 0.1-1 μM<br>+++ < 0.1 μM<br>% at 1.25 μM |
|---|---|---|
| 535 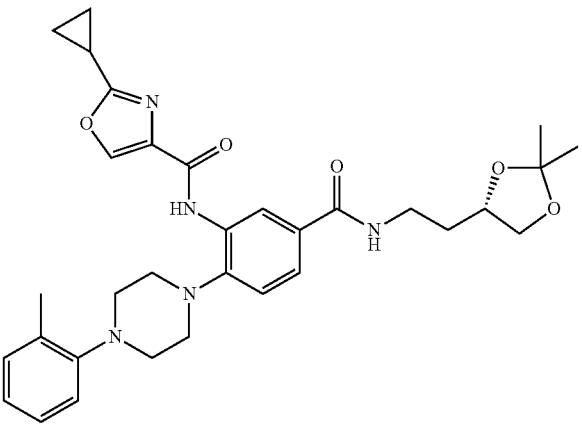 [SMILES: Cc1ccccc1N1CCN(c2ccc(C(=O)NCC[C@H]3COC(C)(C)O3)cc2NC(=O)c2coc(C3CC3)n2)CC1] | | ++ |
| 536 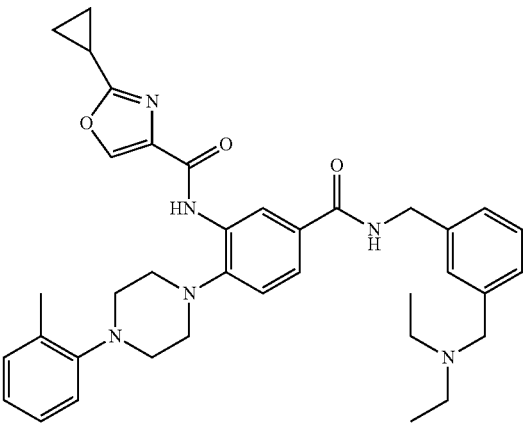 [SMILES: CCN(CC)Cc1cccc(CNC(=O)c2ccc(N3CCN(c4ccccc4C)CC3)c(NC(=O)c3coc(C4CC4)n3)c2)c1] | | ++ |
| 537 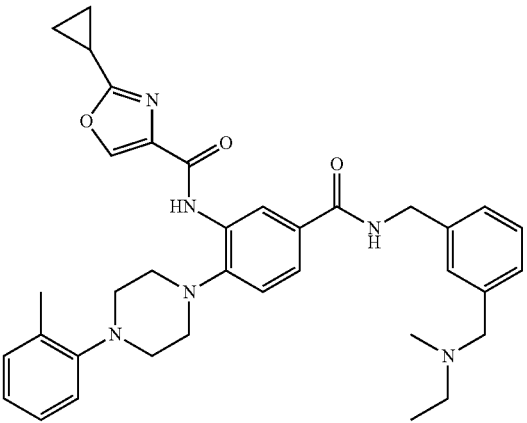 [SMILES: CCN(C)Cc1cccc(CNC(=O)c2ccc(N3CCN(c4ccccc4C)CC3)c(NC(=O)c3coc(C4CC4)n3)c2)c1] | | ++ |

TABLE 2-continued

Further compounds of formulae (I), (I-A), (I-B), (I-C).
Assay A: Example 10; Assay B: Example 11.

| Structure | Assay A<br>0 > 10 μM<br>+ > 1-10 μM<br>++ 0.1-1 μM<br>+++ < 0.1 μM<br>% at 5 μM | Assay B<br>0 > 10 μM<br>+ > 1-10 μM<br>++ 0.1-1 μM<br>+++ < 0.1 μM<br>% at 1.25 μM |
|---|---|---|
| 538 | | ++ |
| 539 | | + |
| 540 | | + |

TABLE 2-continued

Further compounds of formulae (I), (I-A), (I-B), (I-C).
Assay A: Example 10; Assay B: Example 11.

| Structure | Assay A<br>0 > 10 μM<br>+ > 1-10 μM<br>++ 0.1-1 μM<br>+++ < 0.1 μM<br>% at 5 μM | Assay B<br>0 > 10 μM<br>+ > 1-10 μM<br>++ 0.1-1 μM<br>+++ < 0.1 μM<br>% at 1.25 μM |
|---|---|---|
| 541 | | |
| 542 | | ++ |
| 543 | | + |

TABLE 2-continued

Further compounds of formulae (I), (I-A), (I-B), (I-C).
Assay A: Example 10; Assay B: Example 11.

| Structure | Assay A<br>0 > 10 μM<br>+ > 1-10 μM<br>++ 0.1-1 μM<br>+++ < 0.1 μM<br>% at 5 μM | Assay B<br>0 > 10 μM<br>+ > 1-10 μM<br>++ 0.1-1 μM<br>+++ < 0.1 μM<br>% at 1.25 μM |
|---|---|---|
| 544 | | + |
| 545 | | + |
| 546 | | + |
| 547 | | + |

TABLE 2-continued

Further compounds of formulae (I), (I-A), (I-B), (I-C).
Assay A: Example 10; Assay B: Example 11.

| Structure | Assay A<br>0 > 10 μM<br>+ > 1-10 μM<br>++ 0.1-1 μM<br>+++ < 0.1 μM<br>% at 5 μM | Assay B<br>0 > 10 μM<br>+ > 1-10 μM<br>++ 0.1-1 μM<br>+++ < 0.1 μM<br>% at 1.25 μM |
|---|---|---|
| 548 | | + |
| 549 | | ++ |
| 550 | | +++ |

TABLE 2-continued

Further compounds of formulae (I), (I-A), (I-B), (I-C).
Assay A: Example 10; Assay B: Example 11.

| Structure | Assay A<br>0 > 10 μM<br>+ > 1-10 μM<br>++ 0.1-1 μM<br>+++ < 0.1 μM<br>% at 5 μM | Assay B<br>0 > 10 μM<br>+ > 1-10 μM<br>++ 0.1-1 μM<br>+++ < 0.1 μM<br>% at 1.25 μM |
|---|---|---|
| 551 | | +++ |
| 552 | | +++ |
| 553 | | ++ |

TABLE 2-continued

Further compounds of formulae (I), (I-A), (I-B), (I-C).
Assay A: Example 10; Assay B: Example 11.

| Structure | Assay A<br>0 > 10 µM<br>+ > 1-10 µM<br>++ 0.1-1 µM<br>+++ < 0.1 µM<br>% at 5 µM | Assay B<br>0 > 10 µM<br>+ > 1-10 µM<br>++ 0.1-1 µM<br>+++ < 0.1 µM<br>% at 1.25 µM |
|---|---|---|
| 554 | | 40% |
| 555 | | + |
| 556 | | |

TABLE 2-continued
Further compounds of formulae (I), (I-A), (I-B), (I-C).
Assay A: Example 10; Assay B: Example 11.
| Structure | Assay A<br>0 > 10 μM<br>+ > 1-10 μM<br>++ 0.1-1 μM<br>+++ < 0.1 μM<br>% at 5 μM | Assay B<br>0 > 10 μM<br>+ > 1-10 μM<br>++ 0.1-1 μM<br>+++ < 0.1 μM<br>% at 1.25 μM |
|---|---|---|
| 557 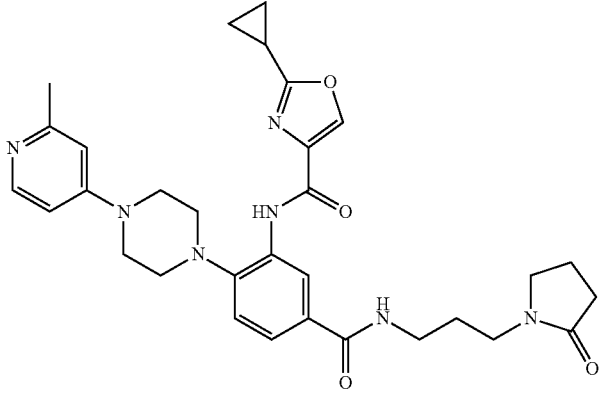 [SMILES: Cc1cc(N2CCN(c3ccc(C(=O)NCCCN4CCCC4=O)cc3NC(=O)c3coc(C4CC4)n3)CC2)ccn1] | | |
| 558 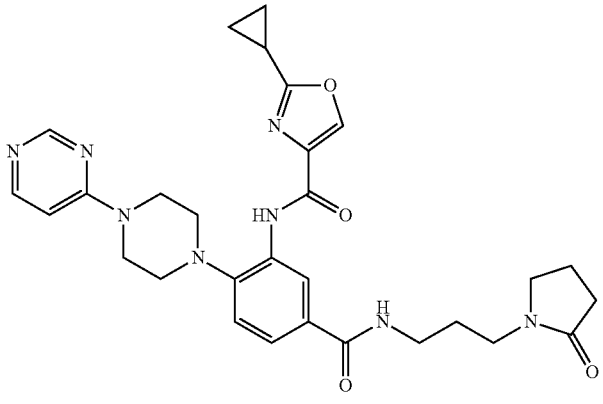 [SMILES: O=C(NCCCN1CCCC1=O)c1ccc(N2CCN(c3ccncn3)CC2)c(NC(=O)c2coc(C3CC3)n2)c1] | | |
| 559 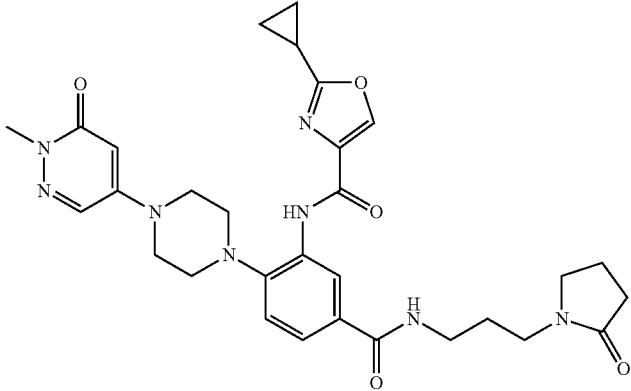 [SMILES: Cn1ncc(N2CCN(c3ccc(C(=O)NCCCN4CCCC4=O)cc3NC(=O)c3coc(C4CC4)n3)CC2)cc1=O] | | |

TABLE 2-continued

Further compounds of formulae (I), (I-A), (I-B), (I-C).
Assay A: Example 10; Assay B: Example 11.

| Structure | Assay A<br>0 > 10 μM<br>+ > 1-10 μM<br>++ 0.1-1 μM<br>+++ < 0.1 μM<br>% at 5 μM | Assay B<br>0 > 10 μM<br>+ > 1-10 μM<br>++ 0.1-1 μM<br>+++ < 0.1 μM<br>% at 1.25 μM |
|---|---|---|
| 560 | | |
| 561 | | + |
| 562 | | ++ |
| 563 | | 0 |

TABLE 2-continued

Further compounds of formulae (I), (I-A), (I-B), (I-C).
Assay A: Example 10; Assay B: Example 11.

| Structure | Assay A<br>0 > 10 µM<br>+ > 1-10 µM<br>++ 0.1-1 µM<br>+++ < 0.1 µM<br>% at 5 µM | Assay B<br>0 > 10 µM<br>+ > 1-10 µM<br>++ 0.1-1 µM<br>+++ < 0.1 µM<br>% at 1.25 µM |
|---|---|---|
| 564 | | ++ |
| 565 | | ++ |
| 566 | | ++ |

TABLE 2-continued

Further compounds of formulae (I), (I-A), (I-B), (I-C).
Assay A: Example 10; Assay B: Example 11.

| Structure | Assay A<br>0 > 10 μM<br>+ > 1-10 μM<br>++ 0.1-1 μM<br>+++ < 0.1 μM<br>% at 5 μM | Assay B<br>0 > 10 μM<br>+ > 1-10 μM<br>++ 0.1-1 μM<br>+++ < 0.1 μM<br>% at 1.25 μM |
|---|---|---|
| 567 | | ++ |
| 568 | | ++ |
| 569 | | + |

TABLE 2-continued

Further compounds of formulae (I), (I-A), (I-B), (I-C).
Assay A: Example 10; Assay B: Example 11.

| Structure | Assay A<br>0 > 10 μM<br>+ > 1-10 μM<br>++ 0.1-1 μM<br>+++ < 0.1 μM<br>% at 5 μM | Assay B<br>0 > 10 μM<br>+ > 1-10 μM<br>++ 0.1-1 μM<br>+++ < 0.1 μM<br>% at 1.25 μM |
|---|---|---|
| 570 | | ++ |
| 571 | | ++ |
| 572 | | +++ |

TABLE 2-continued

Further compounds of formulae (I), (I-A), (I-B), (I-C).
Assay A: Example 10; Assay B: Example 11.

| Structure | Assay A<br>0 > 10 μM<br>+ > 1-10 μM<br>++ 0.1-1 μM<br>+++ < 0.1 μM<br>% at 5 μM | Assay B<br>0 > 10 μM<br>+ > 1-10 μM<br>++ 0.1-1 μM<br>+++ < 0.1 μM<br>% at 1.25 μM |
|---|---|---|
| 573 | | + |
| 574 | | ++ |
| 575 | | +++ |

TABLE 2-continued

Further compounds of formulae (I), (I-A), (I-B), (I-C).
Assay A: Example 10; Assay B: Example 11.

| Structure | Assay A<br>0 > 10 μM<br>+ > 1-10 μM<br>++ 0.1-1 μM<br>+++ < 0.1 μM<br>% at 5 μM | Assay B<br>0 > 10 μM<br>+ > 1-10 μM<br>++ 0.1-1 μM<br>+++ < 0.1 μM<br>% at 1.25 μM |
|---|---|---|
| 576 | | +++ |
| 577 | | |
| 578 | | +++ |

TABLE 2-continued
Further compounds of formulae (I), (I-A), (I-B), (I-C).
Assay A: Example 10; Assay B: Example 11.
| Structure | Assay A<br>0 > 10 μM<br>+ > 1-10 μM<br>++ 0.1-1 μM<br>+++ < 0.1 μM<br>% at 5 μM | Assay B<br>0 > 10 μM<br>+ > 1-10 μM<br>++ 0.1-1 μM<br>+++ < 0.1 μM<br>% at 1.25 μM |
|---|---|---|
| 579 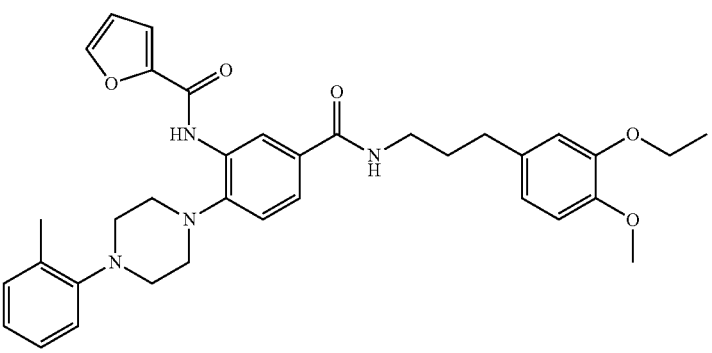 [SMILES: CCOc1cc(CCCNC(=O)c2ccc(N3CCN(c4ccccc4C)CC3)c(NC(=O)c3ccco3)c2)ccc1OC] | | ++ |
| 580 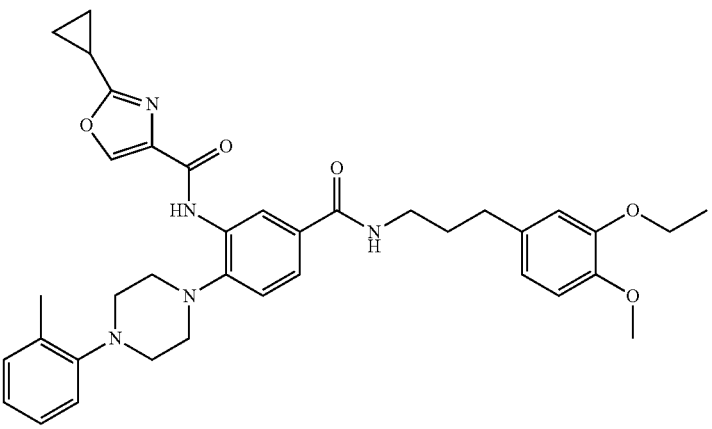 [SMILES: CCOc1cc(CCCNC(=O)c2ccc(N3CCN(c4ccccc4C)CC3)c(NC(=O)c3coc(C4CC4)n3)c2)ccc1OC] | | ++ |
| 581 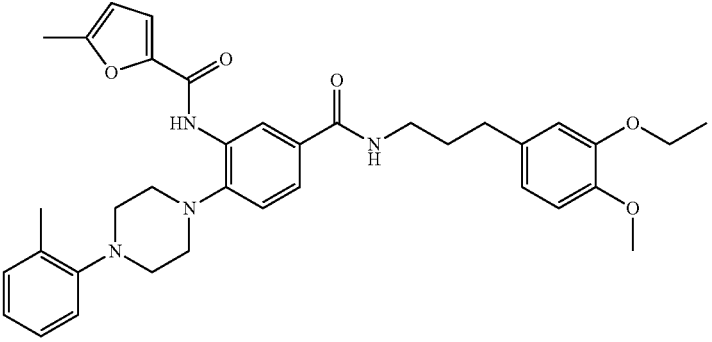 [SMILES: CCOc1cc(CCCNC(=O)c2ccc(N3CCN(c4ccccc4C)CC3)c(NC(=O)c3ccc(C)o3)c2)ccc1OC] | | ++ |

TABLE 2-continued

Further compounds of formulae (I), (I-A), (I-B), (I-C).
Assay A: Example 10; Assay B: Example 11.

| Structure | Assay A<br>0 > 10 μM<br>+ > 1-10 μM<br>++ 0.1-1 μM<br>+++ < 0.1 μM<br>% at 5 μM | Assay B<br>0 > 10 μM<br>+ > 1-10 μM<br>++ 0.1-1 μM<br>+++ < 0.1 μM<br>% at 1.25 μM |
|---|---|---|
| 582 | | ++ |
| 583 | | + |
| 584 | | + |
| 585 | | +++ |

TABLE 2-continued

Further compounds of formulae (I), (I-A), (I-B), (I-C).
Assay A: Example 10; Assay B: Example 11.

| Structure | Assay A<br>0 > 10 μM<br>+ > 1-10 μM<br>++ 0.1-1 μM<br>+++ < 0.1 μM<br>% at 5 μM | Assay B<br>0 > 10 μM<br>+ > 1-10 μM<br>++ 0.1-1 μM<br>+++ < 0.1 μM<br>% at 1.25 μM |
|---|---|---|
| 586 | | |
| 587 | | + |
| 588 | | ++ |
| 589 | | ++ |

TABLE 2-continued

Further compounds of formulae (I), (I-A), (I-B), (I-C).
Assay A: Example 10; Assay B: Example 11.

| Structure | Assay A<br>0 > 10 μM<br>+ > 1-10 μM<br>++ 0.1-1 μM<br>+++ < 0.1 μM<br>% at 5 μM | Assay B<br>0 > 10 μM<br>+ > 1-10 μM<br>++ 0.1-1 μM<br>+++ < 0.1 μM<br>% at 1.25 μM |
|---|---|---|
| 590 | | ++ |
| 591 | | 0 |
| 592 | | + |

TABLE 2-continued
Further compounds of formulae (I), (I-A), (I-B), (I-C).
Assay A: Example 10; Assay B: Example 11.
| Structure | Assay A<br>0 > 10 μM<br>+ > 1-10 μM<br>++ 0.1-1 μM<br>+++ < 0.1 μM<br>% at 5 μM | Assay B<br>0 > 10 μM<br>+ > 1-10 μM<br>++ 0.1-1 μM<br>+++ < 0.1 μM<br>% at 1.25 μM |
|---|---|---|
| 593 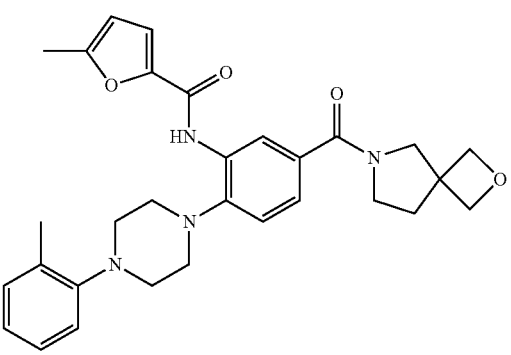 [SMILES: Cc1ccc(C(=O)Nc2cc(C(=O)N3CCC4(COC4)C3)ccc2N2CCN(c3ccccc3C)CC2)o1] | | + |
| 594 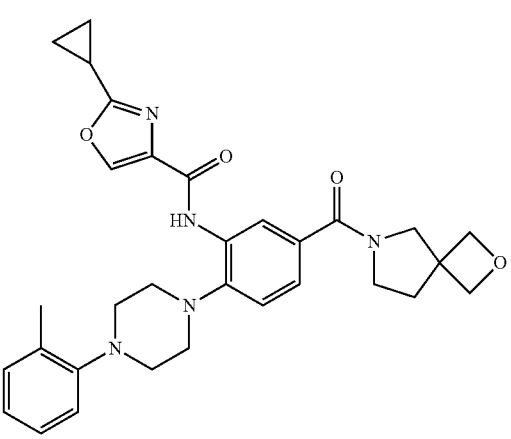 [SMILES: Cc1ccccc1N1CCN(c2ccc(C(=O)N3CCC4(COC4)C3)cc2NC(=O)c2coc(C3CC3)n2)CC1] | | + |
| 595 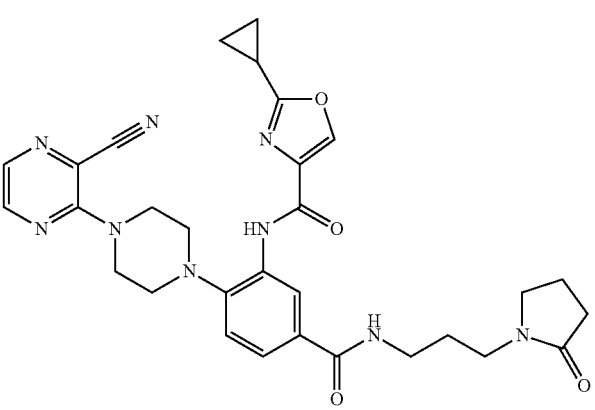 [SMILES: N#Cc1nccnc1N1CCN(c2ccc(C(=O)NCCCN3CCCC3=O)cc2NC(=O)c2coc(C3CC3)n2)CC1] | | + |

TABLE 2-continued

Further compounds of formulae (I), (I-A), (I-B), (I-C).
Assay A: Example 10; Assay B: Example 11.

| Structure | Assay A<br>0 > 10 μM<br>+ > 1-10 μM<br>++ 0.1-1 μM<br>+++ < 0.1 μM<br>% at 5 μM | Assay B<br>0 > 10 μM<br>+ > 1-10 μM<br>++ 0.1-1 μM<br>+++ < 0.1 μM<br>% at 1.25 μM |
|---|---|---|
| 596 | | + |
| 597 | | 0 |
| 598 | | + |

TABLE 2-continued
Further compounds of formulae (I), (I-A), (I-B), (I-C).
Assay A: Example 10; Assay B: Example 11.
| Structure | Assay A<br>0 > 10 μM<br>+ > 1-10 μM<br>++ 0.1-1 μM<br>+++ < 0.1 μM<br>% at 5 μM | Assay B<br>0 > 10 μM<br>+ > 1-10 μM<br>++ 0.1-1 μM<br>+++ < 0.1 μM<br>% at 1.25 μM |
|---|---|---|
| 599 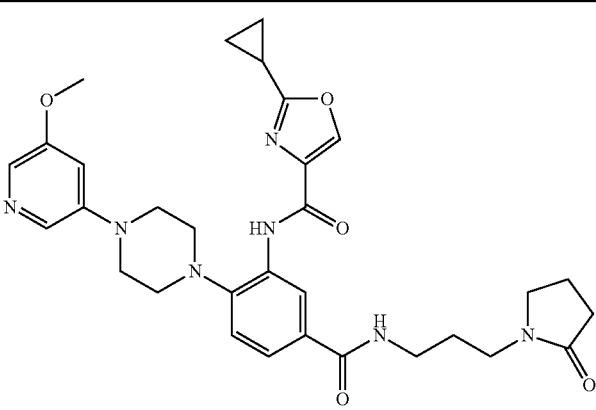 | 0 | |
| 600 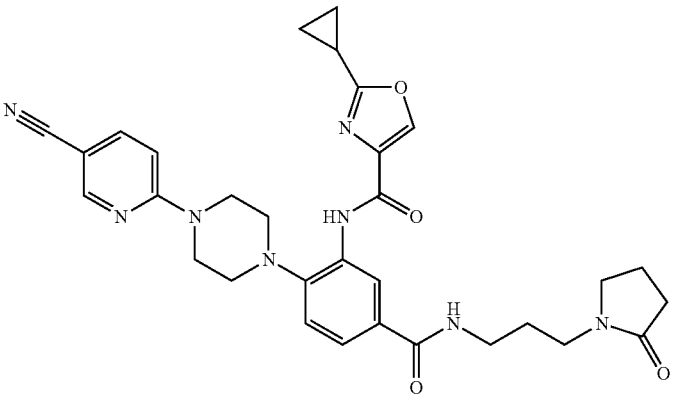 [SMILES: N#Cc1ccc(N2CCN(c3ccc(C(=O)NCCCN4CCCC4=O)cc3NC(=O)c3coc(C4CC4)n3)CC2)nc1] | | |
| 601 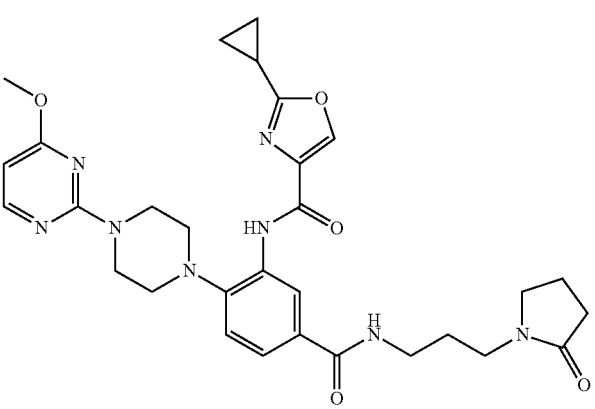 [SMILES: COc1ccnc(N2CCN(c3ccc(C(=O)NCCCN4CCCC4=O)cc3NC(=O)c3coc(C4CC4)n3)CC2)n1] | ++ | + |

TABLE 2-continued

Further compounds of formulae (I), (I-A), (I-B), (I-C).
Assay A: Example 10; Assay B: Example 11.

| Structure | Assay A<br>0 > 10 µM<br>+ > 1-10 µM<br>++ 0.1-1 µM<br>+++ < 0.1 µM<br>% at 5 µM | Assay B<br>0 > 10 µM<br>+ > 1-10 µM<br>++ 0.1-1 µM<br>+++ < 0.1 µM<br>% at 1.25 µM |
|---|---|---|
| 602 | | ++ |
| 603 | | |
| 604 | | |

TABLE 2-continued

Further compounds of formulae (I), (I-A), (I-B), (I-C).
Assay A: Example 10; Assay B: Example 11.

| Structure | Assay A<br>0 > 10 μM<br>+ > 1-10 μM<br>++ 0.1-1 μM<br>+++ < 0.1 μM<br>% at 5 μM | Assay B<br>0 > 10 μM<br>+ > 1-10 μM<br>++ 0.1-1 μM<br>+++ < 0.1 μM<br>% at 1.25 μM |
|---|---|---|
| 605 | | + |
| 606 | | ++ |
| 607 | | ++ |
| 608 | | ++ |

TABLE 2-continued

Further compounds of formulae (I), (I-A), (I-B), (I-C).
Assay A: Example 10; Assay B: Example 11.

| Structure | Assay A<br>0 > 10 μM<br>+ > 1-10 μM<br>++ 0.1-1 μM<br>+++ < 0.1 μM<br>% at 5 μM | Assay B<br>0 > 10 μM<br>+ > 1-10 μM<br>++ 0.1-1 μM<br>+++ < 0.1 μM<br>% at 1.25 μM |
|---|---|---|
| 609 | | ++ |

Highly preferred embodiments are the compounds selected from the group of

369
-continued
370
-continued
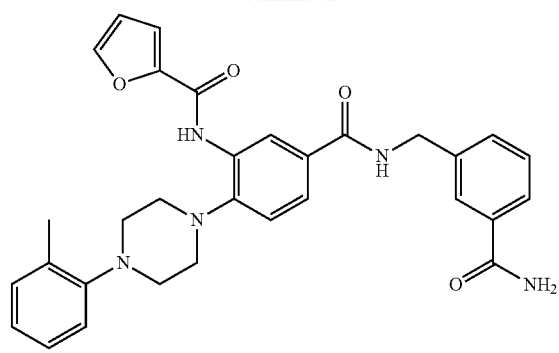
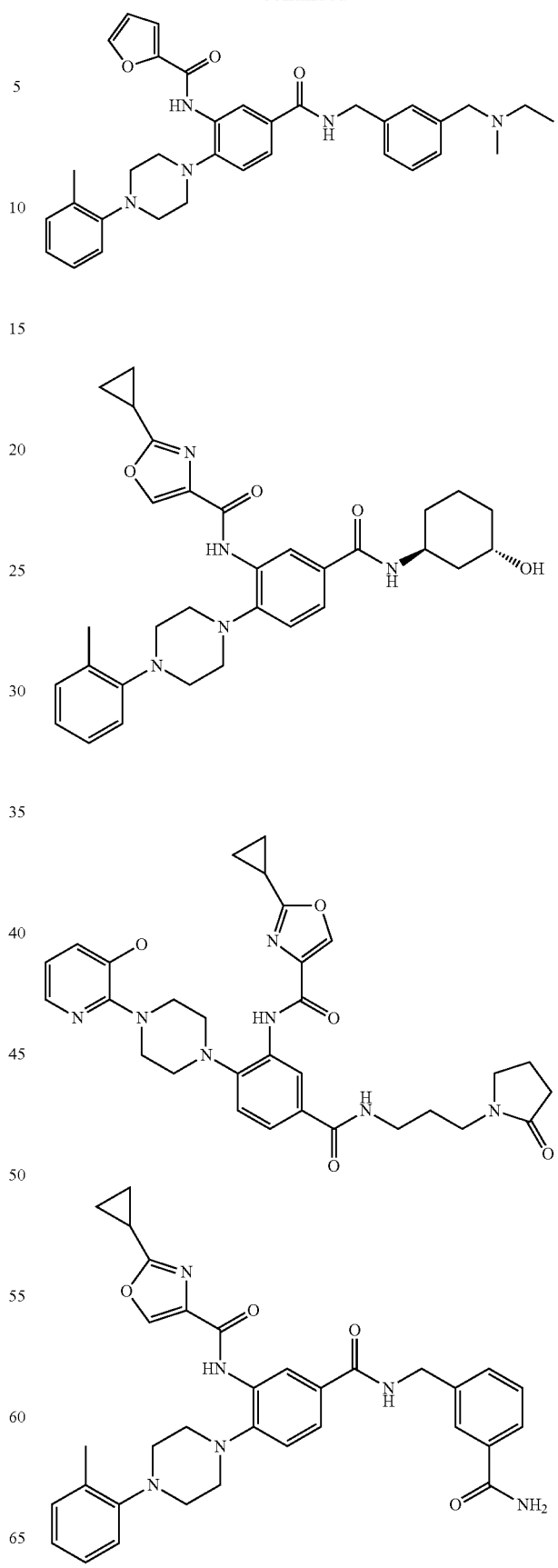

371
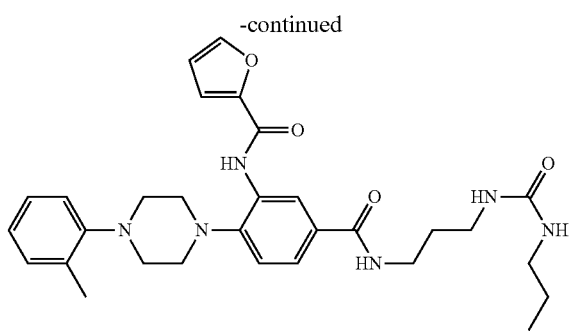
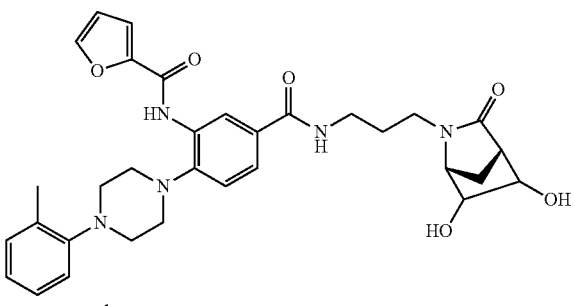
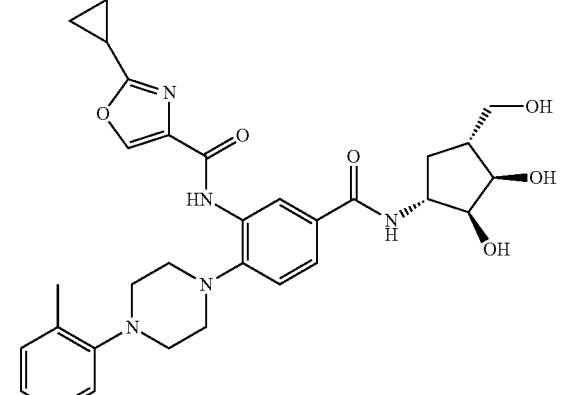
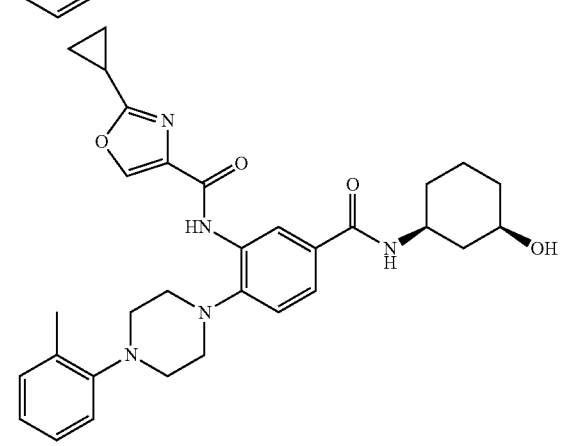
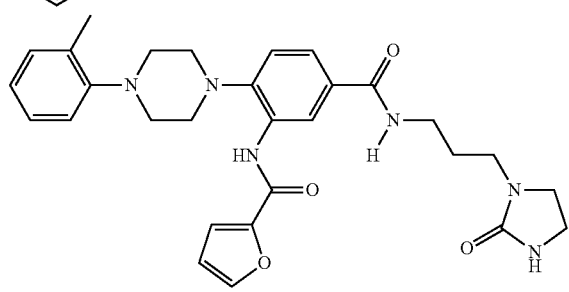
372
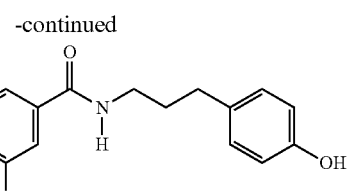
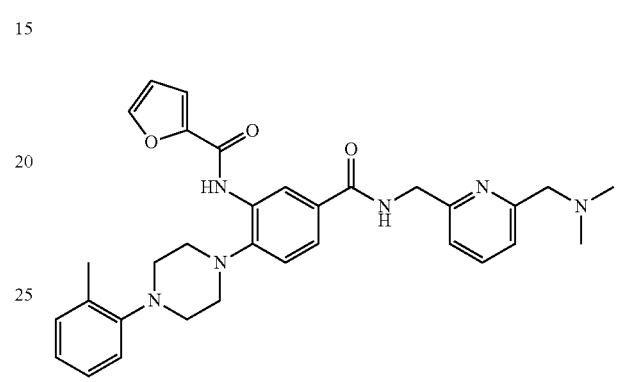
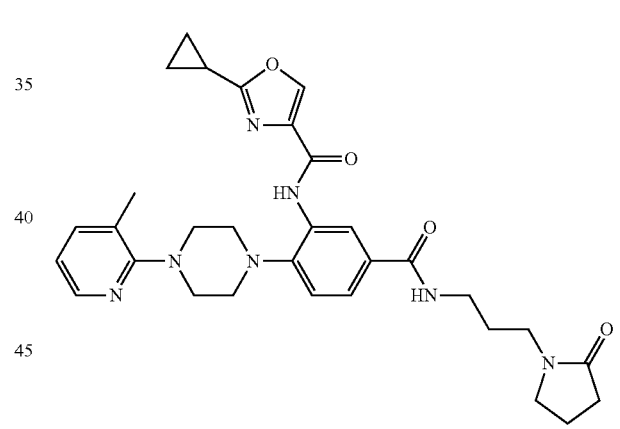
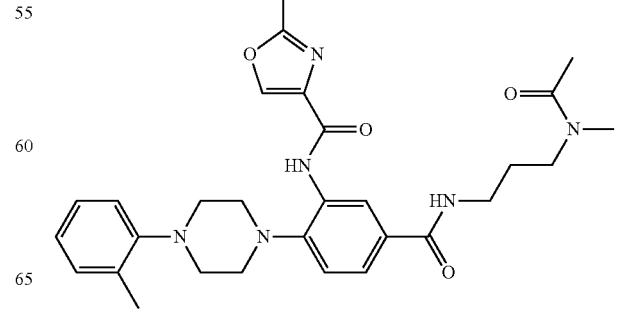
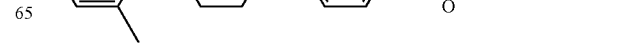

373
-continued
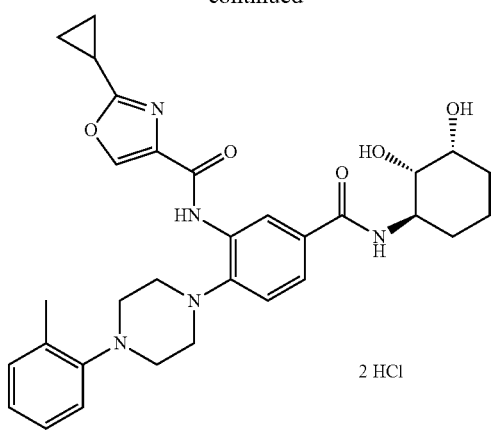
2 HCl
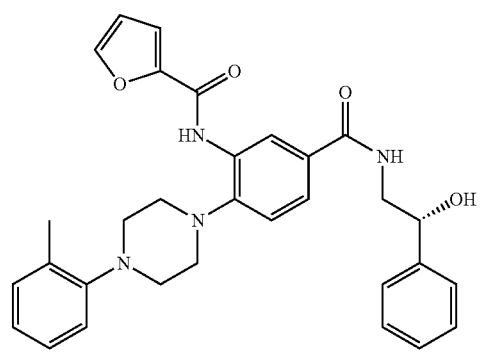
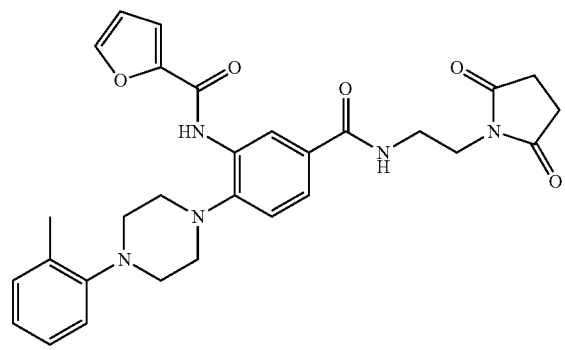
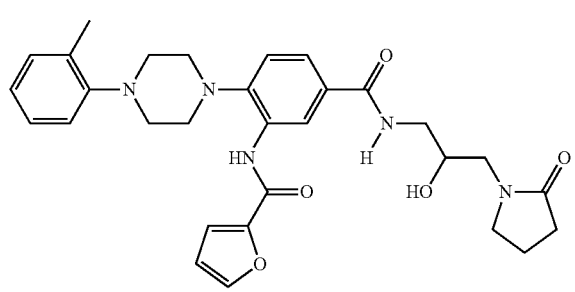
374
-continued
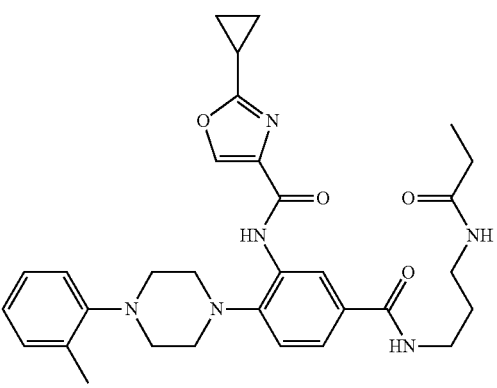
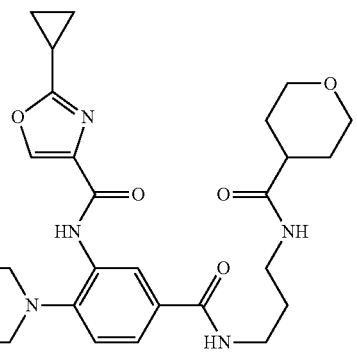
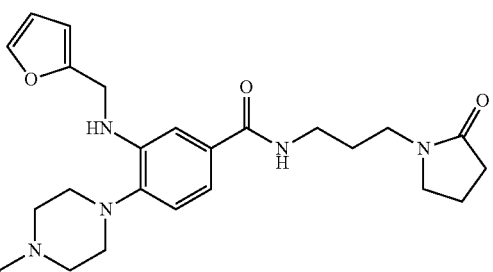

-continued

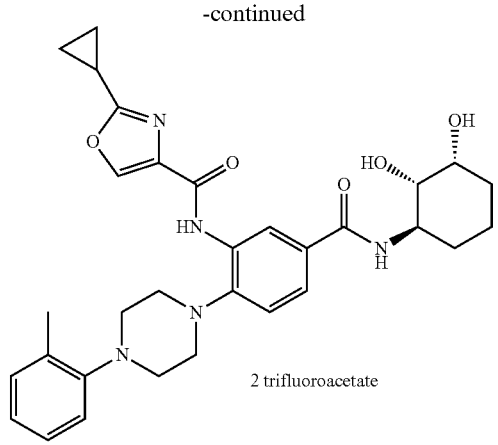

2 trifluoroacetate

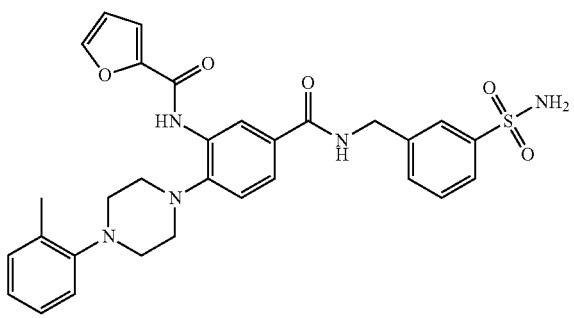

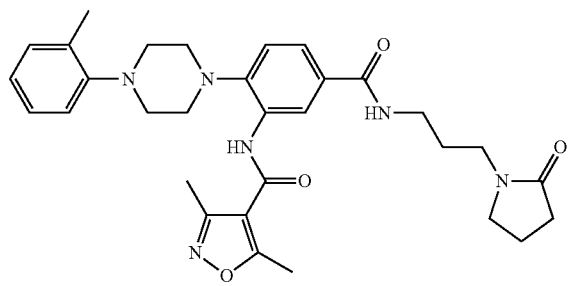

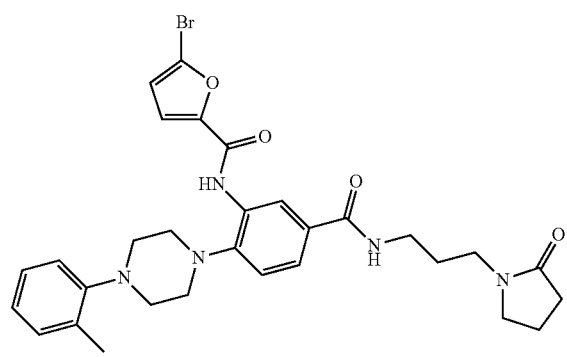

and/or physiologically acceptable salts thereof.

The benzamide derivatives according to formula (I) and the starting materials for its preparation, respectively, are produced by methods known per se, as described in the literature (for example in standard works, such as Houben-Weyl, Methoden der organischen Chemie [Methods of Organic Chemistry], Georg-Thieme-Verlag, Stuttgart), i.e. under reaction conditions that are known and suitable for said reactions.

Use can also be made of variants that are known per se, but are not mentioned in greater detail herein. If desired, the starting materials can also be formed in-situ by leaving them in the un-isolated status in the crude reaction mixture, but immediately converting them further into the compound according to the invention. On the other hand, it is possible to carry out the reaction stepwise.

The reactions are preferably performed under basic conditions. Suitable bases are metal oxides, e.g. aluminum oxide, alkaline metal hydroxide (potassium hydroxide, sodium hydroxide and lithium hydroxide, inter alia), alkaline earth metal hydroxide (barium hydroxide and calcium hydroxide, inter alia), alkaline metal alcoholates (potassium ethanolate and sodium propanolate, inter alia) and several organic bases (piperidine or diethanolamine, inter alia).

The reaction is generally carried out in an inert solvent. Suitable inert solvents are, for example, hydrocarbons, such as hexane, petroleum ether, benzene, toluene or xylene; chlorinated hydrocarbons, such as trichloroethylene, 1,2-dichloroethane, carbon tetrachloride, chloroform or dichloromethane; alcohols, such as methanol, ethanol, isopropanol, n-propanol, n-butanol or tert-butanol; ethers, such as diethyl ether, diisopropyl ether, tetrahydrofuran (THF) or dioxane; glycol ethers, such as ethylene glycol monomethyl or monoethyl ether, ethylene glycol dimethyl ether (diglyme); ketones, such as acetone or butanone; amides, such as acetamide, dimethylacetamide or dimethylformamide (DMF); nitriles, such as acetonitrile; sulfoxides, such as dimethyl sulfoxide (DMSO); carbon disulfide; carboxylic acids, such as formic acid, acetic acid or trifluoroacetic acid (TFA); nitro compounds, such as nitromethane or nitrobenzene; esters, such as ethyl acetate, or mixtures of the said solvents. Particular preference is given to TFA, $H_2O$, THF, tert. butanol, tert. amylalcohol, triethylamine or dioxane.

Depending on the conditions used, the reaction time is between a few minutes and 14 days, the reaction temperature is between about $-30°$ C. and $140°$ C., normally between $-10°$ C. and $130°$ C., preferably between $30°$ C. and $125°$ C.

The present invention also relates to a process for manufacturing compounds of formula (I) comprising the steps of:

(a) reacting a compound of formula (II)

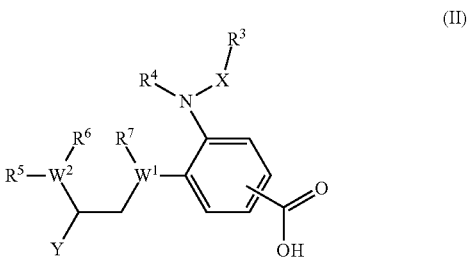

(II)

wherein $W^1$, $W^2$, $R^3$ to $R^7$, $R^6$, X and Y have the meaning as defined above, in the presence of a crosslinking agent and a solvent with a compound of formula (III)

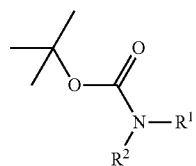

wherein $R^1$ and $R^2$ have the meaning as defined above, to yield a compound of formula (I)

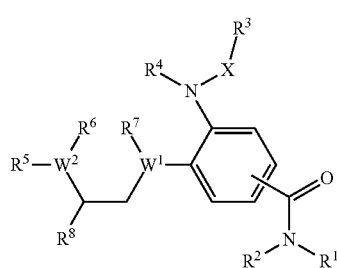

wherein $W^1$, $W^2$, $R^1$ to $R^7$, $R^6$, X and Y have the meaning as defined above,
and optionally
(b) converting a base or an acid of the compound of formula (I) into a salt thereof.

The benzamide derivatives of formula (I) are accessible via the route above. The starting materials, including the compounds of formulae (II) and (III), are usually known to the skilled artisan, or they can be easily prepared by known methods. Accordingly, any compound of formulae (II) and (III) can be purified, provided as intermediate product and used as starting material for the preparation of compounds of formula (I). The process step (a) is preferably performed in the presence of a crosslinking agent which is a carbodiimide derivative, particularly 1-ethyl-3-[3-dimethylaminopropyl] carbodiimide hydrochloride (EDC), and/or in the presence of a solvent, which is an organic acid, particularly TFA. It is more preferred in process step (a) to apply both EDC and TFA. In addition to tert. butyl carbamates (BOC), the skilled artisan knows other protection groups to be used in the compound of formula (III).

The compounds of formula (I) can be modified, like hydrogenated or metal-reduced, to remove the chlorine, or put into a substitution reaction, and/or to be transformed with an acid or base into a salt, preferably with a strong acid. Numerous papers and methods are available and useful for the one skilled in the art in respect for organic chemistry, chemical strategies and tactics, synthetic routes, protection of intermediates, cleavage and purification procedure, isolation and characterization. General chemical modifications are known to the one skilled in the art. Halogenation of aryls or hydroxy substitution by halogens of acids, alcohols, phenols, and their tautomeric structures can be preferably carried out by use of $POCl_3$, or $SOCl_2$, $PCl_5$, $SO_2Cl_2$. In some instances oxalyl chloride is also useful. Temperatures can vary from 0° C. to reflux depending on the task to halogenate a pyridone structure or a carboxylic acid or a sulfonic acid. Time will also be adjusted from minutes to several hours or even over night. Similarly, alkylation, ether formation, ester formation, amide formation are known to the one skilled in the art. Arylation with aryl boronic acids can be performed in presence of a Pd catalyst, appropriate ligand and base, preferably a carbonate, phosphate, borate salt of sodium, potassium or cesium. Organic bases, like $Et_3N$, DIPEA or the more basic DBU can also be used. Solvents can vary too, from toluene, dioxane, THF, diglyme, monoglyme, alcohols, DMF, DMA, NMP, acetonitrile, in some cases even water, and others. Commonly used catalysts like Pd $(PPh_3)_4$, or $Pd(OAc)_2$, $PdCl_2$ type precursors of PdO catalysts have advanced to more complex ones with more efficient ligands. In C—C arylations instead of boronic acids and esters (Stille coupling), aryl-trifluoroborate potassium salts (Suzuki-Miyaura coupling), organo silanes (Hiyama coupling), Grignard reagents (Kumada), zink organyles (Negishi coupling) and tin organyles (Stille coupling) are useful. This experience can be transferred to N- and O-arylations. Numerous papers and methods are available and useful for the one skilled in the art in respect of N-arylation and even of electron deficient anilines (Biscoe et al. JACS 130: 6686 (2008)), and with aryl chlorides and anilines (Fors et al. JACS 130: 13552 (2008) as well as for O-arylation by using Cu catalysis and Pd catalysis.

In the final step of the processes above, a salt of the compounds according to formulae (I) to (III), preferably formula (I), is optionally provided. The said compounds according to the invention can be used in their final non-salt form. On the other hand, the present invention also encompasses the use of these compounds in the form of their pharmaceutically acceptable salts, which can be derived from various organic and inorganic acids and bases by procedures known in the art. Pharmaceutically acceptable salt forms of the compounds according to the invention are for the most part prepared by conventional methods. If the compound according to the invention contains a carboxyl group, one of its suitable salts can be formed by the reaction of the compound with a suitable base to give the corresponding base-addition salt. Such bases are, for example, alkali metal hydroxides, including potassium hydroxide, sodium hydroxide and lithium hydroxide; alkaline earth metal hydroxides, such as barium hydroxide and calcium hydroxide; alkali metal alkoxides, for example potassium ethoxide and sodium propoxide; and various organic bases, such as piperidine, diethanolamine and N-methylglutamine. The aluminum salts of the compounds according to the invention are likewise included. In the case of certain compounds according to the invention, acid-addition salts can be formed by treating these compounds with pharmaceutically acceptable organic and inorganic acids, for example hydrogen halides, such as hydrogen chloride, hydrogen bromide or hydrogen iodide, other mineral acids and corresponding salts thereof, such as sulfate, nitrate or phosphate and the like, and alkyl- and monoarylsulfonates, such as ethanesulfonate, toluenesulfonate and benzenesulfonate, and other organic acids and corresponding salts thereof, such as acetate, trifluoroacetate, tartrate, maleate, succinate, citrate, benzoate, salicylate, ascorbate and the like. Accordingly, pharmaceutically acceptable acid-addition salts of the compounds according to the invention include the following: acetate, adipate, alginate, arginate, aspartate, benzoate, benzenesulfonate (besylate), bisulfate, bisulfite, bromide, butyrate, camphorate, camphorsulfonate, caprylate, chloride, chlorobenzoate, citrate, cyclopentanepropionate, digluconate, dihydrogenphosphate, dinitrobenzoate, dodecylsulfate, ethanesulfonate, fumarate, galacterate (from mucic acid), galacturonate, glucoheptanoate, gluconate, glutamate, glycerophosphate, hemisuccinate, hemisulfate, heptanoate, hexanoate, hippurate, hydrochloride, hydrobromide, hydroiodide, 2-hydroxyethanesulfonate, iodide, isethionate, isobutyrate, lactate, lactobionate, malate, maleate, malonate, mandelate, metaphosphate, methanesulfonate, methylbenzoate, monohydrogenphosphate, 2-naphthalenesulfonate, nicotinate, nitrate, oxalate, oleate, palmoate, pectinate, persulfate, phenylacetate, 3-phenylpropionate, phosphate, phosphonate, phthalate, but this does not represent a restriction.

With regard to that stated above, it can be seen that the expressions "pharmaceutically acceptable salt" and "physiologically acceptable salt", which are used interchangeable herein, in the present connection are taken to mean an active ingredient which comprises a compound according to the invention in the form of one of its salts, in particular if this salt form imparts improved pharmacokinetic properties on the active ingredient compared with the free form of the active ingredient or any other salt form of the active ingredient used earlier. The pharmaceutically acceptable salt form of the active ingredient can also provide this active ingredient for the first time with a desired pharmacokinetic property which it did not have earlier and can even have a positive influence on the pharmacodynamics of this active ingredient with respect to its therapeutic efficacy in the body.

Object of the present invention is also the use of compounds according to formula (I) and/or physiologically acceptable salts thereof for modulating an FSH receptor, particularly in the presence of FSH. The term "modulation" denotes any change in FSHR-mediated signal transduction, which is based on the action of the specific inventive compounds capable to interact with the FSHR target in such a manner that makes recognition, binding and activating possible. The compounds are characterized by such a high affinity to FSHR, which ensures a reliable binding and preferably a positive allosteric modulation of FSHR. More preferably, the substances are mono-specific in order to guarantee an exclusive and directed recognition with the single FSHR target. In the context of the present invention, the term "recognition"—without being limited thereto— relates to any type of interaction between the specific compounds and the target, particularly covalent or non-covalent binding or association, such as a covalent bond, hydrophobic/hydrophilic interactions, van der Waals forces, ion pairs, hydrogen bonds, ligand-receptor interactions, and the like. Such association may also encompass the presence of other molecules such as peptides, proteins or nucleotide sequences. The present receptor/ligand-interaction is characterized by high affinity, high selectivity and minimal or even lacking cross-reactivity to other target molecules to exclude unhealthy and harmful impacts to the treated subject.

A preferred object of the present invention relates to a method for modulating an FSH receptor, preferably in a positive allosteric manner, wherein a system capable of expressing the FSH receptor, preferably expressing the FSH receptor, is contacted, preferably in the presence of FSH, with at least one compound of formula (I) according to the invention and/or physiologically acceptable salts thereof, under conditions such that said FSH receptor is modulated, preferably in a positive allosteric manner. Although a cellular system is preferred in the scope of the invention, an in-vitro translation system can be alternatively used which is based on the protein synthesis without living cells. The cellular system is defined to be any subject provided that the subject comprises cells. Hence, the cellular system can be selected from the group of single cells, cell cultures, tissues, organs and animals. The prior teaching of the present specification concerning the compounds of formula (I), including any preferred embodiment thereof, is valid and applicable without restrictions to the compounds according to formula (I) and their salts when used in the method for modulating FSHR.

The compounds according to the invention preferably exhibit an advantageous biological activity, which is easily demonstrated in cell culture-based assays, for example assays as described herein or in prior art (cf. e.g. WO 2002/09706, which is incorporated herein by reference). In such assays, the compounds according to the invention preferably exhibit and cause an agonistic effect. It is preferred that the compounds of the invention have an FSHR agonist activity, as expressed by an $EC_{50}$ standard, of less than 10 µM, more preferably less than 1 µM, most preferably less than 0.5 µM, highly preferably less than 0.1 µM. "$EC_{50}$" is the effective concentration of a compound at which 50% of the maximal response of that obtained with FSH would be obtained.

As discussed herein, these signaling pathways are relevant for various diseases, preferably fertility disorders. Accordingly, the compounds according to the invention are useful in the prophylaxis and/or treatment of diseases that are dependent on the said signaling pathways by interaction with one or more of the said signaling pathways. The present invention therefore relates to compounds according to the invention as modulators, preferably agonists, more preferably positive allosteric modulators, of the signaling pathways described herein, preferably of the FSHR-mediated signaling pathway. The compounds of the invention are supposed to bind to the intracellular receptor domain without a competitive interaction with FSH, but they act as an allosteric enhancer of FSH on its receptor. The non-competitive interaction refers to the nature of the agonist activity exhibited by the compounds of the invention, wherein the compounds activate FSHR without substantially reducing the magnitude of binding of FSH to FSHR.

The method of the invention can be performed either in-vitro or in-vivo. The susceptibility of a particular cell to treatment with the compounds according to the invention can be particularly determined by in-vitro tests, whether in the course of research or clinical application. Typically, a culture of the cell is combined with a compound according to the invention at various concentrations for a period of time which is sufficient to allow the active agents to modulate FSHR activity, usually between about one hour and one week. In-vitro treatment can be carried out using cultivated cells from a biopsy sample or cell line. In a preferred aspect of the invention, a follicle cell is stimulated for maturation. The viable cells remaining after the treatment are counted and further processed.

The host or patient can belong to any mammalian species, for example a primate species, particularly humans; rodents, including mice, rats and hamsters; rabbits; horses, cows, dogs, cats, etc. Animal models are of interest for experimental investigations, providing a model for treatment of human disease.

For identification of a signal transduction pathway and for detection of interactions between various signal transduction pathways, various scientists have developed suitable models or model systems, for example cell culture models and models of transgenic animals. For the determination of certain stages in the signal transduction cascade, interacting compounds can be utilized in order to modulate the signal. The compounds according to the invention can also be used as reagents for testing FSHR-dependent signal transduction pathways in animals and/or cell culture models or in the clinical diseases mentioned in this application.

The use according to the previous paragraphs of the specification may be either performed in-vitro or in-vivo models. The modulation can be monitored by the techniques described in the course of the present specification. The in-vitro use is preferably applied to samples of humans suffering from fertility disorders. Testing of several specific compounds and/or derivatives thereof makes the selection of that active ingredient possible that is best suited for the treatment of the human subject. The in-vivo dose rate of the chosen derivative is advantageously pre-adjusted to the FSHR susceptibility and/or severity of disease of the respective subject with regard to the in-vitro data. Therefore, the therapeutic efficacy is remarkably enhanced. Moreover, the subsequent teaching of the present specification concerning the use of the compounds according to formula (I) and its derivatives for the production of a medicament for the prophylactic or therapeutic treatment and/or monitoring is considered as valid and applicable without restrictions to the use of the compound for the modulation of FSHR activity if expedient.

The invention furthermore relates to a medicament comprising at least one compound according to the invention and/or pharmaceutically usable derivatives, salts, solvates and stereoisomers thereof, including mixtures thereof in all ratios. Preferably, the invention relates to a medicament comprising at least one compound according to the invention and/or physiologically acceptable salts thereof.

A "medicament" in the meaning of the invention is any agent in the field of medicine, which comprises one or more compounds of formula (I) or preparations thereof (e.g. a pharmaceutical composition or pharmaceutical formulation) and can be used in prophylaxis, therapy, follow-up or aftercare of patients who suffer from diseases, which are associated with FSHR activity, in such a way that a pathogenic modification of their overall condition or of the condition of particular regions of the organism could establish at least temporarily.

Consequently, the invention also relates to a pharmaceutical composition comprising as active ingredient at least one compound of formula (I) according to the invention and/or physiologically acceptable salts thereof together with pharmaceutically tolerable adjuvants and/or excipients. It shall be understood that the compound of the invention is provided in an effective amount.

In the meaning of the invention, an "adjuvant" denotes every substance that enables, intensifies or modifies a specific response against the active ingredient of the invention if administered simultaneously, contemporarily or sequentially. Known adjuvants for injection solutions are, for example, aluminum compositions, such as aluminum hydroxide or aluminum phosphate, saponins, such as QS21, muramyldipeptide or muramyltripeptide, proteins, such as gamma-interferon or TNF, M59, squalen or polyols.

Furthermore, the active ingredient may be administered alone or in combination with other treatments. A synergistic effect may be achieved by using more than one compound in the pharmaceutical composition, i.e. the compound of formula (I) is combined with at least another agent as active ingredient, which is either another compound of formula (I) or a compound of different structural scaffold. The active ingredients can be used either simultaneously or sequentially. The present compounds are suitable for combination with known fertility-inducing agents. Preferably, the other active pharmaceutical ingredient is selected from the group of FSH, α-FSH (Gonal F), β-FSH, LH, hMG and 2-(4-(2-chloro-1,2-diphenylethenyl)-phenoxy)-N,N-diethyl-ethanamine citrate (Chlomifene citrate). Further ovulation adjuncts are known to those of skill in the art (cf. e.g. WO 2002/09706, which is incorporated herein by reference) and are useful with the compounds of the present invention.

The invention also relates to a set (kit) consisting of separate packs of an effective amount of a compound according to the invention and/or pharmaceutically acceptable salts, derivatives, solvates and stereoisomers thereof, including mixtures thereof in all ratios, and an effective amount of a further medicament active ingredient. The set comprises suitable containers, such as boxes, individual bottles, bags or ampoules. The set may, for example, comprise separate ampoules, each containing an effective amount of a compound according to the invention and/or pharmaceutically acceptable salts, derivatives, solvates and stereoisomers thereof, including mixtures thereof in all ratios, and an effective amount of a further medicament active ingredient in dissolved or lyophilized form.

Pharmaceutical formulations can be adapted for administration via any desired suitable method, for example by oral (including buccal or sublingual), rectal, nasal, topical (including buccal, sublingual or transdermal), vaginal or parenteral (including subcutaneous, intramuscular, intravenous or intradermal) methods. Such formulations can be prepared using all processes known in the pharmaceutical art by, for example, combining the active ingredient with the excipient(s) or adjuvant(s).

The pharmaceutical composition of the invention is produced in a known way using common solid or liquid carriers, diluents and/or additives and usual adjuvants for pharmaceutical engineering and with an appropriate dosage. The amount of excipient material that is combined with the active ingredient to produce a single dosage form varies depending upon the host treated and the particular mode of administration. Suitable excipients include organic or inorganic substances that are suitable for the different routes of administration, such as enteral (e.g. oral), parenteral or topical application, and which do not react with compounds of formula (I) or salts thereof. Examples of suitable excipients are water, vegetable oils, benzyl alcohols, alkylene glycols, polyethylene glycols, glycerol triacetate, gelatin, carbohydrates, e.g. lactose or starch, magnesium stearate, talc and petroleum jelly.

Pharmaceutical formulations adapted for oral administration can be administered as separate units, such as, for example, capsules or tablets; powders or granules; solutions or suspensions in aqueous or non-aqueous liquids; edible foams or foam foods; or oil-in-water liquid emulsions or water-in-oil liquid emulsions.

Pharmaceutical formulations adapted for parenteral administration include aqueous and non-aqueous sterile injection solutions comprising antioxidants, buffers, bacteriostatics and solutes, by means of which the formulation is rendered isotonic with the blood of the recipient to be treated; and aqueous and non-aqueous sterile suspensions, which may comprise suspension media and thickeners. The formulations can be administered in single-dose or multi-dose containers, for example sealed ampoules and vials, and stored in freeze-dried (lyophilized) state, so that only the addition of the sterile carrier liquid, for example water for injection purposes, immediately before use is necessary. Injection solutions and suspensions prepared in accordance with the recipe can be prepared from sterile powders, granules and tablets.

It goes without saying that, in addition to the above particularly mentioned constituents, the formulations may also comprise other agents usual in the art with respect to the particular type of formulation; thus, for example, formulations which are suitable for oral administration may comprise flavors.

In a preferred embodiment of the present invention, the pharmaceutical composition is adapted for oral administration. The preparations can be sterilized and/or can comprise auxiliaries, such as carrier proteins (e.g. serum albumin), lubricants, preservatives, stabilizers, fillers, chelating agents, antioxidants, solvents, bonding agents, suspending agents, wetting agents, emulsifiers, salts (for influencing the osmotic pressure), buffer substances, colorants, flavorings and one or more further active substances, for example one or more vitamins. Additives are well known in the art, and they are used in a variety of formulations.

Accordingly, the invention also relates to a pharmaceutical composition comprising as active ingredient at least one compound of formula (I) according to the invention and/or physiologically acceptable salts thereof together with pharmaceutically tolerable adjuvants for oral administration, optionally in combination with at least another active pharmaceutical ingredient. Both active pharmaceutical ingredients are particularly provided in effective amount. The prior teaching of the present specification concerning administration route and combination product, respectively, is valid and applicable without restrictions to the combination of both features if expedient.

The terms "effective amount" or "effective dose" or "dose" are interchangeably used herein and denote an amount of the pharmaceutical compound having a prophylactically or therapeutically relevant effect on a disease or pathological conditions, i.e. which causes in a tissue, system, animal or human a biological or medical response which is sought or desired, for example, by a researcher or physician. A "prophylactic effect" reduces the likelihood of developing a disease or even prevents the onset of a disease. A "therapeutically relevant effect" relieves to some extent one or more symptoms of a disease or returns to normality either partially or completely one or more physiological or biochemical parameters associated with or causative of the disease or pathological conditions. In addition, the expression "therapeutically effective amount" denotes an amount which, compared with a corresponding subject who has not received this amount, has the following consequence: improved treatment, healing, prevention or elimination of a disease, syndrome, condition, complaint, disorder or side-effects or also the reduction in the advance of a disease, complaint or disorder. The expression "therapeutically effective amount" also encompasses the amounts which are effective for increasing normal physiological function.

The respective dose or dosage range for administering the pharmaceutical composition according to the invention is sufficiently high in order to achieve the desired prophylactic or therapeutic effect of reducing symptoms of the aforementioned diseases, cancer and/or fibrotic diseases. It will be understood that the specific dose level, frequency and period of administration to any particular human will depend upon a variety of factors including the activity of the specific compound employed, the age, body weight, general state of health, gender, diet, time and route of administration, rate of excretion, drug combination and the severity of the particular disease to which the specific therapy is applied. Using well-known means and methods, the exact dose can be determined by one of skill in the art as a matter of routine experimentation. The prior teaching of the present specification is valid and applicable without restrictions to the pharmaceutical composition comprising the compounds of formula (I) if expedient.

Pharmaceutical formulations can be administered in the form of dosage units which comprise a predetermined amount of active ingredient per dosage unit. The concentration of the prophylactically or therapeutically active ingredient in the formulation may vary from about 0.1 to 100 wt %. Preferably, the compound of formula (I) or the pharmaceutically acceptable salts thereof are administered in doses of approximately 0.5 to 1000 mg, more preferably between 1 and 700 mg, most preferably 5 and 100 mg per dose unit. Generally, such a dose range is appropriate for total daily incorporation. In other terms, the daily dose is preferably between approximately 0.02 and 100 mg/kg of body weight. The specific dose for each patient depends, however, on a wide variety of factors as already described in the present specification (e.g. depending on the condition treated, the method of administration and the age, weight and condition of the patient). Preferred dosage unit formulations are those which comprise a daily dose or part-dose, as indicated above, or a corresponding fraction thereof of an active ingredient. Furthermore, pharmaceutical formulations of this type can be prepared using a process which is generally known in the pharmaceutical art.

Although a therapeutically effective amount of a compound according to the invention has to be ultimately determined by the treating doctor or vet by considering a number of factors (e.g. the age and weight of the animal, the precise condition that requires treatment, severity of condition, the nature of the formulation and the method of administration), an effective amount of a compound according to the invention for the treatment of neoplastic growth, for example colon or breast carcinoma, is generally in the range from 0.1 to 100 mg/kg of body weight of the recipient (mammal) per day and particularly typically in the range from 1 to 10 mg/kg of body weight per day. Thus, the actual amount per day for an adult mammal weighing 70 kg is usually between 70 and 700 mg, where this amount can be administered as a single dose per day or usually in a series of part-doses (such as, for example, two, three, four, five or six) per day, so that the total daily dose is the same. An effective amount of a salt or solvate or of a physiologically functional derivative thereof can be determined as the fraction of the effective amount of the compound according to the invention per se. It can be assumed that similar doses are suitable for the treatment of other conditions mentioned above.

The pharmaceutical composition of the invention can be employed as medicament in human and veterinary medicine. According to the invention, the compounds of formula (I) and/or physiologically salts thereof are suited for the prophylactic or therapeutic treatment and/or monitoring of diseases that are caused, mediated and/or propagated by FSHR activity. It is particularly preferred that the diseases are fertility disorders. It shall be understood that the host of the compound is included in the present scope of protection according to the present invention.

Particular preference is given to the stimulation of follicular development, ovulation induction, controlled ovarian hyperstimulation, assisted reproductive technology, including in-vitro fertilization, male hypogonadism and male infertility, including some types of failure of spermatogenesis.

The invention also relates to the use of compounds according to formula (I) and/or physiologically acceptable salts thereof for the prophylactic or therapeutic treatment and/or monitoring of diseases that are caused, mediated and/or propagated by FSHR activity. Furthermore, the invention relates to the use of compounds according to formula (I) and/or physiologically acceptable salts thereof for the production of a medicament for the prophylactic or therapeutic treatment and/or monitoring of diseases that are caused, mediated and/or propagated by FSHR activity. Compounds of formula (I) and/or a physiologically acceptable salt thereof can furthermore be employed as intermediate for the preparation of further medicament active ingredients. The medicament is preferably prepared in a non-chemical manner, e.g. by combining the active ingredient with at least one solid, fluid and/or semi-fluid carrier or excipient, and optionally in conjunction with a single or more other active substances in an appropriate dosage form.

Another object of the present invention are compounds of formula (I) according to the invention and/or physiologically acceptable salts thereof for use in the prophylactic or therapeutic treatment and/or monitoring of diseases that are caused, mediated and/or propagated by FSHR activity. Another preferred object of the invention concerns compounds of formula (I) according to the invention and/or physiologically acceptable salts thereof for use in the prophylactic or therapeutic treatment and/or monitoring of fertility disorders. The prior teaching of the present specification concerning the compounds of formula (I), including any preferred embodiment thereof, is valid and applicable without restrictions to the compounds according to formula (I) and their salts for use in the prophylactic or therapeutic treatment and/or monitoring of fertility disorders.

The compounds of formula (I) according to the invention can be administered before or following an onset of disease once or several times acting as therapy. The aforementioned compounds and medical products of the inventive use are particularly used for the therapeutic treatment. A therapeutically relevant effect relieves to some extent one or more symptoms of a disorder, or returns to normality, either partially or completely, one or more physiological or biochemical parameters associated with or causative of a disease or pathological condition.

Monitoring is considered as a kind of treatment provided that the compounds are administered in distinct intervals, e.g. in order to booster the response and eradicate the pathogens and/or symptoms of the disease completely. Either the identical compound or different compounds can be applied. The medicament can also be used to reducing the likelihood of developing a disorder or even prevent the initiation of disorders associated with FSHR activity in advance or to treat the arising and continuing symptoms. The disorders as concerned by the invention are preferably fertility disorders.

In the meaning of the invention, prophylactic treatment is advisable if the subject possesses any preconditions for the aforementioned physiological or pathological conditions, such as a familial disposition, a genetic defect, or a previously passed disease.

It is another object of the invention to provide a method for treating diseases that are caused, mediated and/or propagated by FSHR activity, wherein at least one compound of formula (I) according to the invention and/or physiologically acceptable salts thereof is administered to a mammal in need of such treatment. It is another preferred object of the invention to provide a method for treating fertility disorders, wherein at least one compound of formula (I) according to the invention and/or physiologically acceptable salts thereof is administered to a mammal in need of such treatment. The compound is preferably provided in an effective amount as defined above. The preferred treatment is an oral administration. In another preferred aspect, the method of treatment aims to achieve ovulation induction and/or controlled ovarian hyperstimulation. In still another preferred aspect, the method of treatment forms the basis for a method for in-vitro fertilization comprising the steps of: (a) treating a mammal according to the method of treatment as described above, (b) collecting ova from said mammal, (c) fertilizing said ova, and (d) implanting said fertilized ova into a host mammal. The host mammal can be either the treated mammal (i.e. the patient) or a surrogate. The prior teaching of the invention and its embodiments is valid and applicable without restrictions to the methods of treatment if expedient.

In the scope of the present invention, novel benzamide compounds of formula (I) are provided for the first time. The low molecular weight compounds of the invention are strong and selective modulators of the FSH receptor. Their selectivity to the FSH receptor is 10-fold over the LH receptor and even 100-fold over the TSH receptor while the $IC_{50}$ amounts to more than 10 µM on unrelated G protein-coupled receptors (GPCR) or non-GPCR targets. The current invention comprises the use of present benzamide derivatives in the regulation and/or modulation of the FSHR signal cascade, which can be advantageously applied as research tool, for diagnosis and/or in treatment of any disorder arising from FSHR signaling.

For example, the compounds of the invention are useful in-vitro as unique tools for understanding the biological role of FSH, including the evaluation of the many factors thought to influence, and be influenced by, the production of FSH and the interaction of FSH with the FSHR (e.g. the mechanism of FSH signal transduction/receptor activation). The present compounds are also useful in the development of other compounds that interact with FSHR since the present compounds provide important structure-activity relationship (SAR) information that facilitate that development. Compounds of the present invention that bind to FSHR can be used as reagents for detecting FSHR on living cells, fixed cells, in biological fluids, in tissue homogenates, in purified, natural biological materials, etc. For example, by labeling such compounds, one can identify cells having FSHR on their surfaces. In addition, based on their ability to bind FSHR, compounds of the present invention can be used in in-situ staining, FACS (fluorescence-activated cell sorting), western blotting, ELISA (enzyme-linked immunoadsorptive assay), etc., receptor purification, or in purifying cells expressing FSHR on the cell surface or inside permeabilized cells.

The compounds of the invention can also be utilized as commercial research reagents for various medical research and diagnostic uses. Such uses can include but are not limited to: use as a calibration standard for quantifying the activities of candidate FSH agonists in a variety of functional assays; use as blocking reagents in random compound screening, i.e. in looking for new families of FSH receptor ligands, the compounds can be used to block recovery of the presently claimed FSH compounds; use in the co-crystallization with FSHR receptor, i.e. the compounds of the present invention will allow formation of crystals of the compound bound to FSHR, enabling the determination of receptor/compound structure by x-ray crystallography; other research and diagnostic applications, wherein FSHR is preferably activated or such activation is conveniently calibrated against a known quantity of an FSH agonist, etc.; use in assays as probes for determining the expression of FSHR on the surface of cells; and developing assays for detecting compounds which bind to the same site as the FSHR binding ligands.

The low molecular weight inhibitors can be applied either themselves and/or in combination with physical measurements for diagnostics of treatment effectiveness. Medicaments and pharmaceutical compositions containing said compounds and the use of said compounds to treat FSHR-mediated conditions is a promising, novel approach for a broad spectrum of therapies causing a direct and immediate improvement in the state of health, whether in man and animal. The impact is of special benefit to efficiently combat infertility, either alone or in combination with other fertility-inducing treatments. In particular, the compounds of the invention potentiate the native FSH effect for both ovulation induction and assisted reproductive technology. The orally bioavailable and active new chemical entities of the invention improve convenience for patients and compliance for physicians.

The compounds of the invention are active in the primary screen (CHO with or without FSH), selective in secondary screen (no or low activity against TSHR and LHR) and potent in the granulosa cell estrodiol assay. Neither hERG nor any toxic effects could be observed in-vitro.

The compounds of formula (I), their salts, isomers, tautomers, enantiomeric forms, diastereomers, racemates, derivatives, prodrugs and/or metabolites are characterized by a high specificity and stability, low manufacturing costs and convenient handling. These features form the basis for a reproducible action, wherein the lack of cross-reactivity is included, and for a reliable and safe interaction with the target structure.

All the references cited herein are incorporated by reference in the disclosure of the invention hereby.

It is to be understood that this invention is not limited to the particular compounds, pharmaceutical compositions, uses and methods described herein, as such matter can, of course, vary. It is also to be understood that the terminology used herein is for the purpose of describing particular embodiments only and is not intended to limit the scope of the present invention, which is only defined by the appended claims. As used herein, including the appended claims, singular forms of words such as "a," "an," and "the" include their corresponding plural referents unless the context clearly dictates otherwise. Thus, e.g., reference to "a compound" includes a single or several different compounds, and reference to "a method" includes reference to equivalent steps and methods known to a person of ordinary skill in the art, and so forth. Unless otherwise defined, all technical and scientific terms used herein have the same meaning as commonly understood by a person of ordinary skill in the art to which this invention belongs.

The techniques that are essential according to the invention are described in detail in the specification. Other techniques which are not described in detail correspond to known standard methods that are well known to a person skilled in the art, or the techniques are described in more detail in cited references, patent applications or standard literature. Although methods and materials similar or equivalent to those described herein can be used in the practice or testing of the present invention, suitable examples are described below. The following examples are provided by way of illustration and not by way of limitation. Within the examples, standard reagents and buffers that are free from contaminating activities (whenever practical) are used. The example are particularly to be construed such that they are not limited to the explicitly demonstrated combinations of features, but the exemplified features may be unrestrictedly combined again if the technical problem of the invention is solved. Similarly, the features of any claim can be combined with the features of one or more other claims.

In the following examples, "conventional workup" means: water was added if necessary, the pH was adjusted, if necessary, to a value of between 2 and 10, depending on the constitution of the end product, the mixture was extracted with ethyl acetate or dichloromethane, the phases were separated, the organic phase was dried over sodium sulfate and evaporated, and the product was purified by chromatography on silica gel and/or by crystallization. $R_f$ values were determined on silica gel. The eluent was ethyl acetate/methanol 9:1.

Standard Description of Analytical Equipment

NMR Spectra were acquired on a Varian $^{Unity}$Inova 400 MHz NMR spectrometer equipped with an Automation Triple Broadband (ATB) probe. The ATB probe was simultaneously tuned to $^1H$, $^{19}F$ and $^{13}C$. For typical $^1H$ NMR spectra, the pulse angle was 45 degrees, 8 scans were summed and the spectral width was 16 ppm (−2 ppm to 14 ppm). A total of 32768 complex points were collected during the 5.1 second acquisition time, and the recycle delay was set to 1 second. Spectra were collected at 25° C. $^1H$ NMR Spectra are typically processed with 0.2 Hz line broadening and zero-filling to 131072 points prior to Fourier transformation.

Method A (Rapid LC): A Shimadzu Shim-pack XR-ODS, 3.0×30 mm, 2.2 m, was used at a temperature of 50° C. and at a flow rate of 1.5 mL/min, 2 µL injection, mobile phase: (A) water with 0.1% formic acid and 1% acetonitrile, mobile phase (B) methanol with 0.1% formic acid; retention time given in minutes. Method details: (I) runs on a Binary Pump G1312B with UV/Vis diode array detector G1315C and Agilent 6130 mass spectrometer in positive and negative ion electrospray mode with UV-detection at 220 and 254 nm with a gradient of 15-95% (B) in a 2.2 min linear gradient, (II) hold for 0.8 min at 95% (B), (III) decrease from 95-15% (B) in a 0.1 min linear gradient, and (IV) hold for 0.29 min at 15% (B).

Method B (Polar Stop-Gap): An Agilent Zorbax Bonus RP, 2.1×50 mm, 3.5 m, was used at a temperature of 50° C. and at a flow rate of 0.8 mL/min, 2 µL injection, mobile phase: (A) water with 0.1% formic acid and 1% acetonitrile, mobile phase (B) methanol with 0.1% formic acid; retention time given in minutes. Method details: (I) runs on a Binary Pump G1312B with UV/Vis diode array detector G1315C and Agilent 6130 mass spectrometer in positive and negative ion electrospray mode with UV-detection at 220 and 254 nm with a gradient of 5-95% (B) in a 2.5 min linear gradient, (II) hold for 0.5 min at 95% (B), (III) decrease from 95-5% (B) in a 0.1 min linear gradient, and (IV) hold for 0.29 min at 5% (B).

Preparative HPLC was performed using a system controlled by Chromeleon software and consisting of two Varian PrepStar Model 218 Pumps, a Varian ProStar Model 320 UV/Vis detector, a SEDEX 55 ELSD detector, and a Gilson 215 liquid handler. Typical HPLC mobile phases consist of water and methanol. The standard column is a Varian Dynamax 21.4 mm diameter Microsorb Guard-8 C18 column.

Rt: Retention time

Example 1: Synthetic route towards furan-2-carboxylic acid [5-((S)-1-phenyl-ethylcarbamoyl)-2-(4-o-tolyl-piperazin-1-yl)-phenyl]-amide (compound no. 11)

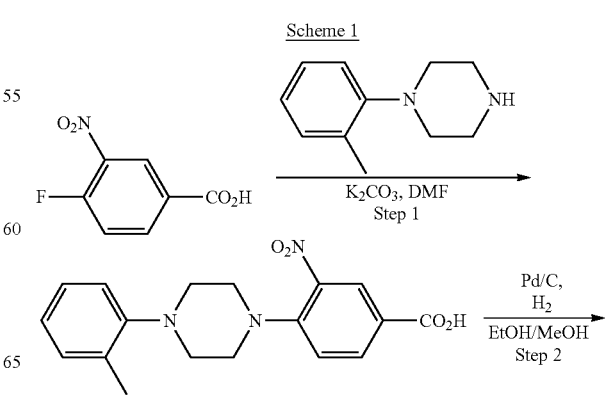

Scheme 1

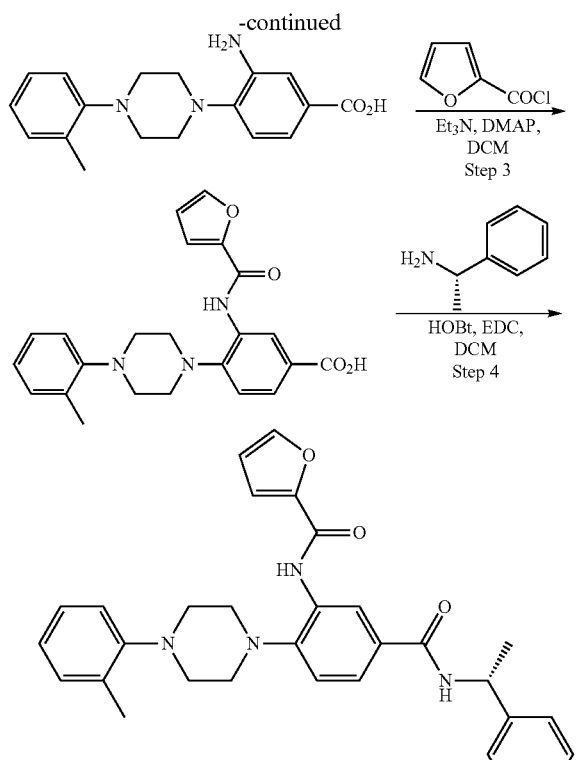

Step 1

To a solution of 4-fluoro-3-nitro-benzoic acid (6.0 g, 32.4 mmol) in DMF (20 mL), $K_2CO_3$ (8.94 g, 64.8 mmol) was added, followed by 1-o-tolyl-piperazine (6.85 g, 38.9 mmol), and the reaction mixture was stirred at room temperature for 16 h. DMF (5.0 mL) was added and filtered. The solid was washed with MeOH (300 mL) and methanol layer was evaporated to give the acid 3-nitro-4-(4-o-tolyl-piperazin-1-yl)-benzoic acid in the first crop (4.0 g, 36%).

Step 2

In a mixture of EtOH (100 mL) and MeOH (100 mL) compound acid 3-nitro-4-(4-o-tolyl-piperazin-1-yl)-benzoic acid (2.0 g, 5.86 mmol) was dissolved and evacuated for 5 min. This was added to a 3-necked flask containing Pd/C (0.2 g of 5 wt %) under nitrogen. The reaction mixture was evacuated and nitrogen purged two times and stirred under a balloon of hydrogen for 4 h. LC-MS indicated the completion of reaction and the contents were evacuated and nitrogen purged and filtered through celite, and concentrated to give the aniline 3-amino-4-(4-o-tolyl-piperazin-1-yl)-benzoic acid (1.7 g, 94%).

Step 3

In $CH_2Cl_2$ (50 mL) aniline 3-amino-4-(4-o-tolyl-piperazin-1-yl)-benzoic acid (1.5 g, 4.8 mmol) was taken with TEA (3.3 mL, 24 mmol) and cooled to 0° C. Furoyl chloride (1.38 g, 10.6 mmol) in $CH_2Cl_2$ (5.0 mL) was added dropwise and the reaction was stirred at 0-25° C. for 6 h. The reaction mixture was concentrated and dissolved in a mixture of MeOH (20 mL) and THF (20 mL) and stirred with a solution of 2N NaOH (20 mL) for 2 h. The solvents were removed and the contents were dissolved in water and the solution was brought to pH 5.0 using 2 N HCl. The solid product 3-[(Furan-2-carbonyl)-amino]-4-(4-o-tolyl-piperazin-1-yl)-benzoic acid was filtered and dried (1.1 g, 56%).

Step 4

To a solution of 3-[(furan-2-carbonyl)-amino]-4-(4-o-tolyl-piperazin-1-yl)-benzoic acid (0.1 g, 0.247 mmol) and HOBt (0.05 g, 0.37 mmol) in $CH_2Cl_2$ (3.0 mL), a-methyl benzyl amine (0.035 g, 0.296 mmol) was added, followed by EDC.HCl (0.05 g, 0.321 mmol), and the reaction mixture was stirred at room temperature for 3 h. The crude was diluted with $CH_2Cl_2$ (10.0 mL) and washed with water, concentrated and purified on silica gel column using $CH_2Cl_2$/MeOH (10%) as eluent to give off-white solid which was treated with 5 mL of 2 M HCl in dioxane followed by ether. The precipitated product was filtered and dried (0.02 g, 16% yield).

LCMS (ESI) 509 (M+H); $^1$H NMR (400 MHz, DMSO-$d_6$) δ ppm 1.40-1.48 (m, 3H) 2.28 (brs, 3H) 3.05 (s, 9H) 5.13 (quin, J=7.42 Hz, 1H) 6.69 (dd, J=3.47, 1.76 Hz, 1H) 6.93-6.99 (m, 1H) 7.06-7.11 (m, 1H) 7.14-7.21 (m, 3H) 7.26-7.31 (m, 3H) 7.33-7.38 (m, 3H) 7.69 (dd, J=8.35, 2.00 Hz, 1H) 7.95-8.00 (m, 1H) 8.57 (d, J=2.00 Hz, 1H) 8.74 (d, J=8.05 Hz, 1H) 9.42 (s, 1H).

The preparation of following compounds was in line with Scheme 1:

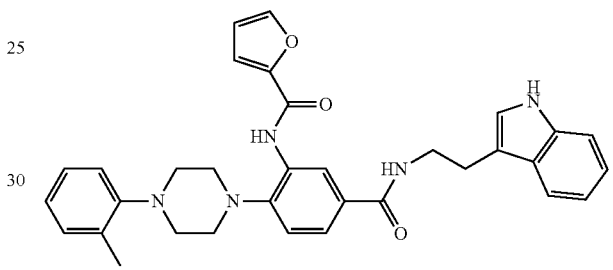

Furan-2-carboxylic acid [5-[2-(1H-indol-3-yl)-ethylcarbamoyl]-2-(4-o-tolyl-piperazin-1-yl)-phenyl]-amide (compound no. 10) was prepared following the same procedure as compound no. 11 from the intermediate acid 3-[(furan-2-carbonyl)-amino]-4-(4-o-tolyl-piperazin-1-yl)-benzoic acid.

LCMS (ESI) 548 (M+H); $^1$H NMR (400 MHz, METHANOL-d4) δ ppm 2.32 (s, 3H) 3.03-3.09 (m, 2H) 3.12 (s, 8H) 3.65 (t, J=7.44 Hz, 2H) 6.67 (dd, J=3.54, 1.78 Hz, 1H) 6.93-7.00 (m, 2H) 7.02-7.08 (m, 1H) 7.10 (s, 1H) 7.13-7.18 (m, 3H) 7.27-7.33 (m, 2H) 7.37 (d, J=8.30 Hz, 1H) 7.54-7.62 (m, 2H) 7.80 (d, J=1.03 Hz, 1H) 8.64 (d, J=2.05 Hz, 1H).

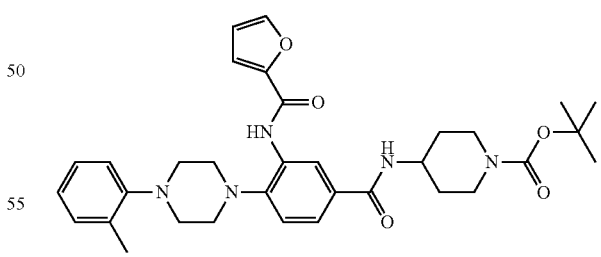

4-[3-[(Furan-2-carbonyl)-amino]-4-(4-o-tolyl-piperazin-1-yl)-benzoylamino]-piperidine-1-carboxylic acid tert-butyl ester (compound no. 49) was prepared following the same procedure as compound no. 11 from the intermediate acid 3-[(furan-2-carbonyl)-amino]-4-(4-o-tolyl-piperazin-1-yl)-benzoic acid.

LCMS (ESI) 588 (M+H); $^1$H NMR (400 MHz, DICHLOROMETHANE-$d_2$) δ ppm 1.36-1.42 (m, 1H) 1.42-1.46 (m, 10H) 1.59 (brs, 1H) 1.93-2.08 (m, 2H) 2.34 (s, 3H) 2.90 (t, J=11.27 Hz, 2H) 3.07-3.22 (m, 8H) 3.94-4.18 (m, 3H) 6.10 (d, J=7.76 Hz, 1H) 6.60 (dd, J=3.51, 1.76 Hz, 1H) 7.01 (td, J=7.33, 1.24 Hz, 1H) 7.09-7.15 (m, 1H) 7.17-7.24 (m, 3H) 7.30-7.36 (m, 1H) 8.80 (d, J=2.10 Hz, 1H) 9.43 (s, 1H).

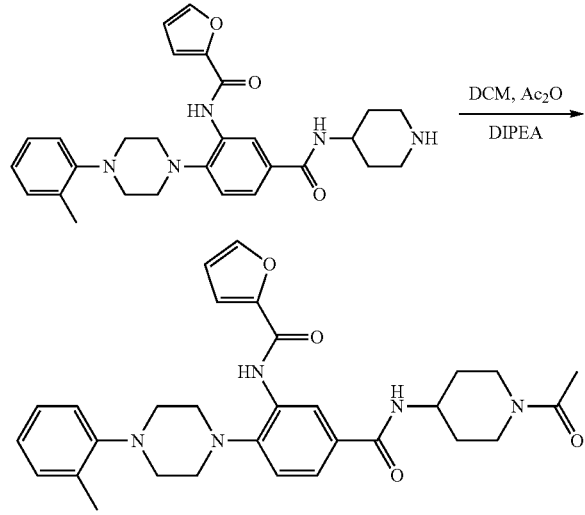

Furan-2-carboxylic acid [5-(1-acetyl-piperidin-4-ylcarbamoyl)-2-(4-o-tolyl-piperazin-1-yl)-phenyl]-amide (compound no. 56) was prepared as follows: 4-[3-[(Furan-2-carbonyl)-amino]-4-(4-o-tolyl-piperazin-1-yl)-benzoylamino]-piperidine-1-carboxylic acid tert-butyl ester (0.35 g, 0.59 mmol) was stirred with a mixture of CH$_2$Cl$_2$ (5.0 mL) and TFA (3.0 mL) for 6 h. The reaction was concentrated to give the intermediate salt (0.225 g). The TFA salt of furan-2-carboxylic acid [5-(piperidin-4-ylcarbamoyl)-2-(4-o-tolyl-piperazin-1-yl)-phenyl]-amide (0.06 g, 0.123 mmol) was dissolved in CH$_2$Cl$_2$ (5.0 mL) and DIPEA (0.2 mL, 1.23 mmol) was added to this followed by acetic anhydride (0.062 g, 0.615 mmol). The reaction mixture was stirred at room temperature for 1 h. Reaction was concentrated and dissolved in methanol and purified on preparative HPLC using MeOH/water as eluent to give the product (0.025 g, 38%).

LCMS (ESI) 530 (M+H); $^1$H NMR (400 MHz, CHLOROFORM-d) δ ppm 1.33-1.52 (m, 3H) 1.96-2.07 (m, 1H) 2.10 (s, 3H) 2.34 (s, 3H) 2.76 (t, J=11.42 Hz, 1H) 3.12 (dd, J=19.38, 5.61 Hz, 8H) 3.19-3.25 (m, 1H) 3.82 (d, J=12.15 Hz, 1H) 4.12-4.26 (m, 1H) 4.59 (d, J=14.10 Hz, 1H) 6.23 (d, J=7.71 Hz, 1H) 6.58 (dd, J=3.47, 1.76 Hz, 1H) 6.99-7.06 (m, 1H) 7.07-7.14 (m, 1H) 7.21 (d, J=5.32 Hz, 1H) 7.25 (s, 1H) 7.31 (d, J=8.30 Hz, 1H) 7.56 (d, J=1.22 Hz, 1H) 7.72 (dd, J=8.27, 2.03 Hz, 1H) 8.76 (d, J=2.10 Hz, 1H) 9.43 (s, 1H).

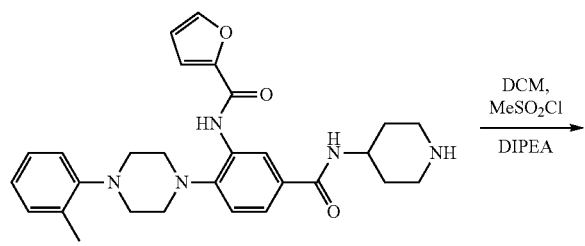

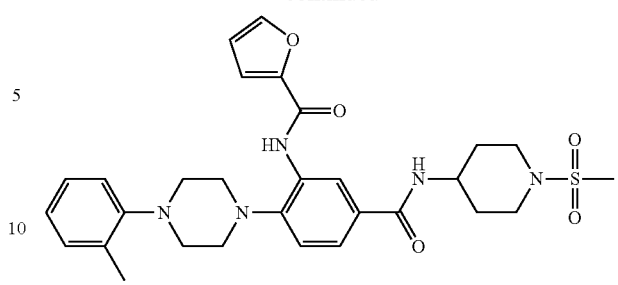

Furan-2-carboxylic acid [5-(1-methanesulfonyl-piperidin-4-ylcarbamoyl)-2-(4-o-tolyl-piperazin-1-yl)-phenyl]-amide (compound no. 58) was prepared as follows: Furan-2-carboxylic acid [5-(piperidin-4-ylcarbamoyl)-2-(4-o-tolyl-piperazin-1-yl)-phenyl]-amide (0.35 g, 0.59 mmol) was stirred with a mixture of CH$_2$Cl$_2$ (5.0 mL) and TFA (3.0 mL) for 6 h. The reaction was concentrated to give the intermediate salt (0.225 g). The TFA salt of furan-2-carboxylic acid [5-(piperidin-4-ylcarbamoyl)-2-(4-o-tolyl-piperazin-1-yl)-phenyl]-amide (0.06 g, 0.123 mmol) was dissolved in CH$_2$Cl$_2$ (5.0 mL) and DIPEA (0.2 mL, 1.23 mmol) was added to this followed by acetic anhydride (0.062 g, 0.615 mmol). The reaction mixture was stirred at room temperature for 1 h. Reaction was concentrated and dissolved in methanol and purified on preparative HPLC using MeOH/water as eluent to give the product (0.025 g, 37%).

LCMS (ESI) 566 (M+H); $^1$H NMR (400 MHz, DMSO-d$_6$) δ ppm 1.57 (qd, J=11.93, 3.69 Hz, 2H) 1.87 (d, J=10.74 Hz, 2H) 2.26 (s, 3H) 2.77-2.83 (m, 3H) 2.84 (s, 3H) 3.04 (s, 8H) 3.54 (d, J=11.91 Hz, 2H) 6.70 (dd, J=3.47, 1.76 Hz, 1H) 6.91-6.99 (m, 1H) 7.05-7.11 (m, 1H) 7.12-7.19 (m, 2H) 7.30 (d, J=2.88 Hz, 1H) 7.35 (d, J=8.35 Hz, 1H) 7.61 (dd, J=8.30, 2.05 Hz, 1H) 7.84-8.03 (m, 1H) 8.27 (d, J=7.76 Hz, 1H) 8.55 (d, J=2.00 Hz, 1H) 9.42 (s, 1H).

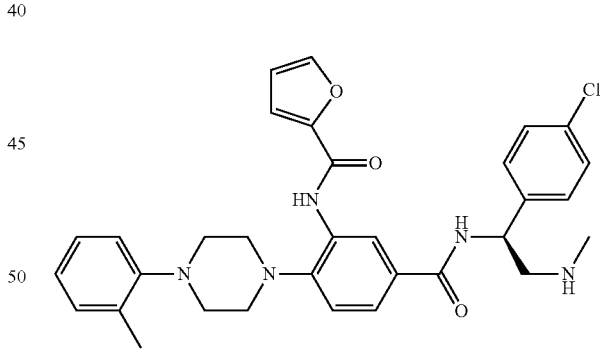

Furan-2-carboxylic acid [5-[(S)-1-(4-chloro-phenyl)-2-methylamino-ethylcarbamoyl]-2-(4-o-tolyl-piperazin-1-yl)-phenyl]-amide (compound no. 55) was prepared following the same procedure as compound no. 11 from the intermediate acid 3-[(furan-2-carbonyl)-amino]-4-(4-o-tolyl-piperazin-1-yl)-benzoic acid.

LCMS (ESI) 570 (M−H); $^1$H NMR (400 MHz, METHANOL-d4) δ ppm 2.32 (s, 3H) 2.79 (s, 3H) 3.14 (s, 8H) 3.48-3.54 (m, 2H) 5.52 (dd, J=8.79, 5.86 Hz, 1H) 6.67 (dd, J=3.47, 1.71 Hz, 1H) 6.91-7.03 (m, 1H) 7.12-7.20 (m, 3H) 7.29 (d, J=3.47 Hz, 1H) 7.38-7.49 (m, 5H) 7.70 (dd, J=8.32, 2.03 Hz, 1H) 7.81 (s, 1H) 8.71 (d, J=2.00 Hz, 1H).

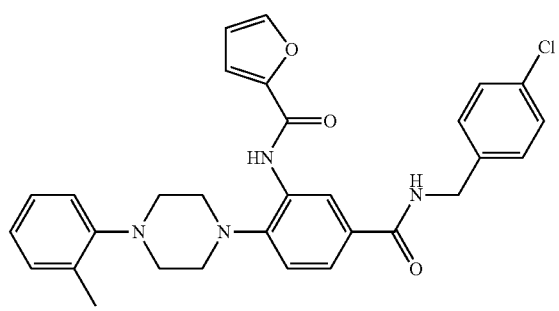 [SMILES: Cc1ccccc1N1CCN(c2ccc(C(=O)NCc3ccc(Cl)cc3)cc2NC(=O)c2ccco2)CC1]

Furan-2-carboxylic acid [5-(4-chloro-benzylcarbamoyl)-2-(4-o-tolyl-piperazin-1-yl)-phenyl]-amide (compound no. 131) was prepared following the same procedure as compound no. 11 from the intermediate acid 3-[(Furan-2-carbonyl)-amino]-4-(4-o-tolyl-piperazin-1-yl)-benzoic acid.

LCMS (ESI) 529 (M+H); $^1$H NMR (400 MHz, DMSO-d6) δ ppm 2.26 (s, 3H) 3.04 (s, 8H) 4.42 (d, J=5.76 Hz, 2H) 6.70 (dd, J=3.49, 1.68 Hz, 1H) 6.90-7.00 (m, 1H) 7.06-7.11 (m, 1H) 7.13-7.19 (m, 2H) 7.26-7.40 (m, 6H) 7.66 (dd, J=8.35, 2.00 Hz, 1H) 7.98 (d, J=1.61 Hz, 1H) 8.61 (d, J=2.00 Hz, 1H) 8.99 (t, J=6.08 Hz, 1H) 9.41 (s, 1H).

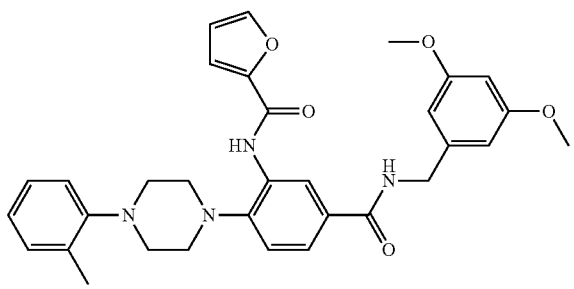 [SMILES: COc1cc(CNC(=O)c2ccc(N3CCN(c4ccccc4C)CC3)c(NC(=O)c3ccco3)c2)cc(OC)c1]

Furan-2-carboxylic acid [5-(3,5-dimethoxy-benzylcarbamoyl)-2-(4-o-tolyl-piperazin-1-yl)-phenyl]-amide (compound no. 95) was prepared following the same procedure as compound no. 11 from the intermediate acid 3-[(furan-2-carbonyl)-amino]-4-(4-o-tolyl-piperazin-1-yl)-benzoic acid.

LCMS (ESI) 555 (M+H); $^1$H NMR (400 MHz, DICHLOROMETHANE-d$_2$) δ ppm 2.39 (s, 3H) 3.19 (d, J=9.71 Hz, 8H) 3.75-3.80 (m, 6H) 4.56 (d, J=5.81 Hz, 2H) 6.38 (t, J=2.25 Hz, 1H) 6.51 (d, J=2.25 Hz, 2H) 6.56-6.63 (m, 2H) 6.98-7.08 (m, 1H) 7.17-7.25 (m, 4H) 7.33-7.40 (m, 1H) 7.55-7.68 (m, 1H) 8.87 (d, J=2.05 Hz, 1H) 9.44 (s, 1H).

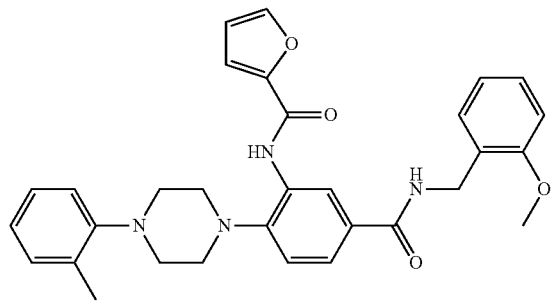 [SMILES: COc1ccccc1CNC(=O)c1ccc(N2CCN(c3ccccc3C)CC2)c(NC(=O)c2ccco2)c1]

Furan-2-carboxylic acid [5-(2-methoxy-benzylcarbamoyl)-2-(4-o-tolyl-piperazin-1-yl)-phenyl]-amide (compound no. 124) was prepared following the same procedure as compound no. 11 from the intermediate acid 3-[(furan-2-carbonyl)-amino]-4-(4-o-tolyl-piperazin-1-yl)-benzoic acid.

LCMS (ESI) 525 (M+H); $^1$H NMR (400 MHz, DICHLOROMETHANE-d$_2$) δ ppm 2.36 (s, 3H) 3.11-3.22 (m, 9H) 3.88-3.92 (m, 3H) 4.60 (d, J=5.86 Hz, 2H) 6.60 (dd, J=3.47, 1.76 Hz, 1H) 6.79 (t, J=5.54 Hz, 1H) 6.89-6.96 (m, 2H) 6.99-7.06 (m, 1H) 7.12-7.38 (m, 6H) 7.55-7.64 (m, 2H) 8.82 (d, J=2.10 Hz, 1H) 9.43 (brs, 1H).

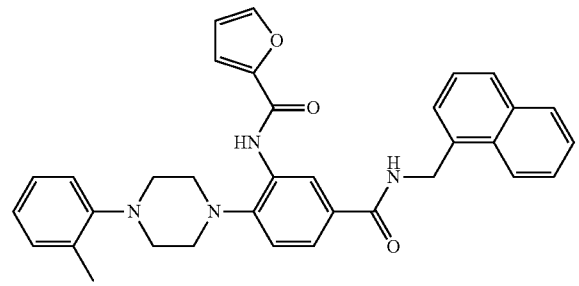 [SMILES: Cc1ccccc1N1CCN(c2ccc(C(=O)NCc3cccc4ccccc34)cc2NC(=O)c2ccco2)CC1]

Furan-2-carboxylic acid [5-[(naphthalen-1-ylmethyl)-carbamoyl]-2-(4-o-tolyl-piperazin-1-yl)-phenyl]-amide Compound no. 96) was prepared following the same procedure as compound no. 11 from 3-[(furan-2-carbonyl)-amino]-4-(4-o-tolyl-piperazin-1-yl)-benzoic acid.

LCMS (ESI) 545 (M+H); $^1$H NMR (400 MHz, DMSO-d$_6$) δ ppm 2.26 (s, 3H) 3.04 (s, 8H) 4.91 (d, J=5.66 Hz, 2H) 6.69 (dd, J=3.49, 1.73 Hz, 1H) 6.92-6.98 (m, 1H) 7.05-7.11 (m, 1H) 7.15 (d, J=7.37 Hz, 2H) 7.29 (d, J=3.22 Hz, 1H) 7.36 (d, J=8.35 Hz, 1H) 7.43-7.47 (m, 2H) 7.48-7.59 (m, 2H) 7.70 (dd, J=8.35, 2.05 Hz, 1H) 7.82 (t, J=4.76 Hz, 1H) 7.90-7.94 (m, 1H) 7.98 (d, J=1.12 Hz, 1H) 8.16 (d, J=8.10 Hz, 1H) 8.64 (d, J=2.05 Hz, 1H) 8.99 (t, J=5.74 Hz, 1H) 9.41 (s, 1H).

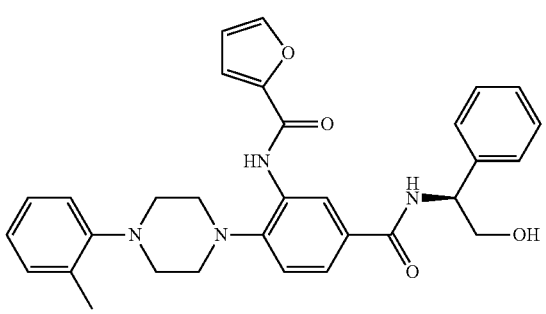 [SMILES: Cc1ccccc1N1CCN(c2ccc(C(=O)N[C@H](CO)c3ccccc3)cc2NC(=O)c2ccco2)CC1]

Furan-2-carboxylic acid [5-((S)-2-hydroxy-1-phenyl-ethylcarbamoyl)-2-(4-o-tolyl-piperazin-1-yl)-phenyl]-amide (compound no. 67) was prepared following the same procedure as compound no. 11 from the intermediate acid 3-[(furan-2-carbonyl)-amino]-4-(4-o-tolyl-piperazin-1-yl)-benzoic acid.

LCMS (ESI) 525 (M+H); $^1$H NMR (400 MHz, METHANOL-d$_4$) δ ppm 2.35 (s, 3H) 3.15 (s, 8H) 3.87 (d, J=6.59 Hz, 2H) 5.18-5.24 (m, 1H) 6.69 (dd, J=3.51, 1.81 Hz, 1H) 6.95-7.02 (m, 1H) 7.17 (dd, J=3.73, 1.93 Hz, 3H) 7.24-7.29 (m, 1H) 7.31 (d, J=3.51 Hz, 1H) 7.35 (t, J=7.57 Hz, 2H) 7.43 (dd, J=7.74, 3.25 Hz, 3H) 7.69 (d, J=2.15 Hz, 1H) 7.81-7.83 (m, 1H).

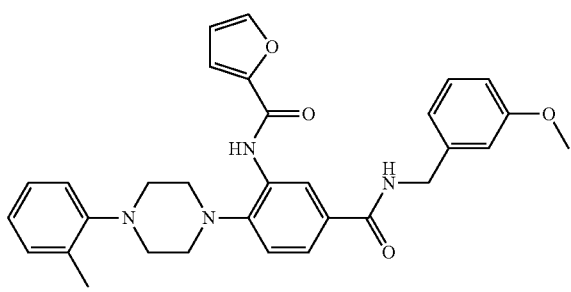 [SMILES: COc1cccc(CNC(=O)c2ccc(N3CCN(c4ccccc4C)CC3)c(NC(=O)c3ccco3)c2)c1]

Furan-2-carboxylic acid [5-(3-methoxy-benzylcarbamoyl)-2-(4-o-tolyl-piperazin-1-yl)-phenyl]-amide (compound no. 93) was prepared following the same procedure as compound no. 11 from the intermediate acid 3-[(furan-2-carbonyl)-amino]-4-(4-o-tolyl-piperazin-1-yl)-benzoic acid.

LCMS (ESI) 525 (M+H); $^1$H NMR (400 MHz, DICHLOROMETHANE-d2) δ ppm 2.45 (s, 3H) 3.29 (d, J=10.20 Hz, 8H) 3.80 (s, 3H) 4.60 (d, J=5.76 Hz, 2H) 6.56-6.63 (m, 2H) 6.80-6.86 (m, 1H) 6.88-6.99 (m, 2H) 7.05-7.14 (m, 1H) 7.26 (dd, J=7.76, 2.44 Hz, 5H) 7.40 (s, 1H) 7.59-7.62 (m, 1H) 7.63-7.69 (m, 1H) 8.86 (s, 1H) 9.41-9.49 (m, 1H).

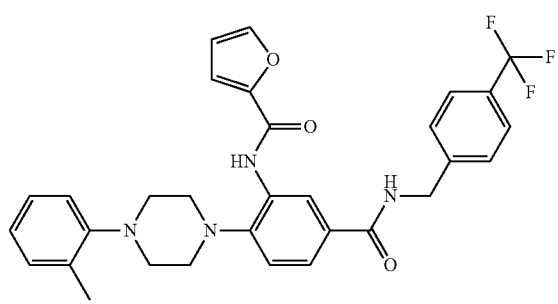 [SMILES: Cc1ccccc1N1CCN(c2ccc(C(=O)NCc3ccc(C(F)(F)F)cc3)cc2NC(=O)c2ccco2)CC1]

Furan-2-carboxylic acid [2-(4-o-tolyl-piperazin-1-yl)-5-(4-trifluoromethyl-benzylcarbamoyl)-phenyl]-amide (compound no. 94) was prepared following the same procedure as compound no. 11 from 3-[(furan-2-carbonyl)-amino]-4-(4-o-tolyl-piperazin-1-yl)-benzoic acid.

LCMS (ESI) 525 (M+H); $^1$H NMR (400 MHz, DICHLOROMETHANE-d2) δ ppm 2.41 (s, 3H) 3.23 (d, J=9.57 Hz, 8H) 4.70 (d, J=5.91 Hz, 2H) 6.61 (dd, J=3.49, 1.78 Hz, 1H) 6.71-6.78 (m, 1H) 7.03-7.11 (m, 1H) 7.20-7.27 (m, 4H) 7.38 (d, J=8.30 Hz, 1H) 7.51 (d, J=8.00 Hz, 2H) 7.59-7.65 (m, 3H) 7.68 (dd, J=8.30, 2.10 Hz, 1H) 8.89 (d, J=2.05 Hz, 1H) 9.38-9.50 (m, 1H).

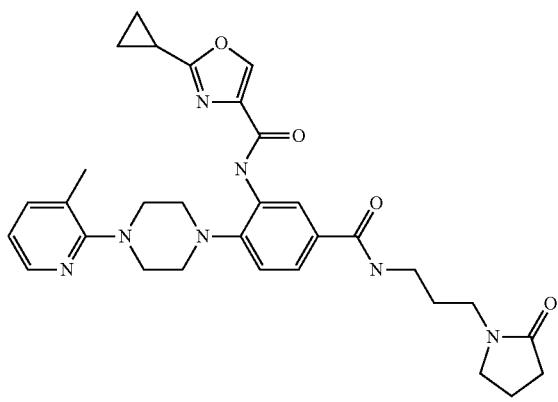 [SMILES: Cc1cccnc1N1CCN(c2ccc(C(=O)NCCCN3CCCC3=O)cc2NC(=O)c2coc(C3CC3)n2)CC1]

2-Cyclopropyl-oxazole-4-carboxylic acid {2-[4-(3-methyl-pyridin-2-yl)-piperazin-1-yl]-5-[3-(2-oxo-pyrrolidin-1-yl)-propylcarbamoyl]-phenyl}-amide LCMS (M+H) 572; $^1$H NMR (400 MHz, DICHLOROMETHANE-d$_2$) δ ppm 1.01-1.19 (m, 4H) 1.75 (t, J=6.08 Hz, 2H) 1.98-2.12 (m, 4H) 2.33 (s, 3H) 2.38 (t, J=8.13 Hz, 2H) 3.06-3.13 (m, 4H) 3.32-3.45 (m, 9H) 6.90 (dd, J=7.30, 4.91 Hz, 1H) 7.27 (d, J=8.25 Hz, 1H) 7.47 (d, J=6.83 Hz, 1H) 7.64 (dd, J=8.27, 2.07 Hz, 2H) 8.12 (s, 1H) 8.18 (dd, J=4.88, 1.46 Hz, 1H) 8.86 (d, J=2.05 Hz, 1H) 9.90 (s, 1H).

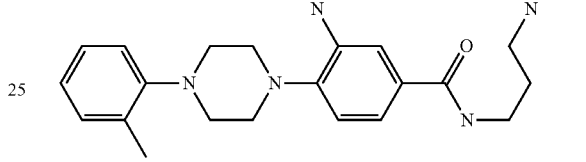

2-Cyclopropyl-oxazole-4-carboxylic acid [5-{3-[(tetrahydro-pyran-4-carbonyl)-amino]-propylcarbamoyl}-2-(4-o-tolyl-piperazin-1-yl)-phenyl]-amide LCMS (M+H) 615; $^1$H NMR (CHLOROFORM-d) δ ppm 9.99 (s, 1H), 8.89 (d, J=1.9 Hz, 1H), 8.13 (s, 1H), 7.72 (dd, J=8.3, 2.0 Hz, 1H), 7.32 (d, J=8.2 Hz, 1H), 7.20-7.26 (m, 2H), 7.15-7.20 (m, 1H), 7.02-7.09 (m, 1H), 6.78 (t, J=5.9 Hz, 1H), 6.70 (t, J=6.3 Hz, 1H), 4.05 (t, J=3.1 Hz, 1H), 4.01 (t, J=3.3 Hz, 1H), 3.53 (q, J=6.3 Hz, 2H), 3.40-3.48 (m, 2H), 3.33 (q, J=6.1 Hz, 2H), 3.17-3.24 (m, 4H), 3.10-3.15 (m, 4H), 2.39-2.46 (m, 1H), 2.38 (s, 3H), 2.07-2.15 (m, 1H), 1.79-1.92 (m, 4H), 1.70-1.78 (m, 2H), 1.11-1.20 (m, 4H).

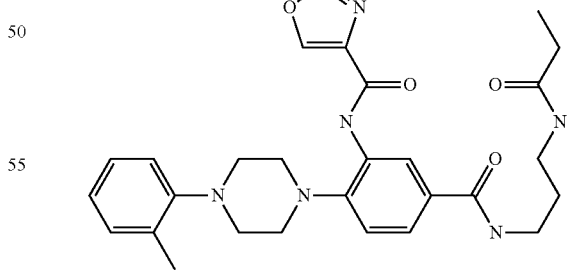

2-Cyclopropyl-oxazole-4-carboxylic acid [5-(3-propionylamino-propylcarbamoyl)-2-(4-o-tolyl-piperazin-1-yl)-phenyl]-amide LCMS (M+H) 559; $^1$H NMR (CHLOROFORM-d) δ ppm 9.98 (s, 1H), 8.90 (d, J=1.9 Hz, 1H), 8.13 (s, 1H), 7.72 (dd, J=8.2, 2.0 Hz, 1H), 7.31 (d, J=8.2 Hz, 1H), 7.20-7.26 (m, 2H), 7.15-7.20 (m, 1H), 7.02-7.08 (m, 1H), 6.84 (t, J=5.7 Hz, 1H), 6.43-6.51 (m, 1H), 3.53 (q, J=6.2 Hz, 2H), 3.34 (q, J=6.2 Hz, 2H), 3.17-3.23 (m, 4H), 3.09-3.16 (m, 4H), 2.38 (s, 3H), 2.28 (q, J=7.6 Hz, 2H), 2.06-2.15 (m, 1H), 1.75 (quin, J=6.0 Hz, 2H), 1.21 (t, J=7.6 Hz, 3H), 1.10-1.18 (m, 4H).

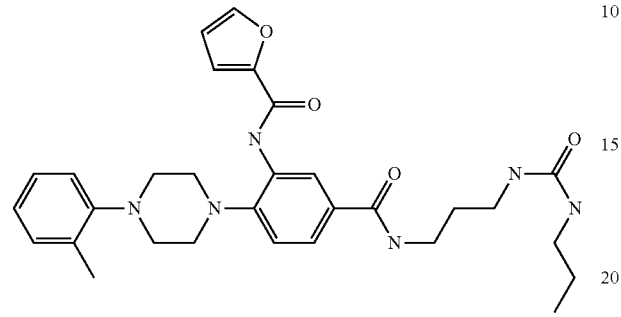

Furan-2-carboxylic acid [5-[3-(3-propyl-ureido)-propylcarbamoyl]-2-(4-o-tolyl-piperazin-1-yl)-phenyl]-amide LCMS (M+H) 547; $^1$H NMR (CHLOROFORM-d) δ ppm 9.48 (s, 1H), 8.88 (d, J=1.9 Hz, 1H), 7.68-7.80 (m, 1H), 7.59 (s, 1H), 7.34 (d, J=8.3 Hz, 1H), 7.24 (d, J=4.9 Hz, 2H), 7.13 (d, J=7.7 Hz, 1H), 7.02-7.09 (m, 1H), 6.94-7.01 (m, 1H), 5.16 (br. s., 1H), 4.64 (br. s., 1H), 3.57 (q, J=6.1 Hz, 2H), 3.33 (q, J=5.9 Hz, 2H), 3.07-3.24 (m, 10H), 2.37 (s, 3H), 1.72-1.82 (m, 2H), 1.52 (sxt, J=7.3 Hz, 2H), 0.92 (t, J=7.4 Hz, 3H).

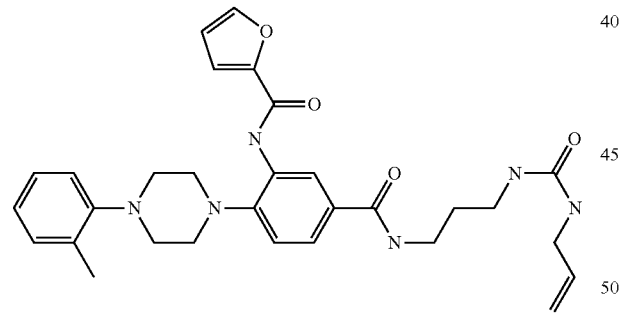

Furan-2-carboxylic acid [5-[3-(3-allyl-ureido)-propylcarbamoyl]-2-(4-o-tolyl-piperazin-1-yl)-phenyl]-amide LCMS (M+H) 545; $^1$H NMR (CHLOROFORM-d) δ ppm 9.48 (s, 1H), 8.89 (d, J=1.7 Hz, 1H), 7.74 (dd, J=8.2, 1.9 Hz, 1H), 7.58 (s, 1H), 7.35 (s, 1H), 7.24 (d, J=4.6 Hz, 2H), 7.13 (d, J=7.8 Hz, 1H), 7.01-7.09 (m, 1H), 6.93 (br. s., 1H), 6.52-6.67 (m, 1H), 5.77-5.96 (m, 1H), 5.15-5.33 (m, 2H), 5.10 (d, J=10.2 Hz, 1H), 4.84 (br. s., 1H), 3.83 (t, J=5.6 Hz, 2H), 3.57 (q, J=5.9 Hz, 2H), 3.34 (q, J=5.9 Hz, 2H), 3.18 (d, J=5.0 Hz, 4H), 3.12 (br. s., 4H), 2.37 (s, 3H), 1.77 (br. s., 2H).

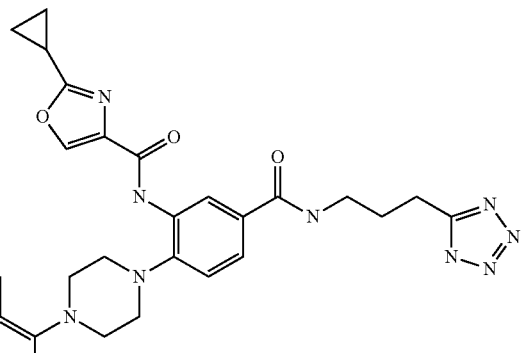

2-Cyclopropyl-oxazole-4-carboxylic acid [5-[3-(1H-tetrazol-5-yl)-propylcarbamoyl]-2-(4-o-tolyl-piperazin-1-yl)-phenyl]-amide LCMS (M+H) 556; $^1$H NMR (CHLOROFORM-d) δ ppm 10.01 (br. s., 1H), 8.93 (s, 1H), 8.16 (s, 1H), 7.83 (d, J=8.4 Hz, 1H), 7.36 (d, J=8.3 Hz, 1H), 7.21-7.26 (m, 2H), 7.14-7.20 (m, 1H), 7.02-7.10 (m, 1H), 3.55 (d, J=5.6 Hz, 2H), 3.21 (d, J=4.0 Hz, 4H), 3.15 (d, J=3.8 Hz, 4H), 3.07-3.12 (m, 2H), 2.38 (s, 3H), 2.08-2.18 (m, 1H), 2.02 (br. s., 2H), 1.10-1.24 (m, 4H).

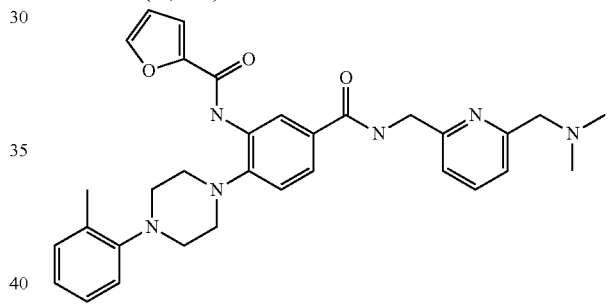

Furan-2-carboxylic acid [5-[(6-dimethylamino-methyl-pyridin-2-ylmethyl)-carbamoyl]-2-(4-o-tolyl-piperazin-1-yl)-phenyl]-amide LCMS (M+H) 553; $^1$H NMR (400 MHz, METHANOL-d$_4$) δ ppm: 2.35 (s, 3H) 2.97 (s, 6H) 3.17 (s, 8H) 3.34-3.39 (m, 1H) 4.46 (s, 2H) 4.76 (s, 2H) 6.64-6.74 (m, 1H) 6.94-7.04 (m, 1H) 7.12-7.23 (m, 3H) 7.29-7.33 (m, 1H) 7.35-7.40 (m, 1H) 7.43-7.51 (m, 2H) 7.69-7.77 (m, 1H) 7.81-7.85 (m, 1H) 7.86-7.93 (m, 1H) 8.75-8.85 (m, 1H).

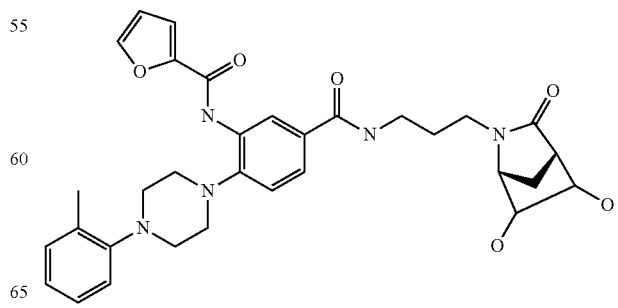

399

Furan-2-carboxylic acid [5-[3-((1R,4S)-5,6-dihydroxy-3-oxo-2-aza-bicyclo[2.2.1]hept-2-yl)-propylcarbamoyl]-2-(4-o-tolyl-piperazin-1-yl)-phenyl]-amide LCMS (M+H) 588; ¹H NMR (400 MHz, METHANOL-d₄) δ ppm 1.77-1.91 (m, 2H) 1.91-1.99 (m, 1H) 2.06-2.14 (m, 1H) 2.35 (s, 3H) 2.54-2.62 (m, 1H) 2.99-3.10 (m, 1H) 3.33-3.39 (m, 1H) 3.40-3.51 (m, 2H) 3.65-3.81 (m, 1H) 3.97 (d, J=1.61 Hz, 2H) 6.63-6.75 (m, 1H) 6.92-7.07 (m, 1H) 7.09-7.24 (m, 3H) 7.27-7.35 (m, 1H) 7.37-7.51 (m, 1H) 7.61-7.71 (m, 1H) 7.74-7.94 (m, 1H) 8.65-8.77 (m, 1H).

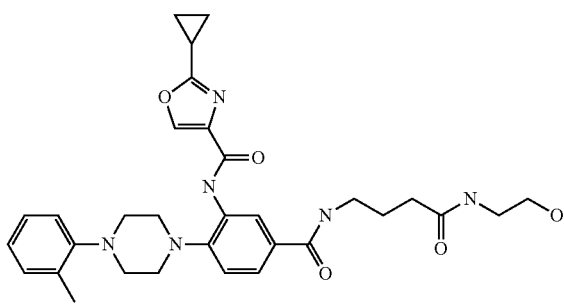 [SMILES: Cc1ccccc1N1CCN(c2ccc(C(=O)NCCCC(=O)NCCO)cc2NC(=O)c2coc(C3CC3)n2)CC1]

2-Cyclopropyl-oxazole-4-carboxylic acid [5-[3-(2-hydroxy-ethylcarbamoyl)-propylcarbamoyl]-2-(4-o-tolyl-piperazin-1-yl)-phenyl]-amide LCMS (M+H) 575; ¹H NMR (400 MHz, DICHLOROMETHANE-d₂) δ ppm 0.99-1.22 (m, 4H) 1.94 (d, J=8.88 Hz, 2H) 2.05-2.17 (m, 1H) 2.22-2.31 (m, 2H) 2.35 (s, 3H) 3.06-3.22 (m, 8H) 3.38 (d, J=4.34 Hz, 2H) 3.48 (d, J=6.25 Hz, 2H) 3.60-3.72 (m, 1H) 6.53-6.64 (m, 1H) 6.81-6.94 (m, 1H) 6.97-7.05 (m, 1H) 7.13-7.24 (m, 3H) 7.31 (d, J=8.30 Hz, 1H) 7.60 (d, J=2.15 Hz, 1H) 8.13 (s, 1H) 8.82 (d, J=2.10 Hz, 1H) 9.86-10.05 (m, 1H).

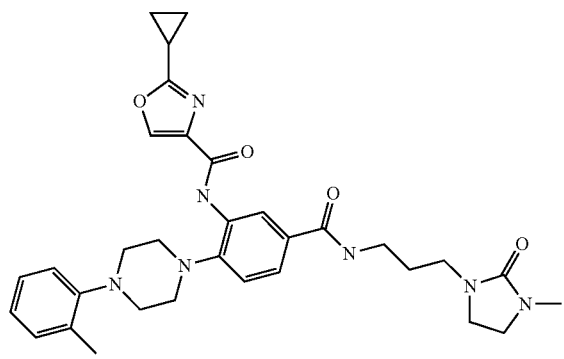 [SMILES: Cc1ccccc1N1CCN(c2ccc(C(=O)NCCCN3CCN(C)C3=O)cc2NC(=O)c2coc(C3CC3)n2)CC1]

2-Cyclopropyl-oxazole-4-carboxylic acid [5-[3-(3-methyl-2-oxo-imidazolidin-1-yl)-propylcarbamoyl]-2-(4-o-tolyl-piperazin-1-yl)-phenyl]-amide LCMS (M+H) 586; ¹H NMR (400 MHz, METHANOL-d₄) δ ppm 1.12 (d, J=6.59 Hz, 4H) 1.71-1.88 (m, 2H) 2.06-2.20 (m, 1H) 2.35 (s, 3H) 2.73 (s, 3H) 3.06-3.15 (m, 4H) 3.17-3.26 (m, 5H) 3.30-3.44 (m, 6H) 6.90-7.06 (m, 1H) 7.09-7.25 (m, 3H) 7.33-7.45 (m, 1H) 7.53-7.67 (m, 1H) 8.16-8.39 (m, 1H) 8.63-8.96 (m, 1H).

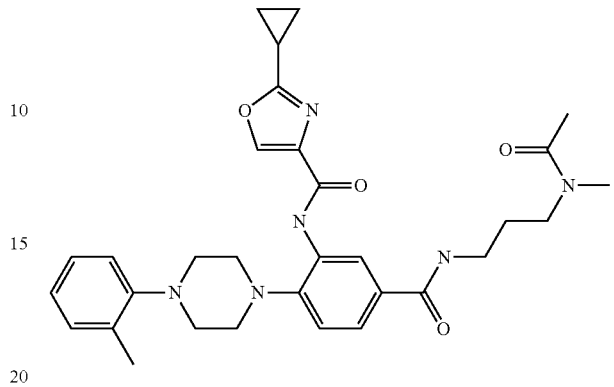

2-Cyclopropyl-oxazole-4-carboxylic acid [5-[3-(acetyl-methyl-amino)-propylcarbamoyl]-2-(4-o-tolyl-piperazin-1-yl)-phenyl]-amide LCMS (M+H) 559; ¹H NMR (400 MHz, DMSO-d₆) δ ppm 9.92 (1H, s) 8.81 (1H, d, J=1.81 Hz) 8.68 (1H, s) 8.35-8.50 (1H, m) 7.56-7.63 (1H, m) 7.42 (1H, d, J=8.25 Hz) 7.18-7.25 (2H, m) 7.11-7.16 (1H, m) 7.01 (1H, t, J=7.27 Hz) 3.34 (2H, br. s.) 3.19-3.29 (2H, m) 3.11 (4H, d, J=4.59 Hz) 3.05 (4H, br. s.) 2.96 (2H, s) 2.79 (1H, s) 2.31 (3H, s) 2.15-2.24 (1H, m) 1.98 (3H, d, J=3.51 Hz) 1.75-1.84 (1H, m) 1.69 (1H, quin, J=6.97 Hz) 1.10-1.17 (2H, m) 1.03-1.09 (2H, m).

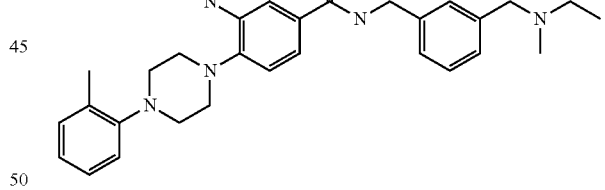

N-(5-((3-((ethyl(methyl)amino)methyl)benzyl)-carbamoyl)-2-(4-(o-tolyl)piperazin-1-yl)phenyl)furan-2-carboxamide LC/MS-ESI: [M+1] 566.33; NMR (DMSO-d₆) δ 9.44 (s, 1, NH—CO), 9.03 (t, 1, CON—H), 8.64 (d, 1, Furan-H), 8.01 (dd, 1, Ar—H), 7.70 (dd, 1, Ar—H), 7.36-7.44 (m, 5, 5×Ar-H), 7.31 (d, 1, Furan-H), 7.18 (t, 2, 2×Ar-H), 7.11 (d, 1, Ar—H), 6.98 (t, 1, Furan-H), 6.72 (dd, 1, Ar—H), 4.50 (d, 2, CON—CH₂), 4.35 (dd, 1, NC—H), 4.19 (dd, 1, NC—H), 3.00-3.16 (m, 10, 2×CH₂CH₂, NCH₂), 2.64 (d, 3, NCH₃), 2.28 (s, 3, Ar—CH₃), 1.19 (t, 3, 3×CH₂CH₂—H).

401

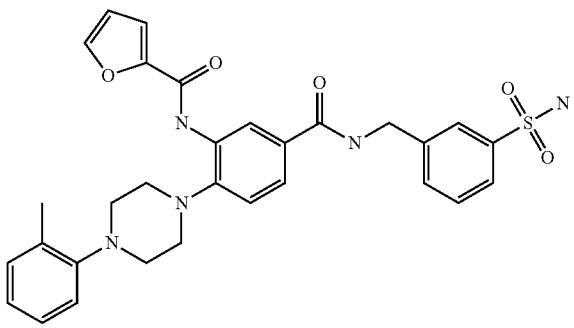 [SMILES: Cc1ccccc1N1CCN(c2ccc(C(=O)NCc3cccc(S(N)(=O)=O)c3)cc2NC(=O)c2ccco2)CC1]

N-(5-((3-sulfamoylbenzoyl)carbamoyl)-2-(4-(o-tolyl)piperazin-1-yl)phenyl)furan-2-carboxamide LC/MS-ESI: [M+1] 574.36; NMR (DMSO-d$_6$) δ 9.48 (s, 1, CON—H), 9.15 (t, 1, CON—H), 8.68 (s, 1, Furan-H), 8.04 (s, 1, Ar—H), 7.81 (s, 1, Ar—H), 7.74 (m, 2, 2×Ar-H), 7.55 (m, 2, 2×Ar-H), 7.43 (d, 1, Ar—H), 7.33-7.39 (m, 3, 2×Ar-H, Furan-H), 7.14 (d, 1, Ar—H), 7.01 (t, 1, Furan-H), 6.75 (m, 1, Ar—H), 4.57 (d, 2, CON—CH2), 3.10 (m, 8, 8×CH$_2$CH$_2$), 2.31 (s, 3, Ar—CH$_3$)

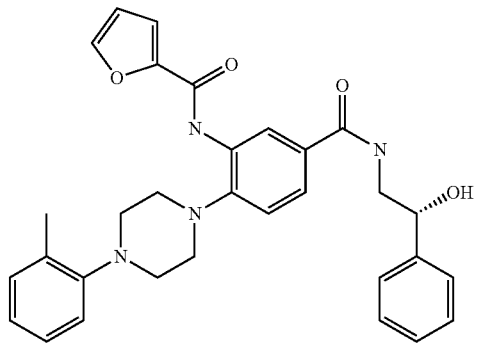 [SMILES: Cc1ccccc1N1CCN(c2ccc(C(=O)NC[C@H](O)c3ccccc3)cc2NC(=O)c2ccco2)CC1]

(R)—N-(5-((2-hydroxy-2-phenylethyl)carbamoyl)-2-(4-(o-tolyl)piperazin-1-yl)phenyl)furan-2-carboxamide LC/MS-ESI: [M+1] 525.3; NMR (DMSO-d$_6$) δ 9.45 (s, 1, CON—H), 8.62 (d, 1, Furan-H), 8.43 (t, 1, CON—H), 8.03 (d, 1, Ar—H), 7.66 (dd, 1, Ar—H), 7.31-7.43 (m, 6, Furan-H, 5×Ar-H), 7.17-7.30 (m, 3, 3×Ar-H), 7.14 (d, 1, Ar—H) 6.98 (t, 1, Furan-H), 6.75 (dd, 1, Ar—H), 5.51 (d, 1, HO—CH), 4.80 (m, 1, O—H), 3.42-3.56 (m, 1, CONC—H), 3.22-3.42 (m, 1, CONC—H), 3.09 (s, 8, 2×CH$_2$CH$_2$), 2.92 (s, 3, Ar—CH$_3$).

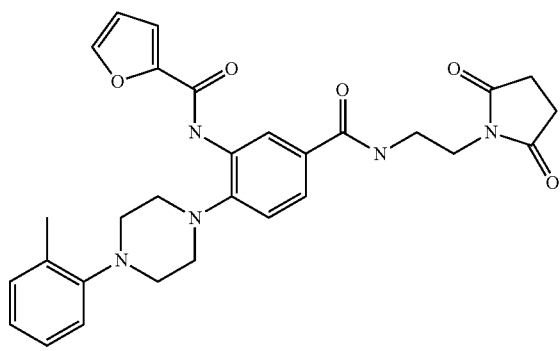 [SMILES: Cc1ccccc1N1CCN(c2ccc(C(=O)NCCN3C(=O)CCC3=O)cc2NC(=O)c2ccco2)CC1]

402

N-(5-((2-(2,5-dioxopyrrolidin-1-yl)ethyl)carbamoyl)-2-(4-(o-tolyl)piperazin-1-yl)phenyl)furan-2-carboxamide LC/MS-ESI: [M+1] 530.20; NMR (DMSO-d$_6$) δ 9.43 (s, 1, CON—H), 8.54 (d, 1, Furan-H), 8.46 (t, 1, CON—H), 8.01 (m, 1, Ar—H), 7.53 (dd, 1, Ar—H), 7.37 (d, 1, Ar—H), 7.32 (d, 1, Furan-H), 7.18 (d, 2, 2×Ar-H), 7.12 (d, 1, Ar—H), 6.98 (t, 1, Furan-H), 6.72 (dd, 1, Ar—H), 3.53 (t, 2, CON—CH$_2$), 3.39 (m, 2, CON—CH$_2$), 3.07 (s, 8, 2×CH$_2$CH$_2$), 2.58 (s, 4, 2×COCH$_2$), 2.29 (s, 3, Ar—CH$_3$).

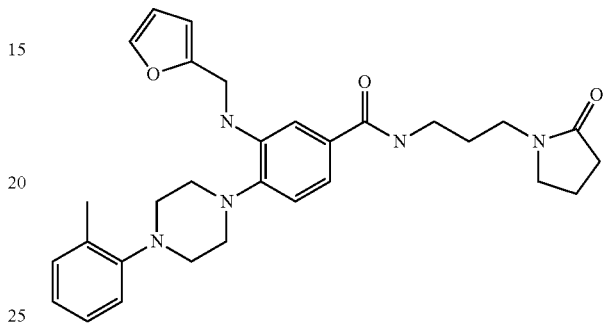

3-((furan-2-ylmethyl)amino)-N-(3-(2-oxopyrrolidin-1-yl)propyl)-4-(4-(o-tolyl)piperazin-1-yl)benzamide LC/MS-ESI: [M+1] 516.00; NMR (DMSO-d$_6$) δ 8.21 (t, 1, CON—H), 7.59 (s, 1, Furan-H), 7.05-7.25 (m, 6, Ar—H) 7.02 (t, 1, Ar—H), 6.39 (t, 1, Furan-H), 6.29 (d, 1, Furan-H), 4.43 (s, 2, Furan-CH$_2$), 3.35 (t, 2, CON—CH$_2$), 3.14-3.28 (m, 4, CON—CH$_2$, CON—CH$_2$), 3.08 (s, 4, CH$_2$CH$_2$), 3.02 (s, 4, CH$_2$CH$_2$), 2.31 (s, 3, Ar—CH$_3$), 2.24 (t, 2, CO—CH$_2$), 1.91 (m, 2, CH$_2$), 1.69 (m, 2, CH$_2$).

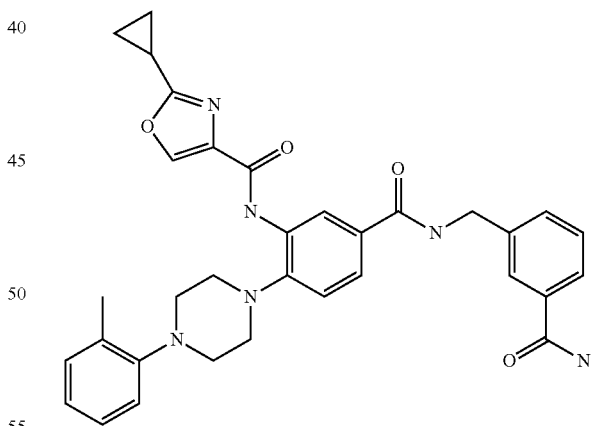

N-(5-((3-carbamoylbenzyl)carbamoyl)-2-(4-(o-tolyl) piperazin-1-yl)phenyl)-2-cyclopropyloxazole-4-carboxamide LC/MS-ESI: [M+1] 579.37; NMR (DMSO-d$_6$) δ 9.91 (s, 1, CON—H), 9.04 (t, 1, CON—H), 8.85 (d, 1, Ar—H), 8.67 (d, 1, Oxazole-H), 7.95 (s, 1, CON—H), 7.82 (s, 1, Ar—H), 7.73 (d, 1, Ar—H), 7.68 (dd, 1, Ar—H), 7.37-7.46 (ddd, 3, 3×Ar-H), 7.32 (s, 1, CON—H), 7.16-7.24 (m, 2, 2×Ar-H), 7.13 (d, 1, Ar—H), 7.00 (t, 1, Ar—H), 4.50 (d, 2, CON—

CH₂), 3.10-3.04 (m, 8, 2×CH2CH2), 2.30 (s, 3, Ar—CH₃), 2.18 (m, 1, CH), 1.01-1.14 (m, 4, 2×CH₂).

403

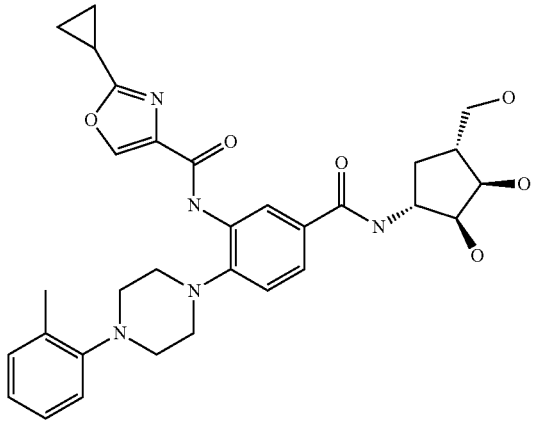 [SMILES: Cc1ccccc1N1CCN(c2ccc(C(=O)N[C@@H]3C[C@H](CO)[C@@H](O)[C@H]3O)cc2NC(=O)c2coc(C3CC3)n2)CC1]

2-cyclopropyl-N-(5-(((1R,2S,3R,4R)-2,3-dihydroxy-4-(hydroxymethyl)cyclopentyl)carbamoyl)-2-(4-(o-tolyl)piperazin-1-yl)phenyl)oxazole-4-carboxamide LC/MS-ESI: [M+1] 576.02; NMR (DMSO-d₆) δ 9.85 (s, 1, CON—H), 8.73 (d, 1, CO—NH), 8.60 (s, 1, Oxazole-H), 8.18 (d, 1, Ar—H), 7.53 (d, 1, Ar—H), 7.34 (t, 1, Ar—H), 7.12 (m, 2, 2×Ar-H), 7.09 (d, 1, Ar—H) 6.93 (t, 1, Ar—H), 4.09 (t, 1, OC—H), 3.69 (dq, 2, OC—H), 3.37 (m, 2, OCH₂), 2.96-3.05 (m, 8, 2×CH₂CH₂), 2.25 (s, 3, Ar—CH₃), 1.75-2.13 (m, 4, OC—H, CH, CH₂), 0.7-1.09 (m, 5, CH₂, CH₂, CH—H).

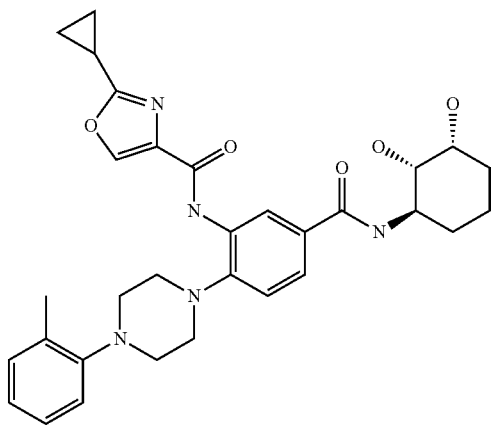 [SMILES: Cc1ccccc1N1CCN(c2ccc(C(=O)N[C@@H]3CCC[C@@H](O)[C@H]3O)cc2NC(=O)c2coc(C3CC3)n2)CC1]

2-cyclopropyl-N-(5-(((1R,2S,3R)-2,3-dihydroxycyclohexyl)carbamoyl)-2-(4-(o-tolyl)piperazin-1-yl)phenyl)oxazole-4-carboxamide trifluoroacetate LC/MS-ESI: [M+1] 560.21; NMR (DMSO-d₆) δ 9.86 (s, 1, CON—H), 8.72 (s, 1, CON—H), 8.60 (s, 1, Oxazole-H), 7.94 (d, 1, Ar—H), 7.56 (d, 1, Ar—H), 7.34 (s, 1, Ar—H), 7.15 (d, 2, 2×Ar-H), 7.09 (d, 1, Ar—H), 6.93 (t, 1, Ar—H), 4.00 (dd, 1, OC—H), 3.80 (s, 1, CON—CH), 3.37 (d, 1, OC—H), 3.04 (s, 4, CH₂CH₂), 2.99 (s, 4, CH₂CH₂), 2.25 (s, 3, Ar—CH₃), 2.13 (m, 1, OC—H, CH, CH₂), 1.01-1.71 (m, 11, 5×CH₂, 5×CH₂, C—H).

404

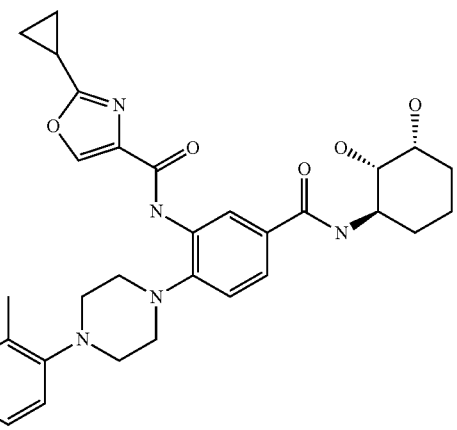

2-cyclopropyl-N-(5-(((1R,2S,3R)-2,3-dihydroxycyclohexyl)-carbamoyl)-2-(4-(o-tolyl)piperazin-1-yl)phenyl)oxazole-4-carboxamide hydrochloride LC/MS-ESI: [M+1] 560.21; NMR (DMSO-d₆) δ 9.93 (s, 1, CON—H), 8.79 (s, 1, CON—H), 8.68 (s, 1, Oxazole-H), 8.02 (d, 1, Ar—H), 7.66 (d, 1, Ar—H), 7.41 (d, 1, Ar—H), 7.10-7.30 (m, 3, 3×Ar-H), 7.03 (t, 1, Ar—H), 4.06 (tq, 1, OC—H), 3.87 (s, 1, CON—CH), 3.44 (dd, 1, OC—H), 3.14 (s, 4, CH₂CH₂), 3.08 (s, 4, CH₂CH₂), 2.51 (s, 3, Ar—CH₃), 2.20 (m, 1, CH), 1.19-1.89 (m, 6, 6×CH₂), 1.00-1.19 (m, 4, CH₂CH₂).

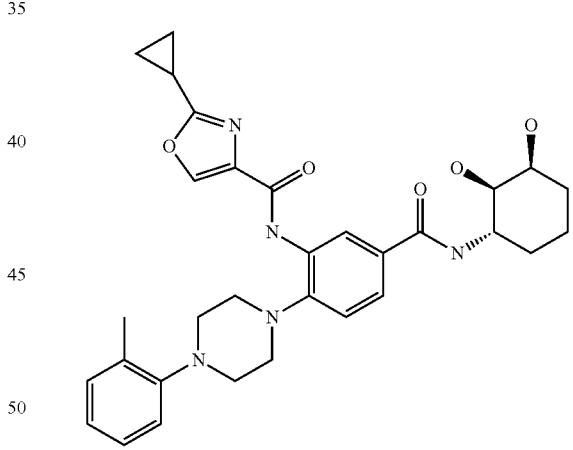

2-cyclopropyl-N-(5-(((1S,2R,3S)-2,3-dihydroxycyclohexyl)carbamoyl)-2-(4-(o-tolyl)piperazin-1-yl)phenyl)oxazole-4-carboxamide LC/MS-ESI: [M+1] 560.07; NMR (DMSO-d6) δ 9.93 (s, 1, CON—H), 8.79 (s, 1, CON—H), 8.68 (s, 1, Oxazole-H), 8.02 (d, 1, Ar—H), 7.66 (d, 1, Ar—H), 7.41 (d, 1, Ar—H), 7.10-7.30 (m, 3, 3×Ar-H), 7.03 (t, 1, Ar—H), 4.06 (tq, 1, OC—H), 3.87 (s, 1, CON—CH), 3.44 (dd, 1, OC—H), 3.14 (s, 4, CH₂CH₂), 3.08 (s, 4, CH₂CH₂), 2.51 (s, 3, Ar—CH₃), 2.20 (m, 1, CH), 1.19-1.89 (m, 6, 6×CH₂), 1.00-1.19 (m, 4, CH₂CH₂).

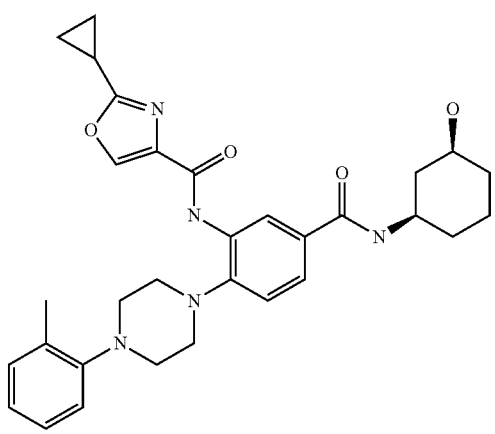 [SMILES: Cc1ccccc1N1CCN(c2ccc(C(=O)N[C@@H]3CCC[C@H](O)C3)cc2NC(=O)c2coc(C3CC3)n2)CC1]

2-cyclopropyl-N-(5-(((1R,3S)-3-hydroxycyclohexyl)carbamoyl)-2-(4-(o-tolyl)piperazin-1-yl)phenyl)oxazole-4-carboxamide LC/MS-ESI: [M+1] 544.09; NMR (DMSO-d$_6$) δ 9.93 (s, 1, CON—H), 8.79 (d, 1, CON—H), 8.67 (s, 1, Oxazole-H), 8.24 (d, 1, Ar—H), 7.60 (dd, 1, Ar—H), 7.41 (d, 1, Ar—H), 7.10-7.30 (m, 3, 3×Ar-H), 7.02 (m, 1, Ar—H), 4.06 (tq, 1, OC—H), 3.24-4.11 (broad, 3) 3.12 (d, 4, CH$_2$CH$_2$), 3.06 (d, 4, CH$_2$CH$_2$), 2.32 (s, 3, Ar—CH$_3$), 2.21 (m, 1, CH), 2.03 (m, 1, CH), 1.63-1.89 (m, 3, 3×CH$_2$), 1.00-1.37 (m, 8, 2×CH$_2$CH$_2$).

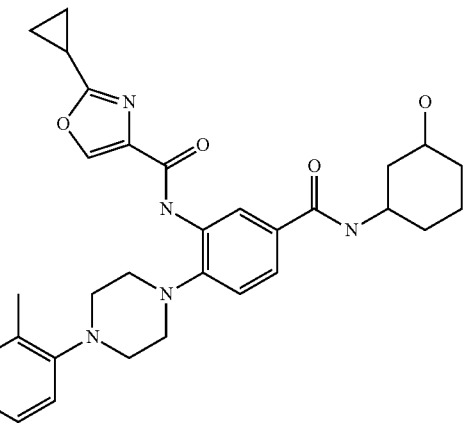

2-cyclopropyl-N-(5-((3-hydroxycyclohexyl)carbamoyl)-2-(4-(o-tolyl)piperazin-1-yl)phenyl)oxazole-4-carboxamide LC/MS-ESI: [M+1] 544.40; NMR (DMSO-d$_6$) δ 9.85 (s, 1, CON—H), 8.71 (d, 1, CO—NH), 8.60 (s, 1, Oxazole-H), 8.16 (dd, 0.46, Ar—H), 7.98 (dd, 0.68, Ar—H), 7.47-7.56 (m, 1, Ar—H), 7.28-7.37 (m, 1, Ar—H), 7.04-7.20 (m, 3, 3×Ar-H), 6.93 (m, 1, Ar—H), 4.06 (tq, 1, OC—H), 3.24-4.11 (broad, 3) 3.12 (d, 4, CH$_2$CH$_2$), 3.06 (d, 4, CH$_2$CH$_2$), 2.25 (s, 3, Ar—CH$_3$), 2.13 (m, 1, CH), 0.91-1.98 (m, 12, 3×CH$_2$CH$_2$).

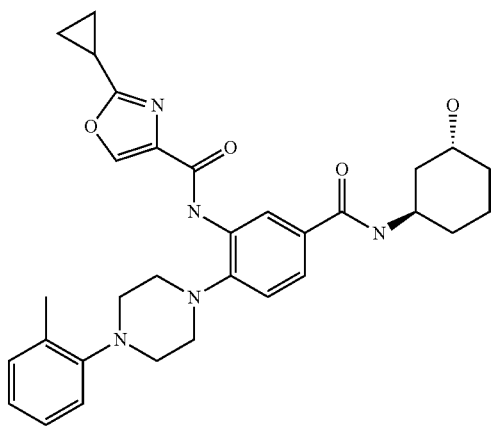 [SMILES: Cc1ccccc1N1CCN(c2ccc(C(=O)N[C@@H]3CCC[C@@H](O)C3)cc2NC(=O)c2coc(C3CC3)n2)CC1]

2-cyclopropyl-N-(5-(((1R,3R)-3-hydroxycyclohexyl)carbamoyl)-2-(4-(o-tolyl)piperazin-1-yl)phenyl)oxazole-4-carboxamide LC/MS-ESI: [M+1] 544.19; NMR (DMSO-d$_6$) δ 9.93 (s, 1, CON—H), 8.77 (d, 1, CON—H), 8.67 (s, 1, Oxazole-H), 8.06 (d, 1, Ar—H), 7.59 (dd, 1, Ar—H), 7.40 (d, 1, Ar—H), 7.10-7.30 (m, 3, 3×Ar-H), 7.02 (m, 1, Ar—H), 4.19 (m, 1), 3.93 (d, 1, OC—H), 3.23-3.84 (broad, 3), 3.12 (d, 4, CH$_2$CH$_2$), 3.05 (d, 4, CH$_2$CH$_2$), 2.32 (s, 3, Ar—CH$_3$), 2.21 (m, 1, CH), 1.19-1.83 (m, 8, 2×CH$_2$CH$_2$), 1.00-1.19 (m, 4, CH$_2$CH$_2$).

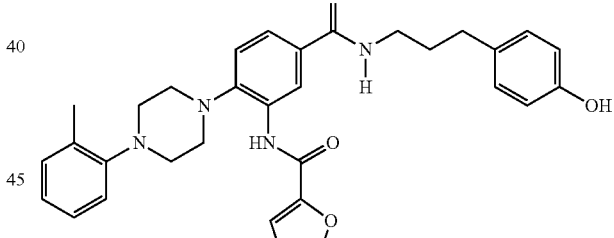

Furan-2-carboxylic acid [5-[3-(4-hydroxy-phenyl)-propylcarbamoyl]-2-(4-o-tolyl-piperazin-1-yl)-phenyl]-amide LCMS: (Method A) 539.2 (M+H), Rt 4.8 min, 96.7% (Max), 97.4% (254 nm).

$^1$H NMR 400 MHz, CDCl$_3$: δ 9.48 (s, 1H), 8.68 (s, 1H), 7.78 (d, J=4.00 Hz, 1H), 7.60 (s, 1H), 7.33 (d, J=8.00 Hz, 1H), 7.30 (t, J=4.00 Hz, 1H), 7.24 (d, J=8.00 Hz, 2H), 7.13 (d, J=8.00 Hz, 1H), 7.04-7.06 (m, 3H), 6.80 (d, J=8.00 Hz, 2H), 6.61-6.62 (m, 1H), 6.53 (s, 1H), 5.83 (s, 1H), 3.46-3.51 (m, 2H), 3.12-3.18 (m, 8H), 2.67 (t, J=4.00 Hz, 2H), 2.37 (s, 3H), 1.91-1.94 (m, 2H).

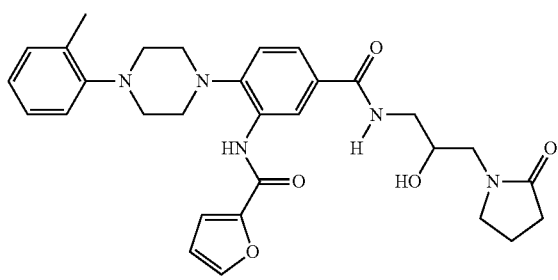 [SMILES: Cc1ccccc1N1CCN(c2ccc(C(=O)NCC(O)CN3CCCC3=O)cc2NC(=O)c2ccco2)CC1]

Furan-2-carboxylic acid [5-[2-hydroxy-3-(2-oxo-pyrrolidin-1-yl)-propylcarbamoyl]-2-(4-o-tolyl-piperazin-1-yl)-phenyl]-amide LCMS: (Method A) 546.3 (M+H), Rt 3.8 min, 97.3% (Max), 98.8% (254 nm).

$^1$H NMR 400 MHz, CDCl$_3$: (9.42 (s, 1H), 8.98 (d, J=4.00 Hz, 1H), 7.73 (d, J=12.00 Hz, 1H), 7.53-7.57 (m, 2H), 7.32 (d, J=8.00 Hz, 1H), 7.28 (s, 1H), 7.23-7.26 (m, 2H), 7.13 (d, J=8.00 Hz, 1H), 7.06-7.08 (m, 1H), 6.60 (d, J=4.00 Hz, 1H), 4.30 (d, J=8.00 Hz, 1H), 4.01-4.02 (m, 1H), 3.73-3.79 (m, 1H), 3.50-3.60 (m, 3H), 3.33-3.43 (m, 2H), 3.17-3.18 (m, 4H), 3.12-3.14 (m, 4H), 2.46 (t, J=8.00 Hz, 2H), 2.37 (s, 3H), 2.05-2.12 (m, 2H).

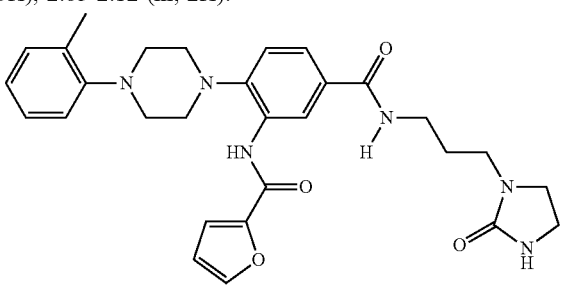

Furan-2-carboxylic acid [5-[3-(2-oxo-imidazolidin-1-yl)-propylcarbamoyl]-2-(4-o-tolyl-piperazin-1-yl)-phenyl]-amide LCMS: (Method A) 531.2 (M+H), Rt 3.9 min, 95.0% (Max). 93.5% (254 nm);

$^1$H NMR 400 MHz, CDCl$_3$: δ 9.46 (s, 1H), 8.88 (s, 1H), 7.76 (d, J=8.00 Hz, 1H), 7.57 (s, 1H), 7.53 (t, J=4.00 Hz, 1H), 7.31 (d, J=8.00 Hz, 2H), 7.23-7.34 (m, 2H), 7.13 (d, J=8.00 Hz, 1H), 7.04-7.07 (m, 1H), 6.59 (s, 1H), 3.47-3.50 (m, 6H), 3.34-3.37 (m, 2H), 3.17-3.18 (m, 4H), 3.11-3.13 (m, 4H), 2.37 (s, 3H), 1.80-1.83 (m, 2H).

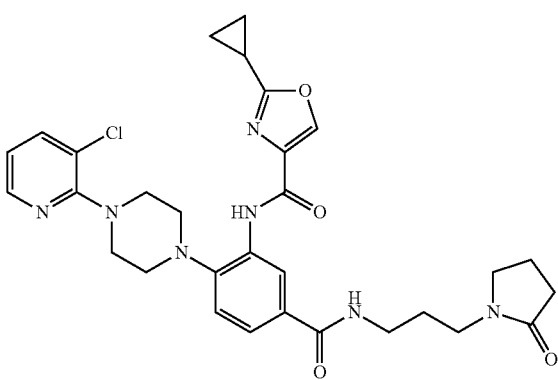 [SMILES: O=C(NCCCN1CCCC1=O)c1ccc(N2CCN(c3ncccc3Cl)CC2)c(NC(=O)c2coc(C3CC3)n2)c1]

2-Cyclopropyl-oxazole-4-carboxylic acid {2-[4-(3-chloro-pyridin-2-yl)-piperazin-1-yl]-5-[3-(2-oxo-pyrrolidin-1-yl)-propylcarbamoyl]-phenyl}-amide LCMS: (Method A) 592.3 (M+H), Rt 4.4 min, 95.4% (Max). 96.4% (254 nm);

$^1$H NMR 400 MHz, CDCl$_3$: δ 9.94 (s, 1H), 8.97 (d, J=4.00 Hz, 1H), 8.23-8.25 (m, 1H), 8.13 (s, 1H), 7.73 (d, J=8.00 Hz, 1H), 7.65 (s, 1H), 7.58-7.63 (m, 1H), 7.26 (s, 1H), 6.88-6.91 (m, 1H), 3.65-3.67 (m, 4H), 3.40-3.45 (m, 6H), 3.11-3.13 (m, 4H), 2.44-2.48 (m, 2H), 2.03-2.11 (m, 3H), 1.81-1.84 (m, 2H), 1.14-1.18 (m, 2H), 1.08-1.09 (m, 2H).

The preparation of all compounds depicted in Table 2 was in line with Scheme 1.

Example 2: Synthetic route towards (R)-3-[3-[(furan-2-carbonyl)-amino]-4-(4-o-tolyl-piperazin-1-yl)-benzoylamino]-piperidine-1-carboxylic acid ethylamide (compound no. 48)

Scheme 2

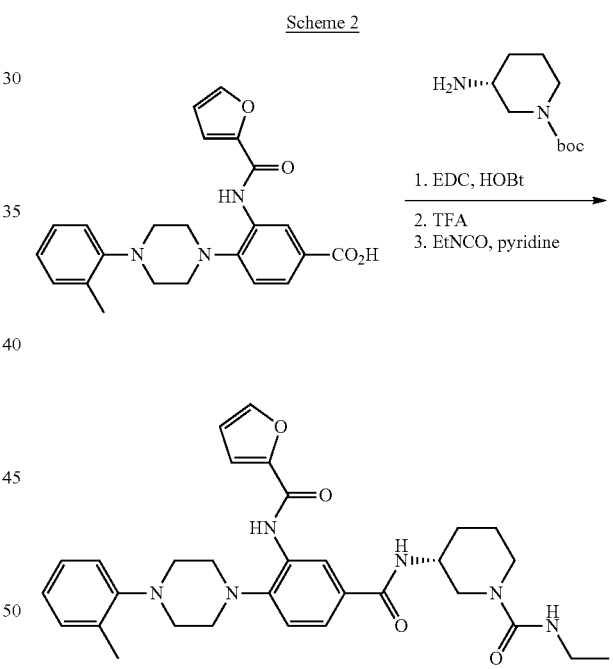

Step 1

The compound was prepared in a similar fashion to compound no. 11 from 3-[(furan-2-carbonyl)-amino]-4-(4-o-tolyl-piperazin-1-yl)-benzoic acid.

Step 2

(R)-3-[3-[(Furan-2-carbonyl)-amino]-4-(4-o-tolyl-piperazin-1-yl)-benzoylamino]-piperidine-1-carboxylic acid tert-butyl ester (0.12 g, 0.204 mmol) was stirred with a mixture of DCM (1.0 mL) and TFA (1.0 mL) for 4 h. LC-MS indicated the completion of deprotection. The mixture was concentrated and dissolved in pyridine (5.0 mL). EtNCO (29 mg, 0.41 mmol) was added and the reaction mixture was stirred at 45° C. for 6 h. Pyridine was rotavaped out and the crude was dissolved in methanol and purified on preparatory HPLC using water/methanol as eluent to give desired product (0.02 g, 18%).

LCMS (ESI) 559 (M+H); ¹H NMR (400 MHz, METHANOL-d4) δ ppm 1.05-1.13 (m, 3H) 1.50-1.68 (m, 2H) 1.73-1.81 (m, 1H) 1.96-2.08 (m, 1H) 2.32 (s, 3H) 2.78-2.96 (m, 2H) 3.12 (s, 9H) 3.17 (q, J=7.19 Hz, 3H) 3.77-4.00 (m, 3H) 6.66 (dd, J=3.51, 1.76 Hz, 1H) 6.96 (td, J=7.11, 1.73 Hz, 1H) 7.08-7.19 (m, 3H) 7.28 (d, J=3.47 Hz, 1H) 7.38 (d, J=8.35 Hz, 1H) 7.61 (dd, J=8.30, 2.10 Hz, 1H) 7.79 (d, J=1.07 Hz, 1H) 8.63 (d, J=2.05 Hz, 1H).

The preparation of following compounds was in line with Scheme 2:

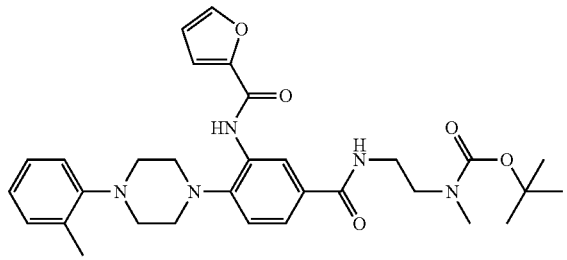 [SMILES: Cc1ccccc1N1CCN(c2ccc(C(=O)NCCN(C)C(=O)OC(C)(C)C)cc2NC(=O)c2ccco2)CC1]

{2-[3-[(Furan-2-carbonyl)-amino]-4-(4-o-tolyl-piperazin-1-yl)-benzoylamino]-ethyl}-methyl-carbamic acid tert-butyl ester (compound no. 64) was prepared comprising the same procedure as compound no. 11 from 3-[(furan-2-carbonyl)-amino]-4-(4-o-tolyl-piperazin-1-yl)-benzoic acid.

LCMS (ESI) 562 (M+H); ¹H NMR (400 MHz, DICHLOROMETHANE-d2) δ ppm 1.40 (s, 9H) 1.54-1.64 (m, 1H) 2.36 (s, 3H) 2.89 (brs, 3H) 3.15 (dd, J=17.01, 5.59 Hz, 8H) 3.48 (brs, 2H) 3.52-3.60 (m, 2H) 6.60 (dd, J=3.39, 1.73 Hz, 1H) 6.97-7.05 (m, 1H) 7.12-7.25 (m, 4H) 7.31 (brs, 1H) 7.56 (brs., 1H) 7.60 (s, 1H) 8.83 (d, J=2.00 Hz, 1H) 9.24-9.52 (m, 1H).

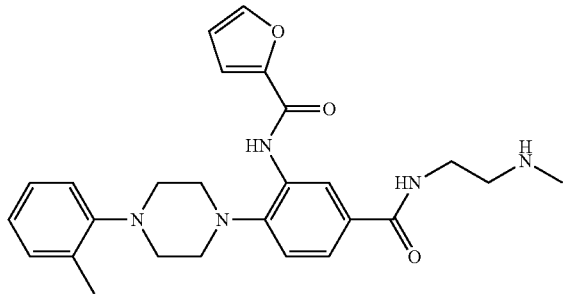 [SMILES: CNCCNC(=O)c1ccc(N2CCN(c3ccccc3C)CC2)c(NC(=O)c2ccco2)c1]

Furan-2-carboxylic acid [5-(2-methylamino-ethylcarbamoyl)-2-(4-o-tolyl-piperazin-1-yl)-phenyl]-amide (compound no. 132) was prepared as follows: {2-[3-[(Furan-2-carbonyl)-amino]-4-(4-o-tolyl-piperazin-1-yl)-benzoylamino]-ethyl}-methyl-carbamic acid tert-butyl ester (0.1 g, 0.17 mmol) was stirred with a mixture of DCM (2.0 mL) and TFA (2.0 mL) for 2 h. Reaction was concentrated to give 0.07 g of the TFA salt.

LCMS (ESI) 462 (M+H); ¹H NMR (400 MHz, METHANOL-d4) δ ppm 2.33 (s, 3H) 2.74 (s, 3H) 3.12-3.19 (m, 8H) 3.23 (t, J=5.66 Hz, 2H) 3.68 (t, J=5.66 Hz, 2H) 6.67 (dd, J=3.54, 1.78 Hz, 1H) 6.94-7.02 (m, 1H) 7.12-7.20 (m, 3H) 7.29 (d, J=2.98 Hz, 1H) 7.41 (d, J=8.35 Hz, 1H) 7.68 (dd, J=8.35, 2.15 Hz, 1H) 7.80 (d, J=1.02 Hz, 1H) 8.72 (d, J=2.10 Hz, 1H).

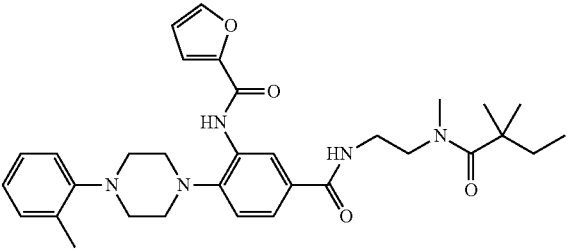 [SMILES: CCC(C)(C)C(=O)N(C)CCNC(=O)c1ccc(N2CCN(c3ccccc3C)CC2)c(NC(=O)c2ccco2)c1]

Furan-2-carboxylic acid [5-{2-[(2,2-dimethyl-butyryl)-methyl-amino]-ethylcarbamoyl}-2-(4-o-tolyl-piperazin-1-yl)-phenyl]-amide (compound no. 133) was prepared as follows: To a solution of furan-2-carboxylic acid [5-(2-methylamino-ethylcarbamoyl)-2-(4-o-tolyl-piperazin-1-yl)-phenyl]-amide (0.04 g, 0.086 mmol) and diisopropylethylamine (0.5 mL) in CH₂Cl₂ (2.0 mL), 2,2-dimethyl butyryl chloride (0.173 mmol) was added at 0° C., and the reaction was stirred at 0-25° C. for 4 h. Reaction was diluted with CH₂Cl₂ and washed with a solution of saturated NaHCO₃. Organic layer was concentrated and dissolved in ACN and purified on preparative HPLC using water/MeOH (0.1% TFA) as eluent to give the product (0.01 g, 21% yield).

LCMS (ESI) 560 (M+H); ¹H NMR (400 MHz, DICHLOROMETHANE-d2) δ ppm 0.81 (t, J=7.49 Hz, 3H) 1.22 (s, 6H) 1.59-1.69 (m, 2H) 2.34 (s, 3H) 3.06-3.19 (m, 11H) 3.54-3.67 (m, 4H) 6.59 (dd, J=3.47, 1.76 Hz, 1H) 7.00 (td, J=7.33, 1.24 Hz, 1H) 7.11-7.15 (m, 1H) 7.17-7.25 (m, 3H) 7.29 (s, 1H) 7.35 (brs, 1H) 7.51 (dd, J=8.27, 2.07 Hz, 1H) 7.57-7.64 (m, 1H) 8.81 (d, J=2.05 Hz, 1H) 9.38 (s, 1H).

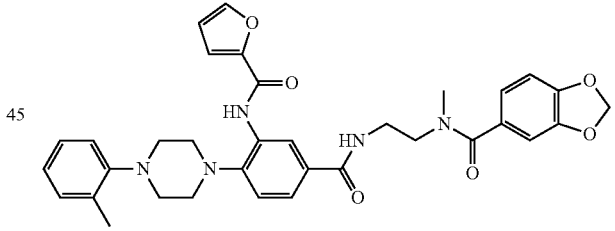

Benzo[1,3]dioxole-5-carboxylic acid {2-[3-[(furan-2-carbonyl)-amino]-4-(4-o-tolyl-piperazin-1-yl)-benzoylamino]-ethyl}-methyl-amide (compound no. 134) was prepared following the same procedure as furan-2-carboxylic acid [5-{2-[(2,2-dimethyl-butyryl)-methyl-amino]-ethylcarbamoyl}-2-(4-o-tolyl-piperazin-1-yl)-phenyl]-amide using piperanoyl chloride.

LCMS (ESI) 610 (M+H); ¹H NMR (400 MHz, DICHLOROMETHANE-d2) S ppm 2.34 (s, 3H) 3.06 (s, 3H) 3.09-3.19 (m, 8H) 3.68 (brs, 4H) 5.98 (s, 2H) 6.60 (dd, J=3.47, 1.76 Hz, 1H) 6.80 (d, J=7.91 Hz, 1H) 6.89-6.96 (m, 1H) 6.97-7.04 (m, 2H) 7.08-7.15 (m, 1H) 7.20 (dd, J=6.83, 5.56 Hz, 2H) 7.25 (d, J=3.42 Hz, 1H) 7.33 (d, J=8.30 Hz, 1H) 7.48-7.56 (m, 1H) 7.57-7.62 (m, 2H) 8.70-8.97 (m, 1H) 9.41 (s, 1H).

Example 3: Synthetic route towards 4-[3-[(5-methyl-furan-2-carbonyl)-amino]-4-(4-o-tolyl-piperazin-1-yl)-benzoylamino]-piperidine-1-carboxylic acid tert-butyl ester (compound no. 175)
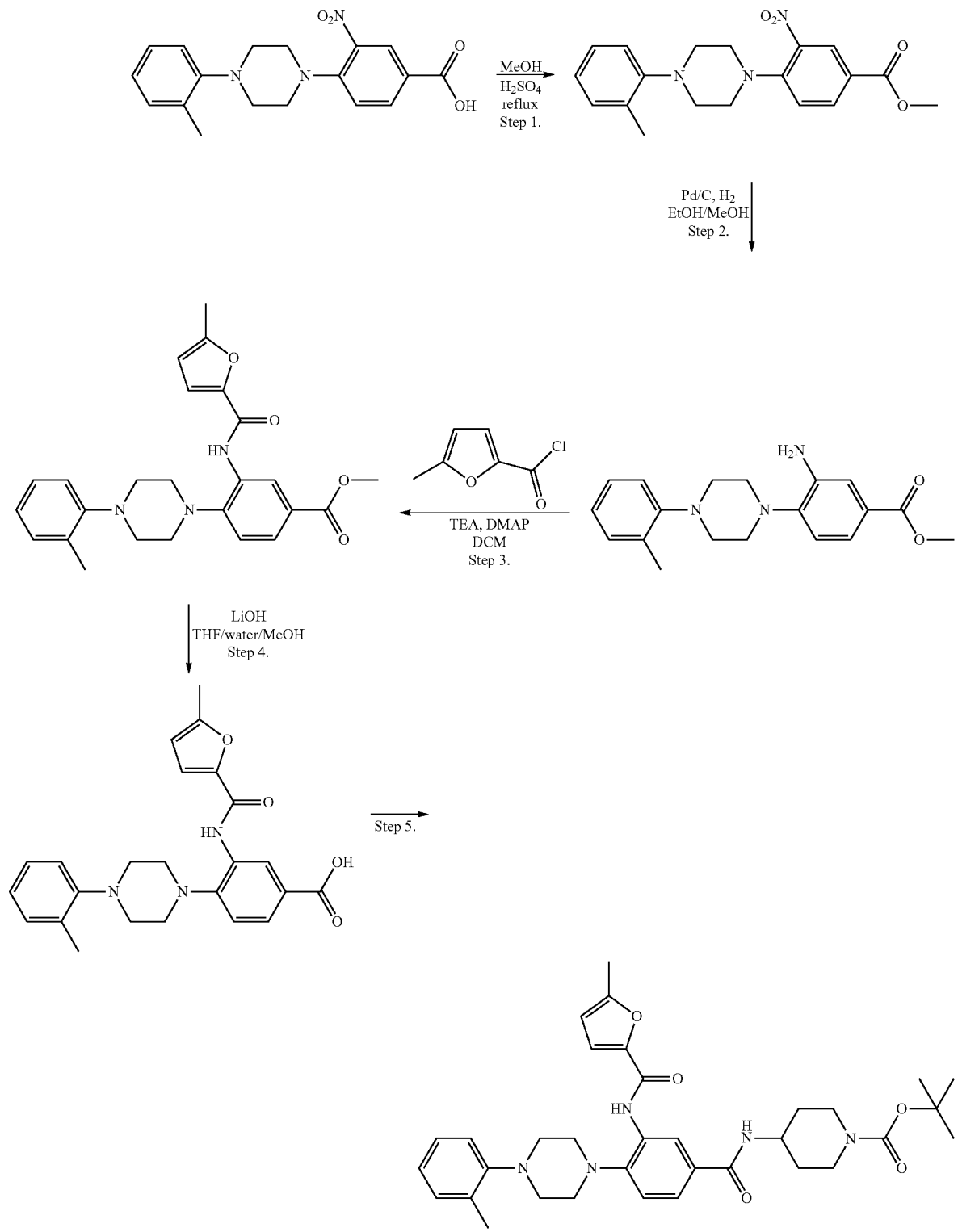

Step 1

3-Nitro-4-(4-o-tolyl-piperazin-1-yl)-benzoic acid (1.0 g, 2.9 mmol) was taken in methanol (100 mL) with sulphuric acid (1.0 mL) and reflux for 16 h. Concentrated and dissolved in ethyl acetate (300 mL) and washed the organic layer with a solution of satd. NaHCO$_3$, dried and concentrated to give 0.37 g of 3-Nitro-4-(4-o-tolyl-piperazin-1-yl)-benzoic acid methyl ester.

Step 2

The same procedure was applied in the preparation of 3-amino-4-(4-o-tolyl-piperazin-1-yl)-benzoic acid.

Step 3 and Step 4

3-amino-4-(4-o-tolyl-piperazin-1-yl)-benzoic acid methyl ester (2.0 g, 6.15 mmol) in CH$_2$Cl$_2$ (50 mL) was added triethylamine (1.7 mL, 12.3 mmol) and cooled to 0° C. 5-Methyl furoyl chloride (1.06 g, 7.38 mmol) in CH$_2$Cl$_2$ (5.0 mL) was added drop wise and the reaction was stirred at 0-25° C. for 6 h. Reaction was diluted CH$_2$Cl$_2$ (100 mL) and washed with a solution of saturated NaHCO$_3$, dried and concentrated to give the crude product, which was dissolved in a mixture of MeOH (60 mL) and THF (60 mL) and stirred with a solution of LiOH.H$_2$O (2.17 g, 53 mmol) in water (20 mL) for 6 h. The solvents were removed and the contents were dissolved in water and acidified to pH 5.0 using 2 N HCl. The 3-[(5-methyl-furan-2-carbonyl)-amino]-4-(4-o-tolyl-piperazin-1-yl)-benzoic acid was filtered and dried (1.37 g, 64%).

Step 5

This was prepared from acid intermediate 3-[(5-methyl-furan-2-carbonyl)-amino]-4-(4-o-tolyl-piperazin-1-yl)-benzoic acid and 4-Amino-piperidine-1-carboxylic acid tert-butyl ester following the EDC amidation procedure described in the preparation of compound no. 11.

LCMS (ESI) 602 (M+H); $^1$H NMR (400 MHz, DICHLOROMETHANE-d$_2$) δ ppm 1.41-1.46 (m, 9H) 1.94-2.03 (m, 2H) 2.36 (s, 3H) 2.43 (s, 3H) 2.81-2.96 (m, 2H) 3.15 (dd, J=15.89, 5.74 Hz, 8H) 4.01-4.16 (m, 3H) 6.07-6.26 (m, 2H) 6.94-7.06 (m, 1H) 7.09-7.14 (m, 2H) 7.16-7.25 (m, 2H) 7.32 (d, J=8.25 Hz, 1H) 7.58 (dd, J=8.25, 2.15 Hz, 1H) 8.78 (d, J=2.10 Hz, 1H) 9.46 (s, 1H).

The preparation of following compounds was in line with Scheme 3:

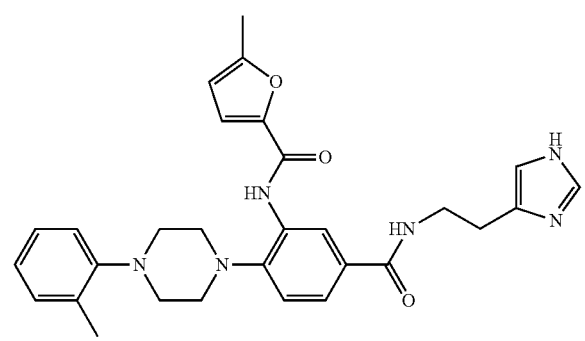 [SMILES: Cc1ccc(C(=O)Nc2cc(C(=O)NCCc3c[nH]cn3)ccc2N2CCN(c3ccccc3C)CC2)o1]

5-Methyl-furan-2-carboxylic acid [5-[2-(1H-imidazol-4-yl)-ethylcarbamoyl]-2-(4-o-tolyl-piperazin-1-yl)-phenyl]-amide (compound no. 185) was prepared comprising the same procedure as compound no. 11 from the intermediate acid 3-[(5-methyl-furan-2-carbonyl)-amino]-4-(4-o-tolyl-piperazin-1-yl)-benzoic acid.

LCMS (ESI) 513 (M+H); $^1$H NMR (400 MHz, DICHLOROMETHANE-d2) δ ppm 1.76 (t, J=6.03 Hz, 2H) 1.99-2.09 (m, 2H) 2.36-2.43 (m, 5H) 3.10-3.15 (m, 4H) 3.25-3.44 (m, 10H) 3.87 (s, 3H) 6.20 (dd, J=3.37, 0.98 Hz, 1H) 6.89-7.05 (m, 4H) 7.11 (d, J=3.32 Hz, 1H) 7.33 (d, J=8.25 Hz, 1H) 7.64 (dd, J=8.25, 2.10 Hz, 2H) 8.87 (d, J=2.10 Hz, 1H) 9.46 (s, 1H).

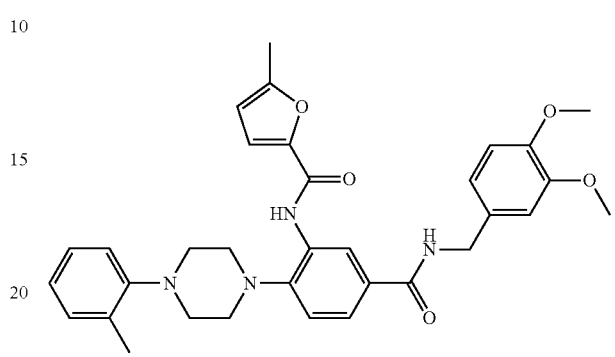

5-Methyl-furan-2-carboxylic acid [5-(3,4-dimethoxy-benzylcarbamoyl)-2-(4-o-tolyl-piperazin-1-yl)-phenyl]-amide (compound no. 171) was prepared comprising the same procedure as compound no. 11 from 3-[(5-methyl-furan-2-carbonyl)-amino]-4-(4-o-tolyl-piperazin-1-yl)-benzoic acid.

LCMS (ESI) 569 (M+H); $^1$H NMR (400 MHz, METHANOL-d4) δ ppm 2.35 (s, 3H) 2.45 (s, 3H) 3.08-3.21 (m, 8H) 3.82 (d, J=8.25 Hz, 6H) 4.52 (s, 2H) 6.31 (dd, J=3.42, 0.93 Hz, 1H) 6.91-6.93 (m, 2H) 6.97-7.02 (m, 2H) 7.12-7.21 (m, 4H) 7.41 (d, J=8.30 Hz, 1H) 7.65 (dd, J=8.30, 2.15 Hz, 1H) 8.74 (d, J=2.10 Hz, 1H).

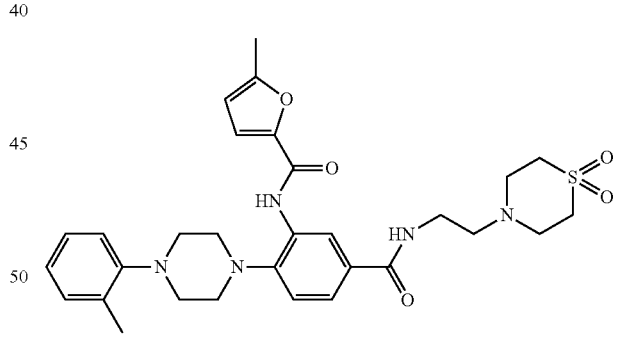

5-Methyl-furan-2-carboxylic acid [5-[2-(1,1-dioxo-1 lambda*6*-thiomorpholin-4-yl)ethylcarbamoyl]-2-(4-o-tolyl-piperazin-1-yl)-phenyl]-amide (compound no. 174) was prepared comprising the same procedure as compound no. 11 from 3-[(5-methyl-furan-2-carbonyl)-amino]-4-(4-o-tolyl-piperazin-1-yl)-benzoic acid.

LCMS (ESI) 580 (M+H); $^1$H NMR (400 MHz, METHANOL-d4) δ ppm 2.35 (s, 3H) 2.45 (s, 3H) 2.77 (t, J=6.35 Hz, 2H) 3.05-3.20 (m, 16H) 3.52 (t, J=6.30 Hz, 2H) 6.31 (dd, J=3.42, 0.98 Hz, 1H) 6.96-7.01 (m, 1H) 7.12-7.21 (m, 4H) 7.42 (d, J=8.30 Hz, 1H) 7.61 (d, J=2.15 Hz, 1H) 8.74 (d, J=2.10 Hz, 1H).

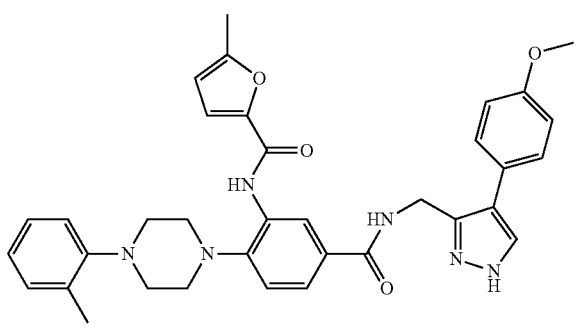 [SMILES: COc1ccc(-c2c[nH]nc2CNC(=O)c2ccc(N3CCN(c4ccccc4C)CC3)c(NC(=O)c3ccc(C)o3)c2)cc1]

5-Methyl-furan-2-carboxylic acid [5-{[4-(4-methoxyphenyl)-1H-pyrazol-3-ylmethyl]-carbamoyl}-2-(4-o-tolyl-piperazin-1-yl)-phenyl]-amide (compound no. 172) was prepared comprising the same procedure as compound no. 11 from 3-[(5-methyl-furan-2-carbonyl)-amino]-4-(4-o-tolyl-piperazin-1-yl)-benzoic acid.

LCMS (ESI) 605 (M+H); $^1$H NMR (400 MHz, METHANOL-d4) δ ppm 2.32-2.37 (m, 3H) 2.45 (s, 3H) 3.15 (q, J=5.81 Hz, 8H) 3.79-3.84 (m, 3H) 4.58 (s, 2H) 6.31 (dd, J=3.42, 0.93 Hz, 1H) 6.94-7.06 (m, 4H) 7.12-7.21 (m, 4H) 7.38 (d, J=8.30 Hz, 1H) 7.51-7.60 (m, 3H) 8.62 (d, J=2.05 Hz, 1H).

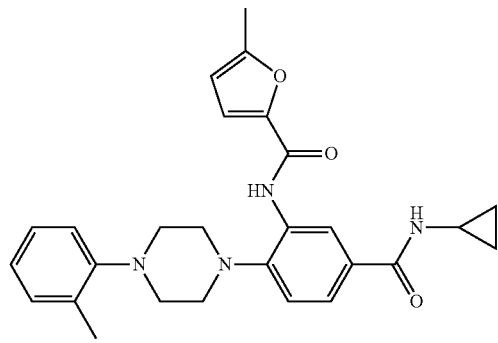 [SMILES: Cc1ccc(C(=O)Nc2cc(C(=O)NC3CC3)ccc2N2CCN(c3ccccc3C)CC2)o1]

5-Methyl-furan-2-carboxylic acid [5-cyclopropylcarbamoyl-2-(4-o-tolyl-piperazin-1-yl)-phenyl]amide (compound no. 195) was prepared comprising the same procedure as compound no. 11 from 3-[(5-methyl-furan-2-carbonyl)-amino]-4-(4-o-tolyl-piperazin-1-yl)-benzoic acid.

LCMS (ESI) 459 (M+H); $^1$H NMR (400 MHz, DICHLOROMETHANE-d$_2$) δ ppm 0.55-0.64 (m, 2H) 0.77-0.86 (m, 2H) 2.41 (d, J=12.30 Hz, 6H) 2.79-2.91 (m, 1H) 3.09-3.27 (m, 8H) 6.21 (dd, J=3.37, 0.98 Hz, 1H) 6.35 (s, 1H) 7.01-7.07 (m, 1H) 7.10-7.26 (m, 4H) 7.33 (d, J=8.30 Hz, 1H) 7.57 (dd, J=8.25, 2.10 Hz, 1H) 8.74 (d, J=2.05 Hz, 1H) 9.45 (brs, 1H).

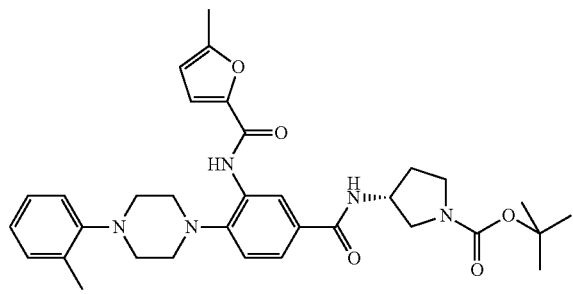 [SMILES: Cc1ccc(C(=O)Nc2cc(C(=O)N[C@@H]3CCN(C(=O)OC(C)(C)C)C3)ccc2N2CCN(c3ccccc3C)CC2)o1]

(R)-3-[3-[(5-Methyl-furan-2-carbonyl)-amino]-4-(4-o-tolyl-piperazin-1-yl)-benzoylamino]-pyrrolidine-1-carboxylic acid tert-butyl ester (compound no. 142) was prepared comprising the same procedure as compound no. 11 from the intermediate acid 3-[(5-methyl-furan-2-carbonyl)-amino]-4-(4-o-tolyl-piperazin-1-yl)-benzoic acid.

LCMS (ESI) 588 (M+H); $^1$H NMR (400 MHz, DICHLOROMETHANE-d$_2$) δ ppm 1.44 (s, 9H) 1.81-2.00 (m, 1H) 2.23 (dq, J=13.47, 6.54 Hz, 1H) 2.35 (s, 3H) 2.43 (s, 3H) 3.07-3.17 (m, 8H) 3.18-3.32 (m, 1H) 3.37-3.51 (m, 2H) 3.64-3.77 (m, 1H) 4.49-4.70 (m, 1H) 6.20 (dd, J=3.37, 0.98 Hz, 1H) 6.46 (d, J=11.37 Hz, 1H) 6.93-7.04 (m, 1H) 7.07-7.13 (m, 2H) 7.14-7.25 (m, 2H) 7.31 (d, J=8.25 Hz, 1H) 7.57 (dd, J=8.22, 2.12 Hz, 1H) 8.78 (d, J=1.90 Hz, 1H) 9.45 (s, 1H).

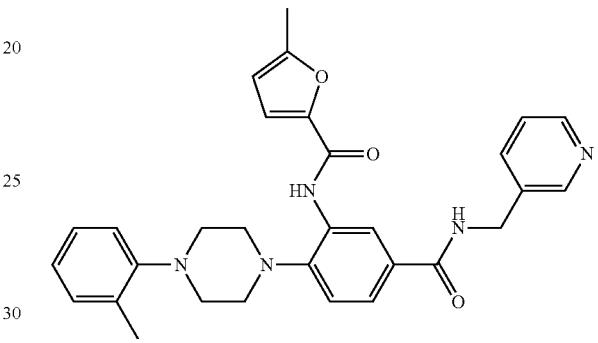

5-Methyl-furan-2-carboxylic acid [5-[(pyridin-3-ylmethyl)-carbamoyl]-2-(4-o-tolyl-piperazin-1-yl)-phenyl]-amide (compound no. 218) was prepared comprising the same procedure as compound no. 11 using 3-[(5-methyl-furan-2-carbonyl)-amino]-4-(4-o-tolyl-piperazin-1-yl)-benzoic acid.

LCMS (ESI) 510 (M+H); $^1$H NMR (400 MHz, DICHLOROMETHANE-d$_2$) δ ppm 2.36 (s, 3H) 2.44 (s, 3H) 3.09-3.20 (m, 8H) 4.70 (d, J=5.86 Hz, 2H) 6.21 (d, J=2.68 Hz, 1H) 6.95-7.06 (m, 2H) 7.11 (d, J=3.66 Hz, 2H) 7.20 (t, J=8.35 Hz, 2H) 7.35 (d, J=8.30 Hz, 1H) 7.51 (brs, 1H) 7.67 (dd, J=8.25, 2.00 Hz, 1H) 8.01 (d, J=7.91 Hz, 1H) 8.52-8.75 (m, 2H) 8.88 (d, J=1.95 Hz, 1H) 9.46 (brs, 1H).

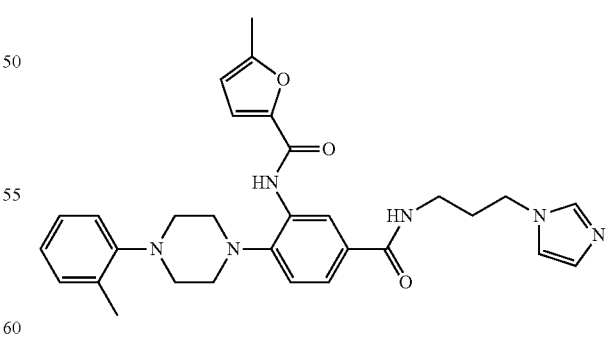

5-Methyl-furan-2-carboxylic acid [5-(3-imidazol-1-yl-propylcarbamoyl)-2-(4-o-tolyl-piperazin-1-yl)-phenyl]-amide (compound no. 210) was prepared comprising the same procedure as compound no. 11 from 3-[(5-methyl-furan-2-carbonyl)-amino]-4-(4-o-tolyl-piperazin-1-yl)-benzoic acid.

LCMS (ESI) 527 (M+H); ¹H NMR (400 MHz, CHLOROFORM-d) δ ppm 2.14 (quin, J=6.80 Hz, 2H) 2.38 (s, 3H) 2.45 (s, 3H) 3.16 (dd, J=16.08, 4.95 Hz, 8H) 3.50 (q, J=6.52 Hz, 2H) 4.07 (t, J=7.05 Hz, 2H) 6.22 (d, J=2.64 Hz, 1H) 6.59 (t, J=5.30 Hz, 1H) 6.96-7.13 (m, 5H) 7.15-7.22 (m, 2H) 7.35 (d, J=8.25 Hz, 1H) 7.52-7.58 (m, 1H) 7.76 (dd, J=8.27, 1.73 Hz, 1H) 8.81 (d, J=1.61 Hz, 1H) 9.51 (s, 1H).

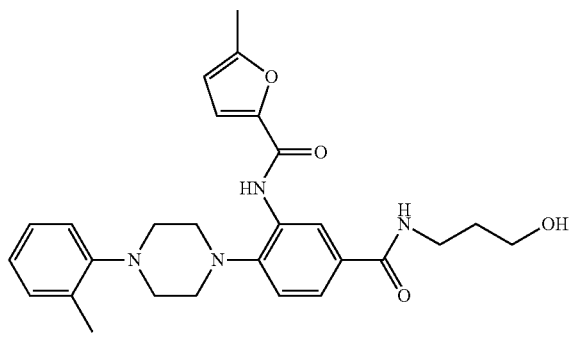 [SMILES: Cc1ccc(C(=O)Nc2cc(C(=O)NCCCO)ccc2N2CCN(c3ccccc3C)CC2)o1]

5-Methyl-furan-2-carboxylic acid [5-(3-hydroxy-propyl-carbamoyl)-2-(4-o-tolyl-piperazin-1-yl)-phenyl]-amide was prepared comprising the same procedure as compound no. 11 from 3-[(5-methyl-furan-2-carbonyl)-amino]-4-(4-o-tolyl-piperazin-1-yl)-benzoic acid.

LCMS (ESI) 477 (M+H); ¹H NMR (400 MHz, DICHLOROMETHANE-d₂) δ ppm 1.69-1.81 (m, 2H) 2.35 (s, 3H) 2.43 (s, 3H) 3.08-3.21 (m, 8H) 3.52-3.69 (m, 4H) 6.21 (d, J=2.59 Hz, 1H) 6.71-6.83 (m, 1H) 6.91-7.04 (m, 1H) 7.07-7.13 (m, 2H) 7.16-7.25 (m, 2H) 7.33 (d, J=8.30 Hz, 1H) 7.64 (dd, J=8.27, 2.07 Hz, 1H) 8.83 (d, J=1.66 Hz, 1H) 9.26-9.58 (m, 1H).

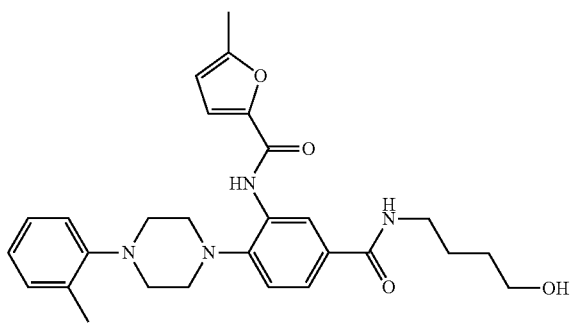 [SMILES: Cc1ccc(C(=O)Nc2cc(C(=O)NCCCCO)ccc2N2CCN(c3ccccc3C)CC2)o1]

5-Methyl-furan-2-carboxylic acid [5-(4-hydroxy-butyl-carbamoyl)-2-(4-o-tolyl-piperazin-1-yl)-phenyl]-amide (compound no. 241) was prepared comprising the same procedure as compound no. 11 from 3-[(5-methyl-furan-2-carbonyl)-amino]-4-(4-o-tolyl-piperazin-1-yl)-benzoic acid.

LCMS (ESI) 491 (M+H); ¹H NMR (400 MHz, CHLOROFORM-d) δ ppm 1.72-1.85 (m, 4H) 2.38 (s, 3H) 2.45 (s, 3H) 3.00 (brs, 1H) 3.15 (dd, J=17.16, 5.49 Hz, 8H) 3.50 (q, J=5.63 Hz, 2H) 3.81-3.88 (m, 2H) 6.21 (d, J=2.64 Hz, 1H) 7.02-7.12 (m, 2H) 7.16 (d, J=3.32 Hz, 1H) 7.20-7.26 (m, 2H) 7.33 (d, J=8.25 Hz, 1H) 7.74 (t, J=4.15 Hz, 1H) 7.81 (dd, J=8.27, 1.98 Hz, 1H) 8.81 (d, J=1.90 Hz, 1H) 9.52 (s, 1H).

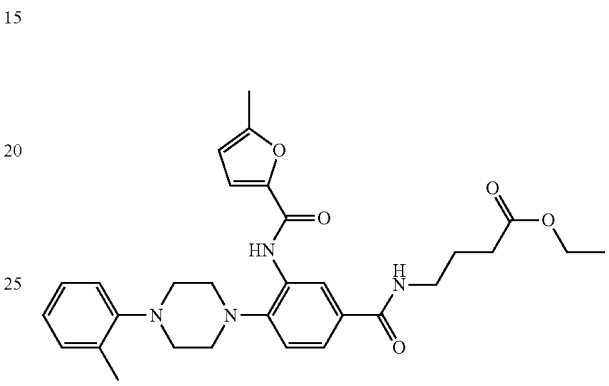

4-[3-[(5-Methyl-furan-2-carbonyl)-amino]-4-(4-o-tolyl-piperazin-1-yl)-benzoylamino]-butyric acid ethyl ester was prepared comprising the same procedure as compound no. 11 from 3-[(5-methyl-furan-2-carbonyl)-amino]-4-(4-o-tolyl-piperazin-1-yl)-benzoic acid.

LCMS (ESI) 533 (M+H); ¹H NMR (400 MHz, DICHLOROMETHANE-d₂) δ ppm 1.19-1.29 (m, 3H) 1.93 (quin, J=7.05 Hz, 3H) 2.33-2.48 (m, 6H) 3.15 (dd, J=15.25, 5.64 Hz, 8H) 3.40-3.52 (m, 3H) 4.11 (q, J=7.13 Hz, 2H) 6.22 (d, J=2.64 Hz, 1H) 6.50 (t, J=5.08 Hz, 1H) 6.98-7.05 (m, 1H) 7.09-7.15 (m, 2H) 7.16-7.25 (m, 2H) 7.33 (d, J=8.25 Hz, 1H) 7.60 (dd, J=8.25, 2.05 Hz, 1H) 8.81 (s, 1H) 9.47 (brs, 1H).

Example 4: Synthetic route towards 5-methyl-furan-2-carboxylic acid [5-(3-amino-propylcarbamoyl)-2-(4-o-tolyl-piperazin-1-yl)-phenyl]-amide Scheme 4

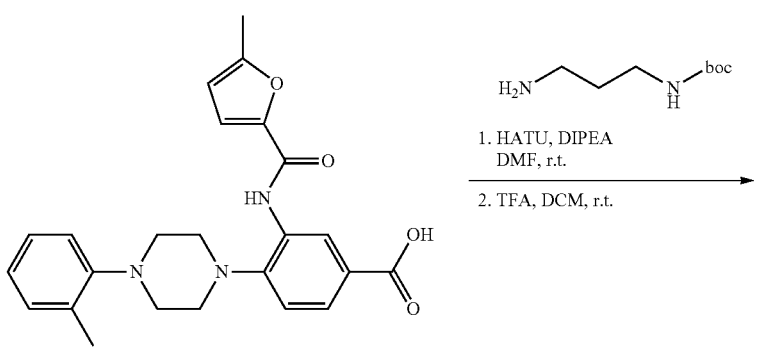

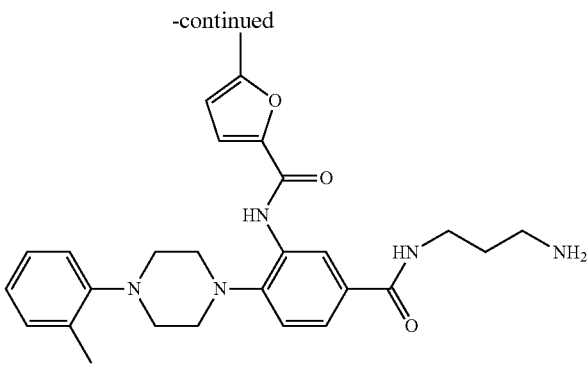

The preparation of following compounds was in line with Scheme 4:

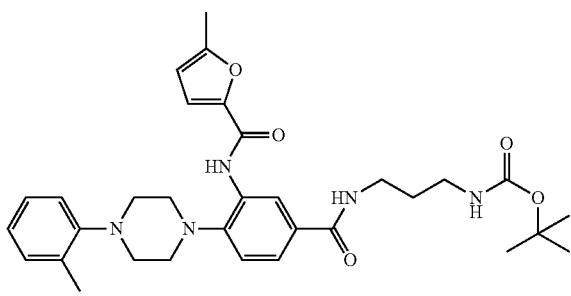 [SMILES: Cc1ccc(C(=O)Nc2cc(C(=O)NCCCNC(=O)OC(C)(C)C)ccc2N2CCN(c3ccccc3C)CC2)o1]

{3-[3-[(5-Methyl-furan-2-carbonyl)-amino]-4-(4-o-tolyl-piperazin-1-yl)-benzoylamino]-propyl}-carbamic acid tert-butyl ester (compound no. 258) was prepared comprising an analogous procedure used for compound no. 11 from the 3-[(5-methyl-furan-2-carbonyl)-amino]-4-(4-o-tolyl-piperazin-1-yl)-benzoic acid.

LCMS (ESI) 576 (M+H); $^1$H NMR (400 MHz, DICHLOROMETHANE-d2) δ ppm 0.81-0.90 (m, 1H) 1.08-1.17 (m, 1H) 1.23-1.31 (m, 1H) 1.43 (s, 9H) 1.65-1.82 (m, 5H) 2.37 (s, 2H) 2.43 (s, 2H) 3.12-3.22 (m, 8H) 3.41 (s, 2H) 6.09-6.25 (m, 1H) 6.97-7.06 (m, 1H) 7.13 (d, J=3.47 Hz, 2H) 7.17-7.24 (m, 1H) 7.35 (s, 1H) 7.52-7.69 (m, 1H) 8.68-8.92 (m, 1H) 9.38-9.59 (m, 1H).

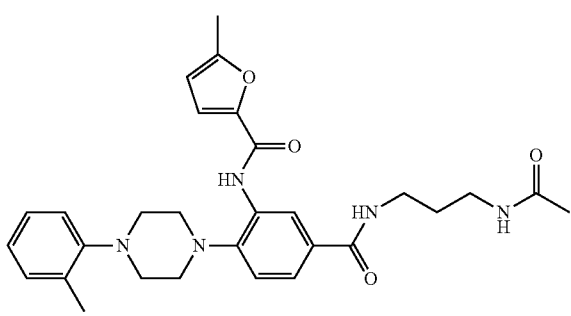 [SMILES: CC(=O)NCCCNC(=O)c1ccc(N2CCN(c3ccccc3C)CC2)c(NC(=O)c2ccc(C)o2)c1]

5-Methyl-furan-2-carboxylicacid [5-(3-acetylaminopropylcarbamoyl)-2-(4-o-tolyl-piperazin-1-yl)-phenyl]-amide (compound no. 259) was prepared as follows: {3-[3-[(5-Methyl-furan-2-carbonyl)-amino]-4-(4-o-tolyl-piperazin-1-yl)-benzoylamino]-propyl}-carbamic acid tert-butyl ester, above, (0.20 g, 0.347 mmol) was stirred with a mixture of CH$_2$Cl$_2$/TFA (5.0 mL/5.0 mL) for 3 h. The reaction was concentrated to give intermediate amine which was taken (0.070 g, 0.147 mmol) in CH$_2$Cl$_2$ (2.0 mL). DIPEA (0.371 g, 2.87 mmol) was added to this followed by acetic anhydride (0.32 g, 3.13 mmol). The reaction was stirred at room temperature for 3 h, concentrated and the crude was purified on preparative HPLC using water/methanol as eluent.

LCMS (ESI) 518 (M+H); $^1$H NMR (400 MHz, METHANOL-d4) δ ppm 1.78 (quin, J=6.81 Hz, 2H) 1.93 (s, 3H) 2.34 (s, 3H) 2.43 (s, 3H) 3.12-3.21 (m, 8H) 3.21-3.26 (m, 2H) 3.26-3.26 (m, 1H) 3.40 (t, J=6.88 Hz, 2H) 6.29 (dd, J=3.39, 0.85 Hz, 1H) 6.96-7.01 (m, 1H) 7.12-7.21 (m, 4H) 7.39 (d, J=8.30 Hz, 1H) 7.61 (dd, J=8.30, 2.15 Hz, 1H) 8.69 (d, J=2.05 Hz, 1H).

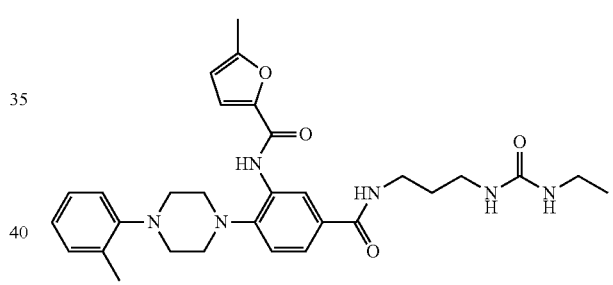

5-Methyl-furan-2-carboxylic acid [5-[3-(3-ethyl-ureido)-propylcarbamoyl]-2-(4-o-tolyl-piperazin-1-yl)-phenyl]-amide was prepared comprising an analogous procedure used for compound no. 48.

LCMS (ESI) 547 (M+H); $^1$H NMR (400 MHz, METHANOL-d4) δ ppm 1.07 (t, J=7.22 Hz, 3H) 1.74 (t, J=6.69 Hz, 2H) 2.35 (s, 3H) 2.42 (s, 3H) 3.08-3.23 (m, 12H) 3.41 (t, J=6.74 Hz, 2H) 6.28 (dd, J=3.32, 0.78 Hz, 1H) 6.93-7.06 (m, 1H) 7.01 (s, 1H) 7.11-7.23 (m, 4H) 7.39 (d, J=8.35 Hz, 1H) 7.61 (dd, J=8.30, 2.10 Hz, 1H) 8.69 (d, J=2.10 Hz, 1H).

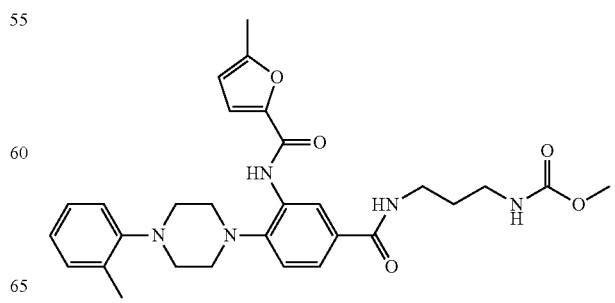

{3-[3-[(5-Methyl-furan-2-carbonyl)-amino]-4-(4-o-tolyl-piperazin-1-yl)-benzoylamino]-propyl}-carbamic acid methyl ester was prepared comprising an analogous procedure used for compound no. 133 from 5-methyl-furan-2-carboxylic acid [5-(3-amino-propylcarbamoyl)-2-(4-o-tolyl-piperazin-1-yl)-phenyl]-amide.

LCMS (ESI) 534 (M+H); $^1$H NMR (400 MHz, METHANOL-d4) δ ppm 1.77 (t, J=6.76 Hz, 2H) 2.34 (s, 3H) 2.42 (s, 3H) 3.09-3.22 (m, 10H) 3.40 (t, J=6.86 Hz, 2H) 3.61 (s, 3H) 6.28 (d, J=3.32 Hz, 1H) 7.00 (dd, J=6.44, 2.10 Hz, 1H) 7.11-7.23 (m, 4H) 7.38 (d, J=8.30 Hz, 1H) 7.60 (dd, J=8.27, 2.07 Hz, 1H) 8.68 (d, J=2.00 Hz, 1H).

Example 5: Synthetic route towards thiophene-2-carboxylic acid [5-[3-(2-oxo-pyrrolidin-1-yl)-propylcarbamoyl]-2-(4-otolyl-piperazin-1-yl)-phenyl]-amide (compound no. 40)

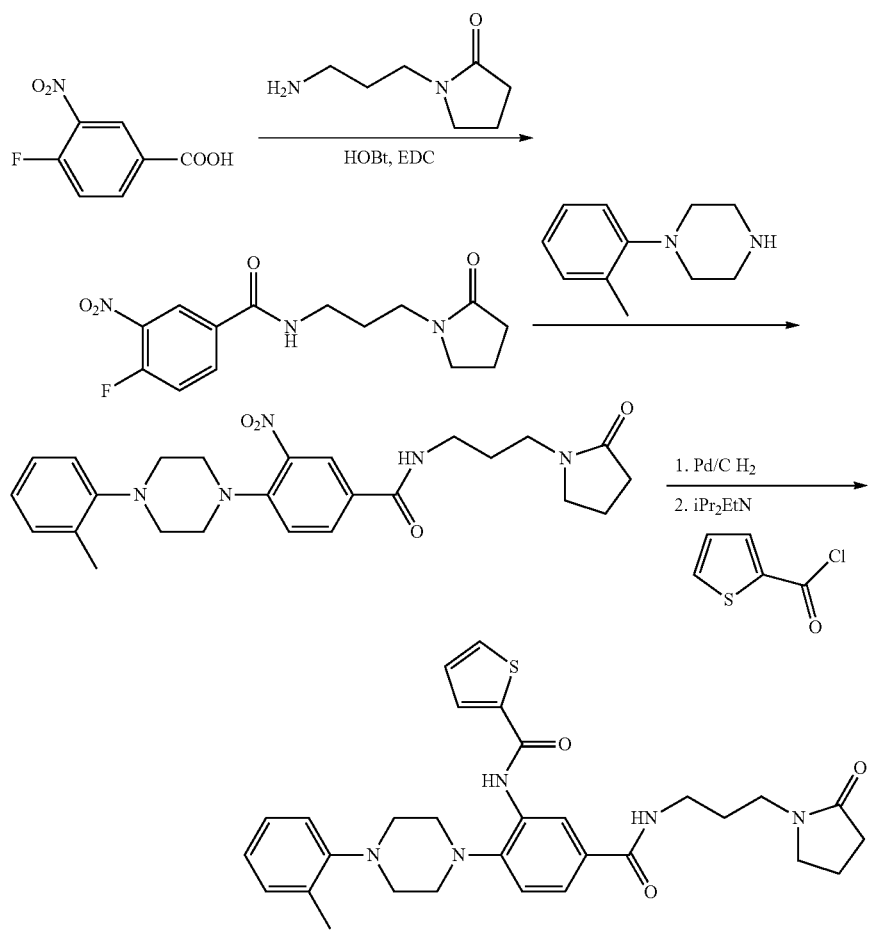

Step 1
To a solution of 4-fluoro-3-nitro-benzoic acid (5.0 g, 27.02 mmol) in CH$_2$Cl$_2$ (150 mL), HOBt (6.5 g, 48.63 mmol) and EDC.HCl (6.2 g, 40.53 mmol) were added followed by DIPEA (6.12 mL, 35.12 mmol). The reaction was stirred at room temperature for 6 h. Water (50.0 mL) was added and the layers were separated. Organic layer was washed with brind and concentrated to give crude product 4-fluoro-3-nitro-N-[3-(2-oxo-pyrrolidin-1-yl)-propyl]-benzamide (7.5 g, 90%). This was taken to the next step without further purification.

Step 2
To a solution of 4-Fluoro-3-nitro-N-[3-(2-oxo-pyrrolidin-1-yl)-propyl]-benzamide (2.0 g, 6.47 mmol) in DMF (10 mL), K$_2$CO$_3$ (1.7 g, 12.94 mmol) was added followed by 1-o-tolyl-piperazine (1.7 g, 9.7 mmol), and the reaction mixture was stirred at room temperature for 16 h. DMF (2.0 mL) was added and filtered. The solid was washed with MeOH (300 mL) and methanol layer was evaporated to give the acid 3-nitro-N-[3-(2-oxo-pyrrolidin-1-yl)-propyl]-4-(4-o-tolyl-piperazin-1-yl)-benzamide in the first crop (1.8 g, 62%).

Step 3
3-Nitro-N-[3-(2-oxo-pyrrolidin-1-yl)-propyl]-4-(4-o-tolyl-piperazin-1-yl)-benzamide (1.5 g, 3.2 mmol) was taken in a mixture of ethanol/methanol (50.0 mL/20.0 mL). This was added to a flask containing Pd/C (5 wt %) (0.15 g). The solution was evacuated and nitrogen purged and stirred under a balloon of hydrogen for 8 h. LC-MS indicated completion of reaction. Reaction was stopped, evacuated and nitrogen purged and filtered on celite. The solvent was rotavaped out to give 3-amino-N-[3-(2-oxo-pyrrolidin-1-yl)-propyl]-4-(4-o-tolyl-piperazin-1-yl)-benzamide (0.7 g, 47%).

Step 4
In 20 mL scintillation vial, under nitrogen, 3-amino-N-[3-(2-oxo-pyrrolidin-1-yl)-propyl]-4-(4-o-tolyl-piperazin-1-yl)-benzamide (0.06 g, 0.137 mmol) was dissolved in CH$_2$Cl$_2$ (2.0 mL), then DIPEA (0.12 mL, 0.685 mmol) and DMAP (0.0016 g, 0.0137 mmol) were added and the mixture was cooled to 0° C. Then the 2-thiophene chloride (0.206 mmol, 0.03 g) in CH$_2$Cl$_2$ (1.0 mL) was added drop by drop. After 40 min the reaction was done. 10.0 mL of CH$_2$Cl$_2$ were added, and then it was washed with 4.0 mL of water followed by 3.0 mL of a saturated sodium bicarbonate solution and 3.0 mL of brine. Organics were dried over anhydrous sodium sulfate, filtered and concentrated. The crude was dissolved in methanol and purified on preparative HPLC using MeOH/Water (0.1% TFA) to give the desired product (0.06 g, 81%).

LCMS (ESI) 546 (M+H); $^1$H NMR (400 MHz, METHANOL-d$_4$) δ ppm 1.84 (quin, J=6.87 Hz, 2H) 2.04 (quin, J=7.60 Hz, 2H) 2.34 (s, 3H) 2.35-2.40 (m, 2H) 3.18 (s, 7H) 3.33-3.40 (m, 4H) 3.44-3.53 (m, 2H) 6.97-7.04 (m, 1H) 7.14-7.24 (m, 4H) 7.38 (d, J=8.40 Hz, 1H) 7.67 (dd, J=8.32, 2.12 Hz, 1H) 7.75 (dd, J=4.98, 1.07 Hz, 1H) 7.86 (dd, J=3.73, 1.05 Hz, 1H) 8.48 (d, J=2.15 Hz, 1H).

The preparation of following compounds was in line with Scheme 5:

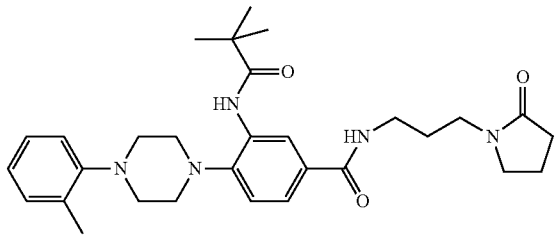 [SMILES: Cc1ccccc1N1CCN(c2ccc(C(=O)NCCCN3CCCC3=O)cc2NC(=O)C(C)(C)C)CC1]

3-(2,2-Dimethyl-propionylamino)-N-[3-(2-oxo-pyrrolidin-1-yl)-propyl]-4-(4-o-tolyl-piperazin-1-yl)-benzamide (compound no. 177) was prepared comprising an analogous procedure used for compound no. 133 from 3-amino-N-[3-(2-oxo-pyrrolidin-1-yl)-propyl]-4-(4-o-tolyl-piperazin-1-yl)-benzamide.

LCMS (ESI) 520 (M+H); $^1$H NMR (400 MHz, DICHLOROMETHANE-d$_2$) δ ppm 1.34 (s, 9H) 1.83 (quin, J=6.32 Hz, 2H) 2.08 (quin, J=7.65 Hz, 2H) 2.38 (s, 3H) 2.51 (t, J=8.13 Hz, 2H) 3.09-3.26 (m, 8H) 3.35-3.52 (m, 6H) 7.03-7.09 (m, 1H) 7.12-7.17 (m, 1H) 7.19-7.25 (m, 2H) 7.36 (d, J=8.35 Hz, 1H) 7.46-7.58 (m, 1H) 7.65 (dd, J=8.30, 2.15 Hz, 1H) 8.74 (d, J=2.10 Hz, 1H) 8.91 (s, 1H).

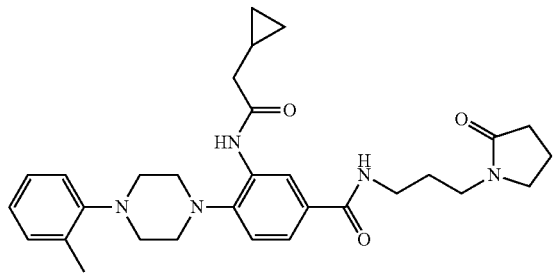 [SMILES: Cc1ccccc1N1CCN(c2ccc(C(=O)NCCCN3CCCC3=O)cc2NC(=O)CC2CC2)CC1]

3-(2-Cyclopropyl-acetylamino)-N-[3-(2-oxo-pyrrolidin-1-yl)-propyl]-4-(4-o-tolyl-piperazin-1-yl)-benzamide (compound no. 219) was prepared comprising an analogous procedure used for compound no. 133 from 3-amino-N-[3-(2-oxo-pyrrolidin-1-yl)-propyl]-4-(4-o-tolyl-piperazin-1-yl)-benzamide.

LCMS (ESI) 518 (M+H); $^1$H NMR (400 MHz, DICHLOROMETHANE-d2) δ ppm 0.04-0.05 (m, 2H) 0.38-0.47 (m, 2H) 0.51-0.59 (m, 1H) 0.79 (dddt, J=12.59, 7.56, 5.05, 2.51, 2.51 Hz, 1H) 0.94-1.00 (m, 1H) 1.44 (quin, J=6.15 Hz, 2H) 1.68-1.77 (m, 2H) 2.01-2.11 (m, 7H) 2.78 (s, 8H) 3.01-3.12 (m, 6H) 6.66-6.73 (m, 1H) 6.76 (d, J=7.27 Hz, 1H) 6.84-6.91 (m, 2H) 7.02 (d, J=8.30 Hz, 1H) 7.24-7.35 (m, 2H) 8.51 (d, J=1.61 Hz, 1H) 8.62 (brs, 1H).

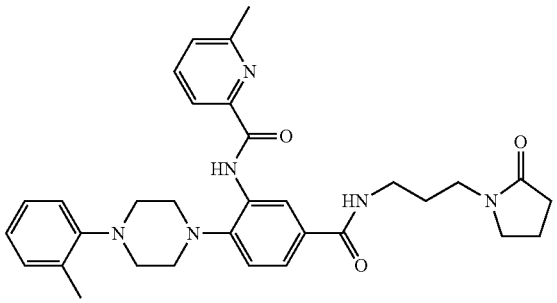 [SMILES: Cc1cccc(C(=O)Nc2cc(C(=O)NCCCN3CCCC3=O)ccc2N2CCN(c3ccccc3C)CC2)n1]

6-Methyl-pyridine-2-carboxylic acid [5-[3-(2-oxo-pyrrolidin-1-yl)-propylcarbamoyl]-2-(4-o-tolyl-piperazin-1-yl)-phenyl]-amide (compound no. 186) was prepared comprising an analogous procedure used for compound no. 133 from 3-amino-N-[3-(2-oxo-pyrrolidin-1-yl)-propyl]-4-(4-o-tolyl-piperazin-1-yl)-benzamide.

LCMS (ESI) 555 (M+H); $^1$H NMR (400 MHz, METHANOL-d$_4$) δ ppm 1.76-1.91 (m, 2H) 2.05 (quin, J=7.59 Hz, 2H) 2.33 (s, 3H) 2.35-2.41 (m, 2H) 2.68 (s, 3H) 3.10-3.16 (m, 4H) 3.20-3.25 (m, 4H) 3.38 (td, J=6.91, 2.05 Hz, 4H) 3.49 (t, J=7.08 Hz, 2H) 6.91-7.00 (m, 1H) 7.10-7.21 (m, 3H) 7.39 (d, J=8.35 Hz, 1H) 7.46 (d, J=7.76 Hz, 1H) 7.62 (dd, J=8.25, 2.10 Hz, 1H) 7.88 (t, J=7.74 Hz, 1H) 8.04 (d, J=7.66 Hz, 1H) 8.93 (d, J=2.05 Hz, 1H).

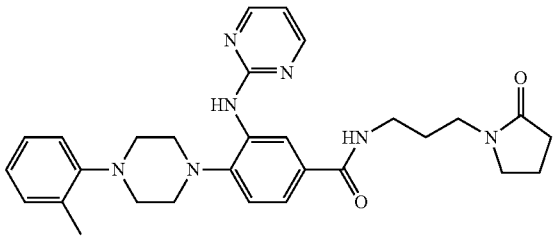 [SMILES: Cc1ccccc1N1CCN(c2ccc(C(=O)NCCCN3CCCC3=O)cc2Nc2ncccn2)CC1]

N-[3-(2-Oxo-pyrrolidin-1-yl)-propyl]-3-(pyrimidin-2-ylamino)-4-(4-o-tolyl-piperazin-1-yl)-benzamide (compound no. 242) was prepared as follows: In a microwavable glass tube, Pd(OAc)$_2$ (0.0025 g, 0.0115 mmol) and X-PHOS (5.4 mg, 0.0115 mmol) were taken in a mixture of t-BuOH:toluene (1:5) (2.0 mL) and stirred. This solution was evacuated for 5 min and purged with nitrogen. 3-Amino-N-[3-(2-oxo-pyrrolidin-1-yl)-propyl]-4-(4-o-tolyl-piperazin-1-yl)-benzamide (0.05 g, 0.115 mmol) and 2-bromo-pyrimidine (2.7 mg, 0.172 mmol) were added to this, evacuated and nitrogen purged. This mixture was stirred at 140° C. under MW for 30 min. LC-MS indicated the product formation along with some other by-products. The reaction mixture was concentrated, dissolved in methanol and purified on preparative HPLC using water/methanol as eluent to give desire product (10.0 mg, 17%).

LCMS (ESI) 514 (M+H); $^1$H NMR (400 MHz, METHANOL-$d_4$) δ ppm 1.15 (t, J=7.03 Hz, 1H) 1.84 (t, J=6.81 Hz, 2H) 1.96-2.10 (m, 2H) 2.27-2.34 (m, 3H) 2.34-2.42 (m, 2H) 3.05-3.14 (m, 8H) 3.37 (q, J=6.74 Hz, 4H) 3.43-3.54 (m, 3H) 6.80-6.99 (m, 2H) 7.04-7.19 (m, 3H) 7.33 (d, J=8.25 Hz, 1H) 7.50 (dd, J=8.25, 2.10 Hz, 1H) 8.49 (d, J=4.83 Hz, 1H) 8.85 (d, J=2.10 Hz, 1H).

2.27 Hz, 1H) 7.12-7.26 (m, 3H) 7.33 (d, J=8.25 Hz, 1H) 7.67 (dd, J=8.18, 1.93 Hz, 2H) 8.85 (d, J=1.90 Hz, 1H) 9.55 (s, 1H).

Example 6: Synthetic route towards 5-ethynyl-furan-2-carboxylic acid [5-[3-(2-oxo-pyrrolidin-1-yl)-propylcarbamoyl]-2-(4-o-tolyl-piperazin-1-yl)-phenyl]-amide (compound no. 176)

Scheme 6

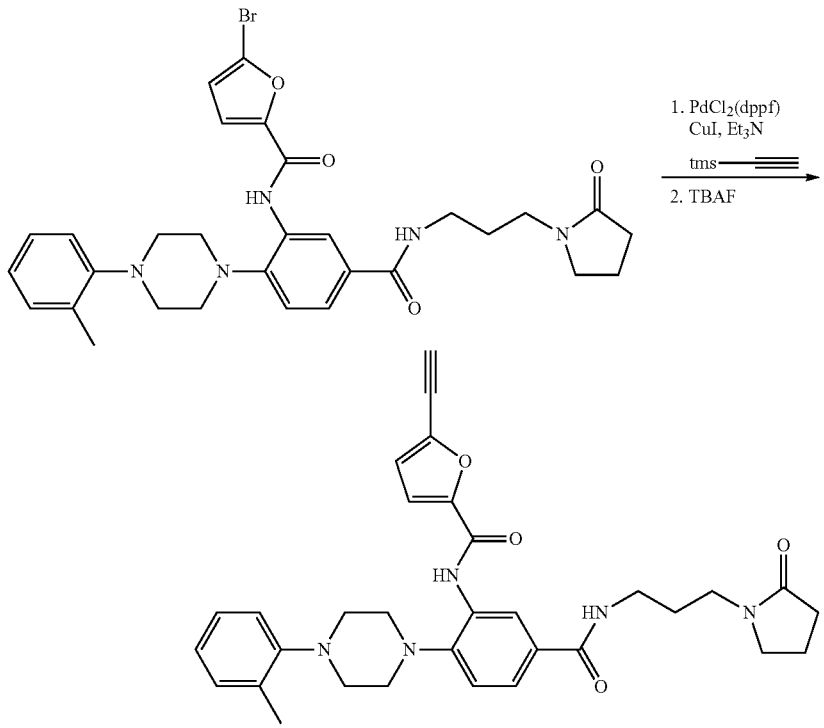

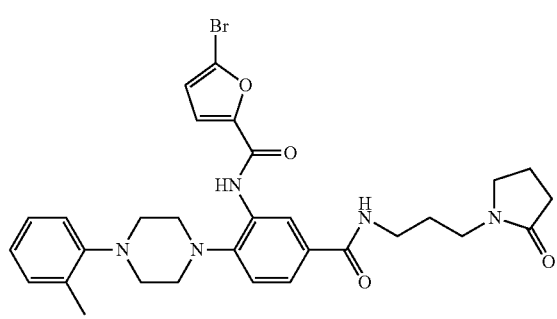 [SMILES: Cc1ccccc1N1CCN(c2ccc(C(=O)NCCCN3CCCC3=O)cc2NC(=O)c2ccc(Br)o2)CC1]

5-Bromo-furan-2-carboxylic acid [5-[3-(2-oxo-pyrrolidin-1-yl)-propylcarbamoyl]-2-(4-o-tolyl-piperazin-1-yl)-phenyl]-amide (compound no. 143) was prepared comprising an analogous procedure used for compound no. 133 from 3-amino-N-[3-(2-oxo-pyrrolidin-1-yl)-propyl]-4-(4-o-tolyl-piperazin-1-yl)-benzamide.

LCMS (ESI) 608 (M+H); $^1$H NMR (400 MHz, DICHLOROMETHANE-$d_2$) δ ppm 1.76 (dt, J=11.99, 6.13 Hz, 4H) 1.95-2.12 (m, 2H) 2.26-2.46 (m, 5H) 2.98-3.25 (m, 8H) 3.27-3.49 (m, 6H) 6.55 (d, J=3.56 Hz, 1H) 7.01 (dd, J=6.52, In a 20 mL scintillation vial, 5-bromo-furan-2-carboxylic acid [5-[3-(2-oxo-pyrrolidin-1-yl)-propylcarbamoyl]-2-(4-o-tolyl-piperazin-1-yl)-phenyl]-amide (0.1 g, 0.231 mmol) was taken in acetonitrile (5.0 mL). Trimethylsilyl acetylene (0.045 g, 0.462 mmol), CuI (0.009 g, 0.046 mmol), triethylamine (0.116 g, 1.155 mmol) and PdCl$_2$(Ph$_3$P) (0.032 g, 0.046 mmol) were added to this, and the solution was evacuated for 5 min and nitrogen purged and stirred at 80° C. for 4 h. LC-MS indicated the completion of the reaction. It was diluted with acetonitrile and filtered through celite and concentrated. The crude was dissolved in THF and stirred with TBAF (2.0 mL of 2 M solution in THF) at room temperature for 16 h. The reaction was concentrated and dissolved in methanol and purified on preparative HPLC using methanol/water as eluent to give the desired product (0.018 g, 14% yield).

LCMS (ESI) 554 (M+H); $^1$H NMR (400 MHz, METHANOL-$d_4$) δ ppm 1.28-1.37 (m, 2H) 1.84 (quin, J=6.87 Hz, 2H) 2.04 (quin, J=7.59 Hz, 2H) 2.31-2.44 (m, 5H) 3.11-3.21 (m, 4H) 3.36 (td, J=6.83, 3.17 Hz, 4H) 3.48 (t, J=7.05 Hz, 2H) 4.18 (s, 1H) 6.88 (d, J=3.61 Hz, 1H) 6.99-7.08 (m, 1H) 7.17-7.31 (m, 4H) 7.39 (d, J=8.30 Hz, 1H) 7.63 (dd, J=8.27, 2.07 Hz, 1H) 8.71 (d, J=2.00 Hz, 1H).

The preparation of following compound was in line with Scheme 6:

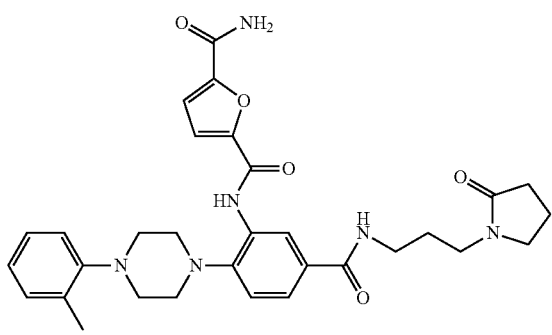 [SMILES: Cc1ccccc1N1CCN(c2ccc(C(=O)NCCCN3CCCC3=O)cc2NC(=O)c2ccc(C(N)=O)o2)CC1]

Furan-2,5-dicarboxylic acid 2-amide 5-{[5-[3-(2-oxo-pyrrolidin-1-yl)-propylcarbamoyl]-2-(4-o-tolyl-piperazin-1-yl)-phenyl]-amide} (compound no. 216) was prepared as follows: 5-Bromo-furan-2-carboxylic acid [5-[3-(2-oxo-pyrrolidin-1-yl)-propylcarbamoyl]-2-(4-o-tolyl-piperazin-1-yl)-phenyl]-amide (0.1 g, 0.164 mmol), Zn(CN)$_2$ (0.038 g, 0.33 mmol), Zn (2.1 mg, 0.033 mmol) were taken in DMA (5.0 mL) and the solution was degassed for 5 min. Pd(t-Bu$_3$P)$_2$ (8.0 mg, 0.016 mmol) was added to this, and the solution was degassed and nitrogen purged again. The reaction mixture was stirred at 85° C. under nitrogen for 5 h. It was cooled, dissolved in MeOH and purified on preparative HPLC using water/methanol as eluent to the intermediate nitrile (0.07 g, 79%). The above nitrile (0.05 g, 0.09 mmol) was taken in DMSO (2.0 mL). K$_2$CO$_3$ (0.074 mg, 0.54 mmol) was added to this followed by H$_2$O$_2$ (0.031 g, 0.27 mmol) and the reaction was stirred at room temperature for 4 h. LC-MS indicated the completion of the reaction. Water (2.0 mL) was added and the product crashed out. It was filtered and dried to give the desired product (0.025 g, 47%).

LCMS (ESI) 573 (M+H); $^1$H NMR (400 MHz, DMSO-d6) δ ppm 1.66 (quin, J=6.97 Hz, 2H) 1.88 (quin, J=7.53 Hz, 2H) 2.15-2.21 (m, 2H) 2.25 (s, 3H) 3.04 (s, 8H) 3.15-3.22 (m, 4H) 3.31 (t, J=6.98 Hz, 2H) 6.84-6.97 (m, 1H) 7.07-7.16 (m, 3H) 7.23 (d, J=3.61 Hz, 1H) 7.29-7.34 (m, 2H) 7.64 (dd, J=8.42, 1.98 Hz, 2H) 8.09 (brs, 1H) 8.36 (t, J=5.64 Hz, 1H) 8.42 (d, J=2.00 Hz, 1H) 9.68 (s, 1H).

Example 7: Synthetic route towards furan-2-carboxylic acid {2-[4-(2-methyl-benzyl)-piperazin-1-yl]-5-[3-(2-oxo-pyrrolidin-1-yl)-propylcarbamoyl]-phenyl}-amide

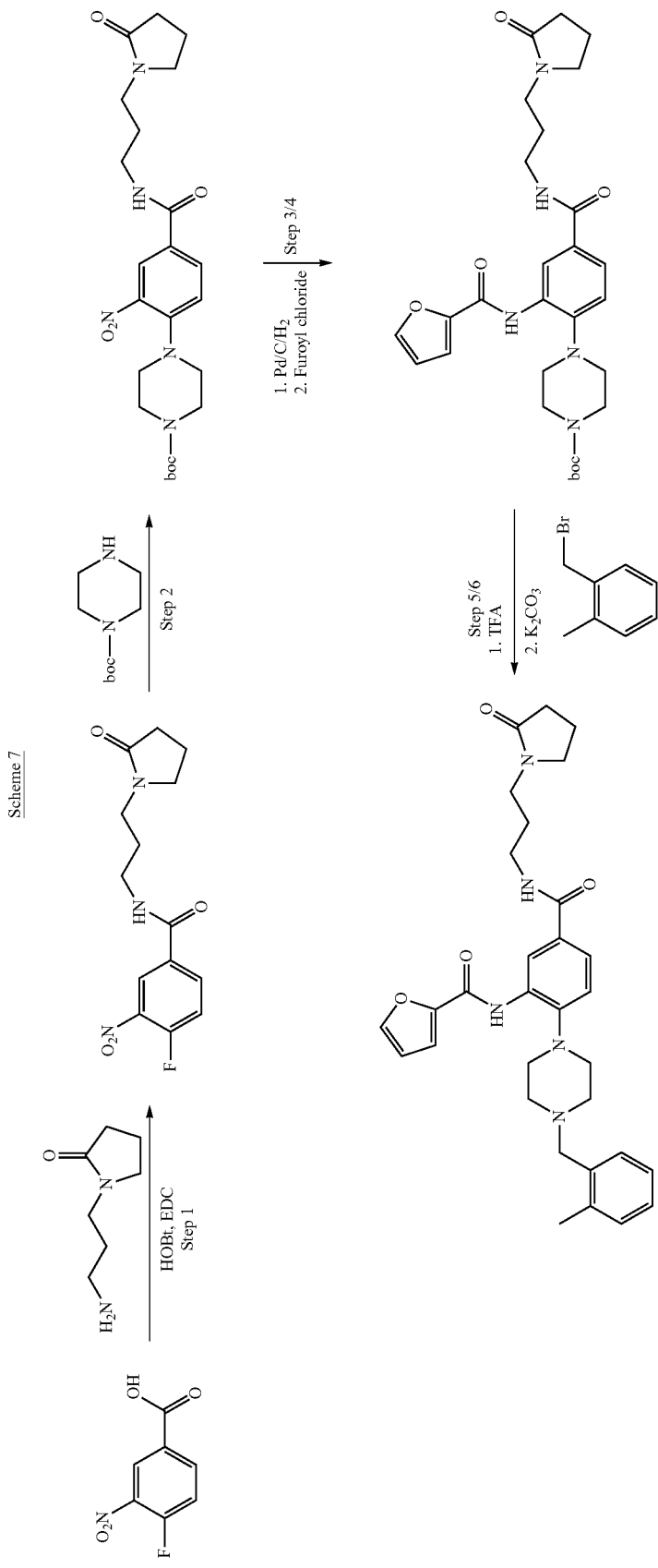

Steps 1, 2, 3 and 4

Reactions were performed in a similar fashion as compound no. 11.

Step 5 and Step 6

To a solution of furan-2-carboxylic acid {5-[3-(2-oxo-pyrrolidin-1-yl)-propylcarbamoyl]-2-piperazin-1-yl-phenyl}-amide (0.1 g, 0.23 mmol) in acetonitrile (3.0 mL) and DMF (0.5 mL), K$_2$CO$_3$ (0.094 g, 0.68 mmol) and 1-bromomethyl-2-methyl-benzene (0.05 g, 0.3 mmol) were added and the reaction was stirred at room temperature for 4 h. Water was added and extracted with DCM, concentrated and the crude was purified on silica gel using DCM/MeOH (10%) to give the product (0.027 g, 22% yield).

LCMS (ESI) 544 (M+H); $^1$H NMR (400 MHz, METHANOL-d4) δ ppm 1.85 (t, J=6.88 Hz, 2H) 2.00-2.11 (m, 2H) 2.38 (d, J=8.25 Hz, 2H) 2.42 (s, 3H) 2.73 (brs, 4H) 2.98 (t, J=4.73 Hz, 4H) 3.34-3.41 (m, 4H) 3.50 (t, J=7.10 Hz, 2H) 3.62 (s, 2H) 6.71 (dd, J=3.56, 1.76 Hz, 1H) 7.10-7.19 (m, 4H) 7.26-7.31 (m, 2H) 7.32 (d, J=8.35 Hz, 1H) 7.61 (dd, J=8.32, 2.12 Hz, 1H) 7.82 (dd, J=1.71, 0.68 Hz, 1H) 8.69 (d, J=2.10 Hz, 1H).

The preparation of following compounds was in line with Scheme 7:

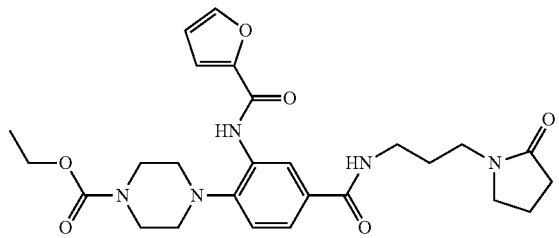 [SMILES: CCOC(=O)N1CCN(c2ccc(C(=O)NCCCN3CCCC3=O)cc2NC(=O)c2ccco2)CC1]

4-{2-[(Furan-2-carbonyl)-amino]-4-[3-(2-oxo-pyrrolidin-1-yl)-propylcarbamoyl]-phenyl}-piperazine-1-carboxylic acid ethyl ester (compound no. 62) was prepared comprising the same procedure as compound no. 11.

LCMS (ESI) 512 (M+H); $^1$H NMR (400 MHz, METHANOL-d4) δ ppm 1.28 (t, J=7.10 Hz, 3H) 1.85 (t, J=6.91 Hz, 2H) 2.01-2.11 (m, 2H) 2.36-2.43 (m, 2H) 2.91-2.99 (m, 4H) 3.34-3.41 (m, 4H) 3.50 (t, J=7.08 Hz, 2H) 3.71 (brs, 4H) 4.16 (q, J=7.08 Hz, 2H) 6.68 (dd, J=3.54, 1.78 Hz, 1H) 7.29 (dd, J=3.56, 0.68 Hz, 1H) 7.33 (d, J=8.35 Hz, 1H) 7.63 (dd, J=8.32, 2.12 Hz, 1H) 7.81 (dd, J=1.73, 0.71 Hz, 1H) 8.69 (d, J=2.05 Hz, 1H).

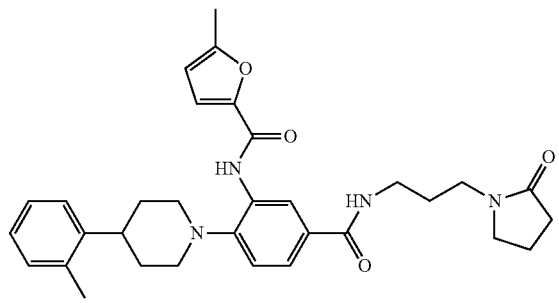 [SMILES: Cc1ccc(C(=O)Nc2cc(C(=O)NCCCN3CCCC3=O)ccc2N2CCC(c3ccccc3C)CC2)o1]

5-Methyl-furan-2-carboxylic acid [5-[3-(2-oxo-pyrrolidin-1-yl)-propylcarbamoyl]-2-(4-o-tolyl-piperidin-1-yl)-phenyl]-amide (compound no. 165) was prepared from the reaction between 4-o-tolyl-piperidine and 4-fluoro-3-nitro-N-[3-(2-oxo-pyrrolidin-1-yl)-propyl]-benzamide, comprising the sequence of reactions described for the synthesis of compound no. 175.

LCMS (ESI) 543 (M+H); $^1$H NMR (400 MHz, METHANOL-d$_4$) δ ppm 1.83 (quin, J=6.91 Hz, 2H) 1.88-1.95 (m, 2H) 1.99-2.09 (m, 4H) 2.13 (s, 1H) 2.34-2.40 (m, 5H) 2.42 (s, 3H) 2.92-3.02 (m, 3H) 3.18 (d, J=11.18 Hz, 2H) 3.32 (s, 1H) 3.36 (td, J=6.87, 3.88 Hz, 4H) 3.48 (t, J=7.08 Hz, 2H) 6.28 (dd, J=3.37, 0.68 Hz, 1H) 7.01-7.20 (m, 4H) 7.34 (d, J=8.35 Hz, 2H) 7.59 (dd, J=8.30, 2.10 Hz, 1H) 8.73 (d, J=2.05 Hz, 1H).

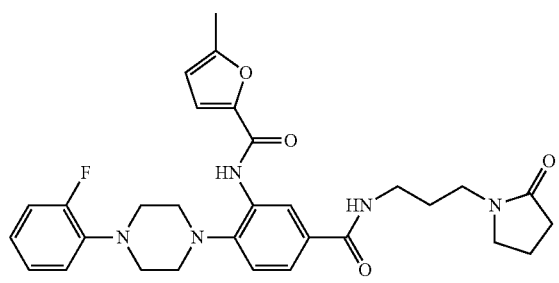 [SMILES: Cc1ccc(C(=O)Nc2cc(C(=O)NCCCN3CCCC3=O)ccc2N2CCN(c3ccccc3F)CC2)o1]

5-Methyl-furan-2-carboxylic acid {2-[4-(2-fluoro-phenyl)-piperazin-1-yl]-5-[3-(2-oxo-pyrrolidin-1-yl)-propylcarbamoyl]-phenyl}-amide (compound no. 130) was prepared from the reaction between 1-(2-fluoro-phenyl)-piperazine and 4-fluoro-3-nitro-N-[3-(2-oxo-pyrrolidin-1-yl)-propyl]-benzamide comprising the sequence of reactions described for the synthesis of compound no. 175.

LCMS (ESI) 548 (M+H); $^1$H NMR (400 MHz, METHANOL-d4) δ ppm 1.84 (t, J=6.91 Hz, 2H) 2.00-2.09 (m, 2H) 2.35 (s, 1H) 2.37-2.41 (m, 4H) 3.11-3.16 (m, 4H) 3.30-3.40 (m, 8H) 3.48 (t, J=7.08 Hz, 2H) 6.28 (dd, J=3.39, 0.95 Hz, 1H) 6.94-7.09 (m, 2H) 7.09-7.12 (m, 2H) 7.15 (d, J=3.47 Hz, 1H) 7.38 (d, J=8.30 Hz, 1H) 7.61 (dd, J=8.30, 2.10 Hz, 1H) 8.70 (d, J=2.10 Hz, 1H).

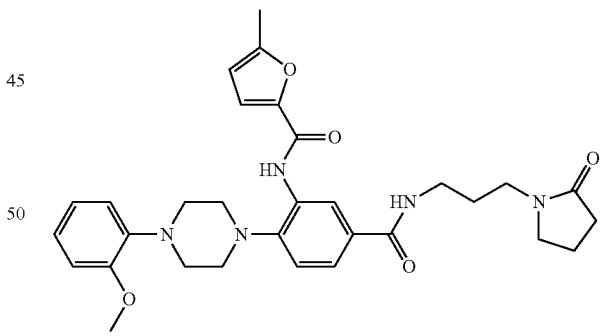

5-Methyl-furan-2-carboxylic acid {2-[4-(2-methoxy-phenyl)-piperazin-1-yl]-5-[3-(2-oxo-pyrrolidin-1-yl)-propylcarbamoyl]-phenyl}-amide (compound no. 173) was prepared from the reaction between 1-(2-methoxy-phenyl)-piperazine and 4-fluoro-3-nitro-N-[3-(2-oxo-pyrrolidin-1-yl)-propyl]-benzamide, comprising the sequence of reactions described for the synthesis of compound no. 175.

LCMS (ESI) 560 (M+H); $^1$H NMR (400 MHz, DICHLOROMETHANE-d2) δ ppm 1.76 (t, J=6.03 Hz, 2H) 1.99-2.09 (m, 2H) 2.36-2.43 (m, 5H) 3.10-3.15 (m, 4H) 3.25-3.44 (m, 10H) 3.87 (s, 3H) 6.20 (dd, J=3.37, 0.98 Hz, 1H) 6.89-7.05

(m, 4H) 7.11 (d, J=3.32 Hz, 1H) 7.33 (d, J=8.25 Hz, 1H) 7.64 (dd, J=8.25, 2.10 Hz, 2H) 8.87 (d, J=2.10 Hz, 1H) 9.46 (s, 1H).

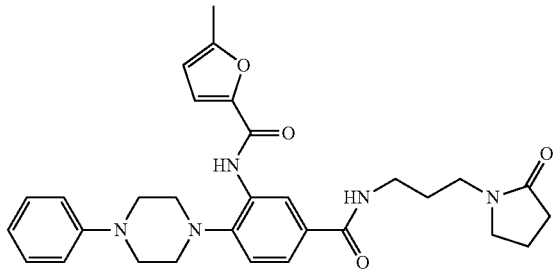

5-Methyl-furan-2-carboxylic acid [5-[3-(2-oxo-pyrrolidin-1-yl)-propylcarbamoyl]-2-(4-phenyl-piperazin-1-yl)-phenyl]-amide (compound no. 167) was prepared from the reaction between 1-phenyl-piperazine and 1-(2-fluoro-phenyl)-piperazine and 4-fluoro-3-nitro-N-[3-(2-oxo-pyrrolidin-1-yl)-propyl]-benzamide, comprising the sequence of reactions described for the synthesis of compound no. 175.

LCMS (ESI) 530 (M+H); $^1$H NMR (400 MHz, METHANOL-d4) δ ppm 1.89 (t, J=6.96 Hz, 2H) 2.05-2.14 (m, 2H) 2.39 (s, 3H) 2.40-2.45 (m, 2H) 3.15-3.20 (m, 4H) 3.38-3.48 (m, 8H) 3.54 (t, J=7.08 Hz, 2H) 6.32 (dd, J=3.42, 0.98 Hz, 1H) 6.91 (t, J=7.35 Hz, 1H) 7.08 (d, J=7.91 Hz, 2H) 7.20 (d, J=3.12 Hz, 1H) 7.27-7.33 (m, 2H) 7.41 (d, J=8.30 Hz, 1H) 7.66 (dd, J=8.30, 2.10 Hz, 1H) 8.75 (d, J=2.05 Hz, 1H).

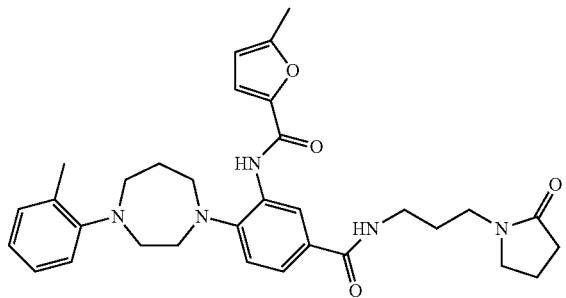 [SMILES: Cc1ccc(C(=O)Nc2cc(C(=O)NCCCN3CCCC3=O)ccc2N2CCCN(c3ccccc3C)CC2)o1]

5-Methyl-furan-2-carboxylic acid [5-[3-(2-oxo-pyrrolidin-1-yl)-propylcarbamoyl]-2-(4-o-tolyl-[1,4]diazepan-1-yl)-phenyl]-amide (compound no. 194) was prepared as follows: In a microwavable glass tube, Pd(OAc)$_2$ (33.6 mg, 0.15 mmol) and X-PHOS (71.4 mg, 0.15 mmol) were taken in a mixture of t-BuOH:toluene (1:5) (4.0 mL) and stirred. This solution was evacuated for 5 min and purged with nitrogen. [1,4]Diazepane-1-carboxylic acid tert-butyl ester (0.2 g, 1.0 mmol) and 1-bromo-2-methyl-benzene (0.255 mg, 1.5 mmol) were added to this, evacuated and nitrogen purged. This mixture was stirred at 140° C. under MW for 30 min. Reaction was cooled, concentrated on celite and purified on silica gel using CH$_2$Cl$_2$/MeOH (10%) to give the intermediate product, 4-o-tolyl-[1,4]diazepane-1-carboxylic acid tert-butyl ester (0.15 g, 51%). This was dissolved in CH$_2$Cl$_2$ (2.0 mL) and stirred with trifluroacetic acid (1.0 mL) for 16 h. The reaction was concentrated and the crude 1-o-tolyl-[1,4]diazepane was used in similar fashion described for compound no. 11.

LCMS (ESI) 558 (M+H); $^1$H NMR (400 MHz, DICHLOROMETHANE-d$_2$) δ ppm 1.67-1.81 (m, 3H) 1.96-2.17 (m, 4H) 2.30-2.41 (m, 8H) 3.22-3.44 (m, 13H) 6.19 (d, J=2.64 Hz, 1H) 6.94 (s, 1H) 7.06-7.21 (m, 4H) 7.31 (d, J=8.30 Hz, 1H) 7.51-7.65 (m, 2H) 8.87 (d, J=2.05 Hz, 1H) 9.55 (s, 1H).

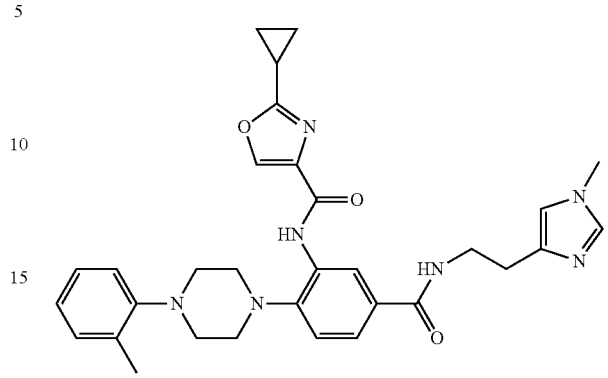

2-Cyclopropyl-oxazole-4-carboxylic acid [5-[2-(1-methyl-1H-imidazol-4-yl)-ethylcarbamoyl]-2-(4-o-tolyl-piperazin-1-yl)-phenyl]-amide was prepared from 2-(1-methyl-1H-imidazol-4-yl)-ethyl amine and 3-[(2-cyclopropyl-oxazole-4-carbonyl)-amino]-4-(4-o-tolyl-piperazin-1-yl)-benzoic acid obtained from the LiOH mediated hydrolysis of 3-[(2-cyclopropyl-oxazole-4-carbonyl)-amino]-4-(4-o-tolyl-piperazin-1-yl)-benzoic acid methyl ester followed by HATU amide coupling using the desired amine.

LCMS (ESI) 554 (M+H); $^1$H NMR (400 MHz, DICHLOROMETHANE-d$_2$) δ ppm 1.06-1.19 (m, 4H) 2.10 (s, 1H) 2.35 (s, 3H) 2.80 (t, J=6.22 Hz, 2H) 3.06-3.20 (m, 8H) 3.59-3.69 (m, 5H) 6.75 (s, 1H) 7.01 (dd, J=7.27, 1.66 Hz, 1H) 7.14-7.23 (m, 3H) 7.29 (d, J=8.25 Hz, 1H) 7.43 (s, 1H) 7.61 (dd, J=8.22, 2.12 Hz, 1H) 7.66-7.77 (m, 1H) 8.13 (s, 1H) 8.87 (d, J=2.05 Hz, 1H) 9.94 (brs, 1H).

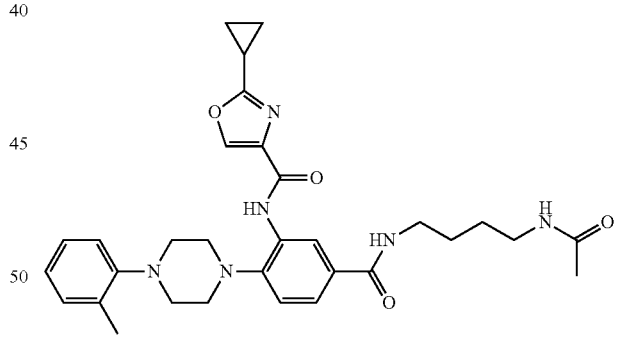

2-Cyclopropyl-oxazole-4-carboxylic acid [5-(4-acetylamino-butylcarbamoyl)-2-(4-o-tolyl-piperazin-1-yl)-phenyl]-amide was prepared from N-(4-amino-butyl)-acetamide and 3-[(2-cyclopropyl-oxazole-4-carbonyl)-amino]-4-(4-o-tolyl-piperazin-1-yl)-benzoic acid obtained from the LiOH mediated hydrolysis of 3-[(2-cyclopropyl-oxazole-4-carbonyl)-amino]-4-(4-o-tolyl-piperazin-1-yl)-benzoic acid methyl ester followed by HATU amide coupling using the desired amine.

LCMS (ESI) 559 (M+H); $^1$H NMR (400 MHz, DICHLOROMETHANE-d$_2$) δ ppm 1.07-1.18 (m, 4H) 1.53-1.70 (m, 4H) 2.00 (s, 3H) 2.05-2.15 (m, 1H) 2.37 (s, 3H) 3.09-3.24 (m, 8H) 3.30 (q, J=6.36 Hz, 2H) 3.43-3.51 (m, 2H) 6.22-6.47

(m, 1H) 6.68 (brs, 1H) 6.97-7.35 (m, 5H) 7.61 (dd, J=8.22, 2.07 Hz, 1H) 8.12 (s, 1H) 8.82 (d, J=2.05 Hz, 1H) 9.94 (s, 1H).

Example 8: Synthetic route towards 2-cyclopropyl-oxazole-4-carboxylic acid [5-[3-(2-methyl-5-oxo-pyrrolidin-1-yl)-propylcarbamoyl]-2-(4-o-tolyl-piperazin-1-yl)-phenyl]-amide

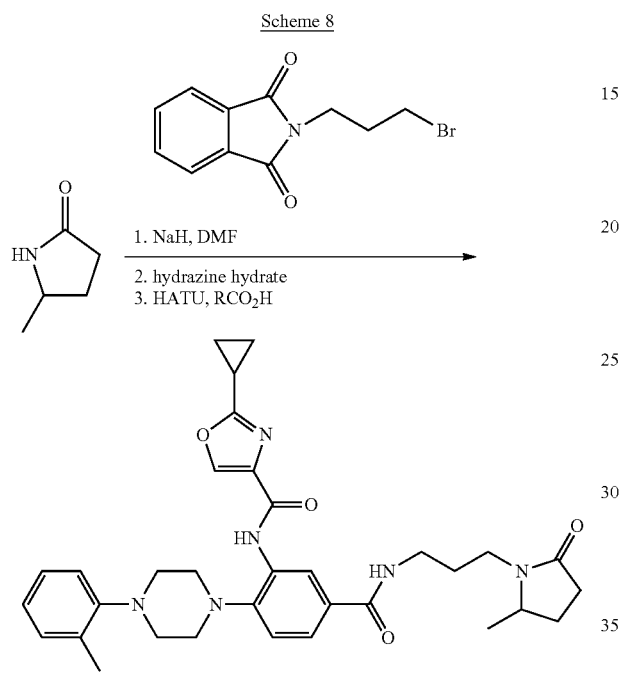

Step 1
To an ice-cold solution of NaH (0.505 g, 12.6 mmol) in DMF (20 mL) 5-methyl-pyrrolidin-2-one (1.0 g, 10.1 mmol) in DMF (10.0 mL) was added slowly. This was stirred for 30 min at 0-25° C. 2-(3-Bromo-propyl)-isoindole-1,3-dione (2.47 g, 9.0 mmol) was added and the reaction was stirred at room temperature for 16 h. A solution of saturated NH₄Cl (10.0 mL) was added and extracted with ethyl acetate. Organic layer was washed with LiCl solution and concentrated. The crude was purified on silica gel using CH$_2$Cl$_2$/MeOH (10%) as eluent to give 2-[3-(3-methyl-2-oxo-pyrrolidin-1-yl)-propyl]-isoindole-1,3-dione (1.2 g, 41%).

Step 2
2-[3-(3-Methyl-2-oxo-pyrrolidin-1-yl)-propyl]-isoindole-1,3-dione (0.5 g, 1.74 mmol) was taken in a mixture of THF/MeOH (3.0 mL/3.0 mL). Hydrazine hydrate (0.44 g, 8.7 mmol) was added to this and the reaction was stirred at 50° C. for 16 h. The precipitate was filtered and the filtrate was concentrated to give the product 1-(3-amino-propyl)-5-methyl-pyrrolidin-2-one (0.12 g, 45%).

Step 3
1-(3-Amino-propyl)-5-methyl-pyrrolidin-2-one was coupled with 3-[(2-cyclopropyl-oxazole-4-carbonyl)-amino]-4-(4-o-tolyl-piperazin-1-yl)-benzoicacid, following HATU coupling procedure.
LCMS (ESI) 585 (M+H); $^1$H NMR (400 MHz, DICHLOROMETHANE-d$_2$) δ ppm 1.06-1.17 (m, 4H) 1.25 (d, J=6.30 Hz, 3H) 1.56-1.69 (m, 1H) 1.72-1.83 (m, 2H) 2.09 (s, 1H) 2.18-2.30 (m, 1H) 2.39 (s, 3H) 2.42 (d, J=8.05 Hz, 2H) 3.11-3.29 (m, 10H) 3.49-3.63 (m, 2H) 3.73 (d, J=6.78 Hz, 1H) 7.01-7.10 (m, 1H) 7.16-7.27 (m, 3H) 7.31 (d, J=8.30 Hz, 1H) 7.64-7.78 (m, 2H) 8.15 (s, 1H) 8.87 (d, J=2.00 Hz, 1H) 9.94 (brs, 1H).

General Scheme for HATU Coupling:

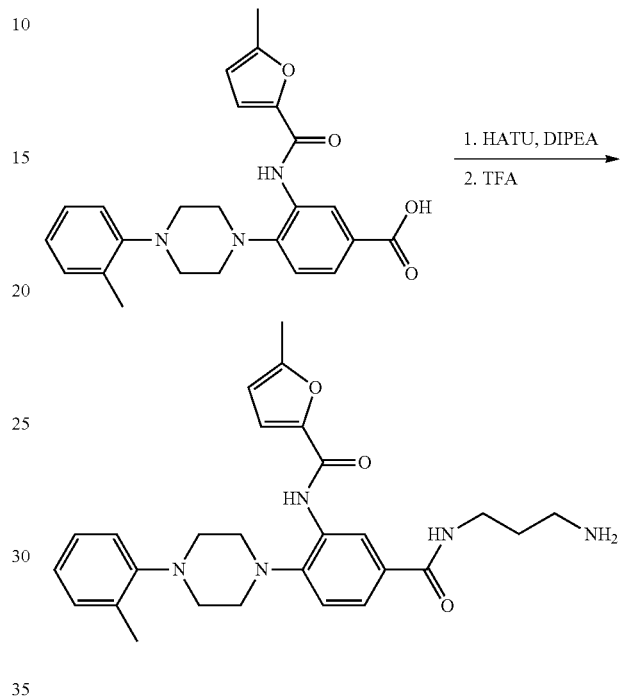

The preparation of following compounds was in line with Scheme 8:

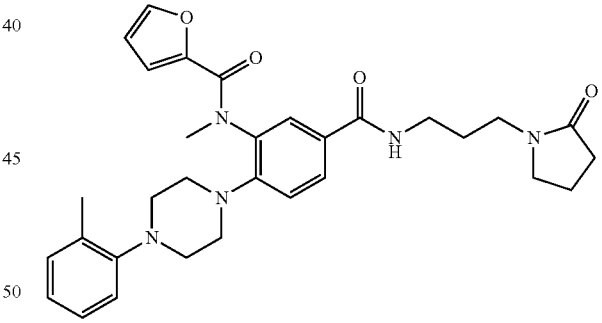

Furan-2-carboxylic acid methyl-[5-[3-(2-oxo-pyrrolidin-1-yl)-propylcarbamoyl]-2-(4-o-tolyl-piperazin-1-yl)-phenyl]-amide (compound no. 169) was prepared comprising the same procedure as compound no. 258 from 3-[(furan-2-carbonyl)-methyl-amino]-4-(4-o-tolyl-piperazin-1-yl) benzoic acid.
LCMS (ESI) 544 (M+H); $^1$H NMR (400 MHz, METHANOL-d4) δ ppm 1.84 (t, J=6.81 Hz, 2H) 2.08 (d, J=7.52 Hz, 2H) 2.41 (t, J=8.10 Hz, 2H) 2.79-2.98 (m, 4H) 3.06-3.18 (m, 2H) 3.37 (q, J=7.08 Hz, 4H) 3.49 (t, J=7.08 Hz, 4H) 6.03-6.18 (m, 1H) 6.24-6.34 (m, 1H) 6.94 (d, J=0.78 Hz, 1H) 7.04 (d, J=0.73 Hz, 1H) 7.15 (t, J=7.88 Hz, 3H) 7.42 (s, 1H) 7.77 (d, J=2.20 Hz, 1H) 7.84 (dd, J=8.44, 2.20 Hz, 1H).

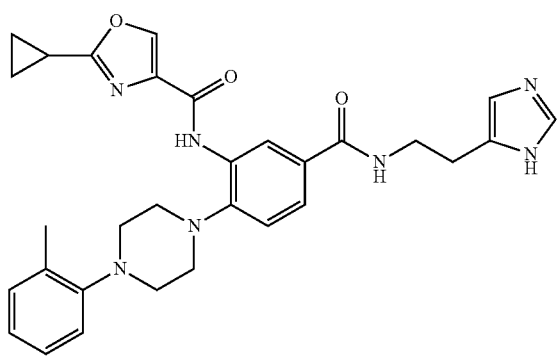 [SMILES: Cc1ccccc1N1CCN(c2ccc(C(=O)NCCc3cnc[nH]3)cc2NC(=O)c2coc(C3CC3)n2)CC1]

2-Cyclopropyl-oxazole-4-carboxylic acid [5-[2-(3H-imidazol-4-yl)-ethylcarbamoyl]-2-(4-o-tolyl-piperazin-1-yl)-phenyl]-amide was prepared comprising the same procedure as compound no. 258 from 3-[(furan-2-carbonyl)-methyl-amino]-4-(4-o-tolyl-piperazin-1-yl) benzoic acid.

LCMS (ESI) 540 (M+H); $^1$H NMR (400 MHz, DMSO-d6) δ ppm 1.06 (s, 2H) 1.14 (s, 2H) 2.20 (s, 1H) 2.32 (s, 3H) 2.84 (s, 2H) 3.05 (brs, 4H) 3.08-3.21 (m, 4H) 3.51 (s, 2H) 7.01 (s, 1H) 7.16 (s, 2H) 7.18-7.29 (m, 2H) 7.42 (s, 1H) 7.56 (s, 1H) 8.29 (s, 1H) 8.54 (s, 1H) 8.67 (s, 1H) 8.79 (s, 1H) 9.92 (s, 1H)

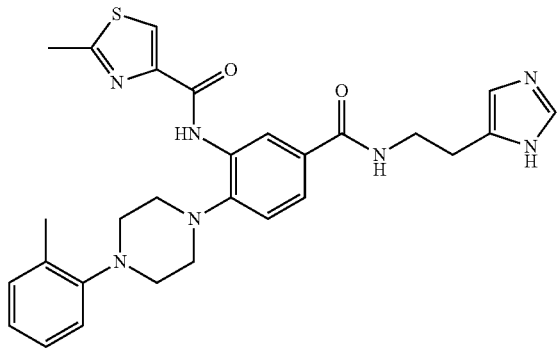 [SMILES: Cc1nc(C(=O)Nc2cc(C(=O)NCCc3cnc[nH]3)ccc2N2CCN(c3ccccc3C)CC2)cs1]

2-Methyl-thiazole-4-carboxylic acid [5-[2-(3H-imidazol-4-yl)-ethylcarbamoyl]-2-(4-o-tolyl-piperazin-1-yl)-phenyl]-amide was prepared comprising the same procedure as compound no. 258 from 3-[(furan-2-carbonyl)-methyl-amino]-4-(4-o-tolyl-piperazin-1-yl) benzoic acid.

LCMS (ESI) 530 (M+H); $^1$H NMR (400 MHz, DMSO-d6) δ ppm 2.31 (s, 3H) 2.77 (s, 3H) 2.80-2.90 (m, 2H) 3.08 (brs, 4H) 3.11-3.23 (m, 4H) 3.47-3.61 (m, 2H) 6.93-7.07 (m, 1H) 7.12 (s, 2H) 7.18-7.27 (m, 2H) 7.36-7.48 (m, 1H) 7.53-7.64 (m, 1H) 8.15-8.24 (m, 1H) 8.33 (s, 1H) 8.47-8.60 (m, 1H) 8.84 (d, J=2.00 Hz, 1H) 10.37-10.48 (m, 1H).

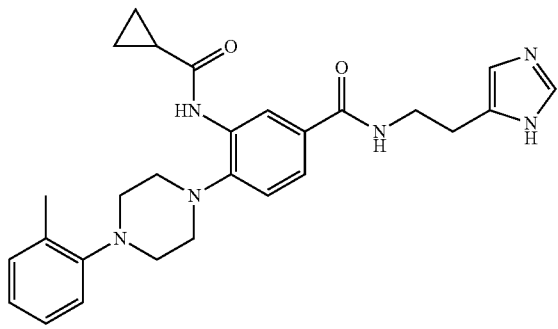 [SMILES: Cc1ccccc1N1CCN(c2ccc(C(=O)NCCc3cnc[nH]3)cc2NC(=O)C2CC2)CC1]

3-(Cyclopropanecarbonyl-amino)-N-[2-(3H-imidazol-4-yl)-ethyl]-4-(4-o-tolyl-piperazin-1-yl)-benzamide was prepared comprising the same procedure as compound no. 258 from 3-[(furan-2-carbonyl)-methyl-amino]-4-(4-o-tolyl-piperazin-1-yl) benzoic acid.

LCMS (ESI) 473 (M+H); $^1$H NMR (400 MHz, DMSO-d6) δ ppm 0.70-0.88 (m, 4H) 1.96-2.12 (m, 1H) 2.30 (s, 3H) 2.69-2.80 (m, 2H) 3.07 (d, J=7.42 Hz, 8H) 3.37-3.56 (m, 2H) 6.94-7.02 (m, 1H) 7.07-7.14 (m, 1H) 7.15-7.21 (m, 2H) 7.21-7.27 (m, 1H) 7.49-7.56 (m, 1H) 7.55-7.64 (m, 1H) 8.20-8.32 (m, 1H) 8.38-8.52 (m, 1H) 9.17-9.29 (m, 1H).

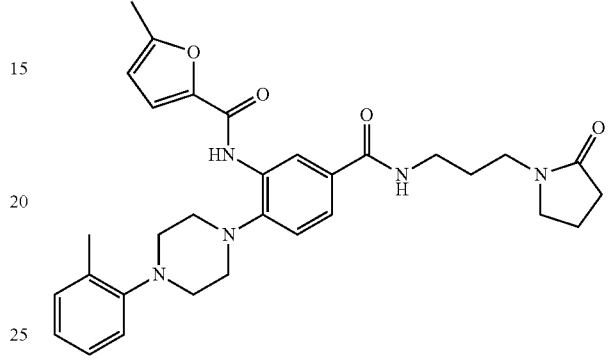

3-[(5-Methyl-furan-2-carbonyl)-amino]-4-(4-m-tolyl-piperazin-1-yl)-benzoic acid 3-(2-oxo-pyrrolidin-1-yl)-propyl ester (compound no. 243) was prepared comprising the same procedure as the aniline intermediate according to compound no 40.

LCMS (ESI) 544 (M+H); $^1$H NMR (400 MHz, CHLOROFORM-d) δ ppm 1.82 (s, 2H) 2.08 (d, J=7.56 Hz, 2H) 2.36 (d, J=1.90 Hz, 6H) 2.45 (t, J=8.10 Hz, 2H) 3.05-3.18 (m, 4H) 3.30-3.48 (m, 10H) 6.17 (dd, J=3.34, 0.95 Hz, 1H) 6.84 (brs, 2H) 7.11-7.30 (m, 4H) 7.45-7.59 (m, 1H) 7.71 (d, J=2.10 Hz, 1H) 8.96 (d, J=2.05 Hz, 1H) 9.38 (s, 1H).

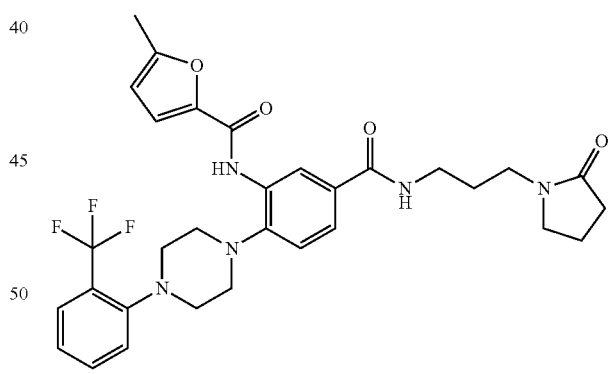

3-[(5-Methyl-furan-2-carbonyl)-amino]-4-[4-(2-trifluoromethyl-phenyl)-piperazin-1-yl]-benzoic acid 3-(2-oxo-pyrrolidin-1-yl)-propyl ester (compound no. 246) was prepared comprising the same procedure as the aniline intermediate according to compound no. 40.

LCMS (ESI) 598 (M+H); $^1$H NMR (400 MHz, CHLOROFORM-d) δ ppm 1.82 (t, J=6.25 Hz, 2H) 1.98-2.15 (m, 2H) 2.35-2.52 (m, 5H) 3.04-3.14 (m, 4H) 3.15-3.25 (m, 4H) 3.28-3.51 (m, 6H) 6.21 (dd, J=3.37, 0.88 Hz, 1H) 7.17 (d, J=3.37 Hz, 1H) 7.28-7.34 (m, 2H) 7.44 (d, J=7.96 Hz, 2H) 7.58 (s, 1H) 7.64-7.78 (m, 2H) 8.96 (d, J=2.05 Hz, 1H) 9.46 (s, 1H) $^{19}$F NMR (376 MHz, CHLOROFORM-d) δ ppm −60.77 (s, 3 F).

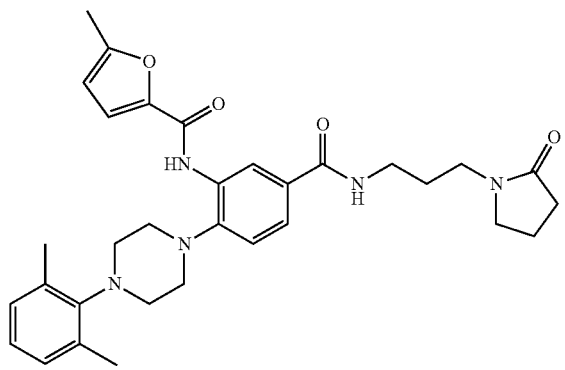 [SMILES: Cc1ccc(C(=O)Nc2cc(C(=O)NCCCN3CCCC3=O)ccc2N2CCN(c3c(C)cccc3C)CC2)o1]

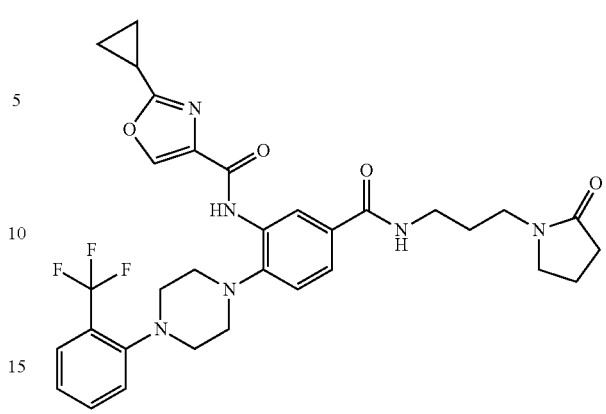

4-[4-(2,6-Dimethyl-phenyl)-piperazin-1-yl]-3-[(5-methyl-furan-2-carbonyl)-amino]-benzoic acid 3-(2-oxo-pyrrolidin-1-yl)-propyl ester was prepared comprising the same procedure as the aniline intermediate according to compound no. 40.

LCMS (ESI) 558 (M+H); $^1$H NMR (400 MHz, CHLOROFORM-d) δ ppm 1.81-1.88 (m, 2H) 2.07 (quin, J=7.58 Hz, 2H) 2.33-2.51 (m, 12H) 3.05 (t, J=4.54 Hz, 4H) 3.36 (brs, 4H) 3.40-3.53 (m, 6H) 6.20 (dd, J=3.37, 0.93 Hz, 1H) 6.94-7.09 (m, 2H) 7.18 (d, J=3.37 Hz, 1H) 7.31 (d, J=8.30 Hz, 1H) 7.53 (t, J=6.10 Hz, 1H) 7.73 (dd, J=8.25, 2.10 Hz, 1H) 8.99 (d, J=2.05 Hz, 1H) 9.48 (s, 1H).

3-[(2-Cyclopropyl-oxazole-4-carbonyl)-amino]-4-[4-(2-trifluoromethyl-phenyl)-piperazin-1-yl]-benzoic acid-3-(2-oxo-pyrrolidin-1-yl)-propyl ester (compound no. 250) was prepared comprising the same procedure as the aniline intermediate according to compound no. 40 (HATU coupling of 2-cyclopropyl-1,3-oxazole-4-carboxylic acid replacing the acid chloride).

LCMS (ESI) 625 (M+H); $^1$H NMR (400 MHz, CHLOROFORM-d) δ ppm 1.05-1.29 (m, 4H) 1.82 (s, 2H) 2.07 (s, 3H) 2.38-2.52 (m, 2H) 3.02-3.12 (m, 4H) 3.21 (d, J=3.95 Hz, 4H) 3.43 (t, J=6.20 Hz, 6H) 7.29 (d, J=8.35 Hz, 2H) 7.54 (s, 3H) 7.64-7.78 (m, 2H) 8.15 (s, 1H) 8.99 (d, J=2.00 Hz, 1H) 9.85-9.97 (m, 1H) $^{19}$F NMR (376 MHz, CHLOROFORM-d) δ ppm −60.76 (s, 3 F).

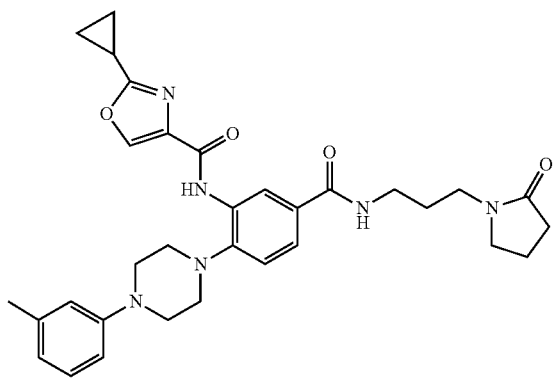 [SMILES: Cc1cccc(N2CCN(c3ccc(C(=O)NCCCN4CCCC4=O)cc3NC(=O)c3coc(C4CC4)n3)CC2)c1]

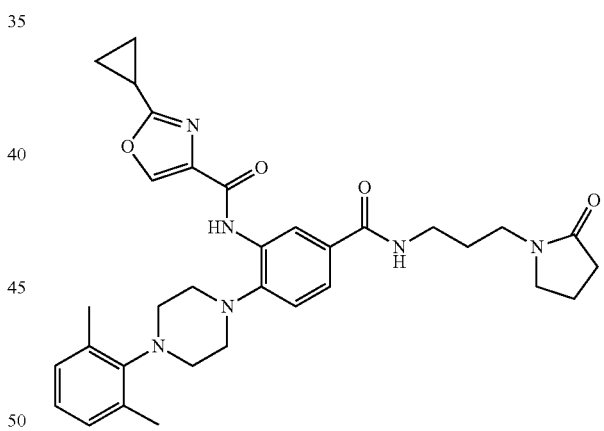

3-[(2-Cyclopropyl-oxazole-4-carbonyl)-amino]-4-(4-m-tolyl-piperazin-1-yl)-benzoic acid 3-(2-oxo-pyrrolidin-1-yl)-propyl ester (compound no. 249) was prepared comprising the same procedure as the aniline intermediate according to compound no. 40 (HATU coupling of 2-cyclopropyl-1,3-oxazole-4-carboxylic acid replacing the acid chloride).

LCMS (ESI) 571 (M+H); $^1$H NMR (400 MHz, CHLOROFORM-d) δ ppm 0.94-1.14 (m, 4H) 1.81 (quin, J=6.21 Hz, 2H) 1.95-2.15 (m, 3H) 2.36 (s, 3H) 2.45 (t, J=8.10 Hz, 2H) 2.96-3.20 (m, 4H) 3.27-3.53 (m, 10H) 6.75 (d, J=7.32 Hz, 1H) 6.80-6.92 (m, 2H) 7.11-7.26 (m, 2H) 7.61 (t, J=6.05 Hz, 1H) 7.73 (dd, J=8.25, 2.00 Hz, 1H) 8.13 (s, 1H) 8.97 (d, J=1.95 Hz, 1H) 9.88 (s, 1H).

3-[(2-Cyclopropyl-oxazole-4-carbonyl)-amino]-4-[4-(2,6-dimethyl-phenyl)-piperazin-1-yl]-benzoic acid 3-(2-oxo-pyrrolidin-1-yl)-propyl ester was prepared comprising the same procedure as the aniline intermediate according to compound no. 40 (HATU coupling of 2-cyclopropyl-1,3-oxazole-4-carboxylic acid replacing the acid chloride).

LCMS (ESI) 585 (M+H); $^1$H NMR (400 MHz, CHLOROFORM-d) δ ppm 1.02-1.24 (m, 4H) 1.74-1.88 (m, 2H) 2.07 (s, 3H) 2.31-2.52 (m, 8H) 3.04 (t, J=4.54 Hz, 4H) 3.29-3.51 (m, 10H) 6.93-7.10 (m, 3H) 7.30 (s, 1H) 7.48-7.59 (m, 1H) 7.68-7.80 (m, 1H) 8.14 (s, 1H) 9.01 (d, J=2.10 Hz, 1H) 9.82-9.94 (m, 1H).

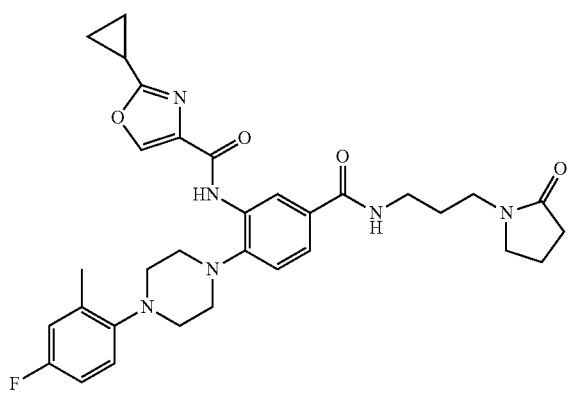 [SMILES: Cc1cc(F)ccc1N1CCN(c2ccc(C(=O)NCCCN3CCCC3=O)cc2NC(=O)c2coc(C3CC3)n2)CC1]

3-[(2-Cyclopropyl-oxazole-4-carbonyl)-amino]-4-[4-(4-fluoro-2-methyl-phenyl)-piperazin-1-yl]-benzoic acid-3-(2-oxo-pyrrolidin-1-yl)-propyl ester was prepared comprising the same procedure as the aniline intermediate according to compound no. 40 (HATU coupling of 2-cyclopropyl-1,3-oxazole-4-carboxylic acid replacing the acid chloride).

LCMS (ESI) 589 (M+H); $^1$H NMR (400 MHz, CHLOROFORM-d) δ ppm 1.00-1.23 (m, 4H) 1.81 (quin, J=6.22 Hz, 2H) 1.96-2.17 (m, 3H) 2.36 (s, 3H) 2.40-2.49 (m, 2H) 2.95-3.20 (m, 8H) 3.31-3.49 (m, 6H) 6.80-6.99 (m, 2H) 7.12 (dd, J=8.71, 5.30 Hz, 1H) 7.28 (s, 1H) 7.64 (t, J=6.05 Hz, 1H) 7.73 (dd, J=8.27, 2.07 Hz, 1H) 8.13 (s, 1H) 8.97 (d, J=2.05 Hz, 1H) 9.94 (s, 1H) $^{19}$F NMR (376 MHz, CHLOROFORM-d) δ ppm −120.69 (td, J=8.74, 5.28 Hz, 1 F).

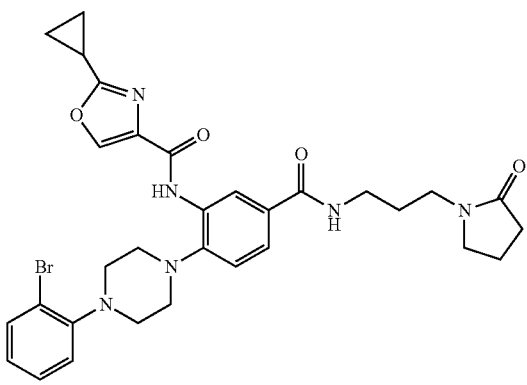 [SMILES: O=C(NCCCN1CCCC1=O)c1ccc(N2CCN(c3ccccc3Br)CC2)c(NC(=O)c2coc(C3CC3)n2)c1]

4-[4-(2-Bromo-phenyl)-piperazin-1-yl]-3-[(2-cyclopropyl-oxazole-4-carbonyl)-amino]-benzoic acid 3-(2-oxo-pyrrolidin-1-yl)-propyl ester was prepared comprising the same procedure as the aniline intermediate according to compound no. 40 (HATU coupling of 2-cyclopropyl-1,3-oxazole-4-carboxylic acid replacing the acid chloride).

LCMS (ESI) 635 (M+H); $^1$H NMR (400 MHz, CHLOROFORM-d) δ ppm 1.00-1.23 (m, 4H) 1.81 (quin, J=6.22 Hz, 2H) 1.92-2.15 (m, 3H) 2.45 (t, J=8.10 Hz, 2H) 3.14 (t, J=4.42 Hz, 4H) 3.32 (brs, 4H) 3.38-3.47 (m, 6H) 6.97 (td, J=7.61, 1.46 Hz, 1H) 7.19 (dd, J=8.00, 1.32 Hz, 1H) 7.28-7.38 (m, 2H) 7.55-7.65 (m, 2H) 7.74 (dd, J=8.27, 2.07 Hz, 1H) 8.13 (s, 1H) 8.97 (d, J=1.95 Hz, 1H) 9.95 (s, 1H).

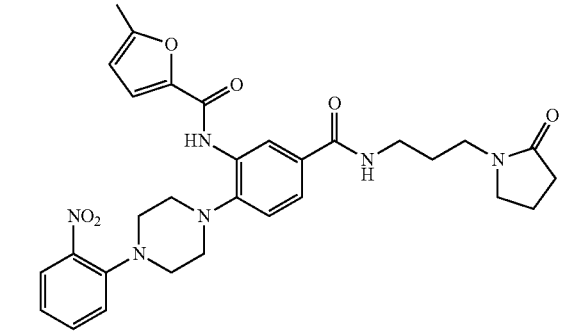 [SMILES: Cc1ccc(C(=O)Nc2cc(C(=O)NCCCN3CCCC3=O)ccc2N2CCN(c3ccccc3[N+](=O)[O-])CC2)o1]

3-[(5-Methyl-furan-2-carbonyl)-amino]-4-[4-(2-nitro-phenyl)-piperazin-1-yl]-benzoic acid 3-(2-oxo-pyrrolidin-1-yl)-propyl ester was prepared comprising the same procedure from the piperazine intermediate according to furan-2-carboxylic acid {2-[4-(2-methyl-benzyl)-piperazin-1-yl]-5-[3-(2-oxo-pyrrolidin-1-yl)-propylcarbamoyl]-phenyl}-amide.

LCMS (ESI) 575 (M+H) $^1$H NMR (400 MHz, CHLOROFORM-d) δ ppm 1.81 (quin, J=6.25 Hz, 2H) 2.03-2.13 (m, 3H) 2.29-2.49 (m, 5H) 3.05-3.17 (m, 4H) 3.25-3.36 (m, 4H) 3.37-3.49 (m, 5H) 6.11-6.25 (m, 1H) 7.05-7.28 (m, 4H) 7.46-7.60 (m, 2H) 7.71 (dd, J=8.25, 2.00 Hz, 1H) 7.81 (dd, J=8.13, 1.29 Hz, 1H) 8.95 (d, J=1.95 Hz, 1H) 9.39 (s, 1H).

Example 9: Synthetic route towards thiophene-3-carboxylic acid [5-[3-(2-oxo-pyrrolidin-1-yl)-propylcarbamoyl]-2-(4-o-tolyl-piperazin-1-yl)-phenyl]-amide

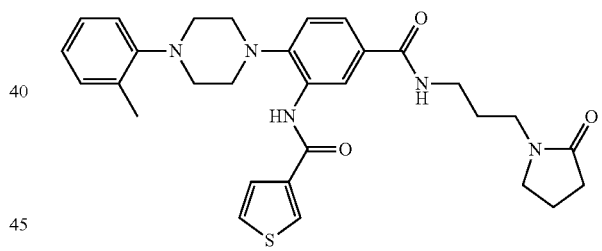

To a suspension of 3-amino-N-[3-(2-oxo-pyrrolidin-1-yl)-propyl]-4-(4-o-tolyl-piperazin-1-yl)-benzamide (0.1 g, 0.229 mmol) in methylene dichloride (5 ml), triethylamine (0.069 g, 0.489 mmol), thiophene-3-carboxylic acid (0.044 g, 0.344 mmol) and 1-propane phosphonic cyclic anhydride (0.21 g, 0.489 mmol) were added. The reaction mixture was stirred for 16 h at room temperature. The reaction mixture was concentrated and extracted with dichloromethane (10 ml×1). The organic layer was washed with water (10 ml×2) and dried over anhydrous sodium sulphate. The organic layer was concentrated and the crude product obtained was purified by flash chromatography using silica gel column to get (0.34 g, 34%) of the titled compound as a brown solid.

LCMS: Mass found (M+546.3).
Method: A—0.1% TFA in water, B—0.1% TFA in ACN: Flow—2 ml/min.
Column: XBridge C8 (50×4.6 mm, 3.5 µm), +ve mode.
Rt (min): 4.17 Area %:—97.91 (Max), 98.87 (254 nm).
$^1$H NMR (400 MHz, CDCl$_3$) δ 9.4 (s, 1H), 8.9 (s, 1H), 8.10 (s, 1H), 7.77 (dd, J=1.52, 6.68 Hz, 1H), 7.69 (s, 1H), 7.57 (d, J=4.2 Hz, 1H), 7.44 (dd, J=3.0, 8.04 Hz, 1H), 7.37 (d, J=8.28 Hz, 1H), 7.25 (t, J=5.36 Hz, 2H), 7.22-7.13 (m, 1H), 7.07-7.03 (m, 1H), 3.45-3.40 (m, 6H), 3.16 (m, 8H), 2.47 ((t, J=7.92 Hz, 2H), 2.36 (s, 3H), 2.11-2.03 (m, 2H), 1.83 (t, J=6.08 Hz, 2H).

The following compounds were prepared in a similar manner unless described otherwise. LCMS and HPLC analysis were performed as follows: Method: A—0.1% TFA in water, B—0.1% TFA in ACN: Flow—2 ml/min; Column: XBridge C8 (50×4.6 mm, 3.5 μm), +ve mode.

2-Bromo-thiazole-5-carboxylic acid [5-[3-(2-oxo-pyrrolidin-1-yl)-propylcarbamoyl]-2-(4-o-tolyl-piperazin-1-yl)-phenyl]-amide

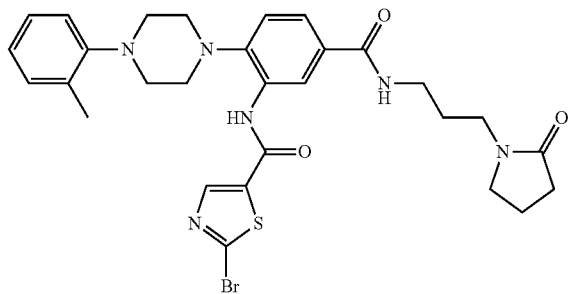 [SMILES: Cc1ccccc1N1CCN(c2ccc(C(=O)NCCCN3CCCC3=O)cc2NC(=O)c2cnc(Br)s2)CC1]

Yield: 25.1%.
Color and appearance: White solid.
LCMS: Mass found (M+625.0).
Rt (min): 4.26 Area %:—95.75 (Max), 95.35 (254 nm).
¹H NMR (400 MHz, CDCl₃) δ 9.38 (s, 1H), 8.83 (s, 1H), 8.17 (s, 1H), 7.81 (d, J=8.08 Hz, 1H) 7.74 (s, 1H), 7.41 (d, J=8.36 Hz, 1H), 7.24 (d, J=7.32 Hz, 2H), 7.16 (d, J=7.68 Hz, 1H), 7.09 (t, J=7.28 Hz, 1H), 3.45-3.40 (m, 6H), 3.21 (m, 8H), 2.49 (t, J=7.88 Hz, 2H), 2.38 (s, 3H), 2.10 (t, J=7.64 Hz, 2H), 1.82 (t, J=5.4 Hz, 2H).

3-(3-Methyl-butyrylamino)-N-[3-(2-oxo-pyrrolidin-1-yl)-propyl]-4-(4-o-tolyl-piperazin-1-yl)-benzamide

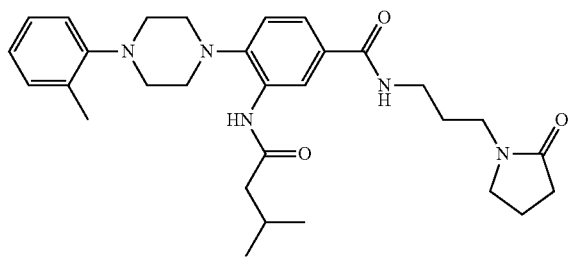 [SMILES: Cc1ccccc1N1CCN(c2ccc(C(=O)NCCCN3CCCC3=O)cc2NC(=O)CC(C)C)CC1]

Yield: 23.4%.
Color and appearance: White solid.
LCMS: Mass found (M+520.3).
Rt (min): 4.26 Area %:—97.85 (Max), 98.03 (254 nm).
¹H NMR (400 MHz, CDCl₃) δ 8.75 (s, 2H), 7.74 (d, J=8.16 Hz, 1H), 7.58 (s, 1H), 7.34 (d, J=8.16 Hz, 1H) 7.25 (t, J=7.32 Hz, 2H), 7.16 (d, J=7.84 Hz, 1H), 7.09 (t, J=7.64 Hz, 1H), 3.44-3.38 (m, 6H), 3.21 (m, 8H), 2.46 (t, J=7.92 Hz, 2H), 2.38 (s, 3H), 2.35 (t, J=6.8 Hz, 2H), 2.28-2.25 (m, 1H), 2.11-2.02 (m, 2H), 1.83-1.79 (m, 2H), 1.11 (d, 6H).

3-Benzoylamino-N-[3-(2-oxo-pyrrolidin-1-yl)-propyl]-4-(4-o-tolyl-piperazin-1-yl)-benzamide

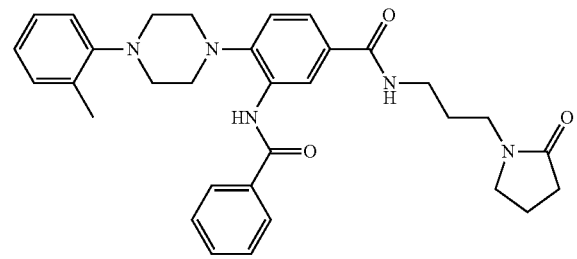

Yield: 53.4%.
Color and appearance: White solid.
LCMS: Mass found (M+540.3).
Rt (min): 4.35 Area %:—95.75 (Max), 98.12 (254 nm).
¹H NMR (400 MHz, CDCL₃) δ 9.38 (s, 1H), 9.04 (s, 1H), 7.98 (dd, J=1.12, 7.84 Hz, 2H), 7.76 (dd, J=2.04, 8.24 Hz, 1H) 7.58-7.51 (m, 4H), 7.36 (d, J=8.28 Hz, 1H), 7.24 (t, J=7.44 Hz, 2H), 7.09-7.02 (m, 2H), 3.45-3.41 (m, 6H), 3.12 (m, 8H), 2.47 (t, J=7.92 Hz, 2H), 2.36 (s, 3H), 2.09 (m, 2H), 1.84 (t, J=6.24 Hz, 2H).

3-(3-Chloro-benzoylamino)-N-[3-(2-oxo-pyrrolidin-1-yl)-propyl]-4-(4-o-tolyl-piperazin-1-yl)-benzamide

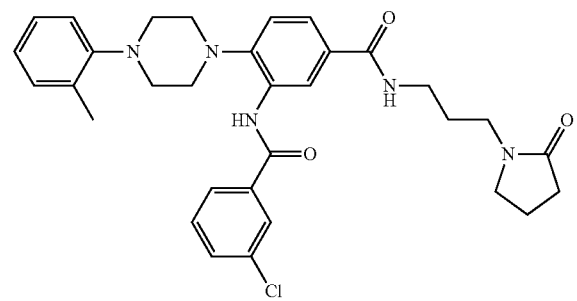

Yield: 34.1%.
Color and appearance: White solid.
LCMS: Mass found (M+574.3).
Rt (min): 4.72 Area %:—96.54 (Max), 97.81 (254 nm).
¹H NMR (400 MHz, CDCL₃) δ 9.46 (s, 1H), 9.00 (s, 1H), 8.00 (s, 1H), 7.86 (d, J=7.52 Hz, 1H) 7.77 (d, J=8.12 Hz, 1H), 7.61 (m, 1H), 7.56 (d, J=7.88 Hz, 1H), 7.49 (t, J=7.8 Hz, 1H), 7.38 (d, J=8.24 Hz, 1H), 7.24 (t, J=7.0 Hz, 2H), 7.13 (d, J=8.12 Hz, 1H), 7.07 (t, J=7.36 Hz, 1H), 3.45-3.43 (m, 6H), 3.15 (m, 8H), 2.48-2.44 (m, 2H), 2.37 (s, 3H), 2.12-2.04 (m, 2H), 1.85-1.79 (m, 2H).

445

3-(4-Chloro-benzoylamino)-N-[3-(2-oxo-pyrrolidin-1-yl)-propyl]-4-(4-o-tolyl-piperazin-1-yl)-benzamide

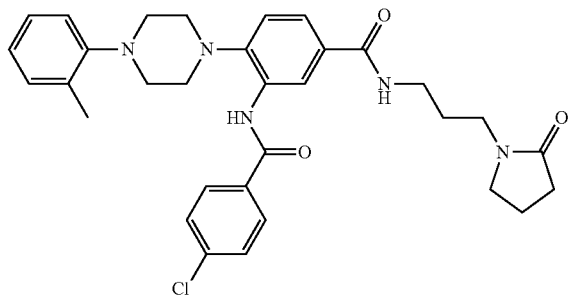

Yield: 44.7%.

Color and appearance: White solid.

LCMS: Mass found (M+574.3).

Rt (min): 4.75 Area %:—98.33 (Max), 98.98 (254 nm).

$^1$H NMR (400 MHz, CDCL$_3$) δ 9.61 (s, 1H), 8.90 (s, 1H), 7.98 (d, J=7.04 Hz, 2H), 7.81 (d, J=7.72 Hz, 1H) 7.73 (s, 1H), 7.52 (d, J=8.28 Hz, 2H), 7.41 (d, J=8.16 Hz, 1H), 7.23 (d, J=5.16 Hz, 2H), 7.13 (d, J=8.12 Hz, 1H), 7.08 (t, J=7.32 Hz, 1H), 3.45-3.41 (m, 6H), 3.22 (m, 8H), 2.48 (t, J=8.00 Hz, 2H), 2.37 (s, 3H), 2.12-2.04 (m, 2H), 1.85-1.79 (m, 2H).

3-(3-Fluoro-benzoylamino)-N-[3-(2-oxo-pyrrolidin-1-yl)-propyl]-4-(4-o-tolyl-piperazin-1-yl)-benzamide

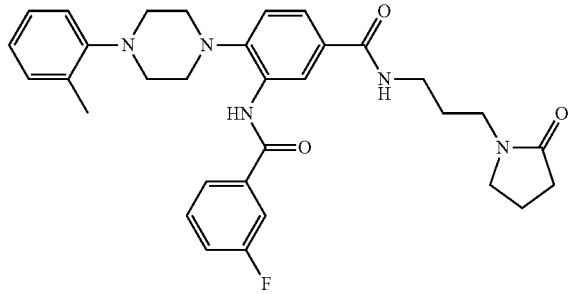 [SMILES: Cc1ccccc1N1CCN(c2ccc(C(=O)NCCCN3CCCC3=O)cc2NC(=O)c2cccc(Cl)c2)CC1]

Yield: 23.5%.

Color and appearance: Brown solid.

LCMS: Mass found (M+558.3).

Rt (min): 4.46 Area %:—95.23 (Max), 97.78 (254 nm).

$^1$H NMR (400 MHz, CDCL$_3$) δ 9.5 (s, 1H), 8.97 (s, 1H), 7.79-7.68 (m, 4H), 7.54-7.48 (m, 1H) 7.39 (d, J=8.28 Hz, 1H), 7.30 (d, J=1.84 Hz, 1H), 7.25 (t, J=4.36 Hz, 2H), 7.13 (d, J=7.84 Hz, 1H), 7.08 (t, J=7.48 Hz, 1H), 3.46-3.41 (m, 6H), 3.17 (m, 8H), 2.48 (t, J=7.92 Hz, 2H), 2.37 (s, 3H), 2.12-2.05 (m, 2H), 1.84 (t, J=6.2 Hz, 2H).

446

3-(4-Fluoro-benzoylamino)-N-[3-(2-oxo-pyrrolidin-1-yl)-propyl]-4-(4-o-tolyl-piperazin-1-yl)-benzamide

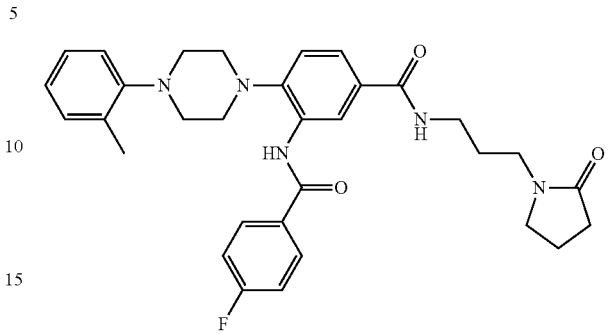

Yield: 39.1%.

Color and appearance: White solid.

LCMS: Mass found (M+558.3).

Rt (min): 4.45 Area %:—94.80 (Max), 96.67 (254 nm).

$^1$H NMR (400 MHz, CDCl$_3$) δ 9.31 (s, 1H), 9.01 (d, J=2.0 Hz, 1H), 7.99-7.96 (m, 2H), 7.76 (dd, J=2.08, 8.28 Hz, 1H) 7.63 (t, J=6.04 Hz, 1H), 7.36 (d, J=8.28 Hz, 1H), 7.23-7.21 (m, 4H), 7.09-7.03 (m, 2H), 3.45-3.41 (m, 6H), 3.3.11 (m, 8H), 2.48 (t, J=7.92 Hz, 2H), 2.36 (s, 3H), 2.11-2.06 (m, 2H), 1.85-1.80 (m, 2H).

3-(3-Cyano-benzoylamino)-N-[3-(2-oxo-pyrrolidin-1-yl)-propyl]-4-(4-o-tolyl-piperazin-1-yl)-benzamide

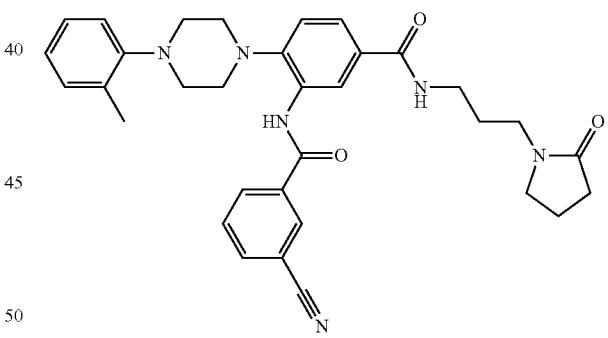

Yield: 23.8%.

Color and appearance: Brown solid.

LCMS: Mass found (M+565.3).

Rt (min): 4.16 Area %:—97.43 (Max), 98.93 (254 nm).

$^1$H NMR (400 MHz, CDCL$_3$) δ 9.49 (s, 1H), 8.97 (s, 1H), 8.32 (s, 1H), 8.21 (s, 1H) 7.87 (d, J=7.68 Hz, 1H), 7.81 (s, 1H), 7.69 (t, J=7.8 Hz, 1H), 7.41 (d, J=8.32 Hz, 1H), 7.26-7.21 (m, 3H), 7.14 (d, J=8.00 Hz, 1H), 7.07 (t, J=7.24 Hz, 1H), 3.46-3.42 (m, 6H), 3.17 (m, 8H), 2.49 (t, J=7.92 Hz, 2H), 2.36 (s, 3H), 2.13-2.07 (m, 2H), 1.83 (t, J=5.68 Hz, 2H).

447

3-(4-Cyano-benzoylamino)-N-[3-(2-oxo-pyrrolidin-1-yl)-propyl]-4-(4-o-tolyl-piperazin-1-yl)-benzamide

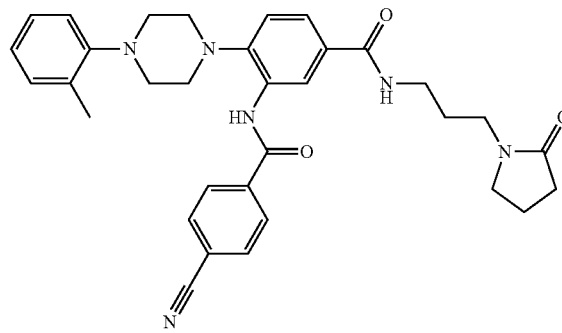

Yield: 39.2%.

Color and appearance: White solid.

LCMS: Mass found (M+565.3).

Rt (min): 4.20 Area %:—96.63 (Max), 96.91 (254 nm).

$^1$H NMR (400 MHz, CDCL$_3$) δ 9.61 (s, 1H), 8.95 (s, 1H), 8.12 (d, J=6.8 Hz, 2H), 7.85-7.81 (m, 4H) 7.42 (d, J=8.2 Hz, 1H), 7.25 (d, J=5.04 Hz, 2H), 7.10 (m, 2H), 3.46-3.41 (m, 6H), 3.18 (m, 8H), 2.49 (t, J=7.96 Hz, 2H), 2.36 (s, 3H), 2.11-2.07 (m, 2H), 1.83 (t, J=5.36 Hz, 2H).

3-(3-Methyl-benzoylamino)-N-[3-(2-oxo-pyrrolidin-1-yl)-propyl]-4-(4-o-tolyl-piperazin-1-yl)-benzamide

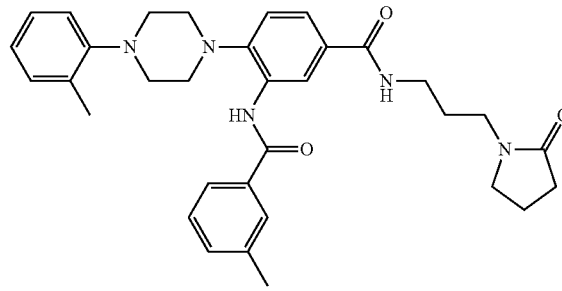

Yield: 53.7%.

Color and appearance: White solid.

LCMS: Mass found (M+554.3).

Rt (min): 4.66 Area %:—95.87 (Max), 97.22 (254 nm).

$^1$H NMR (400 MHz, CDCL$_3$) δ 9.40 (s, 1H), 9.03 (s, 1H), 7.82 (s, 1H), 7.75 (d, J=6.6 Hz, 2H) 7.58 (t, J=5.8 Hz, 1H), 7.43-7.34 (m, 3H), 7.24 (t, J=7.36 Hz, 2H), 7.09-7.02 (m, 2H), 3.45-3.42 (m, 6H), 3.12 (m, 8H), 2.47-2.41 (m, 5H), 2.2.36 (s, 3H), 2.11-2.03 (m, 2H), 1.86-1.80 (m, 2H).

448

3-(4-Methyl-benzoylamino)-N-[3-(2-oxo-pyrrolidin-1-yl)-propyl]-4-(4-o-tolyl-piperazin-1-yl)-benzamide

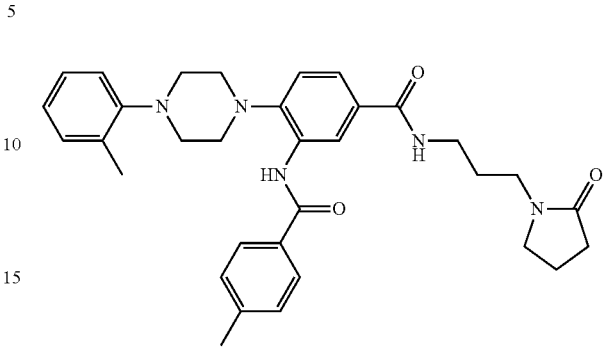

Yield: 39.5%.

Color and appearance: Brown solid.

LCMS: Mass found (M+554.3).

Rt (min): 4.67 Area %:—97.74 (Max), 98.64 (254 nm).

$^1$H NMR (400 MHz, CDCL$_3$) δ 9.38 (s, 1H), 8.99 (s, 1H), 7.89 (d, J=8.08 Hz, 2H), 7.76 (dd, J=1.92, 8.24 Hz, 1H) 7.55 (s, 1H), 7.36 (t, J=8.4 Hz, 3H), 7.24-7.21 (m, 2H), 7.11 (d, J=4.84 Hz, 1H), 7.09 (t, J=11.2 Hz, 1H), 3.45-3.41 (m, 6H), 3.15 (m, 8H), 2.47-2.43 (m, 5H), 2.36 (s, 3H), 2.11-2.03 (m, 2H), 1.85-1.79 (m, 2H).

Pyridine-2-carboxylic acid [5-[3-(2-oxo-pyrrolidin-1-yl)-propylcarbamoyl]-2-(4-o-tolyl-piperazin-1-yl)-phenyl]-amide

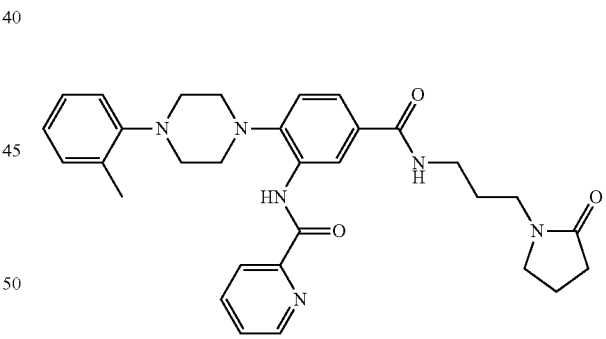

Yield: 69.4%.

Color and appearance: Brown solid.

LCMS: Mass found (M+541.3).

Rt (min): 4.23 Area %:—96.20 (Max), 96.53 (254 nm).

$^1$H NMR (400 MHz, CDCL$_3$) δ 11.07 (s, 1H), 9.06 (s, 1H), 8.66 (d, J=4.4 Hz, 1H), 8.35 (d, J=4.4 Hz, 1H), 7.14 (d, J=7.76 Hz, 1H), 7.94 (d, J=6.32 Hz, 1H), 7.77 (dd, J=1.92, 6.36 Hz, 1H), 7.61 (t, J=5.6 Hz, 1H), 7.50 (t, J=4.76 Hz, 1H), 7.31-7.24 (m, 3H), 7.09 (t, J=7.12 Hz, 1H), 3.46-3.43 (m, 6H), 3.28-3.21 (m, 8H), 2.48-2.41 (m, 5H), 2.09-2.04 (m, 2H), 1.86-1.80 (m, 2H).

449

N-[5-[3-(2-Oxo-pyrrolidin-1-yl)-propylcarbamoyl]-2-(4-o-tolyl-piperazin-1-yl)-phenyl]-nicotinamide

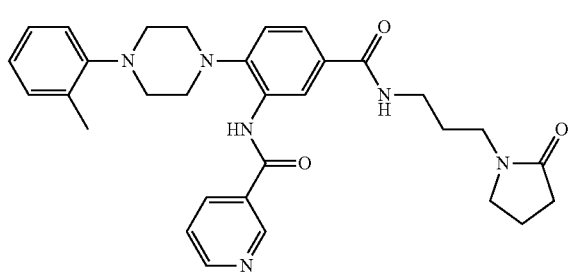 [SMILES: Cc1ccccc1N1CCN(c2ccc(C(=O)NCCCN3CCCC3=O)cc2NC(=O)c2cccnc2)CC1]

Yield: 42.0%.

Color and appearance: White solid.

LCMS: Mass found (M+541.3).

Rt (min): 3.12 Area %:—96.61 (Max), 96.94 (254 nm).

$^1$H NMR (400 MHz, CDCL$_3$) δ 9.52 (s, 1H), 9.21 (s, 1H), 9.00 (s, 1H), 8.81 (d, J=3.68 Hz, 1H), 8.40 (d, J=6.88 Hz, 1H), 7.81-7.75 (m, 2H), 7.80-7.75 (m, 1H), 7.55 (d, J=4.68 Hz, 1H), 7.23-7.20 (m, 2H), 7.13 (d, J=7.76 Hz, 1H), 7.06 (t, J=7.92 Hz, 1H), 3.46-3.41 (m, 6H), 3.16 (m, 8H), 2.49 (t, J=7.92 Hz, 2H), 2.36 (s, 3H), 2.10 (t, J=7.52 Hz, 2H), 1.83 (t, J=5.72 Hz, 2H).

N-[5-[3-(2-Oxo-pyrrolidin-1-yl)-propylcarbamoyl]-2-(4-o-tolyl-piperazin-1-yl)-phenyl]-isonicotinamide

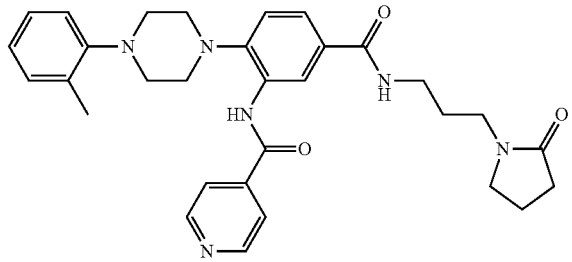 [SMILES: Cc1ccccc1N1CCN(c2ccc(C(=O)NCCCN3CCCC3=O)cc2NC(=O)c2ccncc2)CC1]

Yield: 45.7%.

Color and appearance: White solid.

LCMS: Mass found (M+541.3).

Rt (min): 3.02 Area %:—97.96 (Max), 98.48 (254 nm).

$^1$H NMR (400 MHz, CDCL$_3$) δ 9.48 (s, 1H), 9.04 (s, 1H), 8.86 (d, J=5.96 Hz, 2H), 7.81-7.77 (m, 3H) 7.74 (t, J=6.08 Hz, 1H), 7.39 (d, J=8.32 Hz, 1H), 7.25-7.21 (m, 2H), 7.10-7.05 (m, 2H), 3.46-3.41 (m, 6H), 3.12 (m, 8H), 2.49 (t, J=7.96 Hz, 2H), 2.36 (s, 3H), 2.12-2.07 (m, 2H), 1.83 (t, J=6.04 Hz, 2H).

450

N-[3-(2-Oxo-pyrrolidin-1-yl)-propyl]-4-(4-o-tolyl-piperazin-1-yl)-3-(3-trifluoromethyl-benzoylamino)-benzamide

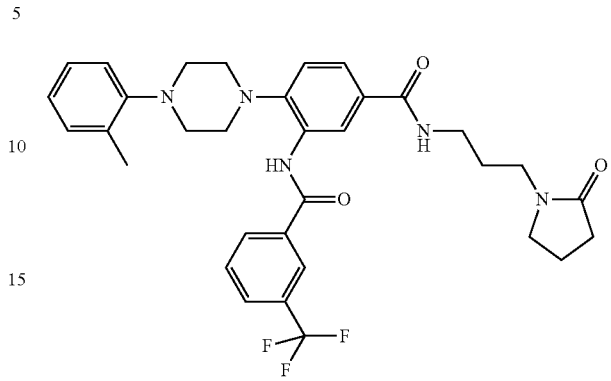

Yield: 32.7%.

Color and appearance: White solid.

LCMS: Mass found (M+608.3).

Rt (min): 4.98 Area %:—98.14 (Max), 99.10 (254 nm).

$^1$H NMR (400 MHz, CDCL$_3$) δ 9.66 (s, 1H), 9.01 (s, 1H), 8.27-8.22 (m, 2H), 7.85-7.67 (m, 4H) 7.41 (d, J=8.24 Hz, 1H), 7.23 (d, J=7.16 Hz, 2H), 7.12 (d, J=8.0 Hz, 1H), 7.08 (d, J=7.28 Hz, 1H), 3.46-3.43 (m, 6H), 317 (m, 8H), 2.49 (t, J=8.0 Hz, 2H), 2.37 (s, 3H), 2.10 (t, J=7.48 Hz, 2H), 1.84 (t, J=6.08 Hz, 2H).

N-[3-(2-Oxo-pyrrolidin-1-yl)-propyl]-4-(4-o-tolyl-piperazin-1-yl)-3-(4-trifluoromethyl-benzoylamino)-benzamide

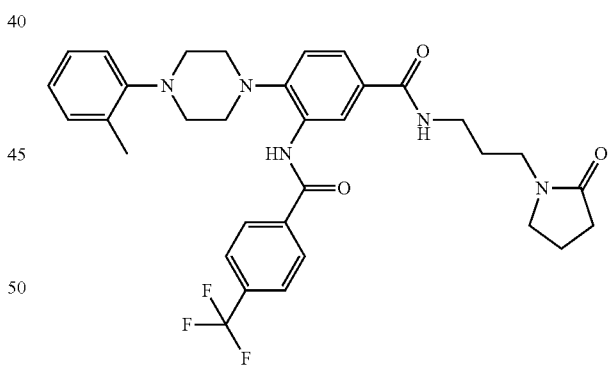

Yield: 60.5%.

Color and appearance: White solid.

LCMS: Mass found (M+608.3).

Rt (min): 5.00 Area %:—99.07 (Max), 98.92 (254 nm).

$^1$H NMR (400 MHz, CDCL$_3$) δ 9.53 (s, 1H), 8.99 (s, 1H), 8.12 (d, J=7.92 Hz, 2H), 7.81-7.78 (m, 3H) 7.72 (s, 1H), 7.41 (d, J=8.28 Hz, 1H), 7.25-7.22 (m, 2H), 7.11-7.03 (m, 2H), 3.46-3.41 (m, 6H), 3.17 (m, 8H), 2.48 (t, J=7.92 Hz, 2H), 2.36 (s, 3H), 2.12-2.06 (m, 2H), 1.85-1.79 (m, 2H).

451

3-(2-Methoxy-benzoylamino)-N-[3-(2-oxo-pyrrolidin-1-yl)-propyl]-4-(4-o-tolyl-piperazin-1-yl)-benzamide

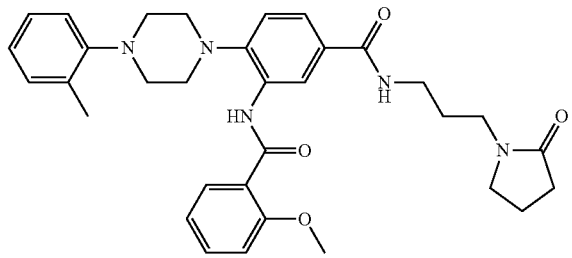

Yield: 60.5%.

Color and appearance: White solid.

LCMS: Mass found (M+570.3).

Rt (min): 4.54 Area %:—97.66 (Max), 98.26 (254 nm).

$^1$H NMR (400 MHz, CDCL$_3$) δ 10.46 (s, 1H), 8.86 (s, 1H), 8.34 (dd, J=1.64, 7.84 Hz, 1H), 7.75 (dd, J=2.0, 8.28 Hz, 1H) 7.54 (m, 1H), 7.44 (t, J=5.48 Hz, 1H), 7.30-7.28 (m, 3H), 7.24-7.17 (m, 1H), 7.10-7.05 (m, 3H), 4.13 (s, 3H), 3.45-3.41 (m, 6H), 3.20-3.18 (m, 8H), 2.46-2.42 (t, J=7.96 Hz, 2H), 2.40 (s, 3H), 2.09 (t, J=7.56 Hz, 2H), 1.84 (t, J=6.2 Hz, 2H).

452

Naphthalene-2-carboxylic acid [5-[3-(2-oxo-pyrrolidin-1-yl)-propylcarbamoyl]-2-(4-o-tolyl-piperazin-1-yl)-phenyl]-amide

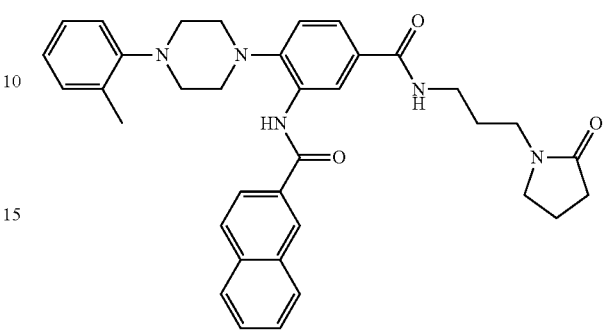

Yield: 16.2%.

Color and appearance: White solid.

LCMS: Mass found (M+590.3).

Rt (min): 4.86 Area %:—98.40 (Max), 97.81 (254 nm).

$^1$H NMR (400 MHz, CDCL$_3$) δ 9.61 (s, 1H), 9.07 (s, 1H), 8.54 (s, 1H), 8.04-7.92 (m, 4H) 7.79 (d, J=8.12 Hz, 1H), 7.67-7.57 (m, 3H), 7.39 (d, J=8.32 Hz, 1H), 7.22 (t, J=6.68 Hz, 2H), 7.11-7.07 (m, 2H), 3.45-3.43 (m, 6H), 3.18 (m, 8H), 2.48 ((t, J=7.92 Hz, 2H), 2.37 (s, 3H), 2.10 (t, J=7.48 Hz, 2H), 1.85 (t, J=5.92 Hz, 2H).

3-(4-Methoxy-benzoylamino)-N-[3-(2-oxo-pyrrolidin-1-yl)-propyl]-4-(4-o-tolyl-piperazin-1-yl)-benzamide

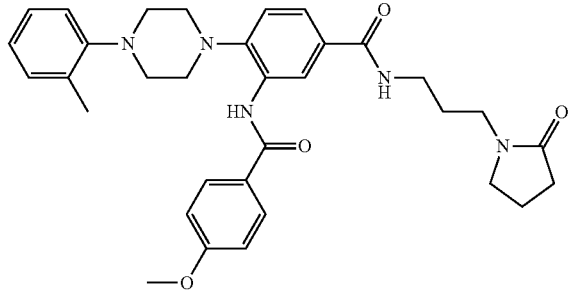 [SMILES: COc1ccc(C(=O)Nc2cc(C(=O)NCCCN3CCCC3=O)ccc2N2CCN(c3ccccc3C)CC2)cc1]

Yield: 21.1%.

Color and appearance: White solid.

LCMS: Mass found (M+570.3).

Rt (min): 4.36 Area %:—94.07 (Max), 94.05 (254 nm).

$^1$H NMR (400 MHz, CDCL$_3$) δ 9.45 (s, 1H), 8.94 (s, 1H), 7.99 (d, J=7.8 Hz, 2H), 7.77 (d, J=7.96 Hz, 1H) 7.56 (s, 1H), 7.38 (d, J=8.32 Hz, 1H), 7.24-7.21 (m, 2H), 7.13 (d, J=8.0 Hz, 1H), 7.08-7.00 (m, 3H), 3.89 (s, 3H), 3.45-3.42 (m, 6H), 3.20 (m, 8H), 2.47 (d, J=8.04 Hz, 2H), 2.37 (s, 3H), 2.11-2.04 (m, 2H), 1.85-1.79 (m, 2H).

Quinoline-8-carboxylic acid [5-[3-(2-oxo-pyrrolidin-1-yl)-propylcarbamoyl]-2-(4-o-tolyl-piperazin-1-yl)-phenyl]-amide

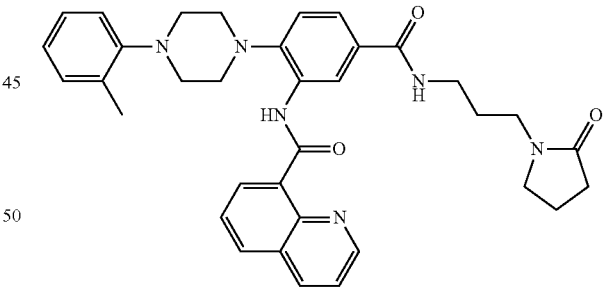

Yield: 50.4%.

Color and appearance: Brown solid.

LCMS: Mass found (M+591.3).

Rt (min): 4.33 Area %:—95.24 (Max), 97.34 (254 nm).

$^1$H NMR (400 MHz, CDCL$_3$) δ 13.54 (s, 1H), 9.20 (dd, J=1.8, 4.28 Hz, 1H), 9.03 (dd, J=1.52, 7.4 Hz, 1H), 8.98 (s, 1H) 8.36 (dd, J=1.76, 8.28 Hz, 1H), 8.06 (dd, J=1.48, 8.12 Hz, 1H), 7.78-7.77 (m, 2H), 7.76-7.75 (m, 1H), 7.58-7.55 (m, 1H), 7.31 (m, 1H), 7.29 (m, 2H), 7.19 (m, 2H), 3.46-3.42 (m, 6H), 3.23-3.14 (m, 8H), 2.46-2.42 (t, J=7.92 Hz, 2H), 2.35 (s, 3H), 2.09-2.07 (m, 2H), 1.84 (m, 2H).

453

4-Methyl-thiazole-5-carboxylic acid [5-[3-(2-oxo-pyrrolidin-1-yl)-propylcarbamoyl]-2-(4-o-tolyl-piperazin-1-yl)-phenyl]-amide

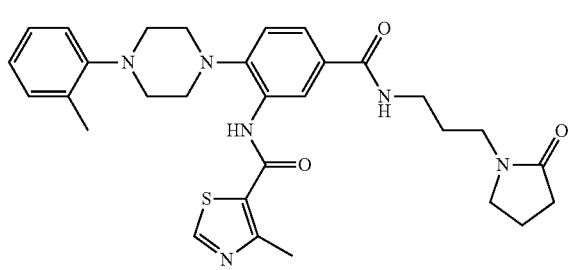 [SMILES: Cc1ccccc1N1CCN(c2ccc(C(=O)NCCCN3CCCC3=O)cc2NC(=O)c2scnc2C)CC1]

Yield: 78%.

Color and appearance: Brown solid.

LCMS: Mass found (M+561.3).

Rt (min): 3.80 Area %:—92.03 (Max), 95.82 (254 nm).

$^1$H NMR (400 MHz, CDCl$_3$) δ 9.17 (s, 1H), 8.93 (s, 1H), 8.78 (s, 1H), 7.76 (dd, J=2.04, 8.32 Hz, 1H), 7.61 (s, 1H), 7.40 (d, J=8.28 Hz, 1H), 7.25 (t, J=7.52 Hz, 2H), 7.13 (d, J=7.72 Hz, 1H), 7.08 (t, J=7.96 Hz, 1H), 3.46-3.40 (m, 6H), 3.17-3.15 (m, 8H), 2.89 (s, 3H), 2.47 (t, J=7.96 Hz, 2H), 2.39 (s, 3H), 2.12-2.04 (m, 2H), 1.85-1.79 (m, 2H).

2-Methyl-4-trifluoromethyl-thiazole-5-carboxylic acid [5-[3-(2-oxo-pyrrolidin-1-yl)-propylcarbamoyl]-2-(4-o-tolyl-piperazin-1-yl)-phenyl]-amide

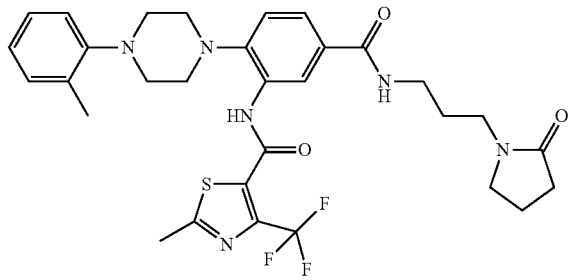 [SMILES: Cc1nc(C(F)(F)F)c(C(=O)Nc2cc(C(=O)NCCCN3CCCC3=O)ccc2N2CCN(c3ccccc3C)CC2)s1]

Yield: 11.7%.

Color and appearance: White solid.

LCMS: Mass found (M+629.3).

Rt (min): 4.30 Area %:—95.39 (Max), 98.27 (254 nm).

$^1$H NMR (400 MHz, CDCL$_3$) δ 9.28 (s, 1H), 8.83 (s, 1H), 7.79 (dd, J=1.76, 8.32 Hz, 1H), 7.6 (s, 1H), 7.41 (d, J=8.28 Hz, 1H), 7.22 (d, J=7.6 Hz, 2H), 7.07-7.01 (m, 2H), 3.45.3.40 (m, 6H), 3.06 (m, 8H), 2.79 (s 3H), 2.47 (t, J=8.0 Hz, 2H), 2.36 (s, 3H), 2.12-2.04 (m, 2H), 1.83-1.80 (m, 2H).

454

2-Bromo-4-methyl-thiazole-5-carboxylic acid [5-[3-(2-oxo-pyrrolidin-1-yl)-propylcarbamoyl]-2-(4-o-tolyl-piperazin-1-yl)-phenyl]-amide

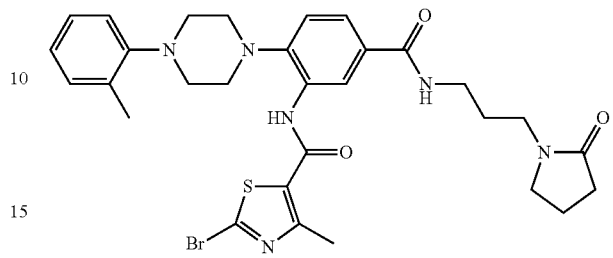

Yield: 15.2%.

Color and appearance: White solid.

LCMS: Mass found (M+639.0).

Rt (min): 4.54 Area %:—94.07 (Max), 94.89 (254 nm).

$^1$H NMR (400 MHz, CDCl$_3$) δ 9.09 (s, 1H), 8.90 (s, 1H), 7.77 (dd, J=1.96, 8.28 Hz, 1H), 7.63 (t, J=5.52 Hz, 1H), 7.40 (d, J=8.32 Hz, 1H), 7.25 (t, J=5.96 Hz, 2H), 7.12 (d, J=7.76 Hz, 1H), 7.08-7.04 (m, 1H), 3.45-3.40 (m, 6H), 3.14-3.12 (m, 8H), 2.83 (s, 3H), 2.47 ((t, J=7.92 Hz, 2H), 2.37 (s, 3H), 2.12-2.04 (m, 2H), 1.84-1.78 (m, 2H).

Thiazole-4-carboxylic acid [5-[3-(2-oxo-pyrrolidin-1-yl)-propylcarbamoyl]-2-(4-o-tolyl-piperazin-1-yl)-phenyl]-amide

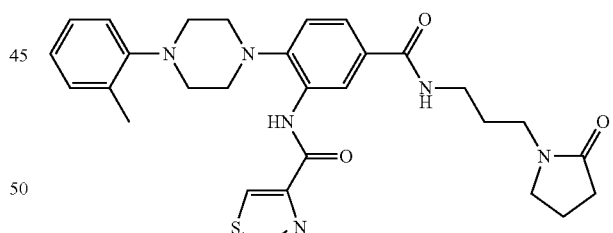

Yield: 40.7%.

Color and appearance: Brown gum.

LCMS: Mass found (M+547.2).

Rt (min): 3.98 Area %:—96.25 (Max), 96.95 (254 nm).

$^1$H NMR (400 MHz, CDCl$_3$) δ 10.37 (s, 1H), 9.03 (s, 1H), 8.84 (s, 1H), 9.32 (d, J=2.04 Hz, 1H), 7.77-7.49 (m, 1H), 7.62 (s, 1H), 7.32 (d, J=8.28 Hz, 1H), 7.24 (m, 3H), 7.08 (s, 1H), 3.45-3.42 (m, 6H), 3.29-3.21 (m, 8H), 2.48-2.43 (m, 5H), 2.11-2.04 (m, 2H), 1.85-1.79 (m, 2H).

2-Methyl-thiazole-4-carboxylic acid [5-[3-(2-oxo-pyrrolidin-1-yl)-propylcarbamoyl]-2-(4-o-tolyl-piperazin-1-yl)-phenyl]-amide

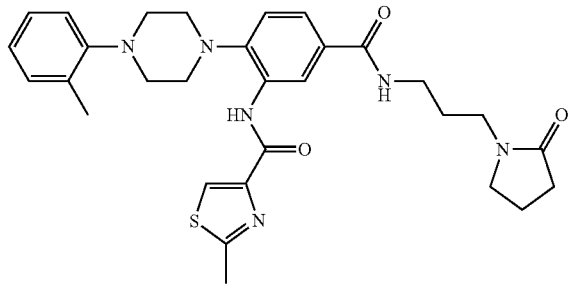

Yield: 35.4%.

Color and appearance: Brown solid.

LCMS: Mass found (M+561.3).

Rt (min): 4.32 Area %:—96.08 (Max), 98.00 (254 nm).

$^1$H NMR (400 MHz, CDCl$_3$) δ 10.36 (s, 1H), 9.02 (s, 1H), 8.09 (s, 1H), 7.751 (dd, J=2.04, 8.24 Hz, 1H), 7.55 (t, J=11.72 Hz, 1H), 7.34-7.22 (m, 4H), 7.17 (t, J=7.88 Hz, 1H), 3.45-3.33 (m, 14H), 2.80 (s, 3H), 2.53 (s, 3H), 2.48 (t, J=7.96 Hz, 2H), 2.11-2.05 (m, 2H), 1.83-1.79 (m, 2H).

2-Methyl-oxazole-4-carboxylic acid [5-[3-(2-oxo-pyrrolidin-1-yl)-propylcarbamoyl]-2-(4-o-tolyl-piperazin-1-yl)-phenyl]-amide

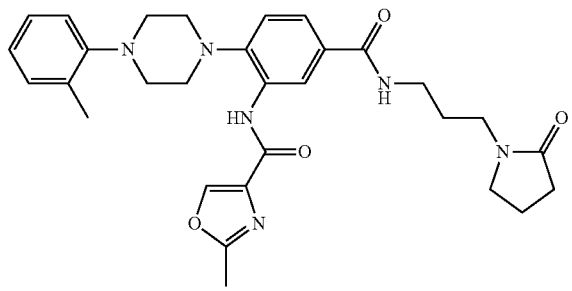 [SMILES: Cc1nc(C(=O)Nc2cc(C(=O)NCCCN3CCCC3=O)ccc2N2CCN(c3ccccc3C)CC2)cs1]

Yield: 54.7%.

Color and appearance: Brown gum.

LCMS: Mass found (M+545.3).

Rt (min): 4.02 Area %:—96.73 (Max), 97.79 (254 nm).

$^1$H NMR (400 MHz, CDCl$_3$) δ 9.91 (s, 1H), 8.99 (s, 1H), 8.19 (s, 1H), 7.75 (dd, J=2.04, 8.32 Hz, 1H), 7.60 (t, J=6.0 Hz, 1H), 7.31 (d, J=8.28 Hz, 1H), 7.24 (t, J=5.56 Hz, 3H), 7.06 (t, J=4.72 Hz, 1H), 3.45-3.40 (m, 6H), 3.26-3.17 (m, 8H), 2.52 (s, 3H), 2.48 (t, J=7.96 Hz, 2H), 2.42 (s, 3H), 2.11-2.03 (m, 2H), 1.84-1.78 (m, 2H).

2-Methyl-5-trifluoromethyl-oxazole-4-carboxylic acid [5-[3-(2-oxo-pyrrolidin-1-yl)-propylcarbamoyl]-2-(4-o-tolyl-piperazin-1-yl)-phenyl]-amide

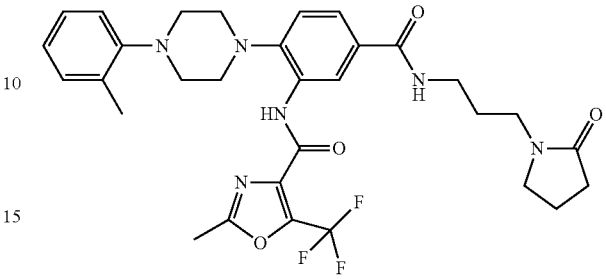

Yield: 63.0%.

Color and appearance: White solid.

LCMS: Mass found (M+613.3).

Rt (min): 4.81 Area %:—98.99 (Max), 99.59 (254 nm).

$^1$H NMR (400 MHz, CDCl$_3$) δ 10.13 (s, 1H), 8.92 (s, 1H), 7.75 (dd, J=1.96, 8.28 Hz, 1H), 7.32 (t, J=8.32 Hz, 2H), 7.25 (t, J=7.64 Hz, 2H), 7.15 (d, J=7.64 Hz, 1H), 7.08 (t, J=7.4 Hz, 1H), 3.46-3.39 (m, 6H), 3.22-3.21 (m, 8H), 2.60 (s, 3H), 2.45 (t, J=8.04 Hz, 2H), 2.39 (s, 3H), 2.11-2.0 (m, 2H), 1.86-1.79 (m, 2H).

5-Ethyl-oxazole-4-carboxylic acid [5-[3-(2-oxo-pyrrolidin-1-yl)-propylcarbamoyl]-2-(4-o-tolyl-piperazin-1-yl)-phenyl]-amide

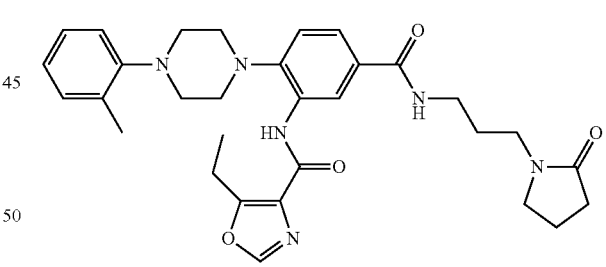

Yield: 51.5%.

Color and appearance: Off white solid.

LCMS: Mass found (M+559.3).

Rt (min): 4.38 Area %:—93.67 (Max), 97.04 (254 nm).

$^1$H NMR (400 MHz, CDCl$_3$) δ 9.9 (s, 1H), 8.9 (s, 1H), 7.76 (s, 1H), 7.73-7.71 (m, 1H), 7.48 (t, J=5.92 Hz, 1H), 7.29-7.21 (m, 3H), 7.16 (d, J=7.64 Hz, 1H), 7.05 (t, J=7.2 Hz, 1H), 3.45-3.3.40 (m, 6H), 3.24-3.18 (m, 10H), 2.46 (t, J=7.96 Hz, 2H), 2.36 (s, 3H), 2.09-2.03 (m, 2H), 1.84 (m, 2H), 1.32 (t, J=7.56 Hz, 3H).

457

5-Methyl-oxazole-4-carboxylic acid [5-[3-(2-oxo-pyrrolidin-1-yl)-propylcarbamoyl]-2-(4-o-tolyl-piperazin-1-yl)-phenyl]-amide

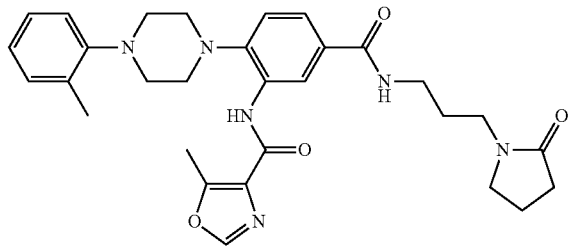 [SMILES: Cc1ccccc1N1CCN(c2ccc(C(=O)NCCCN3CCCC3=O)cc2NC(=O)c2ncoc2C)CC1]

Yield: 27.7%.

Color and appearance: White solid.

LCMS: Mass found (M+545.3).

Rt (min): 4.04 Area %:—91.51 (Max), 97.19 (254 nm).

$^1$H NMR (400 MHz, CDCl$_3$) δ 9.90 (s, 1H), 8.92 (s, 1H), 7.75 (s, 1H), 7.74-7.72 (m, 2H), 7.59 (t, J=6.0 Hz, 2H), 7.30 (t, J=8.48 Hz, 2H), 7.08 (t, J=7.2 Hz, 1H), 3.45-3.40 (m, 6H), 3.25-3.31 (m, 8H), 2.74 (s, 3H), 2.47-2.40 (m, 5H), 2.11-2.05 (m, 2H), 1.84-1.80 (s, 2H).

2-Ethyl-oxazole-4-carboxylic acid [5-[3-(2-oxo-pyrrolidin-1-yl)-propylcarbamoyl]-2-(4-o-tolyl-piperazin-1-yl)-phenyl]-amide

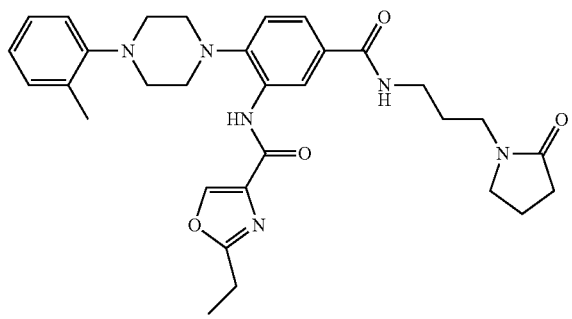 [SMILES: CCc1nc(C(=O)Nc2cc(C(=O)NCCCN3CCCC3=O)ccc2N2CCN(c3ccccc3C)CC2)co1]

Yield: 39.2%.

Color and appearance: White solid.

LCMS: Mass found (M+559.3).

Rt (min): 4.42 Area %:—93.72 (Max), 96.42 (254 nm).

$^1$H NMR (400 MHz, CDCl$_3$) δ 10.00 (s, 1H), 9.00 (s, 1H), 8.20 (s, 1H), 7.75 (dd, J=2.04, 8.24 Hz, 1H), 7.60 (s, 1H), 7.24 (d, J=2.72 Hz, 1H), 7.21-7.19 (m, 2H), 7.13 (d, J=7.6 Hz, 1H), 7.06 (t, J=7.32 Hz, 1H), 3.45-3.40 (m, 6H), 3.21-3.12 (m, 8H), 2.87-2.81 (m, 2H), 2.48 (t, J=7.92 Hz, 2H), 2.38 (s, 3H), 2.09-2.05 (m, 2H), 1.83 (t, J=6.44 Hz, 2H), 1.44 (t, J=7.56 Hz, 3H).

458

3-Methyl-isoxazole-4-carboxylic acid [5-[3-(2-oxo-pyrrolidin-1-yl)-propylcarbamoyl]-2-(4-o-tolyl-piperazin-1-yl)-phenyl]-amide

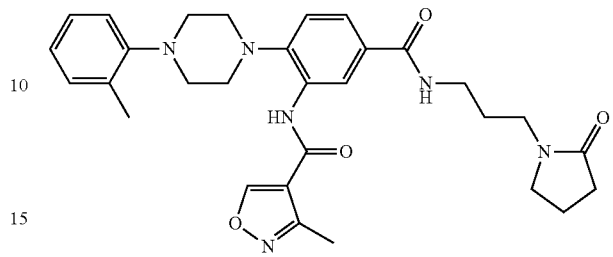

Yield: 18.5%.

Color and appearance: White solid.

LCMS: Mass found (M+545.3).

Rt (min): 3.78 Area %:—96.87 (Max), 98.58 (254 nm).

$^1$H NMR (400 MHz, CDCl$_3$) δ 8.94 (s, 1H), 8.89 (s, 1H), 8.84 (s, 1H), 7.76 (dd, J=1.88, 8.24 Hz, 1H), 7.66 (s, 1H), 7.38 (d, J=8.32 Hz, 1H), 7.24 (t, J=3.96 Hz, 2H), 7.09-7.03 (m, 2H), 3.45-3.40 (m, 6H), 3.09 (m, 8H), 2.65 (s, 3H), 2.48 (t, J=7.96 Hz, 2H), 2.36 (s, 3H), 2.12-2.04 (m, 2H), 1.84-1.78 (m, 2H).

5-Ethyl-3-methyl-isoxazole-4-carboxylic acid [5-[3-(2-oxo-pyrrolidin-1-yl)-propylcarbamoyl]-2-(4-o-tolyl-piperazin-1-yl)-phenyl]-amide

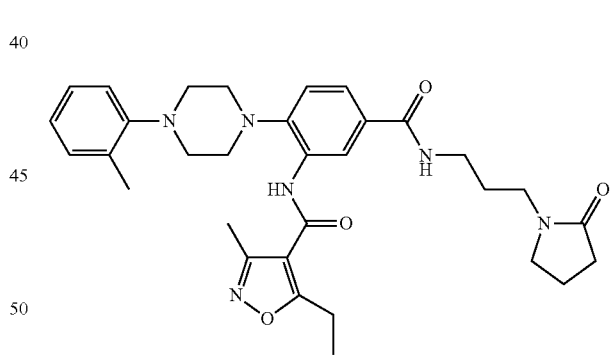

Yield: 13.8%.

Color and appearance: White solid.

LCMS: Mass found (M+573.3).

Rt (min): 4.41 Area %:—95.41 (Max), 97.34 (254 nm).

$^1$H NMR (400 MHz, CDCl$_3$) δ 9.00 (s, 1H), 8.90 (s, 1H), 7.75 (dd, J=2.0, 8.32 Hz, 1H), 7.68 (s, 1H) 7.43 (d, J=8.28 Hz, 1H), 7.23 (t, J=7.2 Hz, 2H), 7.07 (t, J=7.92 Hz, 2H), 3.46-3.42 (m, 6H), 3.09 (m, 8H), 3.06-3.04 (m, 2H), 2.75 (s, 3H), 2.47 (t, J=8.0 Hz, 2H), 2.36 (s, 3H), 2.08-2.04 (m, 2H), 1.85-1.81 (m, 2H), 1.42 (t, J=4.56 Hz, 3H).

459

3-(Cyclohexanecarbonyl-amino)-N-[3-(2-oxo-pyrrolidin-1-yl)-propyl]-4-(4-o-tolyl-piperazin-1-yl)-benzamide

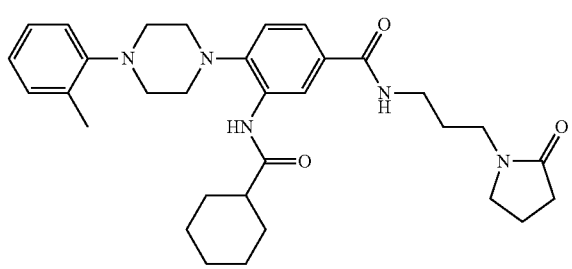 [SMILES: Cc1ccccc1N1CCN(c2ccc(C(=O)NCCCN3CCCC3=O)cc2NC(=O)C2CCCCC2)CC1]

Yield: 64.9%.

Color and appearance: Brown solid.

LCMS: Mass found (M+546.3).

Rt (min): 4.56 Area %:—95.44 (Max), 95.51 (254 nm).

$^1$H NMR (400 MHz, CDCl$_3$) δ 8.8 (s, 1H), 8.6 (s, 1H), 7.70 (dd, J=1.96, 8.24 Hz, 1H), 7.43 (s, 1H), 7.24 (m, 1H), 7.22 (t, J=6.16 Hz, 2H), 7.11 (d, J=7.48 Hz, 1H), 7.06 (t, J=7.36 Hz, 1H), 3.44-3.38 (m, 6H), 3.11-3.07 (m, 8H), 2.45 (t, J=8.0 Hz, 2H), 2.36 (s, 3H), 2.34 (m, 1H), 2.08-2.06 (m, 4H), 2.04-2.00 (m, 1H), 1.88-1.80 (m, 3H), 1.57-1.53 (m, 2H), 1.38-1.25 (m, 4H).

Tetrahydro-furan-2-carboxylic acid [5-[3-(2-oxo-pyrrolidin-1-yl)-propylcarbamoyl]-2-(4-o-tolyl-piperazin-1-yl)-phenyl]-amide

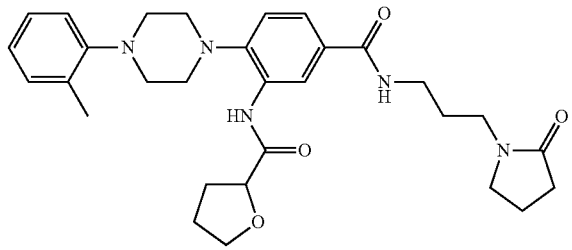

Yield: 75.8%.

Color and appearance: White solid.

LCMS: Mass found (M+534.3).

Rt (min): 3.98 Area %:—98.49 (Max), 98.11 (254 nm).

$^1$H NMR (400 MHz, CDCl$_3$) δ 9.6 (s, 1H), 8.91 (s, 1H), 7.72 (dd, J=2.0, 8.28 Hz, 1H), 7.55 (s, 1H), 7.26-7.20 (m, 3H), 7.13 (d, J=7.12 Hz, 1H), 7.06 (t, J=7.32 Hz, 1H), 4.55-4.51 (m, 1H), 4.10-4.08 (m, 1H), 4.00-3.98 (m, 1H), 3.44-3.41 (m, 6H), 3.18-3.04 (m, 8H), 2.46 (m, 3H), 2.37 (s, 3H), 2.08-2.05 (m, 1H), 1.97-1.94 (m, 2H), 1.83-1.82 (m, 2H), 1.80-1.79 (m, 2H).

460

1-Methyl-piperidine-4-carboxylic acid [5-[3-(2-oxo-pyrrolidin-1-yl)-propylcarbamoyl]-2-(4-o-tolyl-piperazin-1-yl)-phenyl]-amide

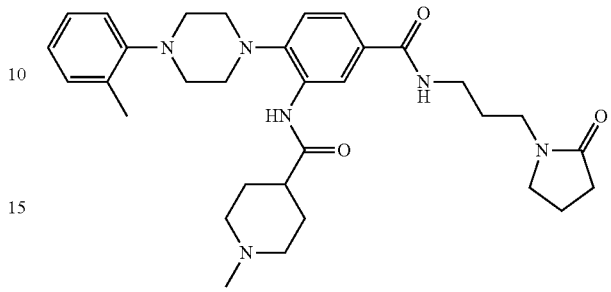

Yield: 19.7%.

Color and appearance: Brown gum.

LCMS: Mass found (M+561.3).

Rt (min): 2.85 Area %:—95.09 (Max), 97.27 (254 nm).

$^1$H NMR (400 MHz, MeOD) δ 8.31 (s, 1H), 7.66 (dd, J=2.08, 8.32 Hz, 1H), 7.33 (d, J=8.4 Hz, 1H), 7.19-7.14 (m, 3H), 6.98 (t, J=1.6 Hz, 1H), 3.52 (t, J=7.08 Hz, 2H), 3.48-3.38 (m, 4H), 3.10 (m, 8H), 3.32-3.31 (m, 2H), 3.01-2.98 (m, 1H), 2.42-2.38 (m, 2H), 2.34-3.32 (m, 3H), 2.17 (s, 3H), 2.08-2.04 (m, 2H), 1.91-1.90 (m, 2H), 1.88-1.87 (m, 2H), 1.85-1.83 (m, 4H).

3-(Cyclopropanecarbonyl-amino)-N-[3-(2-oxo-pyrrolidin-1-yl)-propyl]-4-(4-o-tolyl-piperazin-1-yl)-benzamide

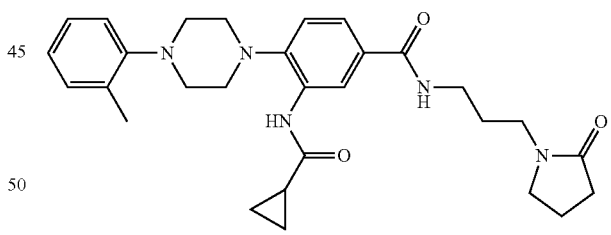

Yield: 67.4%.

Color and appearance: White solid.

LCMS: Mass found (M+504.3).

Rt (min): 3.56 Area %:—95.97 (Max), 97.03 (254 nm).

$^1$H NMR (400 MHz, CDCl$_3$) δ 8.77 (s, 1H), 8.63 (s, 1H), 7.70 (dd, J=2.04, 8.24 Hz, 1H), 7.42 (s, 1H), 7.29 (s, 1H), 7.23 (t, J=7.68 Hz, 2H), 7.12 (d, J=7.8 Hz, 1H), 7.05 (t, J=7.36 Hz, 1H), 3.37 (m, 6H), 3.2 (m, 8H), 2.42 (m, 2H), 2.3 (s, 3H), 2.05-2.02 (m, 2H), 1.83-1.81 (m, 2H), 1.78-1.76 (m, 1H), 1.15-1.11 (m, 2H), 0.98-0.86 (m, 2H).

461
3-(2-Chloro-benzoylamino)-N-[3-(2-oxo-pyrrolidin-1-yl)-propyl]-4-(4-o-tolyl-piperazin-1-yl)-benzamide

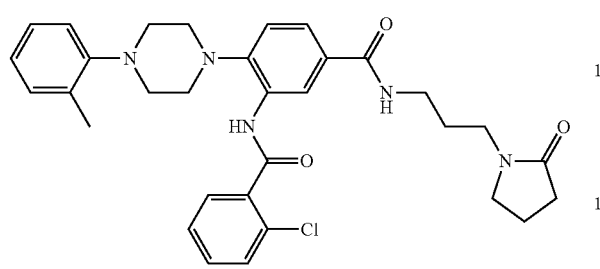

Yield: 51.7%.

Color and appearance: Brown solid.

LCMS: Mass found (M+574.3).

Rt (min): 4.28 Area %:—93.60 (Max), 96.10 (254 nm).

$^1$H NMR (400 MHz, CDCl$_3$) δ 9.35 (s, 1H), 9.06 (s, 1H), 7.84 (d, J=6.96 Hz, 1H), 7.77 (dd, J=1.68, 8.24 Hz, 1H), 7.58 (s, 1H), 7.49-7.46 (m, 1H), 7.44-7.38 (m, 3H), 7.23 (t, J=7.84 Hz, 2H), 7.19 (m, 2H), 3.46-3.42 (m, 6H), 3.19 (m, 8H), 2.47-2.42 (m, 5H), 2.10-2.06 (m, 2H), 1.84-1.79 (m, 2H).

462
3-(3-Dimethylamino-benzoylamino)-N-[3-(2-oxo-pyrrolidin-1-yl)-propyl]-4-(4-o-tolyl-piperazin-1-yl)-benzamide

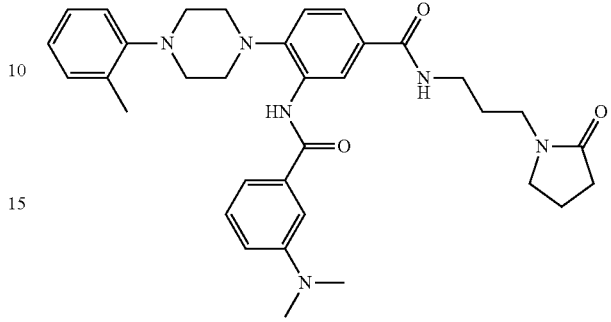

Yield: 45.3%.

Color and appearance: Brown gum.

LCMS: Mass found (M+583.3).

Rt (min): 3.73 Area %:—92.47 (Max), 94.61 (254 nm).

$^1$H NMR (400 MHz, CDCl$_3$) δ 9.41 (s, 1H), 9.04 (s, 1H), 7.76 (dd, J=1.84, 8.24 Hz, 1H), 7.59 (s, 1H), 7.41-7.33 (m, 3H), 7.23 (t, J=7.28 Hz, 3H), 7.07 (m, 2H), 6.92 (s, 1H), 3.46-3.42 (m, 6H), 3.12-3.05 (m, 8H), 3.01 (s, 6H), 2.47 (t, J=7.88 Hz, 2H), 2.36 (s, 3H), 2.11-2.03 (m, 2H), 1.86-1.80 (m, 2H).

3-(2-Fluoro-benzoylamino)-N-[3-(2-oxo-pyrrolidin-1-yl)-propyl]-4-(4-o-tolyl-piperazin-1-yl)-benzamide

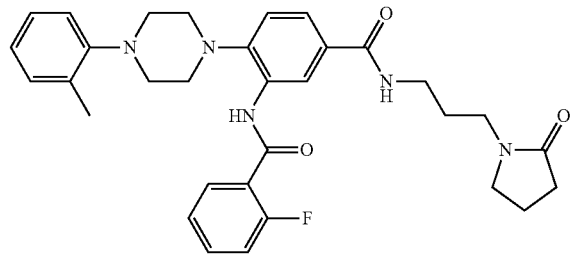 [SMILES: Cc1ccccc1N1CCN(c2ccc(C(=O)NCCCN3CCCC3=O)cc2NC(=O)c2ccccc2F)CC1]

Yield: 36.7%.

Color and appearance: Brown solid.

LCMS: Mass found (M+558.3).

Rt (min): 4.39 Area %:—96.46 (Max), 96.94 (254 nm).

$^1$H NMR (400 MHz, CDCl$_3$) δ 9.96 (s, 1H), 9.09 (s, 1H), 8.29 (t, J=6.4 Hz, 1H), 7.78 (dd, J=2.08, 8.28 Hz, 1H), 7.68 (m, 1H), 7.54-7.52 (m, 1H), 7.40 (d, J=8.28 Hz, 1H), 7.36 (t, J=6.92 Hz, 1H), 7.32 (m, 4H), 7.13 (t, J=4.24 Hz, 1H), 3.46-3.42 (m, 6H), 3.28 (m, 8H), 2.48-2.43 (m, 5H), 2.10-2.06 (m, 2H), 1.85-1.82 (m, 2H).

N-[3-(2-Oxo-pyrrolidin-1-yl)-propyl]-4-(4-o-tolyl-piperazin-1-yl)-3-(2-trifluoromethyl-benzoylamino)-benzamide

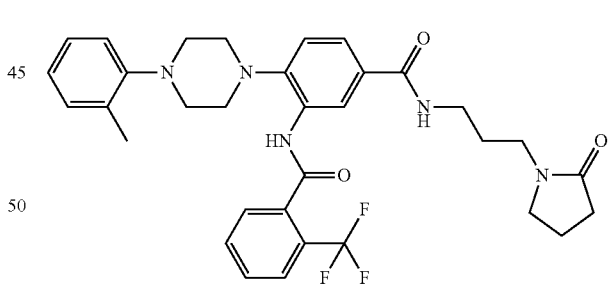

Yield: 32.3%.

Color and appearance: Brown solid.

LCMS: Mass found (M+608.3).

Rt (min): 4.49 Area %:—95.91 (Max), 97.61 (254 nm).

$^1$H NMR (400 MHz, CDCl$_3$) δ 8.94 (s, 2H), 7.79 (t, J=7.6 Hz, 2H), 7.69-7.62 (m, 3H), 7.53 (s, 1H), 7.39 (d, J=8.28 Hz, 1H), 7.22-7.15 (m, 2H), 7.05 (t, J=7.72 Hz, 2H), 3.46-3.42 (m, 6H), 3.13-3.04 (m, 8H), 2.46 (t, J=8.0 Hz, 2H), 2.36 (s, 3H), 2.11-2.04 (m, 2H), 1.85-1.80 (m, 2H).

Naphthalene-1-carboxylic acid [5-[3-(2-oxo-pyrrolidin-1-yl)-propylcarbamoyl]-2-(4-o-tolyl-piperazin-1-yl)-phenyl]-amide

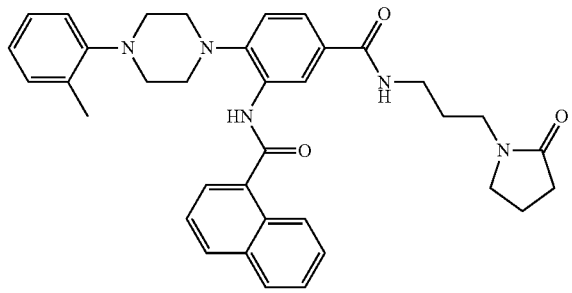 [SMILES: Cc1ccccc1N1CCN(c2ccc(C(=O)NCCCN3CCCC3=O)cc2NC(=O)c2cccc3ccccc23)CC1]

Yield: 10.9%.
Color and appearance: Brown gum.
LCMS: Mass found (M+590.3).
Rt (min): 4.70 Area %:—90.60 (Max), 91.80 (254 nm).
$^1$H NMR (400 MHz, CDCl$_3$) δ 9.1 (s, 2H), 8.52 (d, J=8.92 Hz, 1H), 7.99 (d, J=8.2 Hz, 1H), 7.94 (d, J=7.28 Hz, 1H), 7.80 (t, J=6.72 Hz, 2H), 7.60 (s, 1H), 7.59-7.55 (m, 3H), 7.38 (d, J=8.28 Hz, 1H), 7.20-7.15 (m, 2H), 7.04 (t, J=7.28 Hz, 1H), 6.96 (d, J=8.08 Hz, 1H), 3.47-3.44 (m, 6H), 3.16-3.10 (m, 8H), 2.48 (t, J=8.0 Hz, 2H), 2.35 (s, 3H), 2.10-2.06 (m, 2H), 1.87-1.84 (m, 2H).

Furan-2-carboxylic acid [5-(3-phenyl-propylcarbamoyl)-2-(4-o-tolyl-piperazin-1-yl)-phenyl]-amide

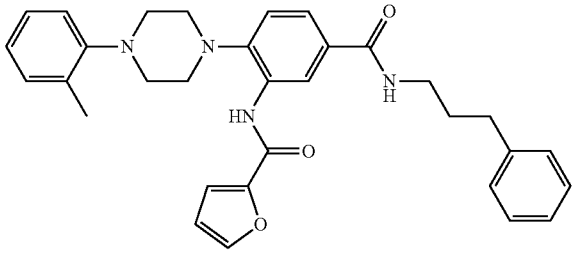 [SMILES: Cc1ccccc1N1CCN(c2ccc(C(=O)NCCCc3ccccc3)cc2NC(=O)c2ccco2)CC1]

To a suspension of 3-[(furan-2-carbonyl)-amino]-4-(4-o-tolyl-piperazin-1-yl)-benzoic acid (0.1 g, 0.246 mmol) in methylene dichloride (5 ml), triethylamine (0.074 g, 0.74 mmol), (3-phenylpropyl)amine (0.044 g, 0.370 mmol) and 1-propane phosphonic cyclic anhydride (0.23 g, 0.74 mmol) were added. The reaction mixture was stirred at room temperature for 16 h. The reaction mixture was concentrated and extracted with dichloromethane (10 ml×1). The organic layer was washed with water (10 ml×2) and dried over anhydrous sodium sulfate. The organic layer was concentrated and the crude product obtained was purified by flash chromatography using silica gel column to get (0.070 g, 67.9%) of the titled compound as a brown solid.
LCMS: Mass found (M+523.3).
Rt (min): 5.42 Area %:—90.74 (Max), 92.59 (254 nm).
$^1$H NMR (400 MHz, CDCl$_3$) δ 9.5 (s, 1H), 8.80 (s, 1H), 7.75 (dd, J=2.08, 8.28 Hz, 1H), 7.58 (s, 1H), 7.34 (d, J=8.32 Hz, 2H), 7.30-7.25 (m, 7H), 7.14 (d, J=8.08 Hz, 1H), 7.05 (m, 1H), 6.61 (s, 1H), 6.60 (s, 1H), 3.51 (m, 2H), 3.18-3.12 (m, 8H), 2.75 (t, J=7.44 Hz, 2H), 2.37 (s, 3H), 1.99-96 (m, 2H).

HPLC: Rt (min) 5.46 Area %:—92.64 (Max), 94.27 (254 nm).

Furan-2-carboxylic acid [5-(3-pyrazol-1-yl-propylcarbamoyl)-2-(4-o-tolyl-piperazin-1-yl)-phenyl]-amide

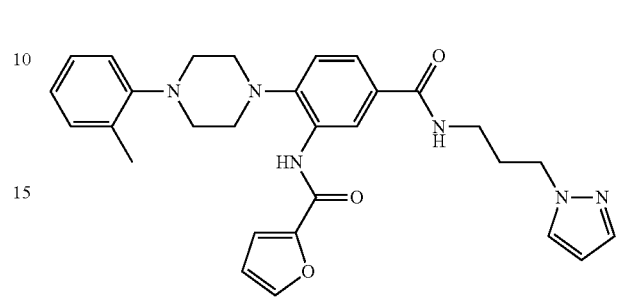

Yield: 64.4%.
Color and appearance: Yellow solid.
LCMS: Mass found (M+513.3).
Rt (min): 4.49 Area %:—99.33 (Max), 99.86 (254 nm).
$^1$H NMR (400 MHz, CDCl$_3$) δ 9.5 (s, 1H), 8.85 (s, 1H), 7.76 (dd, J=2.12, 8.28 Hz, 1H), 7.58 (s, 2H), 7.57 (s, 1H), 7.34 (d, J=8.28 Hz, 1H), 7.29-7.28 (m, 3H), 7.25-7.2481 (m, 2H), 7.23 (m, 1H), 6.60 (s, 1H), 6.27 (s, 1H), 4.30 (t, J=6.4 Hz, 2H), 2.48-2.46 (m, 2H), 3.19-3.13 (m, 8H), 2.37 (s, 3H), 2.18-1.76 (m, 2H).

Furan-2-carboxylic acid [5-(1-cyclopentylcarbamoyl-ethylcarbamoyl)-2-(4-o-tolyl-piperazin-1-yl)-phenyl]-amide

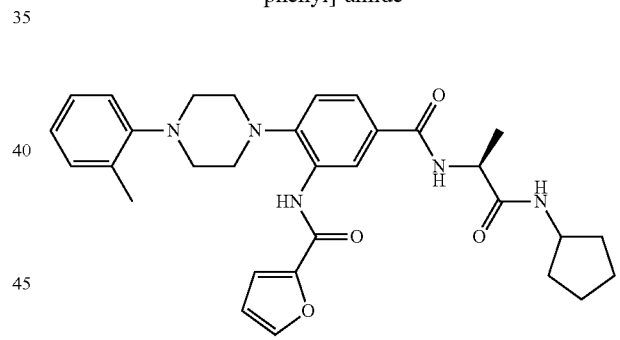

Yield: 48.4%.
Color and appearance: Brown solid.
LCMS: Mass found (M+544.3).
Rt (min): 4.72 Area %:—90.79 (Max), 90.20 (254 nm).
$^1$H NMR (400 MHz, CDCl$_3$) δ 95 (s, 1H), 8.88 (s, 1H), 7.69 (dd, J=2.04, 8.24 Hz, 1H), 7.57 (s, 1H), 7.34 (d, J=8.28 Hz, 1H), 7.29-7.28 (m, 3H), 7.25 (d, J=7.08 Hz, 1H), 7.18 (m, 1H), 7.09 (d, J=7.36 Hz, 1H), 6.85 (d, J=7.48 Hz, 1H), 6.61 (m, 1H), 4.64 (m, 1H), 4.20-4.18 (m, 1H), 3.21-3.18 (m, 8H), 2.40 (s, 3H), 1.98-1.97 (m, 2H), 1.69-1.67 (m, 2H), 1.65-1.58 (m, 2H), 1.49-1.48 (m, 3H), 1.44-1.40 (m, 2H).

Example 10: EC$_{50}$ of Cyclic AMP Production in CHO FSHR Cells+EC$_{20}$ FSH (Assay A)

2500 Cho-FSHR-LUC-1-1-43 cells were plated per well in 5 μl of phenol red free DMEM/F12+1% FBS. Cells were plated in 384 well, solid white low volume plates (Greiner 784075) by Multidrop. Cells were assayed by adding 100 μl of 2×EC$_{20}$ FSH/IBMX in DMEM/F12+0.1% BSA) by Multidrop to 2 μl of test compound stamped in 384 well plates (compounds are diluted 1:50). The final FSH concentration was 0.265 μM, and the final IBMX concentration was 200 μM. The compound plate map was as follows: Column 1: 2 μl of DMSO; Column 2: 2 μl of DMSO; Columns 3-12 and 13-24: 2 μl of test compound, diluted 1:4 in 100% DMSO, or 2 μl of FSH, diluted 1:4 in DMEM/F12+0.1% BSA. The starting concentration for FSH was 50 nM (final concentration was 0.5 nM). Furthermore, Column 23 contained 2 μl of EC$_{10}$ FSH reference (100×) (diluted in DMEM/F12+0.1% BSA) at a final concentration of 0.5 nM, and Column 24 contained 2 μl of 1 mM AS707664/2 reference compound 2. 5 μl of compound+EC$_{20}$ FSH mixture were transferred to cell plates (1:2 dilution into 5 μl of cell media) The plates were incubated at 37° C. for 1 h. 10 μl of mixed HTRF (CisBio #62AM4PEC) reagents were added per well and incubated at room temperature for 1 h. The plates were read on Envision using the cAMP HTRF—low volume 384 well protocol. The readout was the calculated fluorescence ratio (665 nm/620 nm). Values given in percent (%) indicate the percental effect (response) at a certain concentration of agonist relative to the maximum response of the FSH standard. Results are given in Table 1 and 2.

Example 11: Rat Granulosa EC$_{50}$ FSH (Assay B)

The assay was performed pursuant to the teaching of Yanofsky et al. (2006) Allosteric activation of the follicle-stimulating hormone (FSH) receptor by selective, nonpeptide agonists. JBC 281(19): 13226-13233, which is incorporated by reference in the disclosure of the invention. Results are given in Table 1 and 2.

Example 12: Pharmaceutical Preparations (A) Injection vials: A solution of 100 g of an active ingredient according to the invention and 5 g of disodium hydrogen phosphate in 3 l of bidistilled water was adjusted to pH 6.5 using 2 N hydrochloric acid, sterile filtered, transferred into injection vials, lyophilized under sterile conditions and sealed under sterile conditions. Each injection vial contained 5 mg of active ingredient.

(B) Suppositories: A mixture of 20 g of an active ingredient according to the invention was melted with 100 g of soy lecithin and 1400 g of cocoa butter, poured into moulds and allowed to cool. Each suppository contained 20 mg of active ingredient.

(C) Solution: A solution was prepared from 1 g of an active ingredient according to the invention, 9.38 g of NaH$_2$PO$_4$.2H$_2$O, 28.48 g of Na$_2$HPO$_4$.12H$_2$O and 0.1 g of benzalkonium chloride in 940 ml of bidistilled water. The pH was adjusted to 6.8, and the solution was made up to 1 l and sterilized by irradiation. This solution could be used in the form of eye drops.

(D) Ointment: 500 mg of an active ingredient according to the invention were mixed with 99.5 g of Vaseline under aseptic conditions.

(E) Tablets: A mixture of 1 kg of an active ingredient according to the invention, 4 kg of lactose, 1.2 kg of potato starch, 0.2 kg of talc and 0.1 kg of magnesium stearate was pressed to give tablets in a conventional manner in such a way that each tablet contained 10 mg of active ingredient.

(F) Coated tablets: Tablets were pressed analogously to Example E and subsequently coated in a conventional manner with a coating of sucrose, potato starch, talc, tragacanth and dye.

(G) Capsules: 2 kg of an active ingredient according to the invention were introduced into hard gelatin capsules in a conventional manner in such a way that each capsule contained 20 mg of the active ingredient.

(H) Ampoules: A solution of 1 kg of an active ingredient according to the invention in 60 l of bidistilled water was sterile filtered, transferred into ampoules, lyophilized under sterile conditions and sealed under sterile conditions. Each ampoule contained 10 mg of active ingredient.

(I) Inhalation spray: 14 g of an active ingredient according to the invention were dissolved in 10 l of isotonic NaCl solution, and the solution was transferred into commercially available spray containers with a pump mechanism. The solution could be sprayed into the mouth or nose. One spray shot (about 0.1 ml) corresponded to a dose of about 0.14 mg.

The invention claimed is:

1. A compound selected from:

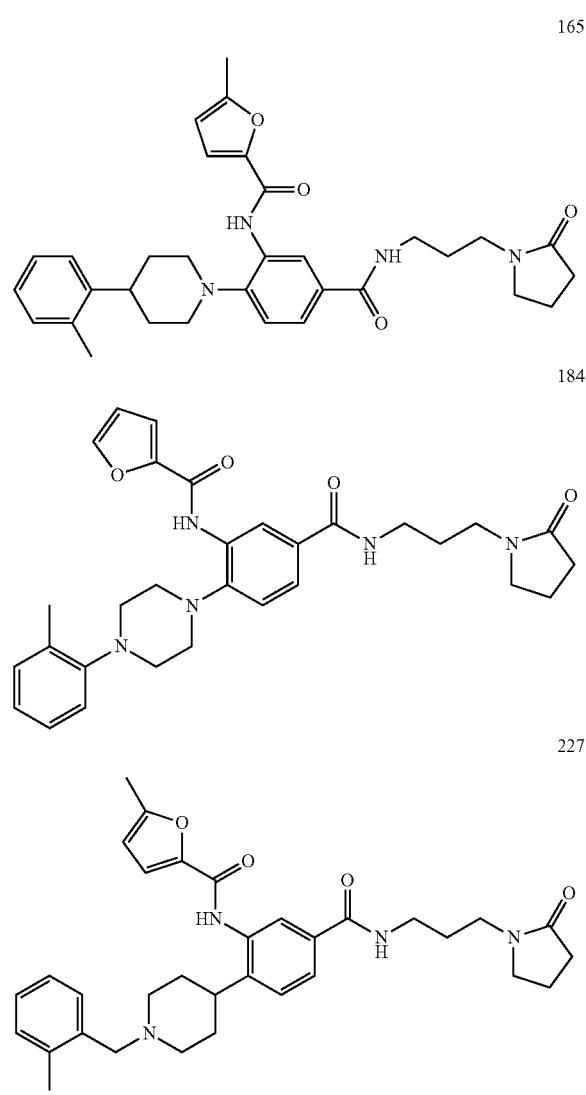

228
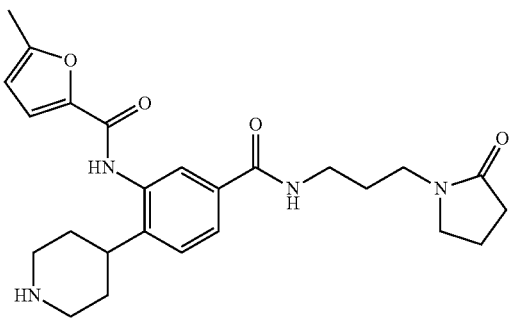
401
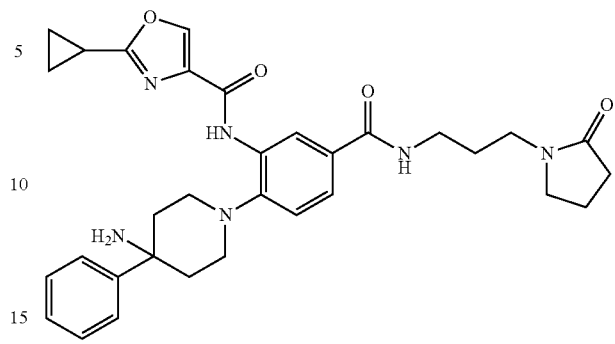
273
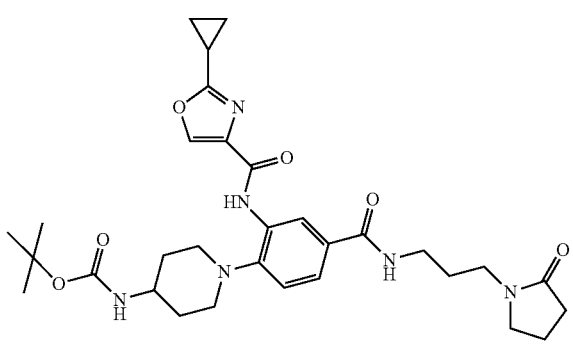
405
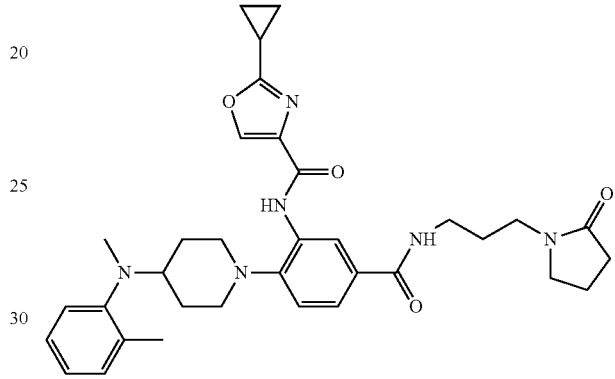
399
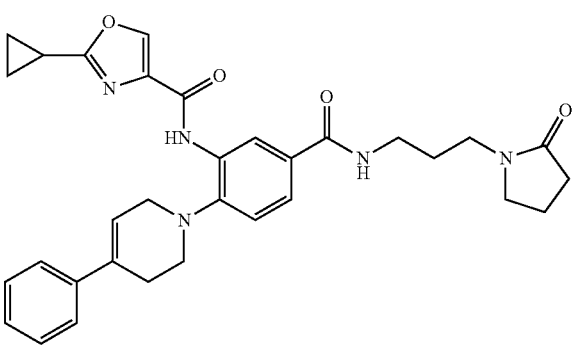
407
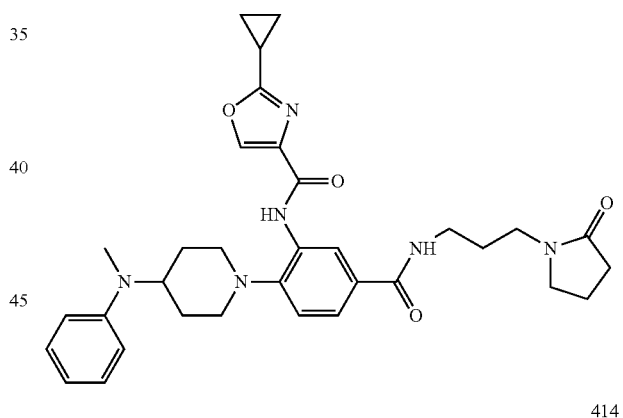
400
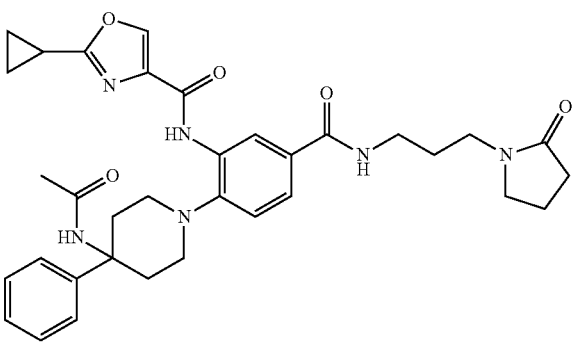
414
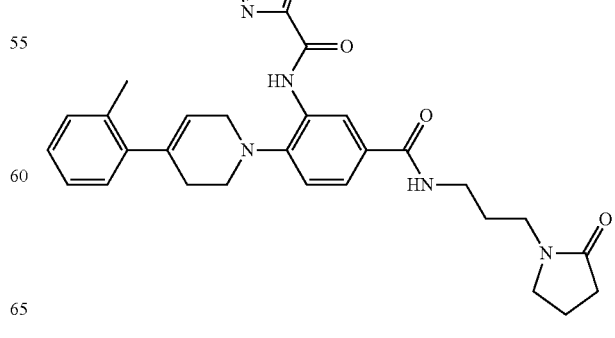

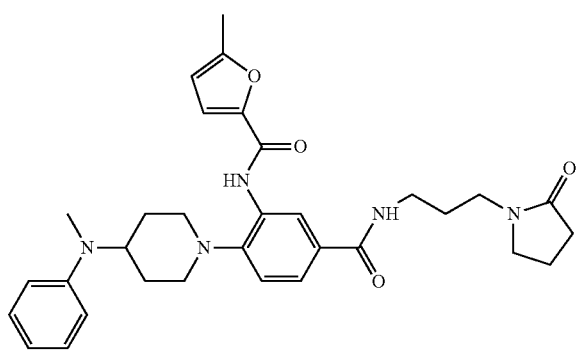

or a physiologically acceptable salt thereof.

2. A method for treating fertility disorders, wherein at least one compound of claim 1 is administered to a mammal in need of such treatment.

3. A method for agonizing an FSH receptor, comprising contacting the FSH receptor with at least one compound of claim 1 under conditions such that the FSH receptor is agonized.

4. A pharmaceutical composition comprising at least one compound according to claim 1 or a physiologically acceptable salt thereof.

5. The pharmaceutical composition according to claim 4, comprising pharmaceutically tolerable adjuvants for oral administration.

6. The pharmaceutical composition according to claim 4, comprising at least a second active pharmaceutical ingredient.

* * * * *